(12) United States Patent
Cole et al.

(10) Patent No.: US 7,781,591 B2
(45) Date of Patent: Aug. 24, 2010

(54) SUBSTITUTED 3-CYANOPYRIDINES AS PROTEIN KINASE INHIBITORS

(75) Inventors: Derek Cecil Cole, New City, NY (US); Diane Harris Boschelli, New City, NY (US); Yanong Daniel Wang, Warren, NJ (US); Magda Asselin, Mahwah, NJ (US); Diane Marie Joseph-McCarthy, Belmont, MA (US); Amarnauth Shastrie Prashad, New City, NY (US); Allan Wissner, Ardsley, NY (US); Russell Dushin, Garrison, NY (US); Biqi Wu, Nanuet, NY (US); Lawrence Nathan Tumey, New Windsor, NY (US); Chuan S. Niu, Cheshire, CT (US); Joan Chen, Flushing, NY (US)

(73) Assignee: Wyeth LLC, Madison, NJ (US)

( * ) Notice: Subject to any disclaimer, the term of this patent is extended or adjusted under 35 U.S.C. 154(b) by 272 days.

(21) Appl. No.: 11/818,119

(22) Filed: Jun. 13, 2007

(65) Prior Publication Data

US 2007/0287708 A1 Dec. 13, 2007

Related U.S. Application Data

(60) Provisional application No. 60/813,060, filed on Jun. 13, 2006.

(51) Int. Cl.
*C07D 401/14* (2006.01)
(52) U.S. Cl. .............. 546/277.4; 546/256; 546/268.4; 546/269.7; 546/270.4; 546/270.7; 546/271.1; 546/271.4; 546/275.4; 546/277.7; 546/281.7; 546/282.4; 546/283.4; 546/283.7; 514/336; 514/339
(58) Field of Classification Search .............. 546/277.4, 546/277.7, 278.1, 256, 268.4, 269.7, 270.4, 546/271.1, 271.4, 275.4, 281.7, 282.4, 270.7
See application file for complete search history.

(56) References Cited

U.S. PATENT DOCUMENTS

| | | | |
|---|---|---|---|
| 6,521,618 B2 * | 2/2003 | Boschelli et al. | 514/231.5 |
| 2003/0187026 A1 * | 10/2003 | Li et al. | 514/332 |
| 2003/0199511 A1 * | 10/2003 | Li et al. | 514/247 |
| 2006/0264460 A1 | 11/2006 | Green et al. | |

FOREIGN PATENT DOCUMENTS

| WO | WO 00/18761 A1 | 4/2000 |
|---|---|---|
| WO | WO 03/050090 A1 | 6/2003 |
| WO | WO 2004/054505 A2 | 7/2004 |
| WO | WO 2004/054505 A3 | 7/2004 |

OTHER PUBLICATIONS

West, Anthony R., Solid State Chemistry and its Applications, Wiley, New York, 1988, pp. 358 & 365.*

* cited by examiner

*Primary Examiner*—Janet L Andres
*Assistant Examiner*—David K O'Dell
(74) *Attorney, Agent, or Firm*—Mabel Ng

(57) ABSTRACT

The present teachings provide compounds of formula I

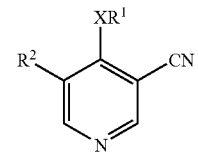

and their pharmaceutically acceptable salts, hydrates, and esters, wherein $R^1$, $R^2$, and X are as defined herein. The present teachings also provide methods of making the compounds of formula I, and methods of treating autoimmune and inflammatory diseases by administering a therapeutically effective amount of a compound or compounds of formula I to a mammal including a human.

20 Claims, No Drawings

SUBSTITUTED 3-CYANOPYRIDINES AS PROTEIN KINASE INHIBITORS

CROSS REFERENCE TO RELATED APPLICATIONS

This application claims priority to and the benefit of U.S. Provisional Patent Application Ser. No. 60/813,060, filed on Jun. 13, 2006, the disclosure of which is incorporated by reference herein in its entirety.

FIELD

The present teachings relate to substituted 3-cyanopyridines (also known as nicotinonitriles) that are capable of inhibiting protein kinases. The present teachings also relate to methods for the preparation of the substituted cyanopyridines and methods of their use. For example, the compounds of the present teachings can be useful for the treatment of autoimmune and inflammatory diseases such as asthma and arthritis.

INTRODUCTION

Protein kinases are enzymes that catalyze the transfer of a phosphate group from adenosine triphosphate (ATP) to an amino acid residue (e.g., tyrosine, serine, threonine or histidine) on a protein. Regulation of these protein kinases is essential for the control of a wide variety of cellular events including proliferation and migration. A large number of diseases including various inflammatory diseases and autoimmune diseases such as asthma, colitis, multiple sclerosis, psoriasis, arthritis, rheumatoid arthritis, osteoarthritis, and joint inflammation, are associated with abnormal cellular events that are mediated by these kinases. See, e.g., Salek-Ardakami, S. et al. (2004), *J. Immunology*, 173(10): 6440-47; Marsland, B. et al. (2004), *J. Exp. Med.*, 200(2): 181-89; Tan, S, et al. (2006), *J. Immunology*, 176: 2872-79; Salek-Ardakami, S. et al. (2005), *J. Immunology*, 175(11): 7635-41; Anderson, K. et al. (2006), *Autoimmunity*, 39(6): 469-78; Healy, A. et al. (2006), *J. Immunology*, 177(3): 1886-93; Sun, Z. et al. (2000), *Nature*, 404: 402-7; and Pfeifhofer, C. et al. (2003), *J. Exp. Med.*, 197(11): 1525-35.

One class of serine/threonine kinases is the protein kinase C (PKC) family. This group of kinases consists of 10 members that share sequence and structural homology. The PKCs are divided into 3 groups and include the classic, the novel, and the atypical isoforms. The theta isoform (PKCθ) is a member of the novel calcium-independent class of PKCs (Baier, G. et al. (1993), *J. Biol. Chem.*, 268: 4997-5004). PKCθ is highly expressed in T cells (Mischak, H. et al. (1993), *FEBS Lett.*, 326: 51-5), with some expression reported in mast cells (Liu, Y. et al. (2001), *J. Leukoc. Biol.*, 69: 831-40), endothelial cells (Mattila, P. et al. (1994), *Life Sci.*, 55: 1253-60), and skeletal muscles (Baier, G. et al. (1994), *Eur. J. Biochem.*, 225: 195-203). It has been shown that PKCθ plays an essential role in T cell receptor (TCR)-mediated signaling (Tan, S. L. et al. (2003), *Biochem. J.*, 376: 545-52). Specifically, it has been observed that inhibiting PKCθ signal transduction, as demonstrated with two independent PKCθ knockout mouse lines, will result in defects in T cell activation and interleukin-2 (IL-2) production (Sun, Z. et al. (2000), *Nature*, 404: 402-7; Pfeifhofer, C. et al. (2003), *J. Exp. Med.*, 197: 1525-35). It also has been shown that PKCθ-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al. (2004), *J. Exp. Med.*, 199: 743-52; Marsland, B. J. et al. (2004), *J. Exp. Med.*, 200: 181-9). The impaired Th2 cell responses result in reduced levels of interleukin-4 (IL-4) and immunoglobulin E (IgE), contributing to the AHR and inflammatory pathophysiology.

Evidence also exists that PKCθ participates in the IgE receptor (FceRI)-mediated response of mast cells (Liu, Y. et al. (2001), *J. Leukoc. Biol.*, 69: 831-840). In human-cultured mast cells (HCMC), it has been demonstrated that PKC kinase activity rapidly localizes (in less than five minutes) to the membrane following FceRI cross-linking (Kimata, M. et al. (1999), *Biochem. Biophys. Res. Commun.*, 257(3): 895-900). A recent study examining in vitro activation of bone marrow mast cells (BMMCs) derived from wild-type and PKCθ-deficient mice shows that upon FceRI cross-linking, BMMCs from PKCθ-deficient mice produced reduced levels of interleukin-6 (IL-6), tumor necrosis factor-alpha (TNFα), and interleukin-13 (IL-13) in comparison with BMMCs from wild-type mice, suggesting a potential role for PKCθ in mast cell cytokine production in addition to T cell activation (Ciarletta, A. B. et al. (2005), poster presentation at the 2005 American Thoracic Society International Conference).

Other serine/threonine kinases include those of the mitogen-activated protein kinase (MAPK) pathway which consists of the MAP kinases (MAPK) (e.g., erk) and the MAPK kinases (MAPKK) (e.g., mek and their substrates). Members of the raf family of kinases phosphorylate residues on mek. The cyclin-dependent kinases (cdks), including cdc2/cyclin B, cdk2/cyclin A, cdk2/cyclin E and cdk4/cyclin D, and others, are serine/threonine kinases that regulate mammalian cell division. Additional serine/threonine kinases include the protein kinases A and B. These kinases, known as PKA or cyclic AMP-dependent protein kinase and PKB (Akt), play key roles in signal transduction pathways.

Tyrosine kinases (TKs) are divided into two classes: the non-transmembrane TKs and transmembrane growth factor receptor TKs (RTKs). Growth factors, such as epidermal growth factor (EGF), bind to the extracellular domain of their partner RTK on the cell surface which activates the RTK, initiating a signal transduction cascade that controls a wide variety of cellular responses. In addition to EGF, there are several other RTKs including FGFR (the receptor for fibroblast growth factor (FGF)); flk-1 (also known as KDR), and flt-1 (the receptors for vascular endothelial growth factor (VEGF)); and PDGFR (the receptor for platelet derived growth factor (PDGF)). Other RTKs include tie-1 and tie-2, colony stimulating factor receptor, the nerve growth factor receptor, and the insulin-like growth factor receptor. In addition to the RTKs there is another family of TKs termed the cytoplasmic protein or non-receptor TKs. The cytoplasmic protein TKs have intrinsic kinase activity, are present in the cytoplasm and nucleus, and participate in diverse signaling pathways. There are a large number of non-receptor TKs including Abl, Jak, Fak, Syk, Zap-70 and Csk, and the Src family of kinases (SFKs) which include Src, Lck, Lyn, Fyn and others.

Certain pyridine and pyrimidine derivatives have been noted as kinase inhibitors. These compounds differ both in nature and placement of substituents at various positions when compared to the compounds of the present teachings.

SUMMARY

The present teachings relate to substituted 3-cyanopyridines of formula I:

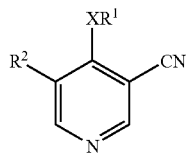

and their pharmaceutically acceptable salts, hydrates, and esters, wherein $R^1$, $R^2$, and X are defined as described herein.

The present teachings also relate to pharmaceutical compositions that include a pharmaceutically effective amount of one or more compounds of formula I (including their pharmaceutically acceptable salts, hydrates, and esters) and a pharmaceutically acceptable carrier or excipient. Another aspect of the present teachings relates to methods of preparing the compounds of formula I and their pharmaceutically acceptable salts, hydrates, and esters. The present teachings also provide methods of using the compounds of formula I and their pharmaceutically acceptable salts, hydrates, and esters. In some embodiments, the present teachings provide methods of treating autoimmune and inflammatory diseases, such as asthma, colitis, multiple sclerosis, psoriasis, arthritis, rheumatoid arthritis, osteoarthritis, and joint inflammation, which include administering a therapeutically effective amount of one or more compounds of formula I (or their pharmaceutically acceptable salts, hydrates, or esters) to a mammal including a human.

DETAILED DESCRIPTION

The present teachings provide compounds of formula I:

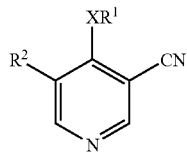

and their pharmaceutically acceptable salts, hydrates, and esters, wherein:

X is selected from a) —$NR^3$—Y—, b) —O—Y—, c) —$S(O)_m$—Y—, d) —$S(O)_m NR^3$—Y—, e) —$NR^3 S(O)_m$—Y—, f) —$C(O)NR^3$—Y—, g) —$C(S)NR^3$—Y—, h) —$NR^3 C(O)$—Y—, i) —$NR^3 C(S)$—Y—, j) —C(O)O—Y—, k) —OC(O)—Y—, and l) a covalent bond;

Y, at each occurrence, independently is selected from a) a divalent $C_{1-10}$ alkyl group, b) a divalent $C_{2-10}$ alkenyl group, c) a divalent $C_{2-10}$ alkynyl group, d) a divalent $C_{1-10}$ haloalkyl group, and e) a covalent bond;

$R^1$ is selected from a) a $C_{1-10}$ alkyl group, b) a $C_{3-14}$ cycloalkyl group, c) a 3-14 membered cycloheteroalkyl group, d) a $C_{8-14}$ polycyclic aryl group, and e) a 5-14 membered heteroaryl group, wherein each group optionally is substituted with 1-4—Y—$R^4$;

$R^2$ is a $C_{6-14}$ aryl group or a 5-14 membered heteroaryl group, wherein each group optionally is substituted with 1-4 groups independently selected from —Y—$R^4$ or —O—Y—$R^4$;

$R^3$, at each occurrence, independently is selected from a) H, b) a $C_{1-10}$ alkyl group, c) a $C_{2-10}$ alkenyl group, d) a $C_{2-10}$ alkynyl group, and e) a $C_{1-10}$ haloalkyl group;

$R^4$, at each occurrence, independently is selected from a) halogen, b) —N, c) —$NO_2$, d) oxo, e) —O—Y—$R^5$, f) —$NR^6$—Y—$R^7$, g) —$N(O)R^6$—Y—$R^7$, h) —$S(O)_m$—Y—$R^5$, i) —$S(O)_m$O—Y—$R^5$, j) —$S(O)_m NR^6$—Y—$R^7$, k) —C(O)—Y—$R^5$, l) —C(O)O—Y—$R^5$, m) —$C(O)NR^6$—Y—$R^7$, n) —$C(S)NR^6$—Y—$R^7$, o) a $C_{1-10}$ alkyl group, p) a $C_{2-10}$ alkenyl group, q) a $C_{2-10}$ alkynyl group, r) a $C_{1-10}$ haloalkyl group, s) a $C_{3-14}$ cycloalkyl group, t) a $C_{6-14}$ aryl group, u) a 3-14 membered cycloheteroalkyl group, and v) a 5-14 membered heteroaryl group, wherein each of o)-v) optionally is substituted with 1-4—Y—$R^8$ groups;

$R^5$, at each occurrence, independently is selected from a) H, b) —$C(O)R^9$, c) —$C(O)OR^9$, d) a $C_{1-10}$ alkyl group, e) a $C_{2-10}$ alkenyl group, f) a $C_{2-10}$ alkynyl group, g) a $C_{1-10}$ haloalkyl group, h) a $C_{3-14}$ cycloalkyl group, i) a $C_{6-14}$ aryl group, j) a 3-14 membered cycloheteroalkyl group, and k) a 5-14 membered heteroaryl group, wherein each of d)-k) optionally is substituted with 1-4-Y—$R^8$ groups;

$R^6$ and $R^7$, at each occurrence, independently are selected from a) H, b) —O—Y—$R^9$, c) —$S(O)_m$—Y—$R^9$, d) —$S(O)_m$O—Y—$R^9$, e) —C(O)—Y—$R^9$, f) —C(O)O—Y—$R^9$, g) —$C(O)NR^{10}$—Y—$R^{11}$, h) —$C(S)NR^{10}$—Y—$R^{11}$, i) a $C_{1-10}$ alkyl group, j) a $C_{2-10}$ alkenyl group, k) a $C_{2-10}$ alkynyl group, l) a $C_{1-10}$ haloalkyl group, m) a $C_{3-14}$ cycloalkyl group, n) a $C_{6-14}$ aryl group, o) a 3-14 membered cycloheteroalkyl group, and p) a 5-14 membered heteroaryl group, wherein each of i)-p) optionally is substituted with 1-4-Y—$R^8$ groups;

$R^8$, at each occurrence, independently is selected from a) halogen, b) —CN, c) —$NO_2$, d) oxo, e) —O—Y—$R^9$, f) —$NR^{10}$—Y—$R^{11}$, g) —$N(O)R^{10}$—Y—$R^{11}$, h) —$S(O)_m$—Y—$R^9$, i) —$S(O)_m$O—Y—$R^9$, j) —$S(O)_m NR^{10}$—Y—$R^{11}$, k) —C(O)—Y—$R^9$, l) —C(O)O—Y—$R^9$, m) —$C(O)NR^{10}$—Y—$R^{11}$, n) —$C(S)NR^{10}$—Y—$R^{11}$, o) a $C_{1-10}$ alkyl group, p) a $C_{2-10}$ alkenyl group, q) a $C_{2-10}$ alkynyl group, r) a $C_{1-10}$ haloalkyl group, s) a $C_{3-14}$ cycloalkyl group, t) a $C_{6-14}$ aryl group, u) a 3-14 membered cycloheteroalkyl group, and v) a 5-14 membered heteroaryl group, wherein each of o)-v) optionally is substituted with 1-4—Y—$R^{12}$ groups;

$R^9$, at each occurrence, independently is selected from a) H, b) —C(O)—$C_{1-10}$ alkyl, c) —C(O)OH, d) —C(O)O—$C_{1-10}$ alkyl, e) a $C_{1-10}$ alkyl group, f) a $C_{2-10}$ alkenyl group, g) a $C_{2-10}$ alkynyl group, h) a $C_{1-10}$ haloalkyl group, i) a $C_{3-14}$ cycloalkyl group, j) a $C_{6-14}$ aryl group, k) a 3-14 membered cycloheteroalkyl group, and l) a 5-14 membered heteroaryl group, wherein each of the $C_{1-10}$ alkyl group, the $C_{2-10}$ alkenyl group, the $C_{2-10}$ alkynyl group, the $C_{1-10}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-4-Y—$R^{12}$ groups;

$R^{10}$ and $R^{11}$, at each occurrence, independently are selected from a) H, b) —OH, c) —SH, d) —$NH_2$, e) —NH—$C_{1-10}$ alkyl, f) —N($C_{1-10}$ alkyl)$_2$, g) —$S(O)_m$—$C_{1-10}$ alkyl, h) —$S(O)_2$OH, i) —$S(O)_m$—O$C_{1-10}$ alkyl, j) —C(O)$C_{1-10}$ alkyl, k) —C(O)OH, l) —C(O)O$C_{1-10}$ alkyl, m) —$C(O)NH_2$, n) —C(O)NH—$C_{1-10}$ alkyl, o) —C(O)N($C_{1-10}$ alkyl)$_2$, p) —$C(S)NH_2$, q) —C(S)NH—$C_{1-10}$ alkyl, r) —C(S)N($C_{1-10}$ alkyl)$_2$, s) a $C_{1-10}$ alkyl group, t) a $C_{2-10}$ alkenyl group, u) a $C_{2-10}$ alkynyl group, v) a $C_{1-10}$ alkoxy group, w) a $C_{1-10}$ haloalkyl group, x) a $C_{3-14}$ cycloalkyl group, y) a $C_{6-14}$ aryl group, z) a 3-14 membered cycloheteroalkyl group, and aa) a 5-14 membered heteroaryl group, wherein each of the $C_{1-10}$ alkyl group, the $C_{2-10}$ alkenyl group, the $C_{2-10}$ alkynyl group, the $C_{1-10}$ alkoxy group, the $C_{1-10}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-4-Y—$R^{12}$ groups;

$R^{12}$, at each occurrence, independently is selected from a) halogen, b) —CN, c) —$NO_2$, d) oxo, e) —OH, f) —$NH_2$, g) —NH($C_{1-10}$ alkyl), h) —N($C_{1-10}$ alkyl)$_2$, i) —SH, j) —S(O)$_m$—$C_{1-10}$ alkyl, k) —S(O)$_2$OH, l) —S(O)$_m$—O$C_{1-10}$ alkyl, m) —C(O)—$C_{1-10}$ alkyl, n) —C(O)OH, o) —C(O)—O$C_{1-10}$ alkyl, p) —C(O)$NH_2$, q) —C(O)NH—$C_{1-10}$ alkyl, r) —C(O)N($C_{1-10}$ alkyl)$_2$, s) —C(S)$NH_2$, t) —C(S)NH—$C_{1-10}$ alkyl, u) —C(S)N($C_{1-10}$ alkyl)$_2$, v) a $C_{1-10}$ alkyl group, w) a $C_{2-10}$ alkenyl group, x) a $C_{2-10}$ alkynyl group, y) a $C_{1-10}$ alkoxy group, z) a $C_{1-10}$ haloalkyl group, aa) a $C_{3-14}$ cycloalkyl group, ab) a $C_{6-14}$ aryl group, ac) a 3-14 membered cycloheteroalkyl group, and ad) a 5-14 membered heteroaryl group; and m is 0, 1, or 2.

In some embodiments, the pyridine ring can be oxidized on the nitrogen atom to provide the corresponding N-oxide having the formula I':

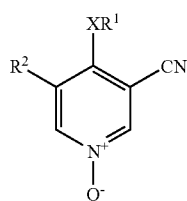

wherein $R^1$, $R^2$, and X are as defined herein.

In some embodiments, X can be selected from —$NR^3$—Y—, —O—Y—, and a covalent bond. For example, X can be selected from —NH—, —N($CH_3$), —NH—$CH_2$—, —NH—$CH_2CH_2$—, —NH—$CH_2CH_2CH_2$—, —O—, and a covalent bond. In particular embodiments, X can be —NH—.

In certain embodiments, $R^1$ can be a $C_{8-14}$ polycyclic (e.g., bicyclic or tricyclic) aryl group or a 5-14 membered heteroaryl group, wherein each of these groups can be optionally substituted with 1-4-Y—$R^4$ groups, wherein Y and $R^4$ are as defined herein. For example, $R^1$ can be selected from a benzimidazolyl group, a benzodioxolyl group, a benzodioxinyl group, a benzodioxanyl group, a benzofuranyl group, a benzothienyl group, a benzoxadiazolyl group, a benzoxazolyl group, a benzisoxazolyl group, a benzothiadiazolyl group, a benzothiazolyl group, a benzisothiazolyl group, a benzo[c]isothiazolyl group, a benzo[c]thienyl group, a benzotriazolyl group, an indazolyl group, an indenyl group, an indanyl group, an indolyl group, an isobenzofuranyl group, an isoindolyl group, an isoquinolinyl group, a naphthyl group, an indolinyl group, a pyrazolyl group, a pyridinyl group, a pyrrolopyridinyl group, a pyrrolyl group, a quinolinyl group, and a tetrahydronaphthalenyl group, wherein each of these groups can be optionally substituted with 1-4-Y—$R^4$ groups, wherein Y and $R^4$ are as defined herein. In particular embodiments, $R^1$ can be an indolyl group or a pyrrolopyridinyl group, wherein each of these groups can be optionally substituted with 1-4-Y—$R^4$ groups, wherein Y and $R^4$ are as defined herein. For example, $R^1$ can be a 1H-indol-4-yl group, a 1H-indol-5-yl group, a 1H-indol-6-yl group, or a 1H-indol-7-yl group, wherein each of these groups can be optionally substituted with 1-4 groups independently selected from a halogen, a $C_{1-4}$ alkyl group, and a $C_{1-4}$ alkoxy group.

In other embodiments, $R^1$ can be a $C_{3-14}$ cycloalkyl group or a 3-14 membered cycloheteroalkyl group, wherein each of these groups can be optionally substituted with 1-4-Y—$R^4$ groups, wherein Y and $R^4$ are as defined herein. For example, $R^1$ can be selected from a cyclobutyl group, a cyclopentyl group, a cyclohexyl group, a cycloheptyl group, a pyrrolidinyl group, a piperidinyl group, a piperazinyl group, a morpholinyl group, and a thiomorpholinyl group, wherein each of these groups can be optionally substituted with 1-4-Y—$R^4$ groups, wherein Y and $R^4$ are as defined herein. In some embodiments, Y, at each occurrence, can be independently a divalent $C_{1-4}$ alkyl group or a covalent bond, and $R^4$, at each occurrence, can be independently —($CH_2$)$_n$—$NR^6$—Y—$R^7$ or a $C_{1-4}$ alkyl group, wherein n can be 0, 1, 2, 3, or 4, and Y, $R^6$, and $R^7$ are as defined herein.

In some embodiments, $R^2$ can be selected from a phenyl group, a $C_{8-14}$ aryl group, and a 5-14 membered heteroaryl group, wherein each of these groups can be optionally substituted with 1-4 groups independently selected from —Y—$R^4$ and —O—Y—$R^4$, wherein Y and $R^4$ are as defined herein. For example, $R^2$ can be selected from a phenyl group, a pyridyl group, a pyrimidyl group, a pyrazinyl group, a furyl group, a thienyl group, a thiazolyl group, an oxazolyl group, a benzofuranyl group, a benzothienyl group, an indolyl group, a benzodioxinyl group, a benzodioxolyl group, a benzodioxanyl group, a dibenzofuranyl group, a dibenzothienyl group, a benzoindolyl group, an indanyl group, an indenyl group, an isothiazolyl group, a pyridazinyl group, a pyrazolyl group, a tetrahydronaphthyl group, an isoxazolyl group, a quinolinyl group, a naphthyl group, an imidazolyl group, and a pyrrolyl group, wherein each of these groups can be optionally substituted with 1-4 groups independently selected from —Y—$R^4$ or —O—Y—$R^4$, wherein Y and $R^4$ are as defined herein.

In certain embodiments, $R^2$ can be

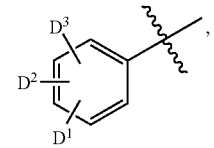

wherein $D^1$, $D^2$, and $D^3$ independently can be H, a —Y—$R^4$ group, or an —O—Y—$R^4$ group, wherein Y and $R^4$ are as defined herein.

For example, at least one of $D^1$, $D^2$, and $D^3$ can be a —Y—$R^4$ group or an —O—Y—$R^4$ group, wherein Y, at each occurrence, can be independently a divalent $C_{1-4}$ alkyl group or a covalent bond, and $R^4$, at each occurrence, can be independently selected from a halogen, —CN, —$NO_2$, —O—Y—$R^5$, —$NR^6$—Y—$R^7$, —S(O)$_2$—Y—$R^5$, —S(O)$_2$$NR^6$—Y—$R^7$, —C(O)—Y—$R^5$, —C(O)O—Y—$R^5$, —C(O)$NR^6$—Y—$R^7$, a $C_{1-10}$ alkyl group, a $C_{1-10}$ haloalkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{1-10}$ haloalkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^8$ groups, wherein Y, $R^5$, $R^6$, $R^7$, and $R^8$ are as defined herein.

In certain embodiments, at least one of $D^1$, $D^2$, and $D^3$ can be an —O—$(CH_2)_n$—$R^4$ group, wherein n, at each occurrence, independently can be 0, 1, 2, 3, or 4, and $R^4$, at each occurrence, can be independently selected from F, Cl, Br, —$NO_2$, —O—Y—$R^5$, —$NR^6$—Y—$R^7$, $S(O)_2$—Y—$R^5$, —$S(O)_2NR^6$—Y—$R^7$, —$C(O)NR^6$—Y—$R^7$, a $C_{1-10}$ alkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^8$ groups, wherein Y, $R^5$, $R^6$, $R^7$, and $R^8$ are as defined herein. In particular embodiments, at least one of $D^1$, $D^2$, and $D^3$ can be —O—$(CH_2)_nNR^6$—Y—$R^7$ or an —O—$(CH_2)_n$— 3-14 membered cycloheteroalkyl group, wherein the 3-14 membered cycloheteroalkyl group can be optionally substituted with 1-4-Y—$R^8$ groups, wherein Y, $R^6$, $R^7$, and $R^8$ are as defined herein, and n, at each occurrence, independently can be 0, 1, 2, 3, or 4.

In some embodiments, at least one of $D^1$, $D^2$, and $D^3$ can be —$(CH_2)_nNR^6$—Y—$R^7$ or a —$(CH_2)_n$— 3-14 membered cycloheteroalkyl group, wherein the 3-14 membered cycloheteroalkyl group can be optionally substituted with 1-4-Y—$R^8$ groups, Y, $R^6$, $R^7$, and $R^8$ are as defined herein, and n, at each occurrence, independently can be 0, 1, 2, 3, or 4.

In embodiments where at least one of $D^1$, $D^2$, and $D^3$ can be an —O—$(CH_2)_nNR^6$—Y—$R^7$ group or a —$(CH_2)_nNR^6$—Y—$R^7$ group, the —O—$(CH_2)_nNR^6$—Y—$R^7$ group and the —$(CH_2)_nNR^6$—Y—$R^7$ group can be —O—$(CH_2)_nNH$—Y—$R^7$ or —O—$(CH_2)_nN(CH_3)$—Y—$R^7$, and —$(CH_2)_nNH$—Y—$R^7$ or —$(CH_2)_nN(CH_3)$—Y—$R^7$, respectively, wherein Y, at each occurrence, can be independently a divalent $C_{1-4}$ alkyl group or a covalent bond, and $R^7$, at each occurrence, can be independently selected from —O—Y—$R^9$, —C(O)—Y—$R^9$, —C(O)O—Y—$R^9$, —$C(O)NR^{10}$—Y—$R^{11}$, a $C_{1-10}$ alkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^{12}$ groups, wherein Y and $R^{12}$ are as defined herein. For example, the $C_{3-14}$ cycloalkyl group, the $C_{6-14}$ aryl group, the 3-14 membered cycloheteroalkyl group, and the 5-14 membered heteroaryl group can be selected from a cyclopentyl group, a cyclohexyl group, a phenyl group, a pyrrolidinyl group, a morpholinyl group, a piperazinyl group, a piperidinyl group, an azepanyl group, a diazepanyl group, a thiomorpholinyl group, a furyl group, an imidazolyl group, and a pyridinyl group, wherein each of these groups can be optionally substituted with 1-4-Y—$R^{12}$ groups, wherein Y and $R^{12}$ are as defined herein.

In embodiments where at least one of $D^1$, $D^2$, and $D^3$ can be an —O—$(CH_2)_n$— 3-14 membered cycloheteroalkyl group or a —$(CH_2)_n$— 3-14 membered cycloheteroalkyl group, the 3-14 membered cycloheteroalkyl group can be selected from a pyrrolidinyl group, a morpholinyl group, a piperazinyl group, a piperidinyl group, an azepanyl group, a diazepanyl group, and a thiomorpholinyl group, wherein each of these groups can be optionally substituted with 1-4-Y—$R^8$ groups, wherein Y and $R^8$ are as defined herein. For example, Y, at each occurrence, can be independently a divalent $C_{1-4}$ alkyl group or a covalent bond, and $R^8$, at each occurrence, can be independently an oxo group, —O—Y—$R^9$, —$NR^{10}$—Y—$R^{11}$, —$S(O)_m$—Y—$R^9$, —C(O)O—Y—$R^9$, a $C_{1-10}$ alkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^{12}$ groups, wherein Y and $R^{12}$ are as defined herein. For example, the $C_{3-14}$ cycloalkyl group, the $C_{6-14}$ aryl group, the 3-14 membered cycloheteroalkyl group, and the 5-14 membered heteroaryl group can be selected from a cyclopentyl group, a cyclohexyl group, a phenyl group, a pyrrolidinyl group, a morpholinyl group, a piperazinyl group, a piperidinyl group, an azepanyl group, a diazepanyl group, a thiomorpholinyl group, a furyl group, an imidazolyl group, and a pyridinyl group, wherein each of these groups can be optionally substituted with 1-4-Y—$R^{12}$ groups, wherein Y and $R^{12}$ are as defined herein.

Alternatively or concurrently, at least one of $D^1$, $D^2$, and $D^3$ can be selected from halogen, —CN, —$NO_2$, —$S(O)_2$—Y—$R^5$, —$S(O)_2NR^6$—Y—$R^7$, —C(O)O—Y—$R^5$, $C(O)NR^6$—Y—$R^7$, a $C_{1-10}$ alkyl group, and a $C_{1-10}$ haloalkyl group, wherein Y, $R^5$, $R^6$, and $R^7$ are as defined herein.

In some embodiments, at least two of $D^1$, $D^2$, and $D^3$ can be —O—$(CH_2)_n$—$R^4$ groups, wherein n, at each occurrence, independently can be 0, 1, 2, 3, or 4, and $R^4$, at each occurrence, can be independently selected from F, Cl, Br, —$NO_2$, —O—Y—$R^5$, —$NR^6$—Y—$R^7$, —$S(O)_2$—Y—$R^5$, —$S(O)_2NR^6$—Y—$R^7$, —$C(O)NR^6$—Y—$R^7$, a $C_{1-10}$ alkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^8$ groups, wherein Y, $R^5$, $R^6$, $R^7$, and $R^8$ are as defined herein.

In certain embodiments, at least two of $D^1$, $D^2$, and $D^3$ can be independently an —O—$CH_3$ group or an —O—$(CH_2)_n$—O—Y—$R^5$ group, wherein Y and $R^5$ are as defined herein, and n, at each occurrence, independently can be 0, 1, 2, 3, or 4. In certain embodiments, two of $D^1$, $D^2$, and $D^3$ can be —O—$CH_3$ groups. In other embodiments, two of $D^1$, $D^2$, and $D^3$ can be —O—$(CH_2)_n$—O—Y—$R^5$ groups or alternatively, an —O—$CH_3$ group and an —O—$(CH_2)_n$—O—Y—$R^5$ group, wherein Y and $R^5$ are as defined herein, and n, at each occurrence, independently can be 0, 1, 2, 3, or 4.

In certain embodiments, at least one of $D^1$, $D^2$, and $D^3$ can be —O—$CH_3$, and at least one of $D^1$, $D^2$, and $D^3$ can be an —O—$(CH_2)_nNR^6$—Y—$R^7$ group or an —O—$(CH_2)_n$— 3-14 membered cycloheteroalkyl group, wherein the 3-14 membered cycloheteroalkyl group can be optionally substituted with 1-4-Y—$R^8$ groups, wherein Y, $R^6$, $R^7$, and $R^8$ are as defined herein, and n, at each occurrence, independently can be 0, 1, 2, 3, or 4.

In some embodiments, one of $D^1$, $D^2$, and $D^3$ can be

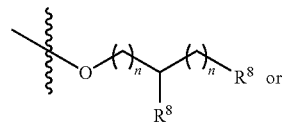 or

-continued

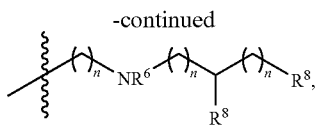

wherein $R^8$, at each occurrence, independently can be selected from —O—Y—$R^9$, —$NR^{10}$—Y—$R^{11}$, a $C_{6-14}$ aryl group, and a 5-14 membered heteroaryl group, wherein each of the $C_{6-14}$ aryl group and the 5-14 membered heteroaryl group can be optionally substituted with 1-4-Y—$R^{12}$ groups, wherein Y, $R^9$, $R^{10}$, $R^{11}$, and $R^{12}$ are as defined herein, and n, at each occurrence, independently can be 0, 1, 2, 3, or 4.

In certain embodiments, at least one of $D^1$, $D^2$, and $D^3$ can be a $C_{6-14}$ aryl group or a 5-14 membered heteroaryl group, wherein each of these groups can be optionally substituted with 1-4 Y—$R^8$ groups, wherein Y and $R^8$ are as defined herein. For example, at least one of $D^1$, $D^2$, and $D^3$ can be selected from a benzothienyl group, a benzofuryl group, a furyl group, a pyridyl group, a pyrimidinyl group, a pyrrolyl group, and a thienyl group, wherein each of these groups can be optionally substituted with 1-4-Y—$R^8$ groups, wherein Y and $R^8$ are as defined herein. In particular embodiments, Y, at each occurrence, can be independently a $C_{1-4}$ alkyl group or a covalent bond, and $R^8$ can be independently selected from a halogen, —CN, —$NO_2$, —O—Y—$R^9$, —$NR^{10}$—Y—$R^{11}$, —C(O)—Y—$R^9$, —C(O)$NR^{10}$—Y—$R^{11}$, —S(O)$_2$—Y—$R^9$, —S(O)$_2NR^{10}$—Y—$R^{11}$, and a 3-14 membered cycloheteroalkyl group optionally substituted with a $C_{1-4}$ alkyl group, wherein Y, $R^9$, $R^{10}$, and $R^{11}$ are as defined herein.

In other embodiments, $R^2$ can be a $C_{8-14}$ bicyclic aryl group or a 5-14 membered heteroaryl group, where each of these groups can be optionally substituted with 1-4 groups independently selected from —Y—$R^4$ groups and —O—Y—$R^4$ groups, wherein Y and $R^4$ are as defined herein.

In particular embodiments, $R^2$ can be selected from a benzothienyl group, a benzofuryl group, a furyl group, a pyridyl group, a pyrimidinyl group, a pyrazinyl group, a thienyl group, an imidazolyl group, an isoxazolyl group, a thiazolyl group, an oxazolyl group, an indolyl group, a benzodioxolyl group, a benzodioxanyl group, and a dibenzofuranyl group, wherein each of these groups can be optionally substituted with 1-4 groups independently selected from a —(CH$_2$)$_n$—$R^4$ group and an —O—(CH$_2$)$_n$—$R^4$ group, wherein n, at each occurrence, independently can be 0, 1, 2, 3, or 4, and $R^4$, at each occurrence, can be independently —$NR^6$—Y—$R^7$ or a 3-14 membered cycloheteroalkyl group optionally substituted with 1-4-Y—$R^8$ group, wherein Y, $R^6$, $R^7$ and $R^8$ are as defined herein.

For example, $R^4$ can be —O—CH$_2$)$_n$NH—Y—$R^7$, —(CH$_2$)$_n$N(CH$_3$)—Y—$R^7$, —(CH$_2$)$_n$NH—Y—$R^7$, or —(CH$_2$)$_n$N(CH$_3$)—Y—$R^7$, wherein Y, at each occurrence, can be independently a divalent $C_{1-4}$ alkyl group or a covalent bond, and $R^7$, at each occurrence, can be independently selected from —O—Y—$R^9$, —C(O)—Y—$R^9$, —C(O)O—Y—$R^9$, —C(O)$NR^{10}$—Y—$R^{11}$, a $C_{1-10}$ alkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^{12}$ groups, wherein Y and $R^{12}$ are as defined herein. In particular embodiments, $R^7$ can be a $C_{3-14}$ cycloalkyl group, a $C_{6-14}$ aryl group, a 3-14 membered cycloheteroalkyl group, or a 5-14 membered heteroaryl group selected from a cyclopentyl group, a cyclohexyl group, a phenyl group, a pyrrolidinyl group, a morpholinyl group, a piperazinyl group, a piperidinyl group, an azepanyl group, a diazepanyl group, a thiomorpholinyl group, a furyl group, an imidazolyl group, and a pyridinyl group, wherein each of these groups can be optionally substituted with 1-4-Y—$R^{12}$ groups, wherein Y and $R^{12}$ are as defined herein.

Alternatively, $R^4$ can be an —O—(CH$_2$)$_n$— 3-14 membered cycloheteroalkyl group or a a —(CH$_2$)$_n$— 3-14 membered cycloheteroalkyl group, wherein the 3-14 membered cycloheteroalkyl group can be selected from a pyrrolidinyl group, a morpholinyl group, a piperazinyl group, a piperidinyl group, an azepanyl group, a diazepanyl group, and a thiomorpholinyl group, wherein each of these groups can be optionally substituted with 1-4-Y—$R^8$ groups, wherein Y and $R^8$ are as defined herein. For example, Y, at each occurrence, can be independently a divalent $C_{1-4}$ alkyl group or a covalent bond, and $R^8$, at each occurrence, can be independently an oxo group, —O—Y—$R^9$, —$NR^{10}$—Y—$R^{11}$, —S(O)$_m$—Y—$R^9$, —C(O)O—Y—$R^9$, a $C_{1-10}$ alkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{3-14}$ cycloalkyl group, the $C_{6-14}$ aryl group, the 3-14 membered cycloheteroalkyl group, and the 5-14 membered heteroaryl group can be optionally substituted with 1-4-Y—$R^{12}$ groups, wherein Y and $R^{12}$ are as defined herein. For example, $R^8$ can be a $C_{3-14}$ cycloalkyl group, a $C_{6-14}$ aryl group, a 3-14 membered cycloheteroalkyl group, and a 5-14 membered heteroaryl group selected from a cyclopentyl group, a cyclohexyl group, a phenyl group, a pyrrolidinyl group, a morpholinyl group, a piperazinyl group, a piperidinyl group, an azepanyl group, a diazepanyl group, a thiomorpholinyl group, a furyl group, an imidazolyl group, and a pyridinyl group, wherein each of these groups can be optionally substituted with 1-4-Y—$R^{12}$ groups, wherein Y and $R^{12}$ are as defined herein.

Compounds of the present teachings include the compounds presented in Table 1 below.

TABLE 1

| Compound | Name |
|---|---|
| 101 | 5-(3,4-dimethoxyphenyl)-4-(1H-indol-5-ylamino)nicotinonitrile |
| 102 | 4-(2,1,3-benzothiadiazol-4-ylamino)-5-(3,4-dimethoxyphenyl)nicotinonitrile |
| 103 | 5-(3,4-dimethoxyphenyl)-4-(isoquinolin-5-ylamino)nicotinonitrile |
| 104 | 5-(3,4-dimethoxyphenyl)-4-(quinolin-5-ylamino)nicotinonitrile |
| 105 | 5-(3,4-dimethoxyphenyl)-4-(5,6,7,8-tetrahydronaphthalen-1-ylamino)nicotinonitrile |
| 106 | 4-(2,3-dihydro-1,4-benzodioxin-6-ylamino)-5-(3,4-dimethoxyphenyl)nicotinonitrile |

TABLE 1-continued

| Compound | Name |
|---|---|
| 107 | 4-(2,3-dihydro-1H-inden-5-ylamino)-5-(3,4-dimethoxyphenyl)nicotinonitrile |
| 108 | 5-(3,4-dimethoxyphenyl)-4-(1H-indol-6-ylamino)nicotinonitrile |
| 109 | 5-(3,4-dimethoxyphenyl)-4-(1H-indol-4-ylamino)nicotinonitrile |
| 110 | 5-(3,4-dimethoxyphenyl)-4-[(2-methyl-1H-indol-5-yl)amino]nicotinonitrile |
| 111 | 4-(1,3-benzodioxol-5-ylamino)-5-(3,4-dimethoxyphenyl)nicotinonitrile |
| 112 | 5-(3,4-dimethoxyphenyl)-4-(2-naphthylamino)nicotinonitrile |
| 113 | 5-(3-bromophenyl)-4-(1H-indol-5-ylamino)nicotinonitrile |
| 114 | 5-(3-bromophenyl)-4-(1H-indol-4-ylamino)nicotinonitrile |
| 115 | 5-(2-bromophenyl)-4-(1H-indol-5-ylamino)nicotinonitrile |
| 116 | 5-(4-bromophenyl)-4-(1H-indol-5-ylamino)nicotinonitrile |
| 117 | 5-(3'-aminobiphenyl-3-yl)-4-(1H-indol-5-ylamino)nicotinonitrile |
| 118 | 5-(4'-cyanobiphenyl-3-yl)-4-(1H-indol-5-ylamino)nicotinonitrile |
| 119 | 5-(4'-aminobiphenyl-3-yl)-4-(1H-indol-5-ylamino)nicotinonitrile |
| 120 | N-{3'-[5-cyano-4-(1H-indol-5-ylamino)pyridin-3-yl]biphenyl-4-yl}acetamide |
| 121 | 4-(1H-indol-5-ylamino)-5-(3-pyridin-4-ylphenyl)nicotinonitrile |
| 122 | 3'-[5-cyano-4-(1H-indol-5-ylamino)pyridin-3-yl]-N,N-dimethylbiphenyl-4-carboxamide |
| 123 | 3'-[5-cyano-4-(1H-indol-5-ylamino)pyridin-3-yl]-N-cyclopentylbiphenyl-4-carboxamide |
| 124 | 4-(1H-indol-5-ylamino)-5-[3-(1H-pyrrol-3-yl)phenyl]nicotinonitrile |
| 125 | 5-(2-bromophenyl)-4-[(7-methyl-1H-indol-5-yl)amino]nicotinonitrile |
| 126 | 5-(2-bromophenyl)-4-(1H-indol-4-ylamino)nicotinonitrile |
| 127 | 4-(1H-indol-5-ylamino)-5-(3'-methylbiphenyl-3-yl)nicotinonitrile |
| 128 | 4-(1H-indol-5-ylamino)-5-(4'-methylbiphenyl-3-yl)nicotinonitrile |
| 129 | 5-(2'-chlorobiphenyl-3-yl)-4-(1H-indol-5-ylamino)nicotinonitrile |
| 130 | 5-(3'-chlorobiphenyl-3-yl)-4-(1H-indol-5-ylamino)nicotinonitrile |
| 131 | 5-(4'-chlorobiphenyl-3-yl)-4-(1H-indol-5-ylamino)nicotinonitrile |
| 132 | 5-(3'-cyanobiphenyl-3-yl)-4-(1H-indol-5-ylamino)nicotinonitrile |
| 133 | 3'-[5-cyano-4-(1H-indol-5-ylamino)pyridin-3-yl]biphenyl-3-carboxylic acid |
| 134 | 3'-[5-cyano-4-(1H-indol-5-ylamino)pyridin-3-yl]biphenyl-4-carboxylic acid |
| 135 | 3'-[5-cyano-4-(1H-indol-4-ylamino)pyridin-3-yl]biphenyl-4-carboxylic acid |
| 136 | 4-(1H-indol-5-ylamino)-5-[3-(2-thienyl)phenyl]nicotinonitrile |
| 137 | 4-(1H-indol-5-ylamino)-5-(3-pyridin-3-ylphenyl)nicotinonitrile |
| 138 | 4-(1H-indol-5-ylamino)-5-(3-pyrimidin-2-ylphenyl)nicotinonitrile |
| 139 | 4-(1H-indol-5-ylamino)-5-[3-(4-methyl-2-thienyl)phenyl]nicotinonitrile |
| 140 | 5-[3-(5-acetyl-2-thienyl)phenyl]-4-(1H-indol-5-ylamino)nicotinonitrile |
| 141 | 4-(1H-indol-5-ylamino)-5-[3-(3-thienyl)phenyl]nicotinonitrile |
| 142 | 5-[3-(3-furyl)phenyl]-4-(1H-indol-5-ylamino)nicotinonitrile |
| 143 | 5-(2'-chlorobiphenyl-2-yl)-4-(1H-indol-5-ylamino)nicotinonitrile |
| 144 | 5-(3'-chlorobiphenyl-2-yl)-4-(1H-indol-5-ylamino)nicotinonitrile |
| 145 | 5-(4'-chlorobiphenyl-2-yl)-4-(1H-indol-5-ylamino)nicotinonitrile |
| 146 | 4-(1H-indol-5-ylamino)-5-[2-(3-thienyl)phenyl]nicotinonitrile |
| 147 | 4-(1H-indol-4-ylamino)-5-[3-(2-thienyl)phenyl]nicotinonitrile |
| 148 | 3'-[5-cyano-4-(1H-indol-4-ylamino)pyridin-3-yl]-N-cyclopentylbiphenyl-4-carboxamide |
| 149 | 4-(1H-indol-4-ylamino)-5-[4'-(pyrrolidin-1-ylcarbonyl)biphenyl-3-yl]nicotinonitrile |
| 150 | 5-[3-(5-formyl-2-thienyl)phenyl]-4-(1H-indol-5-ylamino)nicotinonitrile |
| 151 | 4-(1H-indol-5-ylamino)-5-(3-nitrophenyl)nicotinonitrile |
| 152 | N-{3-[5-cyano-4-(1H-indol-5-ylamino)pyridin-3-yl]phenyl}acetamide |
| 153 | 4-(1H-indol-4-ylamino)-5-[4-methoxy-3-(2-methoxyethoxy)phenyl]nicotinonitrile |
| 154 | 4-(1H-indol-5-ylamino)-5-[4-methoxy-3-(2-methoxyethoxy)phenyl]nicotinonitrile |
| 155 | 4-(1H-indol-6-ylamino)-5-[4-methoxy-3-(2-methoxyethoxy)phenyl]nicotinonitrile |
| 156 | 4-(1,3-benzothiazol-6-ylamino)-5-[4-methoxy-3-(2-methoxyethoxy)phenyl]nicotinonitrile |
| 157 | 5-[4-methoxy-3-(2-methoxyethoxy)phenyl]-4-[(2-methyl-1H-indol-5-yl)amino]nicotinonitrile |
| 158 | 4-(1H-1,2,3-benzotriazol-5-ylamino)-5-[4-methoxy-3-(2-methoxyethoxy)phenyl]nicotinonitrile |
| 159 | 4-(1H-indol-4-ylamino)-5-[3-methoxy-4-(2-methoxyethoxy)phenyl]nicotinonitrile |
| 160 | 4-(1H-indol-5-ylamino)-5-[3-methoxy-4-(2-methoxyethoxy)phenyl]nicotinonitrile |
| 161 | 4-(1H-indol-6-ylamino)-5-[3-methoxy-4-(2-methoxyethoxy)phenyl]nicotinonitrile |
| 162 | 4-(1,3-benzothiazol-6-ylamino)-5-[3-methoxy-4-(2-methoxyethoxy)phenyl]nicotinonitrile |
| 163 | 5-[3-methoxy-4-(2-methoxyethoxy)phenyl]-4-[(2-methyl-1H-indol-5-yl)amino]nicotinonitrile |
| 164 | 4-(1H-indol-4-ylamino)-5-[3-(2-methoxyethoxy)phenyl]nicotinonitrile |
| 165 | 5-[3-(2-chloroethoxy)phenyl]-4-(1H-indol-4-ylamino)nicotinonitrile |
| 166 | 5-[3-(2-chloroethoxy)phenyl]-4-(1H-indol-6-ylamino)nicotinonitrile |

TABLE 1-continued

| Compound | Name |
|---|---|
| 167 | 5-[3-(2-chloroethoxy)phenyl]-4-(1H-indol-5-ylamino)nicotinonitrile |
| 168 | 4-(1H-indol-4-ylamino)-5-{3-[2-(4-methylpiperazin-1-yl)ethoxy]phenyl}nicotinonitrile |
| 169 | 4-(1H-indol-4-ylamino)-5-[3-(2-pyrrolidin-1-ylethoxy)phenyl]nicotinonitrile |
| 170 | 4-(1H-indol-4-ylamino)-5-[3-(2-morpholin-4-ylethoxy)phenyl]nicotinonitrile |
| 171 | 4-(1H-indol-4-ylamino)-5-[3-(2-piperidin-1-ylethoxy)phenyl]nicotinonitrile |
| 172 | 4-(1H-indol-6-ylamino)-5-[3-(2-pyrrolidin-1-ylethoxy)phenyl]nicotinonitrile |
| 173 | 4-(1H-indol-6-ylamino)-5-[3-(2-morpholin-4-ylethoxy)phenyl]nicotinonitrile |
| 174 | 4-(1H-indol-5-ylamino)-5-[3-(2-pyrrolidin-1-ylethoxy)phenyl]nicotinonitrile |
| 175 | 4-(1H-indol-5-ylamino)-5-[3-(2-morpholin-4-ylethoxy)phenyl]nicotinonitrile |
| 176 | 5-(3-{2-[(2-hydroxyethyl)amino]ethoxy}phenyl)-4-(1H-indol-5-ylamino)nicotinonitrile |
| 177 | 4-(1H-indol-5-ylamino)-5-(3-{2-[(2-pyrrolidin-1-ylethyl)amino]ethoxy}phenyl)nicotinonitrile |
| 178 | 5-[3-(2-chloroethoxy)-4-methoxyphenyl]-4-(1H-indol-5-ylamino)nicotinonitrile |
| 179 | 5-{3-[2-(diethylamino)ethoxy]-4-methoxyphenyl}-4-(1H-indol-5-ylamino)nicotinonitrile |
| 180 | 5-{3-[2-(diisopropylamino)ethoxy]-4-methoxyphenyl}-4-(1H-indol-5-ylamino)nicotinonitrile |
| 181 | 5-{3-[2-(benzylamino)ethoxy]-4-methoxyphenyl}-4-(1H-indol-5-ylamino)nicotinonitrile |
| 182 | 4-(1H-indol-5-ylamino)-5-(4-methoxy-3-{2-[(2-methoxyethyl)amino]ethoxy}phenyl)nicotinonitrile |
| 183 | 4-(1H-indol-5-ylamino)-5-(4-methoxy-3-{2-[(5-methyl-1,3,4-thiadiazol-2-yl)amino]ethoxy}phenyl)nicotinonitrile |
| 184 | 4-(1H-indol-5-ylamino)-5-(3-{5-[(4-methylpiperazin-1-yl)methyl]-2-thienyl}phenyl)nicotinonitrile |
| 185 | 4-(1H-indol-5-ylamino)-5-{3-[5-(morpholin-4-ylmethyl)-2-thienyl]phenyl}nicotinonitrile |
| 186 | 4-(1H-indol-5-ylamino)-5-{3-[5-(piperidin-1-ylmethyl)-2-thienyl]phenyl}nicotinonitrile |
| 187 | 5-(3-{5-[(dimethylamino)methyl]-2-thienyl}phenyl)-4-(1H-indol-5-ylamino)nicotinonitrile |
| 188 | 5-(3-bromo-4-methoxyphenyl)-4-(1H-indol-5-ylamino)nicotinonitrile |
| 189 | 4-(1H-indol-5-ylamino)-5-[4-methoxy-3-(2-thienyl)phenyl]nicotinonitrile |
| 190 | 5-(4'-chloro-6-methoxybiphenyl-3-yl)-4-(1H-indol-5-ylamino)nicotinonitrile |
| 191 | 5-(3'-chloro-6-methoxybiphenyl-3-yl)-4-(1H-indol-5-ylamino)nicotinonitrile |
| 192 | 5'-[5-cyano-4-(1H-indol-5-ylamino)pyridin-3-yl]-N-cyclopentyl-2'-methoxybiphenyl-4-carboxamide |
| 193 | 5-(2'-chloro-6-methoxybiphenyl-3-yl)-4-(1H-indol-5-ylamino)nicotinonitrile |
| 194 | 5-[3-(benzyloxy)phenyl]-4-(1H-indol-5-ylamino)nicotinonitrile |
| 195 | 5-[4-(benzyloxy)phenyl]-4-(1H-indol-5-ylamino)nicotinonitrile |
| 196 | 3'-[5-cyano-4-(1H-indol-5-ylamino)pyridin-3-yl]-N-methylbiphenyl-4-carboxamide |
| 197 | N-butyl-3'-[5-cyano-4-(1H-indol-5-ylamino)pyridin-3-yl]biphenyl-4-carboxamide |
| 198 | 3'-[5-cyano-4-(1H-indol-5-ylamino)pyridin-3-yl]-N-(1-ethylpropyl)biphenyl-4-carboxamide |
| 199 | 3'-[5-cyano-4-(1H-indol-5-ylamino)pyridin-3-yl]-N-(2-hydroxyethyl)biphenyl-4-carboxamide |
| 200 | 3'-[5-cyano-4-(1H-indol-5-ylamino)pyridin-3-yl]-N-(2-methoxyethyl)biphenyl-4-carboxamide |
| 201 | 3'-[5-cyano-4-(1H-indol-5-ylamino)pyridin-3-yl]-N-cyclopropylbiphenyl-4-carboxamide |
| 202 | 3'-[5-cyano-4-(1H-indol-5-ylamino)pyridin-3-yl]-N-cyclohexylbiphenyl-4-carboxamide |
| 203 | 3'-[5-cyano-4-(1H-indol-5-ylamino)pyridin-3-yl]-N-(2-pyrrolidin-1-ylethyl)biphenyl-4-carboxamide |
| 204 | N-benzyl-3'-[5-cyano-4-(1H-indol-5-ylamino)pyridin-3-yl]biphenyl-4-carboxamide |
| 205 | 4-(1H-indol-5-ylamino)-5-[4'-(pyrrolidin-1-ylcarbonyl)biphenyl-3-yl]nicotinonitrile |
| 206 | 4-(1H-indol-5-ylamino)-5-[4'-(morpholin-4-ylcarbonyl)biphenyl-3-yl]nicotinonitrile |
| 207 | 4-(1H-indol-5-ylamino)-5-{4'-[(4-methylpiperazin-1-yl)carbonyl]biphenyl-3-yl}nicotinonitrile |

TABLE 1-continued

| Compound | Name |
| --- | --- |
| 208 | 3'-[5-cyano-4-(1H-indol-5-ylamino)pyridin-3-yl]-N-cyclopentylbiphenyl-3-carboxamide |
| 209 | 3'-[5-cyano-4-(1H-indol-5-ylamino)pyridin-3-yl]-N-(4-hydroxybutyl)biphenyl-4-carboxamide |
| 210 | 3'-[5-cyano-4-(1H-indol-5-ylamino)pyridin-3-yl]-N-(3-hydroxypropyl)biphenyl-4-carboxamide |
| 211 | 3'-[5-cyano-4-(1H-indol-5-ylamino)pyridin-3-yl]-N-[2-(methylamino)ethyl]biphenyl-4-carboxamide |
| 212 | 3'-[5-cyano-4-(1H-indol-5-ylamino)pyridin-3-yl]-N-(pyridin-2-ylmethyl)biphenyl-4-carboxamide |
| 213 | 3'-[5-cyano-4-(1H-indol-5-ylamino)pyridin-3-yl]-N-(pyridin-3-ylmethyl)biphenyl-4-carboxamide |
| 214 | 3'-[5-cyano-4-(1H-indol-5-ylamino)pyridin-3-yl]-N-(pyridin-4-ylmethyl)biphenyl-4-carboxamide |
| 215 | N-butyl-3'-[5-cyano-4-(1H-indol-4-ylamino)pyridin-3-yl]biphenyl-4-carboxamide |
| 216 | 3'-[5-cyano-4-(1H-indol-4-ylamino)pyridin-3-yl]-N-(2-hydroxyethyl)biphenyl-4-carboxamide |
| 217 | 5-(3,4-dimethoxyphenyl)-4-[(7-methyl-1H-indol-5-yl)amino]nicotinonitrile |
| 218 | 5-(3,4-dimethoxyphenyl)-4-[(4-methyl-1H-indol-5-yl)amino]nicotinonitrile |
| 219 | 5-(3,4-dimethoxyphenyl)-4-[1H-indol-5-yl(methyl)amino]nicotinonitrile |
| 220 | 5-(3,4-dimethoxyphenyl)-4-(1H-indol-5-yloxy)nicotinonitrile |
| 221 | 5-(3,4-dimethoxyphenyl)-4-(1H-indol-5-yl)nicotinonitrile |
| 222 | 5-(1-benzofuran-2-yl)-4-[(4-methyl-1H-indol-5-yl)amino]nicotinonitrile |
| 223 | 5-(5-formyl-1-benzothien-2-yl)-4-(1H-indol-4-ylamino)nicotinonitrile |
| 224 | 5-{5-[(dimethylamino)methyl]-1-benzothien-2-yl}-4-(1H-indol-4-ylamino)nicotinonitrile |
| 225 | 5-(4-hydroxyphenyl)-4-(1H-indol-4-ylamino)nicotinonitrile |
| 226 | 5-(4-{[(2S)-2-amino-3-phenylpropyl]oxy}phenyl)-4-(1H-indol-4-ylamino)nicotinonitrile |
| 227 | 5-(5-formyl-1-benzothien-2-yl)-4-[(4-methyl-1H-indol-5-yl)amino]nicotinonitrile |
| 228 | 4-[(4-methyl-1H-indol-5-yl)amino]-5-[5-(piperidin-1-ylmethyl)-1-benzothien-2-yl]nicotinonitrile |
| 229 | 5-[5-(hydroxymethyl)-1-benzothien-2-yl]-4-[(4-methyl-1H-indol-5-yl)amino]nicotinonitrile |
| 230 | 4-(1H-indol-5-ylamino)-5-[4-methoxy-3-(2-morpholin-4-ylethoxy)phenyl]nicotinonitrile |
| 231 | 4-(1H-indol-5-ylamino)-5-{4-methoxy-3-[2-(4-methylpiperazin-1-yl)ethoxy]phenyl}nicotinonitrile |
| 232 | 4-(1H-indol-5-ylamino)-5-[4-methoxy-3-(2-piperazin-1-ylethoxy)phenyl]nicotinonitrile |
| 233 | 4-(1H-indol-5-ylamino)-5-[4-methoxy-3-(2-thiomorpholin-4-ylethoxy)phenyl]nicotinonitrile |
| 234 | 5-{3-[2-(4-ethylpiperazin-1-yl)ethoxy]-4-methoxyphenyl}-4-(1H-indol-5-ylamino)nicotinonitrile |
| 235 | 4-(1H-indol-5-ylamino)-5-[4-methoxy-3-(2-piperidin-1-ylethoxy)phenyl]nicotinonitrile |
| 236 | 5-{3-[2-(dimethylamino)ethoxy]-4-methoxyphenyl}-4-(1H-indol-5-ylamino)nicotinonitrile |
| 237 | 5-(3-{2-[bis(2-hydroxyethyl)amino]ethoxy}-4-methoxyphenyl)-4-(1H-indol-5-ylamino)nicotinonitrile |
| 238 | 5-{3-[2-(4-hydroxypiperidin-1-yl)ethoxy]-4-methoxyphenyl}-4-(1H-indol-5-ylamino)nicotinonitrile |
| 239 | 4-(1H-indol-5-ylamino)-5-(4-methoxy-3-{2-[(pyridin-3-ylmethyl)amino]ethoxy}phenyl)nicotinonitrile |
| 240 | 4-(1H-indol-5-ylamino)-5-(4-methoxy-3-{2-[(pyridin-4-ylmethyl)amino]ethoxy}phenyl)nicotinonitrile |
| 241 | 4-(1H-indol-5-ylamino)-5-(4-methoxy-3-{2-[(pyridin-2-ylmethyl)amino]ethoxy}phenyl)nicotinonitrile |
| 242 | 4-(1H-indol-5-ylamino)-5-(4-methoxy-3-{2-[(2-phenylethyl)amino]ethoxy}phenyl)nicotinonitrile |
| 243 | 5-{3-[2-(cyclopentylamino)ethoxy]-4-methoxyphenyl}-4-(1H-indol-5-ylamino)nicotinonitrile |
| 244 | 5-{3-[2-(cyclohexylamino)ethoxy]-4-methoxyphenyl}-4-(1H-indol-5-ylamino)nicotinonitrile |
| 245 | 5-(3-{2-[(2-furylmethyl)amino]ethoxy}-4-methoxyphenyl)-4-(1H-indol-5-ylamino)nicotinonitrile |
| 246 | 5-(2-bromo-4,5-dimethoxyphenyl)-4-(1H-indol-5-ylamino)nicotinonitrile |
| 247 | 5-(2-bromo-4,5-dimethoxyphenyl)-4-[(4-methyl-1H-indol-5-yl)amino]nicotinonitrile |
| 248 | 4-(1H-indol-4-ylamino)-5-[4-methoxy-3-(2-piperidin-1-ylethoxy)phenyl]nicotinonitrile |
| 249 | 5-(3-{2-[(2-hydroxyethyl)amino]ethoxy}-4-methoxyphenyl)-4-(1H-indol-4-ylamino)nicotinonitrile |
| 250 | 4-(1H-indol-5-ylamino)-5-(4-methoxy-3-{2-[(3-phenylpropyl)amino]ethoxy}phenyl)nicotinonitrile |

TABLE 1-continued

| Compound | Name |
|---|---|
| 251 | 4-(1H-indol-5-ylamino)-5-(4-methoxy-3-{2-[(2-pyridin-2-ylethyl)amino]ethoxy}phenyl)nicotinonitrile |
| 252 | 4-(1H-indol-5-ylamino)-5-(4-methoxy-3-{2-[(2-pyridin-3-ylethyl)amino]ethoxy}phenyl)nicotinonitrile |
| 253 | 4-(1H-indol-5-ylamino)-5-(4-methoxy-3-{2-[(2-pyridin-4-ylethyl)amino]ethoxy}phenyl)nicotinonitrile |
| 254 | 5-[3-(dimethylamino)phenyl]-4-(1H-indol-4-ylamino)nicotinonitrile |
| 255 | 4-(1H-indol-4-ylamino)-5-[3-(methylsulfonyl)phenyl]nicotinonitrile |
| 256 | N-{3-[5-cyano-4-(1H-indol-4-ylamino)pyridin-3-yl]phenyl}methanesulfonamide |
| 257 | 4-(1H-indol-5-ylamino)-5-phenylnicotinonitrile |
| 258 | 4-(1H-indol-5-ylamino)-5-(3-thienyl)nicotinonitrile |
| 259 | 4-(1H-indol-5-ylamino)-3,3'-bipyridine-5-carbonitrile |
| 260 | 5-(1,3-benzodioxol-5-yl)-4-(1H-indol-5-ylamino)nicotinonitrile |
| 261 | 4-(1H-indol-5-ylamino)-3,4'-bipyridine-5-carbonitrile |
| 262 | 5-(3-furyl)-4-(1H-indol-5-ylamino)nicotinonitrile |
| 263 | 5-(1H-indol-5-yl)-4-(1H-indol-5-ylamino)nicotinonitrile |
| 264 | 5-(2,3-dihydro-1,4-benzodioxin-6-yl)-4-(1H-indol-5-ylamino)nicotinonitrile |
| 265 | 4-(1H-indol-5-ylamino)-5-pyrimidin-5-ylnicotinonitrile |
| 266 | 4-(1H-indol-5-ylamino)-5-(2-methoxypyrimidin-5-yl)nicotinonitrile |
| 267 | 4-(1H-indol-5-ylamino)-5-(2-thienyl)nicotinonitrile |
| 268 | 5-(1-benzofuran-2-yl)-4-(1H-indol-5-ylamino)nicotinonitrile |
| 269 | 5-(3,5-dimethylisoxazol-4-yl)-4-(1H-indol-5-ylamino)nicotinonitrile |
| 270 | 5-[3-(hydroxymethyl)phenyl]-4-(1H-indol-4-ylamino)nicotinonitrile |
| 271 | 5-{3-[(dimethylamino)methyl]phenyl}-4-(1H-indol-4-ylamino)nicotinonitrile |
| 272 | 4-(1H-indol-4-ylamino)-5-{5-[(prop-2-yn-1-ylamino)methyl]-1-benzothien-2-yl}nicotinonitrile |
| 273 | 5-{5-[(butylamino)methyl]-1-benzothien-2-yl}-4-(1H-indol-4-ylamino)nicotinonitrile |
| 274 | 5-(5-{[(2-hydroxyethyl)amino]methyl}-1-benzothien-2-yl)-4-(1H-indol-4-ylamino)nicotinonitrile |
| 275 | 5-(5-{[(3-hydroxypropyl)amino]methyl}-1-benzothien-2-yl)-4-(1H-indol-4-ylamino)nicotinonitrile |
| 276 | 4-(1H-indol-4-ylamino)-5-(5-{[(3-methoxypropyl)amino]methyl}-1-benzothien-2-yl)nicotinonitrile |
| 277 | 5-(5-{[(4-hydroxybutyl)amino]methyl}-1-benzothien-2-yl)-4-(1H-indol-4-ylamino)nicotinonitrile |
| 278 | 5-{5-[(cyclopropylamino)methyl]-1-benzothien-2-yl}-4-(1H-indol-4-ylamino)nicotinonitrile |
| 279 | 5-(5-{[(cyclopropylmethyl)amino]methyl}-1-benzothien-2-yl)-4-(1H-indol-4-ylamino)nicotinonitrile |
| 280 | 4-(1H-indol-4-ylamino)-5-[5-(pyrrolidin-1-ylmethyl)-1-benzothien-2-yl]nicotinonitrile |
| 281 | 4-(1H-indol-4-ylamino)-5-[5-(morpholin-4-ylmethyl)-1-benzothien-2-yl]nicotinonitrile |
| 282 | 4-(1H-indol-4-ylamino)-5-(5-{[(2-morpholin-4-ylethyl)amino]methyl}-1-benzothien-2-yl)nicotinonitrile |
| 283 | 4-(1H-indol-4-ylamino)-5-[5-(piperidin-1-ylmethyl)-1-benzothien-2-yl]nicotinonitrile |
| 284 | 5-(5-{[4-(hydroxymethyl)piperidin-1-yl]methyl}-1-benzothien-2-yl)-4-(1H-indol-4-ylamino)nicotinonitrile |
| 285 | 5-[5-(hydroxymethyl)-1-benzothien-2-yl]-4-(1H-indol-4-ylamino)nicotinonitrile |
| 286 | 5-{5-[(benzylamino)methyl]-1-benzothien-2-yl}-4-(1H-indol-4-ylamino)nicotinonitrile |
| 287 | 4-(1H-indol-4-ylamino)-5-(5-{[(2-phenylethyl)amino]methyl}-1-benzothien-2-yl)nicotinonitrile |
| 288 | 4-(1H-indol-4-ylamino)-5-(5-{[(pyridin-2-ylmethyl)amino]methyl}-1-benzothien-2-yl)nicotinonitrile |
| 289 | 4-(1H-indol-4-ylamino)-5-(5-{[(pyridin-3-ylmethyl)amino]methyl}-1-benzothien-2-yl)nicotinonitrile |
| 290 | 4-(1H-indol-4-ylamino)-5-(5-{[(pyridin-4-ylmethyl)amino]methyl}-1-benzothien-2-yl)nicotinonitrile |
| 291 | 5-[4-(dimethylamino)phenyl]-4-(pyridin-3-ylamino)nicotinonitrile |
| 292 | 5-[4-(dimethylamino)phenyl]-4-(1H-indazol-5-ylamino)nicotinonitrile |
| 293 | 5-[4-(dimethylamino)phenyl]-4-(1H-indazol-6-ylamino)nicotinonitrile |
| 294 | 5-[4-(dimethylamino)phenyl]-4-[(5-hydroxy-1H-pyrazol-3-yl)amino]nicotinonitrile |
| 295 | 4-(1H-indazol-5-ylamino)-5-(3-methoxyphenyl)nicotinonitrile |
| 296 | 4-(1H-indazol-6-ylamino)-5-(3-methoxyphenyl)nicotinonitrile |
| 297 | 4-[(5-hydroxy-1H-pyrazol-3-yl)amino]-5-(3-methoxyphenyl)nicotinonitrile |
| 298 | 5-(3-bromophenyl)-4-[(4-methyl-1H-indol-5-yl)amino]nicotinonitrile |
| 299 | 4-(1H-indol-4-ylamino)-5-[4-methoxy-3-(2-morpholin-4-ylethoxy)phenyl]nicotinonitrile |
| 300 | 4-(1H-indol-4-ylamino)-5-{4-methoxy-3-[2-(4-methylpiperazin-1-yl)ethoxy]phenyl}nicotinonitrile |

TABLE 1-continued

| Compound | Name |
|---|---|
| 301 | 5-{3-[2-(dimethylamino)ethoxy]-4-methoxyphenyl}-4-(1H-indol-4-ylamino)nicotinonitrile |
| 302 | 5-{3-[2-(4-hydroxypiperidin-1-yl)ethoxy]-4-methoxyphenyl}-4-(1H-indol-4-ylamino)nicotinonitrile |
| 303 | 5-[3-(2-chloroethoxy)-4-methoxyphenyl]-4-(1H-indol-4-ylamino)nicotinonitrile |
| 304 | 4-[(4-methyl-1H-indol-5-yl)amino]-5-[3-(2-thienyl)phenyl]nicotinonitrile |
| 305 | 5-(3,4-dimethoxyphenyl)-4-[(4-ethyl-1H-indol-5-yl)amino]nicotinonitrile |
| 306 | 5-[3-(5-formyl-2-thienyl)phenyl]-4-[(4-methyl-1H-indol-5-yl)amino]nicotinonitrile |
| 307 | 5-(3-{5-[(dimethylamino)methyl]-2-thienyl}phenyl)-4-[(4-methyl-1H-indol-5-yl)amino]nicotinonitrile |
| 308 | 3'-[5-cyano-4-(1H-indol-4-ylamino)pyridin-3-yl]-N-(4-hydroxybutyl)biphenyl-4-carboxamide |
| 309 | 3'-{5-cyano-4-[(4-methyl-1H-indol-5-yl)amino]pyridin-3-yl}-N-(4-hydroxybutyl)biphenyl-4-carboxamide |
| 310 | 4-(1H-indol-4-ylamino)-5-[3-(trifluoromethyl)phenyl]nicotinonitrile |
| 311 | 5-(3-cyanophenyl)-4-(1H-indol-4-ylamino)nicotinonitrile |
| 312 | 3-[5-cyano-4-(1H-indol-4-ylamino)pyridin-3-yl]-N,N-dimethylbenzamide |
| 313 | 3-[5-cyano-4-(1H-indol-4-ylamino)pyridin-3-yl]-N,N-dimethylbenzenesulfonamide |
| 314 | 3-[5-cyano-4-(1H-indol-4-ylamino)pyridin-3-yl]benzamide |
| 315 | 5-(3-{5-[(dimethylamino)methyl]-2-thienyl}phenyl)-4-(1H-indol-4-ylamino)nicotinonitrile |
| 316 | 2-[5-cyano-4-(1H-indol-4-ylamino)pyridin-3-yl]-N,N-dimethylbenzenesulfonamide |
| 317 | N-{4-[5-cyano-4-(1H-indol-4-ylamino)pyridin-3-yl]phenyl}methanesulfonamide |
| 318 | 5-(1-benzofuran-2-yl)-4-(1H-indol-4-ylamino)nicotinonitrile |
| 319 | 5-dibenzo[b,d]furan-4-yl-4-(1H-indol-4-ylamino)nicotinonitrile |
| 320 | 4-(1H-indol-4-ylamino)-5-{1-[(4-methylphenyl)sulfonyl]-1H-indol-3-yl}nicotinonitrile |
| 322 | 5-(1-benzothien-2-yl)-4-(1H-indol-4-ylamino)nicotinonitrile |
| 323 | 4-(1H-indol-4-ylamino)-5-(4-methoxyphenyl)nicotinonitrile |
| 324 | 4-(1H-indol-4-ylamino)-5-(2-methoxyphenyl)nicotinonitrile |
| 325 | 5-(1H-indol-2-yl)-4-(1H-indol-4-ylamino)nicotinonitrile |
| 326 | 4-[5-cyano-4-(1H-indol-4-ylamino)pyridin-3-yl]-N,N-dimethylbenzenesulfonamide |
| 327 | 3-[5-cyano-4-(1H-indol-4-ylamino)pyridin-3-yl]benzoic acid |
| 328 | 5-[3-(aminomethyl)phenyl]-4-(1H-indol-4-ylamino)nicotinonitrile |
| 329 | 5-(3,4-dimethoxyphenyl)-4-[(2-oxo-2,3-dihydro-1H-indol-4-yl)amino]nicotinonitrile |
| 330 | 4-[5-cyano-4-(1H-indol-4-ylamino)pyridin-3-yl]-N-(2-methoxyethyl)benzamide |
| 331 | 4-(1H-indol-4-ylamino)-5-(4-methoxy-3-{2-[(3-phenylpropyl)amino]ethoxy}phenyl)nicotinonitrile |
| 332 | 5-[4-(2-chloroethoxy)phenyl]-4-(1H-indol-4-ylamino)nicotinonitrile |
| 333 | 5-[3-(5-formyl-2-thienyl)phenyl]-4-(1H-indol-4-ylamino)nicotinonitrile |
| 334 | 4-(1H-indol-4-ylamino)-5-[4-(2-morpholin-4-ylethoxy)phenyl]nicotinonitrile |
| 335 | 4-(1H-indol-4-ylamino)-5-{4-[2-(4-methylpiperazin-1-yl)ethoxy]phenyl}nicotinonitrile |
| 336 | 5-(3,4-dimethoxyphenyl)-4-[(5-methyl-1H-indol-4-yl)amino]nicotinonitrile |
| 337 | 5-(2,4-dimethoxyphenyl)-4-(1H-indol-4-ylamino)nicotinonitrile |
| 338 | 4-(1H-indol-4-ylamino)-5-[4-methoxy-3-(2-{[3-(2-oxopyrrolidin-1-yl)propyl]amino}ethoxy)phenyl]nicotinonitrile |
| 339 | 5-[3-(2-{[2-(1H-imidazol-4-yl)ethyl]amino}ethoxy)-4-methoxyphenyl]-4-(1H-indol-4-ylamino)nicotinonitrile |
| 340 | 4-(1H-indol-4-ylamino)-5-(4-methoxy-3-{2-[(3-pyrrolidin-1-ylpropyl)amino]ethoxy}phenyl)nicotinonitrile |
| 341 | 4-(1H-indol-4-ylamino)-5-[4-methoxy-3-(2-{[2-(1-methylpyrrolidin-2-yl)ethyl]amino}ethoxy)phenyl]nicotinonitrile |
| 342 | 5-(4-methoxy-3-{2-[(3-phenylpropyl)amino]ethoxy}phenyl)-4-[(4-methyl-1H-indol-5-yl)amino]nicotinonitrile |
| 343 | 5-{4-methoxy-3-[2-(4-methylpiperazin-1-yl)ethoxy]phenyl}-4-[(4-methyl-1H-indol-5-yl)amino]nicotinonitrile |
| 344 | 5-(3-methoxy-4-{2-[(3-phenylpropyl)amino]ethoxy}phenyl)-4-[(4-methyl-1H-indol-5-yl)amino]nicotinonitrile |
| 345 | 5-{4-[2-(dimethylamino)ethoxy]-3-methoxyphenyl}-4-[(4-methyl-1H-indol-5-yl)amino]nicotinonitrile |
| 346 | 5-(3-bromophenyl)-4-[(2-oxo-2,3-dihydro-1H-indol-4-yl)amino]nicotinonitrile |
| 347 | 4-(1H-indol-4-ylamino)-5-(4-{2-[(3-phenylpropyl)amino]ethoxy}phenyl)nicotinonitrile |
| 348 | 5-[4-(2-chloroethoxy)phenyl]-4-[(4-methyl-1H-indol-5-yl)amino]nicotinonitrile |
| 349 | 5-(3,4-dimethoxyphenyl)-4-[(2-methyl-1H-indol-4-yl)amino]nicotinonitrile |

TABLE 1-continued

| Compound | Name |
|---|---|
| 350 | 4-[(4-methyl-1H-indol-5-yl)amino]-5-{4-[2-(4-methylpiperazin-1-yl)ethoxy]phenyl}nicotinonitrile |
| 351 | 4-[(4-methyl-1H-indol-5-yl)amino]-5-[4-(2-morpholin-4-ylethoxy)phenyl]nicotinonitrile |
| 352 | 5-(1-benzofuran-3-yl)-4-(1H-indol-4-ylamino)nicotinonitrile |
| 353 | 4-(1H-indol-4-ylamino)-5-(4-methoxy-3-{2-[(2-phenylethyl)amino]ethoxy}phenyl)nicotinonitrile |
| 354 | 4-(1H-indol-4-ylamino)-5-(4-methoxy-3-{2-[(2-pyridin-3-ylethyl)amino]ethoxy}phenyl)nicotinonitrile |
| 355 | 4-[(4-methyl-1H-indol-5-yl)amino]-5-(4-{2-[(3-phenylpropyl)amino]ethoxy}phenyl)nicotinonitrile |
| 356 | 6'-[3-(dimethylamino)propoxy]-4-(1H-indol-4-ylamino)-3,3'-bipyridine-5-carbonitrile |
| 357 | 6'-[3-(dimethylamino)propoxy]-4-[(4-methyl-1H-indol-5-yl)amino]-3,3'-bipyridine-5-carbonitrile |
| 358 | 5-(3-hydroxyphenyl)-4-(1H-indol-4-ylamino)nicotinonitrile |
| 359 | 4-(1H-indol-4-ylamino)-5-[5-(piperazin-1-ylmethyl)-1-benzothien-2-yl]nicotinonitrile |
| 360 | N-({2-[5-cyano-4-(1H-indol-4-ylamino)pyridin-3-yl]-1-benzothien-5-yl}methyl)-b-alaninamide |
| 361 | 4-(1H-indol-4-ylamino)-6'-[(2-morpholin-4-ylethyl)amino]-3,3'-bipyridine-5-carbonitrile |
| 362 | 4-[(4-methyl-1H-indol-5-yl)amino]-6'-[(2-morpholin-4-ylethyl)amino]-3,3' bipyridine-5-carbonitrile |
| 363 | 5-{2-chloro-4-[2-(dimethylamino)ethoxy]phenyl}-4-[(4-methyl-1H-indol-5-yl)amino]nicotinonitrile |
| 364 | 4-(1H-indol-4-ylamino)-5-(4-methoxy-3-{2-[(3-morpholin-4-ylpropyl)amino]ethoxy}phenyl)nicotinonitrile |
| 365 | 5-[3-(2-{[3-(1H-imidazol-1-yl)propyl]amino}ethoxy)-4-methoxyphenyl]-4-(1H-indol-4-ylamino)nicotinonitrile |
| 366 | 5-(3-{[(2S)-2-amino-3-phenylpropyl]oxy}phenyl)-4-(1H-indol-4-ylamino)nicotinonitrile |
| 367 | 5-{5-[(benzylamino)methyl]-1-benzothien-2-yl}-4-[(4-methyl-1H-indol-5-yl)amino]nicotinonitrile |
| 368 | 5-{4-[2-(4-butylpiperazin-1-yl)ethoxy]phenyl}-4-[(4-methyl-1H-indol-5-yl)amino]nicotinonitrile |
| 369 | 5-[5-(1,3-dioxan-2-yl)-1-benzofuran-2-yl]-4-(1H-indol-4-ylamino)nicotinonitrile |
| 370 | 5-[5-(1,3-dioxan-2-yl)-1-benzofuran-2-yl]-4-[(4-methyl-1H-indol-5-yl)amino]nicotinonitrile |
| 371 | 5-(2-chloro-4-methoxyphenyl)-4-[(4-methyl-1H-indol-5-yl)amino]nicotinonitrile |
| 372 | 5-[4-(2-chloroethoxy)-3-methoxyphenyl]-4-[(4-methyl-1H-indol-5-yl)amino]nicotinonitrile |
| 373 | 5-(1-benzofuran-2-yl)-4-(1H-indazol-5-ylamino)nicotinonitrile |
| 374 | 5-(4-hydroxyphenyl)-4-[(4-methyl-1H-indol-5-yl)amino]nicotinonitrile |
| 375 | 5-(2-chloro-6-methoxyphenyl)-4-[(4-methyl-1H-indol-5-yl)amino]nicotinonitrile |
| 376 | 5-[3-methoxy-4-(2-piperidin-1-ylethoxy)phenyl]-4-[(4-methyl-1H-indol-5-yl)amino]nicotinonitrile |
| 377 | 5-{3-methoxy-4-[2-(4-methylpiperazin-1-yl)ethoxy]phenyl}-4-[(4-methyl-1H-indol-5-yl)amino]nicotinonitrile |
| 378 | 5-[3-methoxy-4-(2-morpholin-4-ylethoxy)phenyl]-4-[(4-methyl-1H-indol-5-yl)amino]nicotinonitrile |
| 379 | 5-(3,4-dimethoxyphenyl)-4-(1H-indazol-5-ylamino)nicotinonitrile |
| 380 | 5-(2,3-dichlorophenyl)-4-[(4-methyl-1H-indol-5-yl)amino]nicotinonitrile |
| 381 | 5-(4-bromo-2-fluorophenyl)-4-[(4-methyl-1H-indol-5-yl)amino]nicotinonitrile |
| 382 | 5-{5-[(dimethylamino)methyl]-1-benzofuran-2-yl}-4-[(4-methyl-1H-indol-5-yl)amino]nicotinonitrile |
| 383 | 5-(5-{[(2-hydroxyethyl)amino]methyl}-1-benzofuran-2-yl)-4-[(4-methyl-1H-indol-5-yl)amino]nicotinonitrile |
| 384 | 5-(5-{[(3-hydroxypropyl)amino]methyl}-1-benzofuran-2-yl)-4-[(4-methyl-1H-indol-5-yl)amino]nicotinonitrile |
| 385 | 5-(5-{[(2,3-dihydroxypropyl)amino]methyl}-1-benzofuran-2-yl)-4-[(4-methyl-1H-indol-5-yl)amino]nicotinonitrile |
| 386 | 5-(5-{[(2,3-dihydroxypropyl)(methyl)amino]methyl}-1-benzofuran-2-yl)-4-[(4-methyl-1H-indol-5-yl)amino]nicotinonitrile |
| 387 | 5-{5-[(cyclohexylamino)methyl]-1-benzofuran-2-yl}-4-[(4-methyl-1H-indol-5-yl)amino]nicotinonitrile |
| 388 | 4-[(4-methyl-1H-indol-5-yl)amino]-5-[5-(morpholin-4-ylmethyl)-1-benzofuran-2-yl]nicotinonitrile |
| 389 | 4-[(4-methyl-1H-indol-5-yl)amino]-5-[5-(pyrrolidin-1-ylmethyl)-1-benzofuran-2-yl]nicotinonitrile |
| 390 | 4-[(4-methyl-1H-indol-5-yl)amino]-5-(5-{[(2-pyrrolidin-1-ylethyl)amino]methyl}-1-benzofuran-2-yl)nicotinonitrile |

TABLE 1-continued

| Compound | Name |
|---|---|
| 391 | 4-[(4-methyl-1H-indol-5-yl)amino]-5-[5-({[(1-methylpiperidin-4-yl)methyl]amino}methyl)-1-benzofuran-2-yl]nicotinonitrile |
| 392 | 5-(5-{[4-(hydroxymethyl)piperidin-1-yl]methyl}-1-benzofuran-2-yl)-4-[(4-methyl-1H-indol-5-yl)amino]nicotinonitrile |
| 393 | 4-[(4-methyl-1H-indol-5-yl)amino]-5-{5-[(4-pyrrolidin-1-ylpiperidin-1-yl)methyl]-1-benzofuran-2-yl}nicotinonitrile |
| 394 | 5-[5-(1,4'-bipiperidin-1'-ylmethyl)-1-benzofuran-2-yl]-4-[(4-methyl-1H-indol-5-yl)amino]nicotinonitrile |
| 395 | 4-[(4-methyl-1H-indol-5-yl)amino]-5-{5-[(4-morpholin-4-ylpiperidin-1-yl)methyl]-1-benzofuran-2-yl}nicotinonitrile |
| 396 | 5-[5-({4-[2-(dimethylamino)ethyl]piperazin-1-yl}methyl)-1-benzofuran-2-yl]-4-[(methyl-1H-indol-5-yl)amino]nicotinonitrile |
| 397 | 4-[(4-methyl-1H-indol-5-yl)amino]-5-{5-[(4-pyridin-2-ylpiperazin-1-yl)methyl]-1-benzofuran-2-yl}nicotinonitrile |
| 398 | 4-[(4-methyl-1H-indol-5-yl)amino]-5-(5-{[(pyridin-2-ylmethyl)amino]methyl}-1-benzofuran-2-yl)nicotinonitrile |
| 399 | 4-[(4-methyl-1H-indol-5-yl)amino]-5-(5-{[(pyridin-3-ylmethyl)amino]methyl}-1-benzofuran-2-yl)nicotinonitrile |
| 400 | 4-[(4-methyl-1H-indol-5-yl)amino]-5-(5-{[(pyridin-4-ylmethyl)amino]methyl}-1-benzofuran-2-yl)nicotinonitrile |
| 401 | 4-[(4-methyl-1H-indol-5-yl)amino]-5-[5-(morpholin-4-ylmethyl)-2-furyl]nicotinonitrile |
| 402 | 4-[(4-methyl-1H-indol-5-yl)amino]-5-[5-(piperidin-1-ylmethyl)-2-furyl]nicotinonitrile |
| 403 | 5-[5-(1,4'-bipiperidin-1'-ylmethyl)-2-furyl]-4-[(4-methyl-1H-indol-5-yl)amino]nicotinonitrile |
| 404 | 4-[(4-methyl-1H-indol-5-yl)amino]-5-{5-[(4-pyrrolidin-1-ylpiperidin-1-yl)methyl]-2-furyl}nicotinonitrile |
| 405 | 4-[(4-methyl-1H-indol-5-yl)amino]-5-{5-[(4-morpholin-4-ylpiperidin-1-yl)methyl]-2-furyl}nicotinonitrile |
| 406 | 5-{5-[(diethylamino)methyl]-2-furyl}-4-[(4-methyl-1H-indol-5-yl)amino]nicotinonitrile |
| 407 | 5-{5-[(dibutylamino)methyl]-2-furyl}-4-[(4-methyl-1H-indol-5-yl)amino]nicotinonitrile |
| 408 | 5-{5-[(benzylamino)methyl]-2-furyl}-4-[(4-methyl-1H-indol-5-yl)amino]nicotinonitrile |
| 409 | 4-[(4-methyl-1H-indol-5-yl)amino]-5-(5-{[(3-phenylpropyl)amino]methyl}-2-furyl)nicotinonitrile |
| 410 | 4-[(4-methyl-1H-indol-5-yl)amino]-5-[5-(pyrrolidin-1-ylmethyl)-2-furyl]nicotinonitrile |
| 411 | 4-[(4-methyl-1H-indol-5-yl)amino]-5-[5-(thiomorpholin-4-ylmethyl)-2-furyl]nicotinonitrile |
| 412 | 5-(3,4-dimethoxyphenyl)-4-[(6-methyl-1H-indol-5-yl)amino]nicotinonitrile |
| 413 | 5-(1-benzofuran-2-yl)-4-[(6-methyl-1H-indol-5-yl)amino]nicotinonitrile |
| 414 | 5-(4-{2-[(2-hydroxyethyl)amino]ethoxy}phenyl)-4-[(4-methyl-1H-indol-5-yl)amino]nicotinonitrile |
| 415 | 5-(4-{2-[(3-hydroxypropyl)amino]ethoxy}phenyl)-4-[(4-methyl-1H-indol-5-yl)amino]nicotinonitrile |
| 416 | 5-(4-{2-[(2-ethoxyethyl)amino]ethoxy}phenyl)-4-[(4-methyl-1H-indol-5-yl)amino]nicotinonitrile |
| 417 | 5-[4-(2-{[2-(dimethylamino)ethyl]amino}ethoxy)phenyl]-4-[(4-methyl-1H-indol-5-yl)amino]nicotinonitrile |
| 418 | 4-[(4-methyl-1H-indol-5-yl)amino]-5-[4-(2-pyrrolidin-1-ylethoxy)phenyl]nicotinonitrile |
| 419 | 5-{4-[2-(benzylamino)ethoxy]phenyl}-4-[(4-methyl-1H-indol-5-yl)amino]nicotinonitrile |
| 420 | 4-[(4-methyl-1H-indol-5-yl)amino]-5-(4-{2-[(1-methylpiperidin-4-yl)amino]ethoxy}phenyl)nicotinonitrile |
| 421 | 4-[(4-methyl-1H-indol-5-yl)amino]-5-[4-(2-{[(1-methylpiperidin-4-yl)methyl]amino}ethoxy)phenyl]nicotinonitrile |
| 422 | 5-(4-{2-[4-(hydroxymethyl)piperidin-1-yl]ethoxy}phenyl)-4-[(4-methyl-1H-indol-5-yl)amino]nicotinonitrile |
| 423 | 4-[(4-methyl-1H-indol-5-yl)amino]-5-{4-[2-(4-pyrrolidin-1-ylpiperidin-1-yl)ethoxy]phenyl}nicotinonitrile |
| 424 | 4-[(4-methyl-1H-indol-5-yl)amino]-5-{4-[2-(4-morpholin-4-ylpiperidin-1-yl)ethoxy]phenyl}nicotinonitrile |
| 425 | 5-{4-[2-(4-ethylpiperazin-1-yl)ethoxy]phenyl}-4-[(4-methyl-1H-indol-5-yl)amino]nicotinonitrile |
| 426 | 5-{4-[2-(4-methyl-1,4-diazepan-1-yl)ethoxy]phenyl}-4-[(4-methyl-1H-indol-5-yl)amino]nicotinonitrile |
| 427 | 5-(4-{2-[4-(2-hydroxyethyl)piperazin-1-yl]ethoxy}phenyl)-4-[(4-methyl-1H-indol-5-yl)amino]nicotinonitrile |
| 428 | 5-[4-(2-{4-[2-(dimethylamino)ethyl]piperazin-1-yl}ethoxy)phenyl]-4-[(4-methyl-1H-indol-5-yl)amino]nicotinonitrile |
| 429 | 5-[4-(2-{[3-(1H-imidazol-1-yl)propyl]amino}ethoxy)phenyl]-4-[(4-methyl-1H-indol-5-yl)amino]nicotinonitrile |

TABLE 1-continued

| Compound | Name |
|---|---|
| 430 | 4-[(4-methyl-1H-indol-5-yl)amino]-5-{4-[2-(4-pyridin-2-ylpiperazin-1-yl)ethoxy]phenyl}nicotinonitrile |
| 431 | 4-[(4-methyl-1H-indol-5-yl)amino]-5-{4-[2-(4-pyridin-4-ylpiperazin-1-yl)ethoxy]phenyl}nicotinonitrile |
| 432 | 4-[(4-methyl-1H-indol-5-yl)amino]-5-(4-{2-[(pyridin-2-ylmethyl)amino]ethoxy}phenyl)nicotinonitrile |
| 433 | 4-[(4-methyl-1H-indol-5-yl)amino]-5-(4-{2-[(pyridin-3-ylmethyl)amino]ethoxy}phenyl)nicotinonitrile |
| 434 | 4-[(4-methyl-1H-indol-5-yl)amino]-5-(4-{2-[(pyridin-4-ylmethyl)amino]ethoxy}phenyl)nicotinonitrile |
| 435 | 4-[(4-methyl-1H-indol-5-yl)amino]-5-{4-[2-(4-phenylpiperidin-1-yl)ethoxy]phenyl}nicotinonitrile |
| 436 | 5-(5-{[4-(dimethylamino)piperidin-1-yl]methyl}-2-furyl)-4-[(4-methyl-1H-indol-5-yl)amino]nicotinonitrile |
| 437 | 5-{5-[(4-isopropylpiperazin-1-yl)methyl]-2-furyl}-4-[(4-methyl-1H-indol-5-yl)amino]nicotinonitrile |
| 438 | 4-[(4-methyl-1H-indol-5-yl)amino]-5-{5-[2-(4-methylpiperazin-1-yl)ethoxy]-1-benzofuran-2-yl}nicotinonitrile |
| 439 | 5-(3,4-dimethoxyphenyl)-4-{[2-(4-methylpiperazin-1-yl)ethyl]amino}nicotinonitrile |
| 440 | 5-(3,4-dimethoxyphenyl)-4-{[3-(4-methylpiperazin-1-yl)propyl]amino}nicotinonitrile |
| 441 | 4-({[trans-4-(aminomethyl)cyclohexyl]methyl}amino)-5-(3,4-dimethoxyphenyl)nicotinonitrile |
| 442 | 4-{[(trans-4-aminocyclohexyl)methyl]amino}-5-(3,4-dimethoxyphenyl)nicotinonitrile |
| 443 | 4-({[cis-3-(aminomethyl)cyclohexyl]methyl}amino)-5-(3,4-dimethoxyphenyl)nicotinonitrile |
| 444 | 5-(3,4-dimethoxyphenyl)-4-[(2-piperidin-4-ylethyl)amino]nicotinonitrile |
| 445 | 5-(3,4-dimethoxyphenyl)-4-[(piperidin-4-ylmethyl)amino]nicotinonitrile |
| 446 | 4-[(cis-4-aminocyclohexyl)amino]-5-(3,4-dimethoxyphenyl)nicotinonitrile |
| 447 | 5-(3,4-dimethoxyphenyl)-4-{[2-(1-methylpiperidin-4-yl)ethyl]amino}nicotinonitrile |
| 448 | 5-(3,4-dimethoxyphenyl)-4-{[(1-methylpiperidin-4-yl)methyl]amino}nicotinonitrile |
| 449 | 4-[(4-methyl-1H-indol-5-yl)amino]-5-{4-[(4-methylpiperazin-1-yl)methyl]phenyl}nicotinonitrile |
| 450 | 4-[(4-methyl-1H-indol-5-yl)amino]-5-[4-(pyrrolidin-1-ylmethyl)phenyl]nicotinonitrile |
| 451 | 4-[(4-methyl-1H-indol-5-yl)amino]-5-[4-(morpholin-4-ylmethyl)phenyl]nicotinonitrile |
| 452 | 5-{4-[(dimethylamino)methyl]phenyl}-4-[(4-methyl-1H-indol-5-yl)amino]nicotinonitrile |
| 453 | 4-[(4-methyl-1H-indol-5-yl)amino]-2'-(morpholin-4-ylmethyl)-3,4'-bipyridine-5-carbonitrile |
| 454 | 4-[(4-methyl-1H-indol-5-yl)amino]-5-{3-[(4-methylpiperazin-1-yl)methyl]phenyl}nicotinonitrile |
| 455 | 4-[(4-methyl-1H-indol-5-yl)amino]-5-[3-(pyrrolidin-1-ylmethyl)phenyl]nicotinonitrile |
| 456 | 4-[(4-methyl-1H-indol-5-yl)amino]-5-[3-(morpholin-4-ylmethyl)phenyl]nicotinonitrile |
| 457 | 5-{3-[(dimethylamino)methyl]phenyl}-4-[(4-methyl-1H-indol-5-yl)amino]nicotinonitrile |
| 458 | 5-(4-{[(2R)-2-amino-3-phenylpropyl]oxy}phenyl)-4-(1H-indol-4-ylamino)nicotinonitrile |
| 459 | 5-{2-fluoro-4-[(4-methylpiperazin-1-yl)methyl]phenyl}-4-[(4-methyl-1H-indol-5-yl)amino]nicotinonitrile |
| 460 | 5-[4-(3-chloropropoxy)phenyl]-4-[(4-methyl-1H-indol-5-yl)amino]nicotinonitrile |
| 461 | 4-[(4-methyl-1H-indol-5-yl)amino]-5-[5-(piperidin-1-ylmethyl)-1-benzofuran-2-yl]nicotinonitrile |
| 462 | 4-[(4-methyl-1H-indol-5-yl)amino]-5-{5-[(4-methylpiperazin-1-yl)methyl]-1-benzofuran-2-yl}nicotinonitrile |
| 463 | 5-(5-formyl-2-thienyl)-4-[(4-methyl-1H-indol-5-yl)amino]nicotinonitrile |
| 464 | 4-[(4-methyl-1H-indol-5-yl)amino]-5-{5-[(4-methylpiperazin-1-yl)methyl]-2-thienyl}nicotinonitrile |
| 465 | 5-(5-formyl-1-benzofuran-2-yl)-4-[(4-methyl-1H-indol-5-yl)amino]nicotinonitrile |
| 466 | 5-(3-methyl-1-benzofuran-2-yl)-4-[(4-methyl-1H-indol-5-yl)amino]nicotinonitrile |
| 467 | 4-[(4-methyl-1H-indol-5-yl)amino]-3,4'-bipyridine-5-carbonitrile |
| 468 | 4-[(4-methyl-1H-indol-5-yl)amino]-5-{5-[(4-methylpiperazin-1-yl)methyl]-2-furyl}nicotinonitrile |
| 469 | 2'-chloro-4-[(4-methyl-1H-indol-5-yl)amino]-3,4'-bipyridine-5-carbonitrile |
| 470 | 5-{2-chloro-4-[2-(4-methylpiperazin-1-yl)ethoxy]phenyl}-4-[(4-methyl-1H-indol-5-yl)amino]nicotinonitrile |
| 471 | 2'-chloro-4-[(4-methyl-1H-indol-5-yl)amino]-3,3'-bipyridine-5-carbonitrile |

TABLE 1-continued

| Compound | Name |
|---|---|
| 472 | 4-[(4-methyl-1H-indol-5-yl)amino]-5-{4-[3-(4-methylpiperazin-1-yl)propoxy]phenyl}nicotinonitrile |
| 473 | 4-[(4-methyl-1H-indol-5-yl)amino]-5-[4-(3-morpholin-4-ylpropoxy)phenyl]nicotinonitrile |
| 474 | 4-[(4-methyl-1H-indol-5-yl)amino]-5-[4-(3-piperidin-1-ylpropoxy)phenyl]nicotinonitrile |
| 475 | 5-{4-[3-(dimethylamino)propoxy]phenyl}-4-[(4-methyl-1H-indol-5-yl)amino]nicotinonitrile |
| 477 | 5-[3,4-bis(2-methoxyethoxy)phenyl]-4-[(4-methyl-1H-indol-5-yl)amino]nicotinonitrile |
| 478 | 5-[3-methoxy-4-(2-methoxyethoxy)phenyl]-4-[(4-methyl-1H-indol-5-yl)amino]nicotinonitrile |
| 481 | 5-[5-(hydroxymethyl)-1-benzofuran-2-yl]-4-[(4-methyl-1H-indol-5-yl)amino]nicotinonitrile |
| 482 | 5-[4-(2-methoxyethoxy)phenyl]-4-[(4-methyl-1H-indol-5-yl)amino]nicotinonitrile |
| 483 | 5-[3-(2-methoxyethoxy)phenyl]-4-[(4-methyl-1H-indol-5-yl)amino]nicotinonitrile |
| 484 | 5-(5-formyl-1-benzofuran-2-yl)-4-(1H-indol-5-ylamino)nicotinonitrile |
| 485 | 4-(1H-indol-5-ylamino)-5-{5-[(4-methylpiperazin-1-yl)methyl]-1-benzofuran-2-yl}nicotinonitrile |
| 486 | 5-{5-[(4-cyclopentylpiperazin-1-yl)methyl]-2-furyl}-4-[(4-methyl-1H-indol-5-yl)amino]nicotinonitrile |
| 487 | 5-{5-[(1,1-dioxidothiomorpholin-4-yl)methyl]-2-furyl}-4-[(4-methyl-1H-indol-5-yl)amino]nicotinonitrile |
| 488 | 5-(3,4-dimethoxyphenyl)-4-(1H-pyrrolo[2,3-b]pyridin-5-ylamino)nicotinonitrile |
| 489 | 5-(5-formyl-2-furyl)-4-[(4-methyl-1H-indol-5-yl)amino]nicotinonitrile |
| 490 | 5-[4-(4-chlorobutoxy)phenyl]-4-[(4-methyl-1H-indol-5-yl)amino]nicotinonitrile |
| 491 | 4-[(4-methyl-1H-indol-5-yl)amino]-5-{4-[4-(4-methylpiperazin-1-yl)butoxy]phenyl}nicotinonitrile |
| 492 | 4-[(4-chloro-1H-pyrrolo[2,3-b]pyridin-5-yl)amino]-5-[3-methoxy-4-(2-methoxyethoxy)phenyl]nicotinonitrile |
| 494 | 5-[4-(2-chloroethoxy)phenyl]-4-[(6-methyl-1H-indol-5-yl)amino]nicotinonitrile |
| 495 | 5-(5-formyl-1-benzofuran-2-yl)-4-[(6-methyl-1H-indol-5-yl)amino]nicotinonitrile |
| 496 | 4-[(6-methyl-1H-indol-5-yl)amino]-5-{4-[2-(4-methylpiperazin-1-yl)ethoxy]phenyl}nicotinonitrile |
| 497 | 4-[(6-methyl-1H-indol-5-yl)amino]-5-{5-[(4-methylpiperazin-1-yl)methyl]-1-benzofuran-2-yl}nicotinonitrile |
| 498 | 4-[(7-chloro-4-methyl-1H-indol-5-yl)amino]-5-(3,4-dimethoxyphenyl)nicotinonitrile |
| 499 | 5-[5-(hydroxymethyl)-1-benzofuran-2-yl]-4-[(6-methyl-1H-indol-5-yl)amino]nicotinonitrile |
| 500 | 5-{5-[(diethylamino)methyl]-1-benzofuran-2-yl}-4-[(6-methyl-1H-indol-5-yl)amino]nicotinonitrile |
| 501 | 5-[3-(4-chlorobutoxy)phenyl]-4-[(4-methyl-1H-indol-5-yl)amino]nicotinonitrile |
| 502 | 4-[(4-methyl-1H-indol-5-yl)amino]-5-{3-[4-(4-methylpiperazin-1-yl)butoxy]phenyl}nicotinonitrile |
| 503 | 4-[(4-methyl-1H-indol-5-yl)amino]-5-{5-[(4-methylpiperazin-1-yl)methyl]-3-furyl}nicotinonitrile |
| 504 | 4-[(6-methyl-1H-indol-5-yl)amino]-5-[4-(2-piperidin-1-ylethoxy)phenyl]nicotinonitrile |
| 505 | 5-{4-[2-(4-hydroxypiperidin-1-yl)ethoxy]phenyl}-4-[(6-methyl-1H-indol-5-yl)amino]nicotinonitrile |
| 506 | 4-[(6-methyl-1H-indol-5-yl)amino]-5-{4-[2-(4-pyrrolidin-1-ylpiperidin-1-yl)ethoxy]phenyl}nicotinonitrile |
| 507 | 4-[(4-methyl-1H-indol-5-yl)amino]-6'-morpholin-4-yl-3,3'-bipyridine-5-carbonitrile |
| 508 | 4-[(4-methyl-1H-indol-5-yl)amino]-6'-piperidin-1-yl-3,3'-bipyridine-5-carbonitrile |
| 509 | 4-[(4-methyl-1H-indol-5-yl)amino]-5-pyrimidin-5-ylnicotinonitrile |
| 510 | 4-[(4-methyl-1H-indol-5-yl)amino]-5-(2-piperidin-1-ylpyrimidin-5-yl)nicotinonitrile |
| 511 | 4-[(4-methyl-1H-indol-5-yl)amino]-5-(2-morpholin-4-ylpyrimidin-5-yl)nicotinonitrile |
| 512 | 4-[(4-methyl-1H-indol-5-yl)amino]-5-(2-pyrrolidin-1-ylpyrimidin-5-yl)nicotinonitrile |
| 513 | 5-[2-(dimethylamino)pyrimidin-5-yl]-4-[(4-methyl-1H-indol-5-yl)amino]nicotinonitrile |
| 514 | 5-(1-benzothien-2-yl)-4-[(4-methyl-1H-indol-5-yl)amino]nicotinonitrile |
| 515 | 5-[4-(2-chloroethoxy)phenyl]-4-(1H-indol-5-ylamino)nicotinonitrile |
| 516 | 5-(5-formyl-3-thienyl)-4-[(4-methyl-1H-indol-5-yl)amino]nicotinonitrile |
| 517 | 5-(4-formyl-2-furyl)-4-[(4-methyl-1H-indol-5-yl)amino]nicotinonitrile |

TABLE 1-continued

| Compound | Name |
|---|---|
| 518 | 4-[(4-methyl-1H-indol-5-yl)amino]-5-{5-[(4-methylpiperazin-1-yl)methyl]-3-thienyl}nicotinonitrile |
| 519 | 4-[(4-methyl-1H-indol-5-yl)amino]-3,3'-bipyridine-5-carbonitrile |
| 520 | 4-(1H-indol-5-ylamino)-5-{4-[2-(4-methylpiperazin-1-yl)ethoxy]phenyl}nicotinonitrile |
| 521 | 4-[(4-methyl-1H-indol-5-yl)amino]-5-{5-[(4-methylpiperazin-1-yl)methyl]-1-benzothien-2-yl}nicotinonitrile |
| 522 | 4-[(4-chloro-1H-pyrrolo[2,3-b]pyridin-5-yl)amino]-5-(3,4-dimethoxyphenyl)nicotinonitrile |
| 523 | 5-(3,4-dimethoxyphenyl)-4-(1H-indol-5-ylamino)nicotinonitrile 1-oxide |
| 524 | 4-[(trans-4-aminocyclohexyl)amino]-5-(3,4-dimethoxyphenyl)nicotinonitrile |
| 525 | 1-butyl-3-(4-{5-cyano-4-[(4-methyl-1H-indol-5-yl)amino]pyridin-3-yl}phenyl)urea |
| 526 | methyl (4-{5-cyano-4-[(4-methyl-1H-indol-5-yl)amino]pyridin-3-yl}phenyl)carbamate |
| 527 | benzyl (4-{5-cyano-4-[(4-methyl-1H-indol-5-yl)amino]pyridin-3-yl}-2-fluorophenyl)carbamate |
| 528 | 4-methoxybenzyl (4-{5-cyano-4-[(4-methyl-1H-indol-5-yl)amino]pyridin-3-yl}-2-fluorophenyl)carbamate |
| 529 | 4-[(7-chloro-4-methyl-1H-indol-5-yl)amino]-5-{5-[(4-methylpiperazin-1-yl)methyl]-1-benzofuran-2-yl}nicotinonitrile |
| 530 | 5-(3,4-dimethoxyphenyl)-4-[(4-methyl-1H-indol-7-yl)amino]nicotinonitrile |
| 531 | 5-(1-benzofuran-2-yl)-4-[(7-chloro-4-methyl-1H-indol-5-yl)amino]nicotinonitrile |
| 532 | 4-[(7-chloro-4-methyl-1H-indol-5-yl)amino]-5-(5-formyl-1-benzofuran-2-yl)nicotinonitrile |
| 533 | 5-[4-(2-chloroethoxy)phenyl]-4-[(7-chloro-4-methyl-1H-indol-5-yl)amino]nicotinonitrile |
| 534 | 4-[(7-chloro-4-methyl-1H-indol-5-yl)amino]-5-{4-[2-(dimethylamino)ethoxy]phenyl}nicotinonitrile |
| 535 | 4-[(7-chloro-4-methyl-1H-indol-5-yl)amino]-5-{4-[2-(4-methylpiperazin-1-yl)ethoxy]phenyl}nicotinonitrile |
| 536 | tert-butyl 4-[(2-{5-cyano-4-[(4-methyl-1H-indol-5-yl)amino]pyridin-3-yl}-1-benzofuran-5-yl)methyl]piperazine-1-carboxylate |
| 537 | 5-(2-formyl-1-methyl-1H-imidazol-5-yl)-4-[(4-methyl-1H-indol-5-yl)amino]nicotinonitrile |
| 538 | 4-[(4-methyl-1H-indol-5-yl)amino]-5-(5-{[4-(methylsulfonyl)piperazin-1-yl]methyl}-1-benzofuran-2-yl)nicotinonitrile |
| 539 | 4-[(4-methyl-1H-indol-5-yl)amino]-5-{1-methyl-2-[(4-methylpiperazin-1-yl)methyl]-1H-imidazol-5-yl}nicotinonitrile |
| 540 | 4-[(4-methyl-1H-indol-5-yl)amino]-5-[5-(piperazin-1-ylmethyl)-1-benzofuran-2-yl]nicotinonitrile |
| 541 | 4-[(4-methyl-1H-indol-5-yl)amino]-5-(1,3-thiazol-2-yl)nicotinonitrile |
| 542 | 5-(1-methyl-1H-imidazol-2-yl)-4-[(4-methyl-1H-indol-5-yl)amino]nicotinonitrile |
| 543 | 4-[(4-methyl-1H-indol-5-yl)amino]-5-(1,3-thiazol-4-yl)nicotinonitrile |
| 544 | 5-(3,4-dimethoxyphenyl)-4-(1H-indol-7-ylamino)nicotinonitrile |
| 545 | 5-(3,4-dimethoxyphenyl)-4-[(4-methoxy-1H-indol-5-yl)amino]nicotinonitrile |
| 546 | 5-(3,4-dimethoxyphenyl)-4-[(4-fluoro-1H-indol-5-yl)amino]nicotinonitrile |
| 547 | 4-[(7-chloro-4-methyl-1H-indol-5-yl)amino]-5-[5-(piperazin-1-ylmethyl)-1-benzofuran-2-yl]nicotinonitrile |
| 548 | tert-butyl 4-[(2-{4-[(7-chloro-4-methyl-1H-indol-5-yl)amino]-5-cyanopyridin-3-yl}-1-benzofuran-5-yl)methyl]piperazine-1-carboxylate |
| 549 | 5-(3,4-dimethoxyphenyl)-4-[(2,4-dimethyl-1H-indol-5-yl)amino]nicotinonitrile |
| 550 | 5-{2-[(dimethylamino)methyl]phenyl}-4-[(4-methyl-1H-indol-5-yl)amino]nicotinonitrile |
| 551 | 5-(5-formyl-2-methoxyphenyl)-4-[(4-methyl-1H-indol-5-yl)amino]nicotinonitrile |
| 552 | 5-{2-methoxy-5-[(4-methylpiperazin-1-yl)methyl]phenyl}-4-[(4-methyl-1H-indol-5-yl)amino]nicotinonitrile |
| 553 | 5-{5-[(4-ethylpiperazin-1-yl)methyl]-1-benzofuran-2-yl}-4-[(4-methyl-1H-indol-5-yl)amino]nicotinonitrile |
| 554 | 4-[(4-methyl-1H-indol-5-yl)amino]-5-{5-[(4-methyl-4-oxidopiperazin-1-yl)methyl]-1-benzofuran-2-yl}nicotinonitrile |
| 555 | 5-(3,4-dimethoxyphenyl)-4-[(1,4-dimethyl-1H-indol-5-yl)amino]nicotinonitrile |
| 556 | 3-{5-cyano-4-[(4-methyl-1H-indol-5-yl)amino]pyridin-3-yl}benzoic acid |
| 557 | 5-(2-methoxyphenyl)-4-[(4-methyl-1H-indol-5-yl)amino]nicotinonitrile |
| 558 | 5-(3-methoxyphenyl)-4-[(4-methyl-1H-indol-5-yl)amino]nicotinonitrile |
| 559 | 5-(4-methoxyphenyl)-4-[(4-methyl-1H-indol-5-yl)amino]nicotinonitrile |
| 560 | 4-[(4-methyl-1H-indol-5-yl)amino]-5-phenylnicotinonitrile |
| 561 | 4-[(4-methyl-1H-indol-5-yl)amino]-5-(2-thienyl)nicotinonitrile |
| 562 | 4-[(4-methyl-1H-indol-5-yl)amino]-5-(3-thienyl)nicotinonitrile |
| 563 | 5-(3-furyl)-4-[(4-methyl-1H-indol-5-yl)amino]nicotinonitrile |

TABLE 1-continued

| Compound | Name |
|---|---|
| 564 | 5-(1-methyl-1H-imidazol-5-yl)-4-[(4-methyl-1H-indol-5-yl)amino]nicotinonitrile |
| 565 | 4'-[(4-methyl-1H-indol-5-yl)amino]-2,3'-bipyridine-5'-carbonitrile |
| 566 | 1-(4-{5-cyano-4-[(4-methyl-1H-indol-5-yl)amino]pyridin-3-yl}phenyl)-3-cyclopropylurea |
| 567 | 1-(4-{5-cyano-4-[(4-methyl-1H-indol-5-yl)amino]pyridin-3-yl}phenyl)-3-methylurea |
| 568 | 3-(4-{5-cyano-4-[(4-methyl-1H-indol-5-yl)amino]pyridin-3-yl}phenyl)-1,1-dimethylurea |
| 569 | N-(4-{5-cyano-4-[(4-methyl-1H-indol-5-yl)amino]pyridin-3-yl}phenyl)morpholine-4-carboxamide |
| 570 | 4-[(4-methyl-1H-indol-5-yl)amino]-5-(4-nitrophenyl)nicotinonitrile |
| 571 | 5-(4-aminophenyl)-4-[(4-methyl-1H-indol-5-yl)amino]nicotinonitrile |
| 572 | 5-(3-aminophenyl)-4-[(4-methyl-1H-indol-5-yl)amino]nicotinonitrile |
| 573 | 5-(2-aminophenyl)-4-[(4-methyl-1H-indol-5-yl)amino]nicotinonitrile |
| 574 | 5-[4-(dimethylamino)phenyl-4-[(4-methyl-1H-indol-5-yl)amino]nicotinonitrile |
| 575 | 5-[3-(dimethylamino)phenyl]-4-[(4-methyl-1H-indol-5-yl)amino]nicotinonitrile |
| 576 | N-(4-{5-cyano-4-[(4-methyl-1H-indol-5-yl)amino]pyridin-3-yl}phenyl)acetamide |
| 577 | N-(2-{5-cyano-4-[(4-methyl-1H-indol-5-yl)amino]pyridin-3-yl}phenyl)acetamide |
| 578 | N-(3-{5-cyano-4-[(4-methyl-1H-indol-5-yl)amino]pyridin-3-yl}phenyl)acetamide |
| 579 | N-(4-{5-cyano-4-[(4-methyl-1H-indol-5-yl)amino]pyridin-3-yl}phenyl)-2-methylpropanamide |
| 580 | 4-{5-cyano-4-[(4-methyl-1H-indol-5-yl)amino]pyridin-3-yl}-N-methylbenzamide |
| 581 | 4-[(4-methyl-1H-indol-5-yl)amino]-5-(1-naphthyl)nicotinonitrile |
| 582 | 4-[(4-methyl-1H-indol-5-yl)amino]-5-(2-naphthyl)nicotinonitrile |
| 583 | 4-[(4-methyl-1H-indol-5-yl)amino]-5-(1-methyl-1H-pyrazol-5-yl)nicotinonitrile |
| 584 | 4-[(4-methyl-1H-indol-5-yl)amino]-5-(1H-pyrazol-4-yl)nicotinonitrile |
| 585 | 5-(1-benzothiophen-3-yl)-4-[(4-methyl-1H-indol-5-yl)amino]nicotinonitrile |
| 586 | 5-(1-methyl-1H-indol-2-yl)-4-[(4-methyl-1H-indol-5-yl)amino]nicotinonitrile |
| 587 | 5-(1H-indol-5-yl)-4-[(4-methyl-1H-indol-5-yl)amino]nicotinonitrile |
| 588 | 5-(1H-indol-6-yl)-4-[(4-methyl-1H-indol-5-yl)amino]nicotinonitrile |
| 589 | 4-[(4-methyl-1H-indol-5-yl)amino]-5-quinolin-3-ylnicotinonitrile |
| 590 | 4-[(4-methyl-1H-indol-5-yl)amino]-5-quinolin-8-ylnicotinonitrile |
| 591 | 5-(1-benzofuran-5-yl)-4-[(4-methyl-1H-indol-5-yl)amino]nicotinonitrile |
| 592 | 4-(4-methyl-1H-indol-5-ylamino)-5-(quinolin-5-yl)nicotinonitrile |
| 593 | 5-(dibenzo[b,d]thiophen-3-yl)-4-(4-methyl-1H-indol-5-ylamino)nicotinonitrile |
| 594 | 5-(benzo[b]thiophen-5-yl)-4-(4-methyl-1H-indol-5-ylamino)nicotinonitrile |
| 595 | 5-(1H-indol-4-yl)-4-(4-methyl-1H-indol-5-ylamino)nicotinonitrile |
| 596 | 4-[(2,4-dimethyl-1H-indol-5-yl)amino]-5-{5-[(4-methylpiperazin-1-yl)methyl]-1-benzofuran-2-yl}nicotinonitrile |
| 597 | 4-[(2,4-dimethyl-1H-indol-5-yl)amino]-5-[5-(piperazin-1-ylmethyl)-1-benzofuran-2-yl]nicotinonitrile |
| 598 | 4-[(4-methyl-1H-indol-5-yl)amino]-5-{6-[(4-methylpiperazin-1-yl)methyl]-1-benzofuran-2-yl}nicotinonitrile |
| 599 | 4-[(4-methyl-1H-indol-5-yl)amino]-5-[6-(piperazin-1-ylmethyl)-1-benzofuran-2-yl]nicotinonitrile |
| 600 | 4-[(4-methyl-1H-indol-5-yl)amino]-5-{4-[(piperazin-1-yl)methyl]phenyl}nicotinonitrile |
| 601 | 4-[(2,4-dimethyl-1H-indol-5-yl)amino]-5-{4-[(4-methylpiperazin-1-yl)methyl]phenyl}nicotinonitrile |
| 602 | 4-(2,4-dimethyl-1H-indol-5-ylamino)-5-{3-[2-(4-methylpiperazin-1-yl)ethoxy]phenyl}nicotinonitrile |
| 603 | 5-{4-[2-(dimethylamino)ethoxy]-3-methoxyphenyl}-4-[(2,4-dimethyl-1H-indol-5-yl)amino]nicotinonitrile |
| 604 | 4-[(2,4-dimethyl-1H-indol-5-yl)amino]-5-{4-[2-(4-methylpiperazin-1-yl)ethoxy]phenyl}nicotinonitrile |
| 605 | 4-[(4-methyl-1H-indol-5-yl)amino]-5-{4-[2-(piperazin-1-yl)ethoxy]phenyl}nicotinonitrile |
| 606 | 4-(4-methyl-1H-indol-5-ylamino)-2'-((4-methylpiperazin-1-yl)methyl)-3,4'-bipyridine-5-carbonitrile |
| 607 | 4-(4-methyl-1H-indol-5-ylamino)-2'-((piperazin-1-yl)methyl)-3,4'-bipyridine-5-carbonitrile |
| 608 | 4'-(4-methyl-1H-indol-5-ylamino)-5-((4-methylpiperazin-1-yl)methyl)-2,3'-bipyridine-5'-carbonitrile |
| 609 | 4'-(4-methyl-1H-indol-5-ylamino)-5-(morpholinomethyl)-2,3'-bipyridine-5'-carbonitrile |
| 610 | 4'-(4-methyl-1H-indol-5-ylamino)-5-((piperazin-1-yl)methyl)-2,3'-bipyridine-5'-carbonitrile |

TABLE 1-continued

| Compound | Name |
|---|---|
| 611 | 4'-(4-methyl-1H-indol-5-ylamino)-6-((4-methylpiperazin-1-yl)methyl)-2,3'-bipyridine-5'-carbonitrile |
| 612 | 4'-(4-methyl-1H-indol-5-ylamino)-6-(morpholinomethyl)-2,3'-bipyridine-5'-carbonitrile |
| 613 | 4'-(4-methyl-1H-indol-5-ylamino)-6-((piperazin-1-yl)methyl)-2,3'-bipyridine-5'-carbonitrile |
| 614 | 4'-(4-methyl-1H-indol-5-ylamino)-4-(morpholinomethyl)-2,3'-bipyridine-5'-carbonitrile |
| 615 | 4'-(4-methyl-1H-indol-5-ylamino)-4-((4-methylpiperazin-1-yl)methyl)-2,3'-bipyridine-5'-carbonitrile |
| 616 | 4'-(4-methyl-1H-indol-5-ylamino)-4-((piperazin-1-yl)methyl)-2,3'-bipyridine-5'-carbonitrile |
| 617 | 4-(4-methyl-1H-indol-5-ylamino)-5'-((4-methylpiperazin-1-yl)methyl)-3,3'-bipyridine-5-carbonitrile |
| 618 | 4-(4-methyl-1H-indol-5-ylamino)-5'-((piperazin-1-yl)methyl)-3,3'-bipyridine-5-carbonitrile |
| 619 | 4-(4-methyl-1H-indol-5-ylamino)-5'-(morpholinomethyl)-3,3'-bipyridine-5-carbonitrile |
| 620 | 4-(4-methyl-1H-indol-5-ylamino)-6'-((4-methylpiperazin-1-yl)methyl)-3,3'-bipyridine-5-carbonitrile |
| 621 | 4-(4-methyl-1H-indol-5-ylamino)-6'-((piperazin-1-yl)methyl)-3,3'-bipyridine-5-carbonitrile |
| 622 | 4-(4-methyl-1H-indol-5-ylamino)-6'-(morpholinomethyl)-3,3'-bipyridine-5-carbonitrile |
| 623 | 4-(4-methyl-1H-indol-5-ylamino)-5-(3-(piperazin-1-ylmethyl)phenyl)nicotinonitrile |
| 624 | 4-(4-methyl-1H-indol-5-ylamino)-5-(4-(piperazin-1-ylmethyl)phenyl)nicotinonitrile |
| 625 | 4-({[cis-4-(aminomethyl)cyclohexyl]methyl}amino)-5-(3,4-dimethoxyphenyl)nicotinonitrile |

Pharmaceutically acceptable salts of the compounds of formula I, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, benzenesulfonic, benzoic, camphorsulfonic, citric, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, and toluenesulfonic, as well as other known pharmaceutically acceptable acids.

Esters of the compounds of formula I can include various pharmaceutically acceptable esters known in the art that can be metabolized into the free acid form (e.g., a free carboxylic acid form) in a mammal. Examples of such esters include alkyl esters (e.g., of 1 to 10 carbon atoms), cycloalkyl esters (e.g., of 3-10 carbon atoms), aryl esters (e.g., of 6-14 carbon atoms, including of 6-10 carbon atoms), and heterocyclic analogues thereof (e.g., of 3-14 ring atoms, 1-3 of which can be selected from oxygen, nitrogen, and sulfur heteroatoms), wherein the alcohol residue can include further substituents. In some embodiments, esters of the compounds disclosed herein can be $C_{1-10}$ alkyl esters, such as methyl esters, ethyl esters, propyl esters, isopropyl esters, butyl esters, isobutyl esters, t-butyl esters, pentyl esters, isopentyl esters, neopentyl esters, and hexyl esters; $C_{3-10}$ cycloalkyl esters, such as cyclopropyl esters, cyclopropylmethyl esters, cyclobutyl esters, cyclopentyl esters, and cyclohexyl esters; or aryl esters, such as phenyl esters, benzyl esters, and tolyl esters.

Also provided in accordance with the present teachings are prodrugs of the compounds disclosed herein. As used herein, "prodrug" refers to a moiety that produces, generates or releases a compound of the present teachings when administered to a mammalian subject. Prodrugs can be prepared by modifying functional groups present in the compounds in such a way that the modifications are cleaved, either by routine manipulation or in vivo, from the parent compounds. Examples of prodrugs include compounds as described herein that contain one or more molecular moieties appended to a hydroxyl, amino, sulfhydryl, or carboxyl group of the compound, and that when administered to a mammalian subject, is cleaved in vivo to form the free hydroxyl, amino, sulfhydryl, or carboxyl group, respectively. Examples of prodrugs can include acetate, formate, and benzoate derivatives of alcohol and amine functional groups in the compounds of the present teachings. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, the entire disclosures of which are incorporated by reference herein for all purposes.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington: The Science and Practice of Pharmacy,* 20th edition, ed. Alfonso R. Gennaro, Lippincott Williams & Wilkins, Baltimore, Md. (2000), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be useful for treating a pathological condition or disorder in a mammal, for example, a human. As used herein, "treating" refers to partially or completely alleviating and/or ameliorating the condition and/or symptoms thereof. The present teachings accordingly include a method of providing to a mammal a pharmaceutical composition that includes a compound of the present teachings in combination or association with a pharmaceutically acceptable carrier. Compounds of the present teachings can be administered alone or in combination with other therapeutically effective compounds or therapies for the treatment of a pathological condition or disorder. As used herein, "therapeutically effective" refers to a substance or an amount that elicits a desirable biological activity or effect.

The present teachings also include use of the compounds disclosed herein as active therapeutic substances for the treatment of a pathological condition or disorder mediated by a protein kinase such as protein kinase C (PKC) and its theta isoform (PKCθ). The pathological condition or disorder can include inflammatory diseases and autoimmune diseases such as asthma, colitis, multiple sclerosis, psoriasis, arthritis, rheumatoid arthritis, osteoarthritis, and joint inflammation. Accordingly, the present teachings further provide methods of treating these pathological conditions and disorders using the compounds described herein. In some embodiments, the methods include identifying a mammal having a pathological condition or disorder mediated by a protein kinase such as PKC and PKCθ, and providing to the mammal an effective amount of a compound as described herein. In some embodiments, the method includes administering to a mammal a pharmaceutical composition that includes a compound disclosed herein in combination or association with a pharmaceutically acceptable carrier.

The present teachings further include use of the compounds disclosed herein as active therapeutic substances for the prevention and/or inhibition of the pathological condition or disorder listed above. Accordingly, the present teachings further provide methods of preventing and/or inhibiting these pathological conditions and disorders using the compounds described herein. In some embodiments, the methods include identifying a mammal having a pathological condition or disorder mediated by a protein kinase such as PKC and PKCθ, and providing to the mammal an effective amount of a compound as described herein. In some embodiments, the method includes administering to a mammal a pharmaceutical composition that includes a compound disclosed herein in combination or association with a pharmaceutically acceptable carrier.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiinflammatory agents. Oral formulations containing an active compound disclosed herein can include any conventionally used oral form, including tablets, capsules, buccal forms, troches, lozenges and oral liquids, suspensions or solutions. In powders, the carrier can be a finely divided solid, which is an admixture with a finely divided active compound. In tablets, an active compound can be mixed with a carrier having the necessary compression properties in suitable proportions and compacted in the shape and size desired. The powders and tablets may contain up to 99% of the active compound.

Capsules can contain mixtures of active compound(s) with inert filler(s) and/or diluent(s) such as the pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Preferred surface modifying agents include nonionic and anionic surface modifying agents. Representative examples of surface modifying agents include poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the active compound(s). The oral formulation can also comprise a compound as described herein in water or fruit juice, containing appropriate solubilizers or emulsifiers as needed.

Liquid carriers can be used in preparing solutions, suspensions, emulsions, syrups, elixirs, and for inhaled delivery. A compound described herein can be dissolved or suspended in a pharmaceutically acceptable liquid carrier such as water, an organic solvent, or a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include water (particularly containing additives as described above, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the active compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form may contain from about 1 mg/kg of active compound to about 500 mg/kg of active compound, and can be given in a single dose or in two or more doses. Such doses can be administered in any manner useful in directing the active compound(s) to the recipient's bloodstream, including orally, via implants, parenterally (including intravenous, intraperitoneal and subcutaneous injections), rectally, vaginally, and transdermally. Such administrations can be carried out using the compounds of the present teachings including pharmaceutically acceptable salts thereof, in lotions, creams, foams, patches, suspensions, solutions, and suppositories (rectal and vaginal).

When administered for the treatment or inhibition of a particular disease state or disorder, it is understood that an effective dosage can vary depending upon many factors such as the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases, for example those in which the lung is the targeted organ, it may be desirable to administer a compound directly to the airways of the patient, using devices such as metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these active compounds or pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In preferred embodiments, the form is sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, and esters thereof, in lotions, creams, foams, patches, suspensions, solutions, and suppositories (rectal and vaginal). Topical formulations that deliver active compound(s) through the epidermis can be useful for localized treatment of inflammation and arthritis.

Transdermal administration can be accomplished through the use of a transdermal patch containing an active compound and a carrier that can be inert to the active compound, can be non-toxic to the skin, and can allow delivery of the active compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active compound can also be suitable. A variety of occlusive devices can be used to release the active compound into the blood stream, such as a semi-permeable membrane covering a reservoir containing the active compound with or without a carrier, or a matrix containing the active compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For inflammatory diseases, other active compounds (i.e., other active ingredients or agents) effective in their treatment, and particularly in the treatment of asthma and arthritis, can be administered with active compounds of the present teachings. The other agents can be administered at the same time or at different times than the compounds disclosed herein.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components. The use of the term "include" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

As used herein, a "compound" refers to the compound itself and its pharmaceutically acceptable salts, hydrates and esters, unless otherwise understood from the context of the description or expressly limited to one particular form of the compound, i.e., the compound itself, or a pharmaceutically acceptable salt, hydrate or ester thereof.

As used herein, "halo" or "halogen" refers to fluoro, chloro, bromo, and iodo.

As used herein, "oxo" refers to a double-bonded oxygen (i.e., =O).

As used herein, as a moiety or part of a moiety, "alkyl" refers to a straight-chain or branched saturated hydrocarbon group. In some embodiments, an alkyl group can have from 1 to 10 carbon atoms (e.g, from 1 to 6 carbon atoms). Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. In some embodiments, alkyl groups can be substituted with up to four independently selected —Y—$R^4$, —Y—$R^8$ or $R^{12}$ groups, where Y, $R^4$, $R^8$ and $R^{12}$ are as described herein. A lower alkyl group typically has up to 6 carbon atoms, i.e., one to six carbon atoms. Examples of lower alkyl groups include methyl, ethyl, propyl (e.g., n-propyl and isopropyl), and butyl groups (e.g., n-butyl, isobutyl, s-butyl, t-butyl).

As used herein, as a moiety or part of a moiety, "alkenyl" refers to a straight-chain or branched alkyl group having one or more carbon-carbon double bonds. In some embodiments, an alkenyl group can have from 2 to 10 carbon atoms (e.g., from 2 to 6 carbon atoms). Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In some embodiments, alkenyl groups can be substituted with up to four independently selected —Y—$R^8$ or $R^{12}$ groups, where Y, $R^8$, and $R^{12}$ are as described herein.

As used herein, as a moiety or part of a moiety, "alkynyl" refers to a straight-chain or branched alkyl group having one or more carbon-carbon triple bonds. In some embodiments, an alkynyl group can have from 2 to 10 carbon atoms (e.g., from 2 to 6 carbon atoms). Examples of alkynyl groups include ethynyl, propynyl, butynyl, pentynyl, and the like. The one or more carbon-carbon triple bonds can be internal (such as in 2-butyne) or terminal (such as in 1-butyne). In some embodiments, alkynyl groups can be substituted with up to four independently selected —Y—$R^8$ or $R^{12}$ groups, where Y, $R^8$, and $R^{12}$ are as described herein.

As used herein, "alkoxy" refers to an —O-alkyl group. In some embodiments, an alkoxy group can have from 1 to 10 carbon atoms (e.g., from 1 to 6 carbon atoms). Examples of alkoxy groups include methoxy, ethoxy, propoxy (e.g., n-propoxy and isopropoxy), t-butoxy groups, and the like.

As used herein, "alkylthio" refers to an —S-alkyl group. Examples of alkylthio groups include methylthio, ethylthio, propylthio (e.g., n-propylthio and isopropylthio), t-butylthio groups, and the like.

As used herein, "haloalkyl" refers to an alkyl group having one or more halogen substituents. In some embodiments, a haloalkyl group can have from 1 to 10 carbon atoms (e.g., from 1 to 6 carbon atoms). Examples of haloalkyl groups include $CF_3$, $C_2F_5$, $CHF_2$, $CH_2F$, $CCl_3$, $CHCl_2$, $CH_2C_1$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl."

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted with up to four independently selected —Y—$R^4$, —Y—$R^8$ or $R^{12}$ groups, where Y, $R^4$, $R^8$, and $R^{12}$ are as described herein. For example, cycloalkyl groups can include substitution of one or more oxo groups.

As used herein, "heteroatom" refers to an atom of any element other than carbon or hydrogen and includes, for example, nitrogen, oxygen, sulfur, phosphorus, and selenium.

As used herein, "cycloheteroalkyl" refers to a non-aromatic cycloalkyl group that contains at least one ring heteroatom selected from O, N and S, which may be the same or different, and optionally contains one or more double or triple bonds. A cycloheteroalkyl group, as a whole, can have, for example, from 3 to 14 ring atoms and contains from 1 to 5 ring heteroatoms (e.g., from 3-7 ring atoms for a monocyclic cycloheteroalkyl group and from 7 to 14 ring atoms for a polycyclic cycloheteroalkyl group). One or more N or S atoms in a cycloheteroalkyl ring may be oxidized (e.g., morpholine N-oxide, thiomorpholine S-oxide, thiomorpholine S,S-dioxide). In some embodiments, nitrogen atoms of cycloheteroalkyl groups can bear a substituent, for example, a —Y—$R^8$ group or an $R^{12}$ group, where Y, $R^8$, and $R^{12}$ as described herein. Cycloheteroalkyl groups can also contain one or more oxo groups, such as piperidone, oxazolidinone, pyrimidine-2,4(1H,3H)-dione, pyridin-2(1H)-one, and the like. Examples of cycloheteroalkyl groups include, among others, morpholine, thiomorpholine, pyran, imidazolidine, imidazoline, oxazolidine, pyrazolidine, pyrazoline, pyrrolidine, pyrroline, tetrahydrofuran, tetrahydrothiophene, piperidine, piperazine, and the like. In some embodiments, cycloheteroalkyl groups can be optionally substituted with up to four independently selected —Y—$R^4$, —Y—$R^8$ or $R^{12}$ groups, where Y, $R^4$, $R^8$, and $R^{12}$ are as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 14 carbon atoms in its ring system, which can include multiple fused rings. In some embodiments, a polycyclic aryl group can have from 8 to 14 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups optionally contain up to four independently selected $R^4$, —Y—$R^4$, —O—Y—$R^4$, —Y—$R^8$, or $R^{12}$ groups, where Y, $R^4$, $R^8$, and $R^{12}$ are as described herein.

As used herein, "heteroaryl" refers to an aromatic monocyclic ring system containing at least 1 ring heteroatom selected from oxygen (O), nitrogen (N) and sulfur (S) or a polycyclic ring system where at least one of the rings present in the ring system is aromatic and contains at least 1 ring heteroatom. When more than one ring heteroatoms are present they may be the same or different. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 14 ring atoms and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered monocyclic and 5-6 bicyclic ring systems shown below:

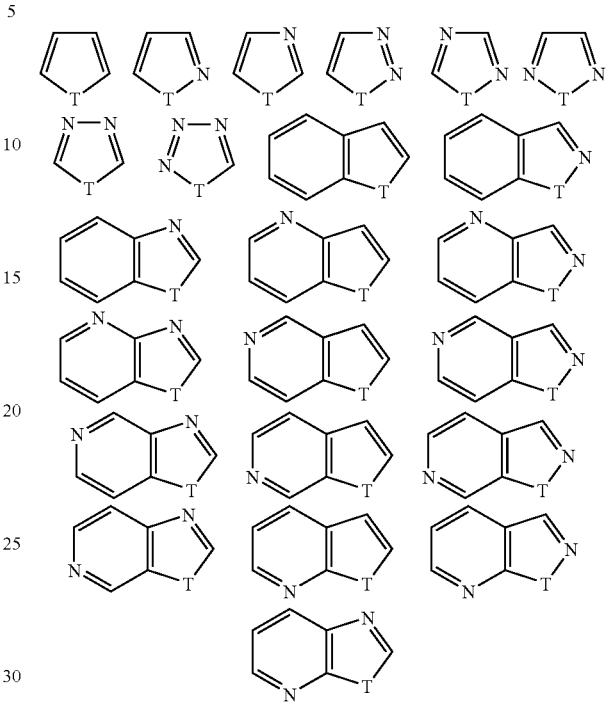

wherein T is O, S, NH, N—Y—$R^4$, N—Y—$R^8$, or $NR^{12}$; and Y, $R^4$, $R^8$, and $R^{12}$ are as described herein. Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted with up to four substituents independently selected from $R^4$, —Y—$R^4$, O—Y—$R^4$, —Y—$R^8$, or $R^{12}$ groups, where Y, $R^4$, $R^8$, and $R^{12}$ are as described herein.

The compounds of the present teachings can include a "divalent group" defined herein as a lining group capable of forming a covalent bond with two other moieties. For example, compounds described herein can include a divalent $C_{1-10}$ alkyl group, such as, for example, a methylene group.

At various places in the present specification, substituents of compounds are disclosed in groups or in ranges. It is specifically intended that the description include each and every individual subcombination of the members of such groups and ranges. For example, the term "$C_{1-10}$ alkyl" is specifically intended to individually disclose $C_1$, $C_2$, $C_3$, $C_4$, $C_5$, $C_6$, $C_7$, $C_8$, $C_9$, $C_{10}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, and $C_9$-$C_{10}$ alkyl. By way of other examples, the term "5-14 membered heteroaryl group" is specifically intended to individually disclose a heteroaryl group having 5, 6, 7, 8, 9, 10, 11, 12, 13, 14, 5-14, 5-13, 5-12, 5-11, 5-10, 5-9, 5-8, 5-7, 5-6, 6-14, 6-13, 6-12, 6-11, 6-10, 6-9, 6-8, 6-7, 7-14, 7-13, 7-12, 7-11, 7-10, 7-9, 7-8, 8-14, 8-13, 8-12, 8-11, 8-10, 8-9, 9-14, 9-13, 9-12, 9-11, 9-10, 10-14, 10-13, 10-12, 10-11, 11-14, 11-13, 11-12, 12-14, 12-13, and 13-14 ring atoms; and the phrase "optionally substituted with 1-4 substituents" is specifically intended to individually disclose a chemical group that can include 0, 1, 2, 3, 4, 0-4, 0-3, 0-2, 0-1, 1-4, 1-3, 1-2, 2-4, 2-3, and 3-4 substituents.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such optical isomers (enantiomers) and diastereomers (geometric isomers), as well as the racemic and resolved, enantiomerically pure stereoisomers, as well as other mixtures of the R and S stereoisomers and pharmaceutically acceptable salts thereof. Optical isomers can be obtained in pure form by standard procedures known to those skilled in the art, which include diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include column chromatography, thin-layer chromatography, and high-performance liquid chromatography.

Throughout the specification, structures may or may not be presented with chemical names. Where any question arises as to nomenclature, the structure prevails.

An aspect of the present teachings relates to methods of preparing the compounds disclosed herein. The compounds of the present teachings can be prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, and/or by chromatography such as high performance liquid chromatograpy (HPLC) or thin layer chromatography.

Preparation of Compounds can Involve the Protection and Deprotection of Various chemical groups. The need for protection and deprotection and the selection of appropriate protecting groups can be readily determined by one skilled in the art. The chemistry of protecting groups can be found, for example, in Greene, et al., *Protective Groups in Organic Synthesis*, 4th Ed., Wiley & Sons, 2006, the entire disclosure of which is incorporated by reference herein for all purposes.

The reactions of the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Scheme 1 below depicts an exemplary synthetic route for the preparation of an intermediate of compounds of formula I.

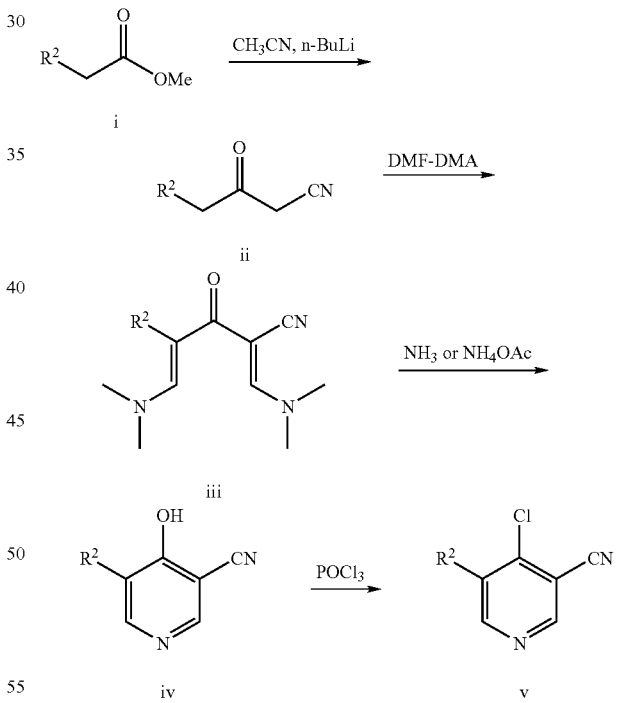

Acetic acid ester i is converted to 3-oxo-butyronitrile ii by reaction with the anion of acetonitrile prepared by reaction of acetonitrile ($CH_3CN$) with a strong base such as n-butyl lithium (n-BuLi) in a solvent such as THF. Reaction of oxo-butyronitrile ii with dimethylformamide-dimethyl acetal (DMF-DMA) in a solvent such as DMF at high temperature (e.g., 122° C.) results in the formation of bisdimethylami-nomethylene intermediate iii which is converted to 4-hydroxy-nicotinonitrile iv by reaction with ammonia ($NH_3$) or ammonium acetate ($NH_4OAc$) in a solvent such as ethanol at reflux. Reaction of the hydroxypyridine with refluxing phosphorous oxychloride (POCl₃) with or without catalytic DMF for 2 to 6 hours results in conversion to 4-chloro-nicotinonitrile v.

Scheme 2 below shows an alternative procedure for the preparation of 3-oxo-butyronitrile ii. This alternative procedure involves conversion of acetic acid vi to the corresponding acid chloride by reaction with a chlorinating agent such as thionyl chloride (SOCl₂) followed by reaction of the anion of tert-butylcyanoacetate prepared by reaction of tert-butylcyanoacetate with a base such as sodium hydride (NaH) in a solvent such as THF to give 2-cyano-3-oxo-butanoic acid tert-butyl ester vii, which undergoes deprotection of the ester and decarboxylation to give 3-oxo-butyronitrile ii by reaction with an acid such as trifluoroacetic acid (TFA).

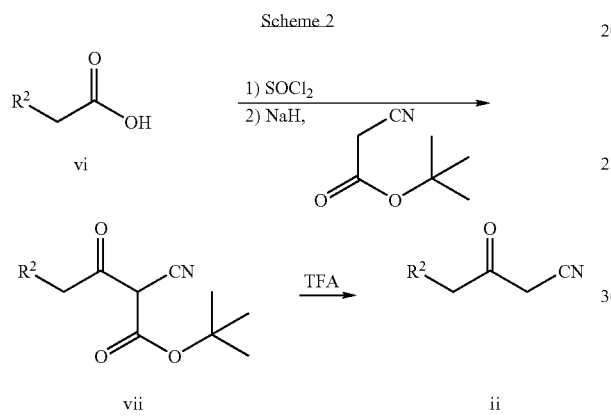

Alternatively, as shown in Scheme 3 below, the bisdimethylaminemethylene intermediate iii obtained by reaction of 3-oxo-butyronitrile ii with DMF-DMA can be reacted with 3,4-dimethoxybenzylamine at reflux in a solvent such as toluene to give 1-(3,4-dimethoxybenzyl)-4-oxo-1,4-dihydro-pyridine-3-carbonitrile viii. Reaction of viii with excess LiCl in refluxing POCl₃ results in removal of the dimethoxybenzyl group and conversion to the corresponding 4-chloro-nicotinonitrile v.

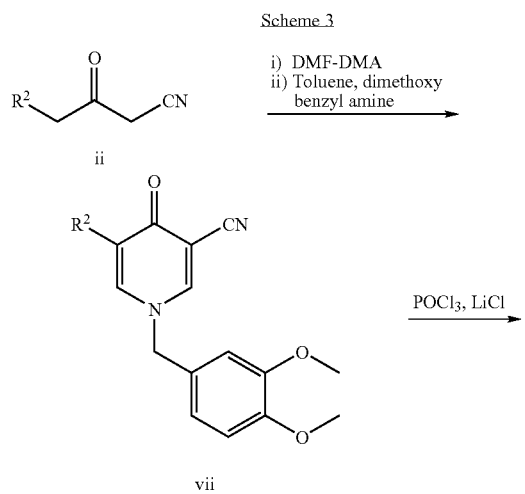

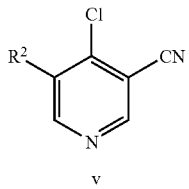

Scheme 4 below depicts an exemplary synthetic route for the preparation of compounds of formula I.

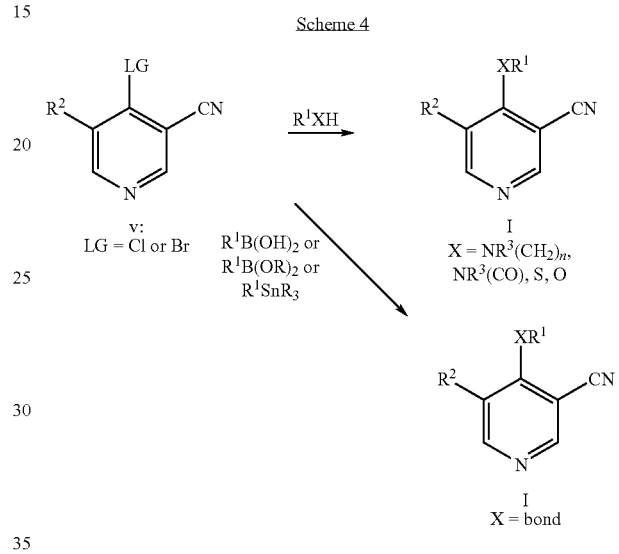

To prepare compounds of formula I where X is —NR³—(CH₂)ₙ—, —NR³(CO)—, —O—, or —S—, where n=0-10, a C-5 substituted 4-chloro-3-cyanopyridine v can be reacted with R¹XH under one of the following reaction conditions: 1) in a solvent such as ethanol (EtOH), propanol, butanol, 2-ethoxyethanol (EtEtOH), 2-methoxyethanol, or 2-butoxyethanol at elevated temperature of 60-180° C., optionally in the presence of pyridine hydrochloride (Pyr.HCl); 2) using an alkali base such as sodium hydride (NaH) in a solvent such as tetrahydrofuran (THF) or dimethylformamide (DMF) at elevated temperatures of 60-120° C.; 3) using a palladium catalyst such as tris(dibenzylidene)acetone dipalladium (Pd₂(dba)₃) and a phosphine ligand such as 2-dicyclohexylphosphino-2'-(N,N-dimethylamino)biphenyl (DavePhos) or tributylphosphine, in the presence of a base such as potassium phosphate (K₃PO₄) or potassium t-butoxide at elevated temperatures of 80-150° C.; 4) using an organic base such as triethylamine (TEA), pyridine, or diisopropylethylamine (DIEA) in a solvent such as DMF, N-methyl-2-pyrrolidone (NMP) or EtEtOH at elevated temperatures of 80-150° C.; 5) using an inorganic base such as cesium carbonate (Cs₂CO₃) in a solvent such as acetonitrile (CH₃CN) or DMF at elevated temperatures of 80-150° C.

When X is a covalent bond, compounds of formula I can be prepared by a coupling reaction of C-5 substituted 4-chloro-3-cyanopyridine v with a boronic acid of formula R¹B(OH)₂, or boronic ester of formula R¹B(OR)₂, where R is an alkyl group (e.g., a lower alkyl group), mediated by a palladium catalyst such as tetrakis(triphenylphosphine)-palladium (0) [(Ph₃P)₄Pd] or palladium (II) acetate (Pd(OAc)₂) in a solvent such as a mixture of dimethoxyethane (DME) and aqueous sodium bicarbonate (aq. NaHCO$_3$) or aqueous sodium carbonate (aq. Na$_2$CO$_3$), optionally in the presence of a phosphine ligand such as triphenyl phosphine (Ph$_3$P). Alternatively, 4-chloro-3-cyanopyridine v can be treated with a stannane R$^1$SnR$_3$, wherein R is an alkyl group (e.g., a lower alkyl group), to yield compounds of formula I.

Referring to Scheme 5 below, additional compounds of formula I where R$^2$ is substituted with an R$^4$ group selected from an aryl group, a heteroaryl group, an alkenyl group and an alkynyl group (formula Ib) can be prepared from compounds of formula I where R$^2$ is substituted with a leaving group (LG) such as bromide (Br), iodide (I), chloride (Cl) or trifluoromethane sulfonate (OTf) (formula Ia) as described in Scheme 5 below.

Scheme 5

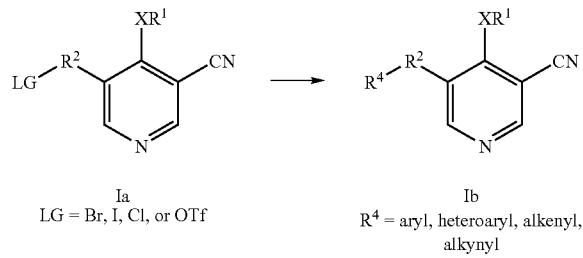

Ia
LG = Br, I, Cl, or OTf

Ib
R$^4$ = aryl, heteroaryl, alkenyl, alkynyl

More specifically, compounds of formula Ib where R$^4$ is an aryl group or a heteroaryl group can be prepared by treatment of compounds of formula Ia with a boronic acid (R$^4$B(OH)$_2$), a boronic ester (R$^4$B(OR)$_2$, where R is a lower alkyl group) or with an organic stannane reagent (e.g., R$^4$SnBu$_3$) mediated by a palladium catalyst (e.g., (Ph$_3$P)$_4$Pd or Pd(OAc)$_2$) in a solvent such as a mixture of DME and aq. NaHCO$_3$ or aq. Na$_2$CO$_3$, optionally in the presence of a phosphine ligand such as Ph$_3$P.

Similarly, compounds of formula Ib where R$^4$ is an alkenyl group or an alkynyl group can be prepared by treating compounds of formula Ia with an alkene or alkyne of formula R$^4$—H or with a boronic acid or ester of or an organic stannane reagent in the presence of a palladium catalyst (e.g., (Ph$_3$P)$_4$Pd, dichlorobis(triphenylphosphine)palladium (II), or Pd(OAc)$_2$) in a solvent such as DMF, NMP, dioxane, or DME, in the presence of a ligand such as Ph$_3$P or tri-o-tolylphosphine and a base (e.g., potassium carbonate (K$_2$CO$_3$) or Na$_2$CO$_3$), optionally with the addition of an organic base such as TEA. A catalytic amount of copper(I) iodide can be optionally used for this coupling reaction.

Scheme 6 depicts a synthetic route for preparing additional compounds of formula I where both R$^2$ and R$^4$ are aryl or heteroaryl groups and R$^4$ is further substituted with an amide (formula Id).

Scheme 6

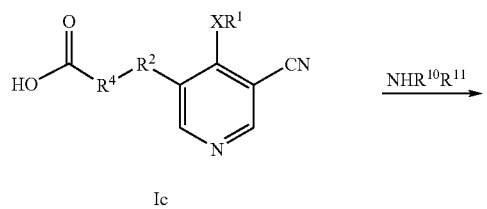

Ic

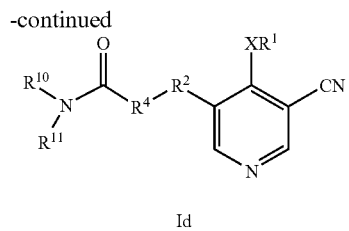

Id

Compounds of formula I where R$^2$ is substituted by an aryl or heteroaryl group substituted by a carboxylic acid (formula Ic) can be treated with an amine of formula NHR$^{10}$R$^{11}$ in the presence of a catalyst (e.g., benzotriazol-1-yloxytris(dimethyl amino)phosphonium hexafluorophosphate (BOP)) and an organic amine (e.g., TEA, DIEA, or pyridine) in a solvent such as MeOH or EtOH at ambient temperature to elevated temperatures of 50-80° C. to provide compounds of formula Id as described.

Additional compounds of formula I where R$^2$ is substituted with —O—Y—NR$^6$R$^7$ (formula If) can be prepared as depicted in Scheme 7 below, by treating compounds of formula I where R$^2$ is substituted with —O—Y-LG (formula Ie), where LG is Cl, Br, methanesulfonyl (mesyl, OMs), or p-toluenesulfonyl (tosyl, OTs), with an amine of formula NHR$^6$R$^7$ in a solvent such as EtOH, DME or DMF optionally in the presence of NaI or a base such as K$_2$CO$_3$.

Scheme 7

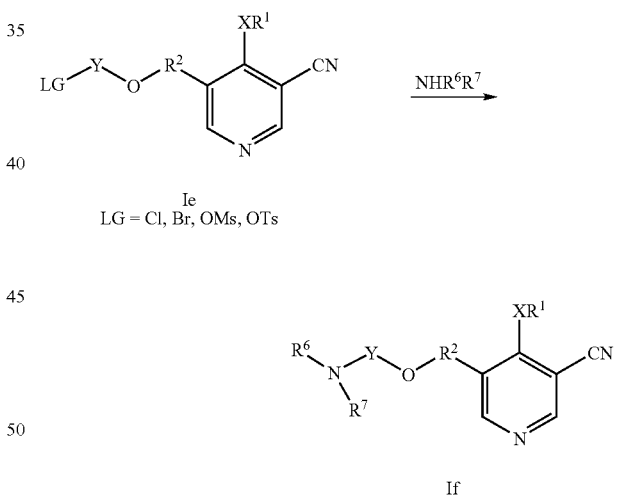

As depicted in Scheme 8, compounds of formula I wherein R$^2$ is substituted by —CH$_2$—NR$^6$YR$^7$ (formula Ih), can be prepared by treating compounds of formula I where R$^2$ contains an aldehyde functionality (formula Ig), with an amine of formula HNR$^6$YR$^7$ in the presence of a reducing agent (e.g., sodium triacetoxyborohydride (Na(OAc)$_3$BH) or sodium cyanoborohydride) in a solvent such as dichloromethane (CH$_2$Cl$_2$) or THF with the optional addition of DMF or NMP and preferably in the presence of acetic acid. Compounds of formula I wherein R$^2$ is substituted by —CH$_2$—OH (formula II) can be formed as a b-byproduct of this reductive amination reaction.

Scheme 8

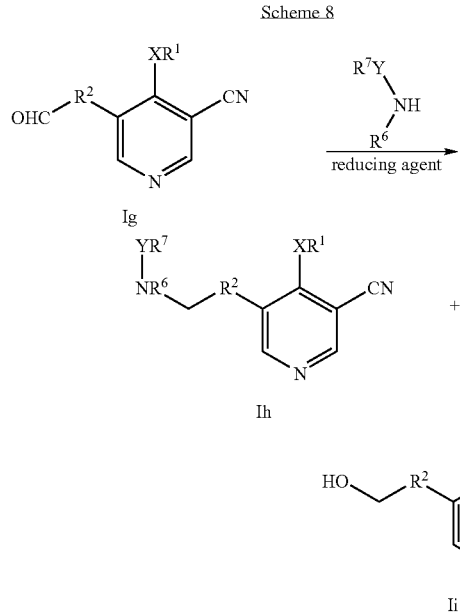

As depicted in Scheme 9, compounds of formula I where $R^2$ is substituted by —$OYR^5$ (formula Ik) can be prepared by treating compounds of formula I where $R^2$ contains a hydroxyl functionality (formula Ij), with an alcohol of formula $R^5YOH$ under Mitsunobu conditions. This reaction can be conducted in a solvent such as THF in the presence of $Ph_3P$ and either diethyl azodicarboxylate or di-t-butyl azodicarboxylate.

Scheme 9

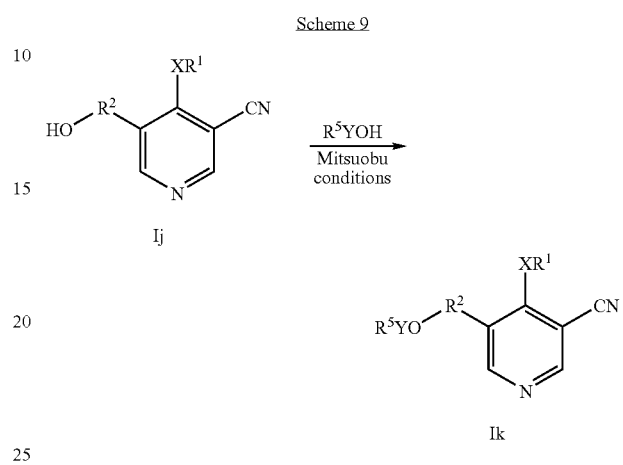

Additional compounds of formula I wherein X is not a bond can be prepared as shown in Scheme 10, Scheme 11, and Scheme 12 below.

Scheme 10

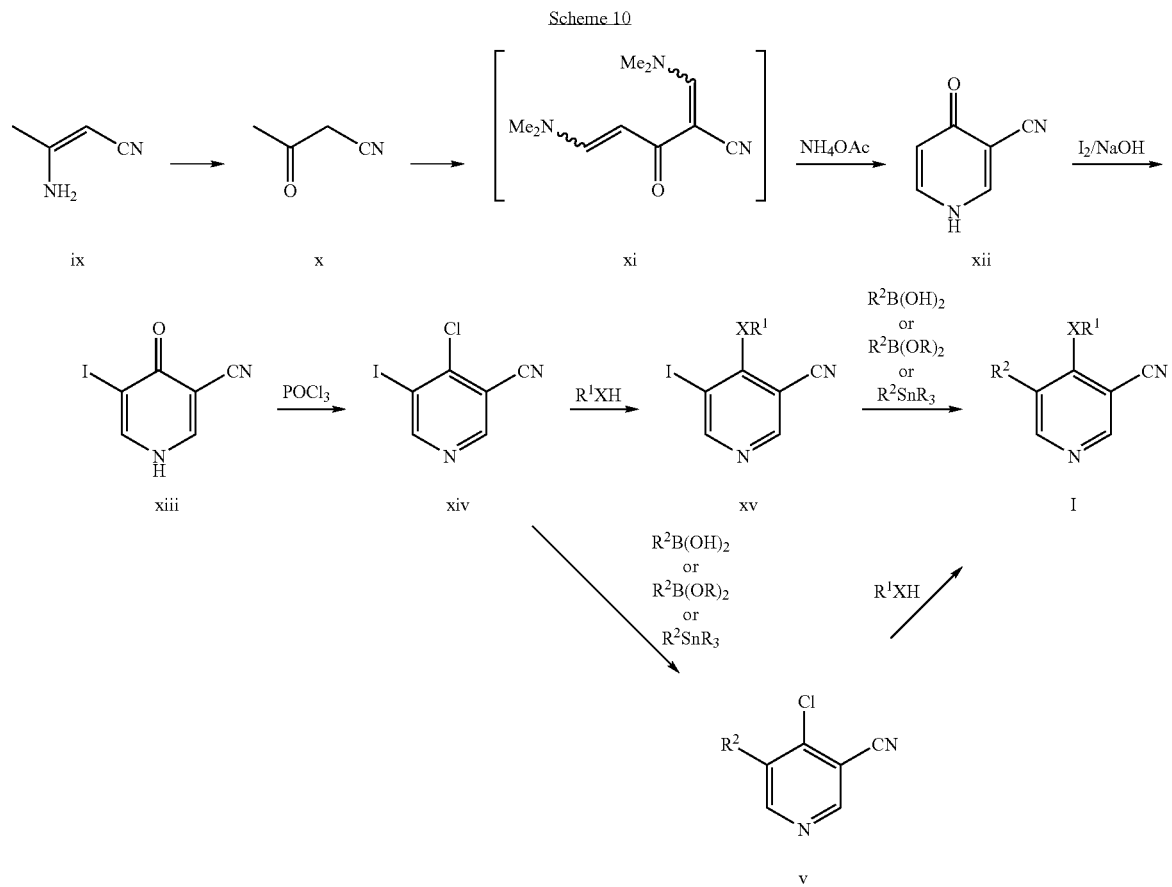

A mixture of 3-aminobut-2-enenitrile ix is heated in acid (e.g., aqueous HCl) to yield acetoacetonitrile x. Acetoacetonitrile x is treated with t-butoxybis(dimethyl amino)methane and DMF-DMA at an elevated temperature to yield 5-(dimethylamino)-2-[(dimethylamino)methylene]-3-oxopent-4-enenitrile xi, which is then treated with ammonium acetate in EtOH at reflux to produce 4-hydroxynicotinonitrile xii. (An alternate synthesis of 4-hydroxynicotinonitrile was reported in the literature: Broekman, F. W. et al., *Recueil des Travaux Chimiques des Pays-Bas*, 81: 792-796 (1962)). A mixture of 4-hydroxynicotinonitrile xii, iodine and NaOH in water is heated overnight to yield 4-hydroxy-5-iodonicotinonitrile xiii, which is then treated with POCl$_3$ at an elevated temperature to yield 4-chloro-5-iodonicotinonitrile xiv. Intermediate xiv can then be treated with R$^1$XH, wherein X is not a bond (e.g., R$^1$NH$_2$, R$^1$OH, R$^1$SH, etc.) to yield the 4-substituted 5-iodo-nicotinonitrile xv. Further treatment with a boronic acid R$^2$B(OH)$_2$, boronic acid ester R$^2$B(OR)$_2$ or stannane R$^2$SnR$_3$ (where R, in each case, is a lower alkyl group) yields compounds of formula I. Alternatively, intermediate xiv can be treated with a boronic acid R$^2$B(OH)$_2$, a boronic acid ester R$^2$B(OR)$_2$ or a stannane R$^2$SnR$_3$ (where R, in each case, is a lower alkyl group), followed by a reaction with R$^1$XH to provide compounds of formula I.

Scheme 11

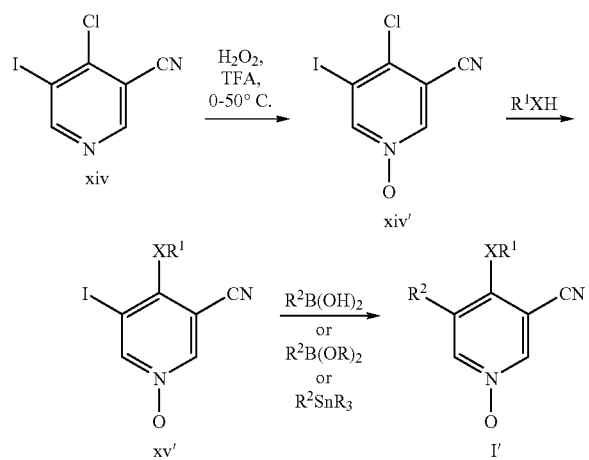

As depicted in Scheme 11, treatment of 4-chloro-5-iodonicotinonitrile xiv with an oxidizing agent, preferably hydrogen peroxide, in trifluoroacetic acid at temperatures of 0-50° C., provides 4-chloro-5-iodo-1-oxy-nicotinonitrile xiv'. Addition of R$^1$XH under the conditions noted previously provides compounds of formula xv'. Addition of a boronic acid, ester, or an organostannane under the conditions noted previously provides compounds of formula I'.

Scheme 12

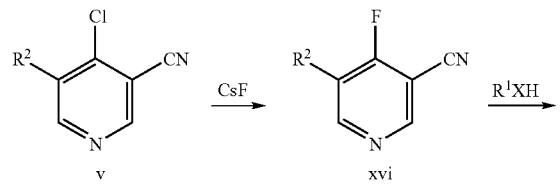

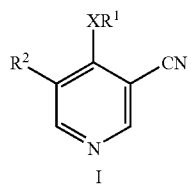

As shown in Scheme 12, treatment of compounds of formula v with CsF in a solvent such as DMF provides a 4-fluoro analog xvi. Subsequent displacement of the 4-fluoro group with R$^1$XH in a solvent such as DMSO provides compounds of formula I.

Aspects of the present teachings can be further understood in light of the following examples, which should not be construed as limiting the scope of the present teachings in any way.

More specifically, the following examples illustrate various synthetic routes which can be used to prepare compounds of formula I. HPLC conditions used in the examples are listed as the following:

(a): column: Prodigy ODS3, 4.6×150 mm, from Phenomenex (Torrance, Calif.); mobile phase A: 0.02% trifluoroacetic acid (TFA) in water; mobile phase B: 0.02% TFA in CH$_3$CN, 10-95% B in 20 minutes (min.); flow rate: 1.0 mL/min.; column temperature: 40° C.; detection wavelength: 215 nm;

(b): column: Prodigy ODS3, 4.6×150 mm, from Phenomenex (Torrance, Calif.); mobile phase A: 0.02% trifluoroacetic acid (TFA) in water; mobile phase B: CH$_3$CN, 10-90% B; flow rate: 1.0 mL/min.; detection wavelength: 215 nm;

(c): column: Prodigy ODS3, 4.6×150 mm, from Phenomenex (Torrance, Calif.); mobile phase A: 0.02% formic acid in water; mobile phase B: 0.02% formic acid in acetonitrile, 10-95% B in 3 min., 95-10% B in 1 min.; column temperature: 40° C.; detection wavelength: 215 nm;

(d): column: YMC C18, 4.6×50 mm, 5 microns, from YMC (Kyoto, Japan); mobile phase A: 90% water+10% MeOH+ 0.02% H$_3$PO$_4$; mobile phase B: 90% MeOH+10% water+ 0.02% H$_3$PO$_4$, 1-100% B in 2 min., up to 10 min. 100% B, then 100-1% B in 1 min.;

(e): column: Aquasil C18, 2.1×50 mm, from Thermo Fisher Scientific, Inc. (Waltham, Mass.); 5.5 min. gradient CH$_3$CN in water/formic acid; flow rate: 0.8 mL/min.; detection wavelength: 254 nm;

(f): column: Xterra MS C18, 3.5 µm, 2.1×30 mm, from Waters Corp. (Milford, Mass.); 5 min. gradient CH$_3$CN in water/formic acid; flow rate: 1.0 mL/min.; detection wavelength: 215 nm;

(g): column: Prodigy ODS3, 4.6×150 mm, from Phenomenex (Torrance, Calif.); 20 min. gradient CH$_3$CN in water/ TFA; flow rate: 1.0 mL/min.; detection wavelength: 215 nm;

(h): column: Prodigy ODS3, 4.6×150 mm, from Phenomenex (Torrance, Calif.); 20 min. gradient methanol (MeOH) in water/TFA; flow rate: 1.0 mL/min.; detection wavelength: 215 nm;

(i) column: XBridge C18, 4.6×50 mm, from Waters Corp. (Milford, Mass.); 5.5 min. gradient CH$_3$CN in water/formic acid; flow rate: 0.8 mL/min.; detection wavelength: 254 nm;

(j): column: Pursuits PFP, 4.6×150 mm, from Varian, Inc. (Palo Alto, Calif.); 20 min. gradient CH$_3$CN in water/TFA; flow rate: 1.0 mL/min.; detection wavelength: 215 nm; and (k): column: Aquasil C18, 2.1×50 mm, from Thermo Fisher Scientific, Inc. (Waltham, Mass.); mobile phase A:

0.1% formic acid in water; mobile phase B: 0.1% formic acid in CH₃CN, 0-100% B in 2.5 min; flow rate: 0.8 mL/min; column temperature: 40° C.; detection wavelength: 254 nm.

Example 1

Preparation of 5-(3,4-dimethoxyphenyl)-4-(1H-indol-5-ylamino)nicotinonitrile

A solution of 3,4-dimethoxyphenyl acetic acid (50 mM) in MeOH (100 mL) with concentrated sulfuric acid (conc. H₂SO₄, 1 mL) or concentrated hydrochloric acid (conc. HCl) was heated at reflux overnight. Concentration to dryness on a rotary evaporator and high vacuum pump overnight gave the ester as an oil which was used directly in the next step.

To a 1.0 L three-necked round-bottomed flask was added 50 mL of THF and the reaction mixture was cooled to −78° C. Butyl lithium (BuLi, 1.6 M, 14.4 mL, 23 mmol) was added dropwise keeping the temperature below −70° C. Acetonitrile (1.3 mL, 25 mmol) in 30 mL of THF was added dropwise to the flask amidst stirring and cooling. After 2 hours (h) of stirring, (3,4-dimethoxyphenyl)acetic acid methyl ester (2.3 g, 11 mmol) was added to the resulting white colloidal mixture in the flask. The reaction mixture was stirred for a further 2 h, followed by the addition of saturated ammonium chloride solution (NH₄Cl, 75 mL) at −78° C. The organic layer was separated, dried with sodium sulfate (Na₂SO₄), filtered to remove the drying agent and evaporated to dryness to give the crude product. This crude product was purified by silica gel column chromatography, eluting with 30-70% ethyl acetate (EtOAc) in hexanes to yield 4-(3,4-dimethoxyphenyl)-3-oxo-butyronitrile in the form of a solidifying amber oil, 1.8 g (75%).

To a solution of 4-(3,4-dimethoxyphenyl)-3-oxo-butyronitrile (5.0 g, 23 mmol) in DMF (12 mL) was added dimethyl-formamide-dimethylacetal (DMF-DMA, 13.5 mL, 101 mmol) and the solution heated at 122° C. overnight. Concentration on a rotary evaporator under high vacuum gave an orange-red solid. This solid was dissolved in EtOH (100 mL) and excess ammonium acetate was added and the reaction mixture was heated at 85° C. for 1 h. The reaction mixture was allowed to cool to room temperature (r.t.) for 1 h then the solids were collected by filtration and washed with EtOH (cold) to give 5-(3,4-dimethoxyphenyl)-4-hydroxynicotinonitrile (4.1 g, 69%) as a brown solid. The filtrate was concentrated on a rotary evaporator and the residue purified on silica gel with 0-25% MeOH in CH₂Cl₂ to give an additional amount of 5-(3,4-dimethoxyphenyl)-4-hydroxynicotinonitrile.

A solution of 5-(3,4-dimethoxyphenyl)-4-hydroxynicotinonitrile (4 g, 15.7 mmol) in phosphorus oxychloride (POCl₃, 25 mL) was heated at 125° C. for 1.5 h, then cooled to r.t. and poured into an ice/3 N sodium hydroxide (NaOH)/EtOAc mixture. The mixture was stirred and the layers separated. The organic layer was dried over magnesium sulfate (MgSO₄), filtered and concentrated to give 4-chloro-5-(3,4-dimethoxyphenyl)nicotinonitrile (3.9 g, 91%) as a brown solid.

A mixture of 4-chloro-5-(3,4-dimethoxyphenyl)nicotinonitrile (824 mg, 3 mmol), 5-aminoindole (396 mg, 3 mmol) and Pyr.HCl (345 mg, 3 mmol) in EtEtOH (25 mL) was heated at reflux for 8 h, cooled to r.t. and concentrated. The residue was purified by flash silica gel column chromatography eluting with 0-25% MeOH in CH₂Cl₂ to give 977 mg (88% yield) of a yellow-brown oil, that was triturated with MeOH/ethyl ether to give 525 mg (47%) of 5-(3,4-dimethoxyphenyl)-4-(1H-indol-5-ylamino)nicotinonitrile 101 as a yellow-brown solid. MS 371.2 (M+H), HPLC retention time: 1.70 min.[a].

Following procedures analogous to those described for preparing compound 101 and using the appropriate amine in the last step, the compounds in Table 2 were prepared.

TABLE 2

| Compound | Compound Name | HPLC Retention Time (min.) | Observed Ion m/e [M + H] |
|---|---|---|---|
| 102 | 4-(2,1,3-benzothiadiazol-4-ylamino)-5-(3,4-dimethoxyphenyl)nicotinonitrile | 1.85[a] | 390 |
| 103 | 5-(3,4-dimethoxyphenyl)-4-(isoquinolin-5-ylamino)nicotinonitrile | 1.50[a] | 383 |
| 104 | 5-(3,4-dimethoxyphenyl)-4-(quinolin-5-ylamino)nicotinonitrile | 1.61[a] | 383 |
| 105 | 5-(3,4-dimethoxyphenyl)-4-(5,6,7,8-tetrahydronaphthalen-1-ylamino)nicotinonitrile | 2.06[a] | 386 |
| 106 | 4-(2,3-dihydro-1,4-benzodioxin-6-ylamino)-5-(3,4-dimethoxyphenyl)nicotinonitrile | 1.75[a] | 390 |
| 107 | 4-(2,3-dihydro-1H-inden-5-ylamino)-5-(3,4-dimethoxyphenyl)nicotinonitrile | 2.03[a] | 372 |
| 108 | 5-(3,4-dimethoxyphenyl)-4-(1H-indol-6-ylamino)nicotinonitrile | 1.65[a] | 371 |
| 109 | 5-(3,4-dimethoxyphenyl)-4-(1H-indol-4-ylamino)nicotinonitrile | 1.62[a] | 371 |
| 110 | 5-(3,4-dimethoxyphenyl)-4-[(2-methyl-1H-indol-5-yl)amino]nicotinonitrile | 2.15[a] | 385 |
| 111 | 4-(1,3-benzodioxol-5-ylamino)-5-(3,4-dimethoxyphenyl)nicotinonitrile | 2.01[a] | 376.1 |
| 112 | 5-(3,4-dimethoxyphenyl)-4-(2-naphthylamino)nicotinonitrile | 2.22[a] | 382.1 |

Example 2

Preparation of 5-(3-bromophenyl)-4-(1H-indol-5-ylamino)nicotinonitrile 113

Following procedures analogous to those described for preparing 4-chloro-5-(3,4-dimethoxyphenyl)nicotinonitrile (Example 1), 5-(3-bromophenyl)-4-chloronicotinonitrile was prepared from 3-bromophenylacetic acid. 5-(3-Bromophenyl)-4-(1H-indol-5-ylamino)nicotinonitrile 113 was then prepared using two methods.

Method A: Following procedures analogous to those described for preparing compound 101 (Example 1), the title compound was prepared from 5-(3-bromophenyl)-4-chloronicotinonitrile and purified by flash silica gel column chromatography eluting with 0-25% MeOH in $CH_2Cl_2$. MS: 389.0 (M+H), HPLC retention time: 1.92 min.[a].

Method B: A solution of 5-(3-bromophenyl)-4-chloronicotinonitrile (4.42 g, 15 mmol), 5-aminoindole (1.99 g, 15 mmol) in EtEtOH (44 mL) was heated at reflux for 12 h, then cooled to r t. The reaction mixture was poured into saturated aq. $NaHCO_3$ solution, whereupon the crude product precipitated. The latter was filtered and the crude solid was dissolved in $CH_2Cl_2$, dried over $Na_2SO_4$, concentrated and purified by flash chromatography on silica gel eluting with 1:1 EtOAc/hexane to give 4.2 g (72% yield) of the title compound as a foamy yellow solid. MS: 389.0 (M+H), HPLC retention time: 1.92 min.[a].

Example 3

Preparation of 5-(3-bromophenyl)-4-(1H-indol-4-ylamino)nicotinonitrile 114

Following procedures analogous to those described in Example 2, Method B, 5-(3-bromophenyl)-4-(1H-indol-4-ylamino)nicotinonitrile was prepared from 5-(3-bromophenyl)-4-chloronicotinonitrile and 4-aminoindole. MS: 389.2 (M+H).

Example 4

Preparation of 5-(2-bromophenyl)-4-(1H-indol-5-ylamino)nicotinonitrile 115

Following procedures analogous to those described for preparing 4-chloro-5-(3,4-dimethoxyphenyl)nicotinonitrile (Example 1), 5-(2-bromophenyl)-4-chloronicotinonitrile was prepared from 2-bromophenylacetic acid. Following procedures analogous to those described for preparing compound 113 (Example 2, Method B), 5-(2-bromophenyl)-4-(1H-indol-5-ylamino)nicotinonitrile 115 was prepared from 5-(2-bromophenyl)-4-chloronicotinonitrile. MS: 389.0 (M+H).

Example 5

Preparation of 5-(4-bromophenyl)-4-(1H-indol-5-ylamino)nicotinonitrile 116

Following procedures analogous to those described for preparing 4-chloro-5-(3,4-dimethoxyphenyl)nicotinonitrile (Example 1), 5-(4-bromophenyl)-4-chloronicotinonitrile was prepared from 4-bromophenylacetic acid. Following procedures analogous to those described for preparing compound 113 (Example 2, Method B), 5-(4-bromophenyl)-4-(1H-indol-5-ylamino)nicotinonitrile 116 was prepared from 5-(4-bromophenyl)-4-chloronicotinonitrile. MS: 389.0 (M+H).

Example 6

Preparation of 5-[3-methoxy-4-(2-methoxyethoxy)phenyl]-4-[(4-methyl-1H-indol-5-yl)amino]nicotinonitrile 478

Following procedures analogous to those described for preparing compound 113 (Method B), 5-[3-methoxy-4-(2-methoxyethoxy)phenyl]-4-[(4-methyl-1H-indol-5-yl)amino]nicotinonitrile was prepared. HPLC retention time: 8.0 min.[g]; melting range: 208-210° C.; and HRMS: 429.19278.

Example 7

Preparation of 5-(3'-aminobiphenyl-3-yl)-4-(1H-indol-5-ylamino)nicotinonitrile 117

A mixture of 5-(3-bromophenyl)-4-(1H-indol-5-ylamino)nicotinonitrile 113 (39 mg, 0.1 mmol), $(Ph_3P)_4Pd$ (2.3 mg, 0.002 mmol) and 2M aq. $Na_2CO_3$ (0.1 mL) in DME (2 mL) was degassed by bubbling nitrogen for 5 min., then 3-aminophenylboronic acid (17 mg, 0.11 mmol) was added and the mixture was heated at reflux for 12 h. After cooling to r.t., the mixture was filtered and the filtrate was purified by preparative HPLC to give 5-(3'-aminobiphenyl-3-yl)-4-(1H-indol-5-ylamino)nicotinonitrile 117. MS: 402 (M+H), HPLC retention time: 1.72 min.[a].

Following procedures analogous to those described for preparing compound 117, compounds 118-150 in Table 3 were synthesized from 5-(3-bromophenyl)-4-(1H-indol-5-ylamino)nicotinonitrile 113, 5-(3-bromophenyl)-4-(1H-indol-4-ylamino)nicotinonitrile 114, 5-(2-bromophenyl)-4-(1H-indol-5-ylamino)nicotinonitrile 115 or 5-(4-bromophenyl)-4-(1H-indol-5-ylamino)nicotinonitrile 116 and the appropriate boronic acid.

TABLE 3

| Compound | Compound Name | HPLC Retention Time (min.) | Observed Ion m/e [M + H] | Melting Range (° C.) |
|---|---|---|---|---|
| 118 | 5-(4'-cyanobiphenyl-3-yl)-4-(1H-indol-5-ylamino)nicotinonitrile | 2.01[a] | 412 | N/A |
| 119 | 5-(4'-aminobiphenyl-3-yl)-4-(1H-indol-5-ylamino)nicotinonitrile | 1.71[a] | 402 | N/A |
| 120 | N-{3'-[5-cyano-4-(1H-indol-5-ylamino)pyridin-3-yl]biphenyl-4-yl}acetamide | 1.87[a] | 444 | N/A |
| 121 | 4-(1H-indol-5-ylamino)-5-(3-pyridin-4-ylphenyl)nicotinonitrile | 1.50[a] | 388 | N/A |

TABLE 3-continued

| Compound | Compound Name | HPLC Retention Time (min.) | Observed Ion m/e [M + H] | Melting Range (° C.) |
|---|---|---|---|---|
| 122 | 3'-[5-cyano-4-(1H-indol-5-ylamino) pyridin-3-yl]-N,N-dimethylbiphenyl-4-carboxamide | 1.88[a] | 458 | N/A |
| 123 | 3'-[5-cyano-4-(1H-indol-5-ylamino) pyridin-3-yl]-N-cyclopentylbiphenyl-4-carboxamide | 2.04[a] | 498 | N/A |
| 124 | 4-(1H-indol-5-ylamino)-5-[3-(1H-pyrrol-3-yl)phenyl]nicotinonitrile | 1.84[a] | 374 | N/A |
| 125 | 5-(2-bromophenyl)-4-[(7-methyl-1H-indol-5-yl)amino]nicotinonitrile | N/A | 403.0 | N/A |
| 126 | 5-(2-bromophenyl)-4-(1H-indol-4-yl amino)nicotinonitrile | 9.3[a] | 389.0 | N/A |
| 127 | 4-(1H-indol-5-ylamino)-5-(3'-methyl biphenyl-3-yl)nicotinonitrile | 2.20[a] | 401.5 | N/A |
| 128 | 4-(1H-indol-5-ylamino)-5-(4'-methyl biphenyl-3-yl)nicotinonitrile | 2.20[a] | 401.5 | N/A |
| 129 | 5-(2'-chlorobiphenyl-3-yl)-4-(1H-indol-5-ylamino)nicotinonitrile | 2.18[a] | 421.9 | N/A |
| 130 | 5-(3'-chlorobiphenyl-3-yl)-4-(1H-indol-5-ylamino)nicotinonitrile | 2.23[a] | 421.9 | N/A |
| 131 | 5-(4'-chlorobiphenyl-3-yl)-4-(1H-indol-5-ylamino)nicotinonitrile | 2.24[a] | 421.9 | N/A |
| 132 | 5-(3'-cyanobiphenyl-3-yl)-4-(1H-indol-5-ylamino)nicotinonitrile | 2.04[a] | 412.5 | N/A |
| 133 | 3'-[5-cyano-4-(1H-indol-5-ylamino) pyridin-3-yl]biphenyl-3-carboxylic acid | 2.80[a] | 431.5 | N/A |
| 134 | 3'-[5-cyano-4-(1H-indol-5-ylamino) pyridin-3-yl]biphenyl-4-carboxylic acid | 1.91[a] | 431.5 | N/A |
| 135 | 3'-[5-cyano-4-(1H-indol-4-ylamino) pyridin-3-yl]biphenyl-4-carboxylic acid | N/A | 431.1 | N/A |
| 136 | 4-(1H-indol-5-ylamino)-5-[3-(2-thienyl) phenyl]nicotinonitrile | 2.08[a] | 393.5 | N/A |
| 137 | 4-(1H-indol-5-ylamino)-5-(3-pyridin-3-ylphenyl)nicotinonitrile | 1.59[a] | 388.5 | N/A |
| 138 | 4-(1H-indol-5-ylamino)-5-(3-pyrimidin-2-ylphenyl)nicotinonitrile | 1.80[a] | 389.4 | N/A |
| 139 | 4-(1H-indol-5-ylamino)-5-[3-(4-methyl-2-thienyl)phenyl]nicotinonitrile | 2.50[a] | 405.1 | N/A |
| 140 | 5-[3-(5-acetyl-2-thienyl)phenyl]-4-(1H-indol-5-ylamino)nicotinonitrile | 2.31[a] | 433.1 | N/A |
| 141 | 4-(1H-indol-5-ylamino)-5-[3-(3-thienyl)phenyl]nicotinonitrile | 2.39[a] | 391.1 | N/A |
| 142 | 5-[3-(3-furyl)phenyl]-4-(1H-indol-5-ylamino)nicotinonitrile | 2.30[a] | 375.1 | N/A |
| 143 | 5-(2'-chlorobiphenyl-2-yl)-4-(1H-indol-5-ylamino)nicotinonitrile | 2.37[a] | 419.1 | N/A |
| 144 | 5-(3'-chlorobiphenyl-2-yl)-4-(1H-indol-5-ylamino)nicotinonitrile | 2.38[a] | 419.1 | N/A |
| 145 | 5-(4'-chlorobiphenyl-2-yl)-4-(1H-indol-5-ylamino)nicotinonitrile | 2.40[a] | 419.1 | N/A |
| 146 | 4-(1H-indol-5-ylamino)-5-[2-(3-thienyl)phenyl]nicotinonitrile | 2.28[a] | 391.1 | N/A |
| 147 | 4-(1H-indol-4-ylamino)-5-[3-(2-thienyl)phenyl]nicotinonitrile | N/A | 393.2 | N/A |
| 148 | 3'-[5-cyano-4-(1H-indol-4-ylamino) pyridin-3-yl]-N-cyclopentylbiphenyl-4-carboxamide | N/A | 498.3 | N/A |
| 149 | 4-(1H-indol-4-ylamino)-5-[4'-(pyrrolidin-1-ylcarbonyl)biphenyl-3-yl]nicotinonitrile | N/A | 484.3 | N/A |
| 150 | 5-[3-(5-formyl-2-thienyl)phenyl]-4-(1H-indol-5-ylamino)nicotinonitrile | N/A | 421.1 | 196-199 (decom.) |

Example 8

Preparation of 4-(1H-indol-5-ylamino)-5-(3-nitrophenyl)nicotinonitrile 151

3-Nitrophenyl acetic acid (9.5 g, 52 mmol) and thionyl chloride (20 mL) were stirred overnight at r.t., then evaporated to dryness. In a separate flask NaH (60% dispersion in oil, 5.5 g, 1.4 mmol) was suspended in THF (100 mL) and the mixture was cooled to 0° C. and tert-butylcyanoacetate (8.8 g, 62 mmol) was added. After 15 min., a solution of 3-nitrophenylacetyl chloride from above in THF was added dropwise. The reaction mixture was allowed to warm to r.t. and stirred for 4 h, quenched by the addition of brine, and extracted with EtOAc (2×200 mL). The combined organic extracts were dried over $MgSO_4$ and concentrated. The residue was used in the next step without further purification.

To a solution of 2-cyano-4-(3-nitrophenyl)-3-oxo-butyric acid tert-butyl ester (9.5 g, 31 mmol) in toluene (40 mL) was added TFA (4 mL) and the solution was heated at reflux for 2 h, then the solvent evaporated in vacuo. The residue was purified by flash chromatography on silica gel to give 4.0 g of 4-(3-nitrophenyl)-3-oxo-butyronitrile (37% over 2 steps).

Following procedures analogous to those described for preparing compound 101 (Example 1), 4-(3-nitrophenyl)-3-oxo-butyronitrile was converted to 4-(1H-indol-5-ylamino)-5-(3-nitrophenyl)-nicotinonitrile 151. MS: 356 (M+H), HPLC retention time: 2.50 min.[a].

Example 9

Preparation of N-{3-[5-cyano-4-(1H-indol-5-ylamino)pyridin-3-yl]phenyl}acetamide 152

To a solution of 4-(1H-indol-5-ylamino)-5-(3-nitrophenyl) nicotinonitrile 151 (9 mg, 0.025 mmol) in MeOH (1 mL) were added hydrazine (20 uL) and Raney-Nickel (2-5 mg). The mixture was stirred for 2 h then filtered through celite and the filtrate was concentrated to give the crude reduced product which was then dissolved in $CH_2Cl_2$ (1 mL) and pyridine (20 uL), and acetyl chloride (20 uL) was added. After stirring for 1 h, the reaction mixture was evaporated and the residue was purified by preparative HPLC to give the title compound (4 mg). MS: 366.0 (M+H), HPLC retention time: 1.61 min.[a].

Example 10

Preparation of 4-(1H-indol-4-ylamino)-5-[4-methoxy-3-(2-methoxyethoxy)phenyl]nicotinonitrile 153

To a stirred solution of 3-hydroxy-4-methoxyphenyl acetic acid (24.8 g, 136 mmol) in 200 mL of MeOH was added 1 mL of $H_2SO_4$ and the reaction mixture was heated at reflux overnight. The methanol was removed by evaporation in vacuo and the residue was poured into saturated $NaHCO_3$ solution and extracted with EtOAc (3×150 mL). Combined organic extracts were then washed with brine, dried over anhydrous $MgSO_4$, filtered, and concentrated in vacuo to yield 23.9 g (90% yield) of 3-hydroxy-4-methoxyphenyl acetic acid methyl ester as a yellow oil.

To a stirred solution of 3-hydroxy-4-methoxyphenyl acetic acid methyl ester (5.0 g, 25.5 mmol), tetrabutylammonium iodide (TBAI, 0.941 g, 2.5 mmol), and 2-bromoethylmethyl ether (4.6 mL, 50.9 mmol) in 150 mL of acetone was added $Cs_2CO_3$ (17.4 g, 53.4 mmol). The mixture was stirred for 21.5 h at reflux. The mixture was concentrated and the residue was partitioned between water and EtOAc. The combined organic extracts were dried over anhydrous $Na_2SO_4$, filtered, and concentrated in vacuo to yield 8.15 g of an orange oil, which was purified by flash chromatography on silica gel eluting with 10-50% EtOAc in hexane to give 5.33 g (82% yield) of 4-methoxy-3-(2-methoxyethoxy)phenylacetic acid methyl ester as a light yellow oil.

To a 250 mL three-necked round-bottomed flask was added 10 mL of anhydrous THF and cooled to −78° C. n-Butyl lithium (2.5 M in hexane, 8.06 mL, 12.9 mmol) was added and the mixture was stirred for 5 min. Anhydrous $CH_3CN$ (0.696 mL, 13.3 mmol) in 5 mL of anhydrous THF was added dropwise at −78° C. After 1 h of stirring, 4-methoxy-3-(2-methoxyethoxy)phenylacetic acid methyl ester (1.10 g, 4.3 mmol) in 10 mL of anhydrous THF was added dropwise to the resulting white colloidal mixture. The reaction mixture was stirred for an additional 2 h, followed by the addition of saturated $NH_4Cl$ solution at −78° C. The solution was warmed to r.t., diluted with 100 mL water and extracted with EtOAc (3×100 mL). The combined organics were washed with brine, dried with anhydrous $MgSO_4$, filtered, and concentrated in vacuo. The crude product was purified by flash chromatography on silica gel eluting with gradient 30-60% EtOAc in hexanes to yield 769 mg (68% yield) of 4-[4-methoxy-3-(2-methoxyethoxy)phenyl]-3-oxo-butyronitrile as a colorless oil.

To a stirred solution of 4-[4-methoxy-3-(2-methoxyethoxy)phenyl]-3-oxo-butyronitrile (9.91 g, 34.5 mmol) in 20 mL of anhydrous DMF was added DMF-DMA (20.2 mL, 152 mmol). The resulting mixture was heated at 100° C. for 15 h and was concentrated in vacuo. The crude material was mixed with 3,4-dimethoxybenzylamine (0.687 mL, 41.4 mmol) in 20 mL of anhydrous toluene and the mixture was heated at reflux for 2 h. The reaction mixture was cooled, concentrated in vacuo, and purified by flash chromatography on silica gel eluting with gradient 50-100% EtOAc/hexane to yield 8.5 g (55% yield) of 1-(3,4-dimethoxybenzyl)-5-[4-methoxy-3-(2-methoxyethoxy)phenyl]-4-oxo-1,4-dihydro-pyridine-3-carbonitrile as a yellow/orange foam.

A solution of 1-(3,4-dimethoxybenzyl)-5-[4-methoxy-3-(2-methoxyethoxy)phenyl]-4-oxo-1,4-dihydro-pyridine-3-carbonitrile (300 mg, 0.666 mmol) and lithium chloride (LiCl, 254 mg, 6 mmol) in 2.5 mL of $POCl_3$ was heated at reflux for 2.5 h. The excess $POCl_3$ was removed by evaporating in vacuo and then was co-evaporated with toluene. The residue was dissolved in 100 mL ethyl acetate and washed with ice-cold 1 N aqueous sodium hydroxide. The organic layer was separated, dried over anhydrous $MgSO_4$, filtered, and concentrated in vacuo, and the resulting solid was triturated with isopropyl alcohol to yield 166 mg (78% yield) of 4-chloro-5-[4-methoxy-3-(2-methoxyethoxy)phenyl]-nicotinonitrile as an off-white solid.

To a stirred solution of 4-chloro-5-[4-methoxy-3-(2-methoxyethoxy)phenyl]-nicotinonitrile (100 mg, 0.313 mmol), 4-aminoindole (62 mg, 0.47 mmol), DavePhos (37 mg, 0.094 mmol), and $K_3PO_4$ (99.8 mg, 0.47 mmol) in 4 mL of anhydrous ethylene glycol dimethyl ether was added $Pd_2(dba)_3$ (28.7 mg, 0.031 mmol). The mixture was heated to 90° C. for 2 h, then cooled, filtered through celite, concentrated in vacuo, and crystallized by tritration with ether/hexane to yield 42.5 mg (33% yield) of the title compound 153 as a tan solid. MS: 415.1 (M+H), HPLC retention time: 7.70 min[b].

Following procedures analogous to those described for preparing compound 153 and using the appropriate amine, the compounds in Table 4 were prepared.

TABLE 4

| Compound | Compound Name | HPLC Retention Time (min.) | Observed Ion m/e [M + H] |
|---|---|---|---|
| 154 | 4-(1H-indol-5-ylamino)-5-[4-methoxy-3-(2-methoxyethoxy)phenyl]nicotinonitrile | 7.70[b] | 415.2 |
| 155 | 4-(1H-indol-6-ylamino)-5-[4-methoxy-3-(2-methoxyethoxy)phenyl]nicotinonitrile | 8.50[b] | 415.2 |
| 156 | 4-(1,3-benzothiazol-6-ylamino)-5-[4-methoxy-3-(2-methoxyethoxy)phenyl]nicotinonitrile | 7.85[b] | 433.1 |
| 157 | 5-[4-methoxy-3-(2-methoxyethoxy)phenyl]-4-[(2-methyl-1H-indol-5-yl)amino]nicotinonitrile | 8.50[b] | 429.1 |
| 158 | 4-(1H-1,2,3-benzotriazol-5-ylamino)-5-[4-methoxy-3-(2-methoxyethoxy)phenyl]nicotinonitrile | 10.7[b] | 417.0 |

Example 11

Preparation of 4-(1H-indol-4-ylamino)-5-[3-methoxy-4-(2-methoxyethoxy)phenyl]nicotinonitrile 159

Following procedures analogous to those described for preparing 4-methoxy-3-(2-methoxyethoxy)phenylacetic acid methyl ester in Example 9, ethyl[3-methoxy-4-(2-methoxyethoxy)phenyl]acetate was prepared from 4-hydroxy-3-methoxyphenylacetic acid ethyl ester. 4-(1H-Indol-4-ylamino)-5-[3-methoxy-4-(2-methoxyethoxy)phenyl]nicotinonitrile 159 was then prepared following procedures analogous to those described for preparing 4-(1H-indol-4-ylamino)-5-[4-methoxy-3-(2-methoxyethoxy)phenyl]-nicotinonitrile 153 (Example 9). MS: 415.2 (M+H), HPLC retention time: 7.9 min[b].

Compounds in Table 5 were prepared following procedures described for preparing compound 153 from 4-chloro-5-[3-methoxy-4-(2-methoxyethoxy)phenyl]nicotinonitrile.

TABLE 5

| Compound | Compound Name | HPLC Retention Time (min.) | Observed Ion m/e [M + H] |
|---|---|---|---|
| 160 | 4-(1H-indol-5-ylamino)-5-[3-methoxy-4-(2-methoxyethoxy)phenyl]nicotinonitrile | 7.8[b] | 415.2 |
| 161 | 4-(1H-indol-6-ylamino)-5-[3-methoxy-4-(2-methoxyethoxy)phenyl]nicotinonitrile | 8.6[b] | 415.2 |
| 162 | 4-(1,3-benzothiazol-6-ylamino)-5-[3-methoxy-4-(2-methoxyethoxy)phenyl]nicotinonitrile | 7.8[b] | 433.0 |
| 163 | 5-[3-methoxy-4-(2-methoxyethoxy)phenyl]-4-[(2-methyl-1H-indol-5-yl)amino]nicotinonitrile | 8.7[b] | 429.1 |

Example 12

Preparation of 4-(1H-indol-4-ylamino)-5-[3-(2-methoxyethoxy)phenyl]nicotinonitrile 164

Following procedures analogous to those described in Example 9, 4-(1H-indol-4-ylamino)-5-[3-(2-methoxyethoxy)phenyl]nicotinonitrile 164 was prepared from 3-hydroxyphenylacetic acid. MS: 385.2 (M+H), HPLC retention time: 7.10 min.[b].

Example 13

Preparation of 5-[3-(2-chloroethoxy)phenyl]-4-(1H-indol-4-ylamino)-nicotinitrile 165

To a stirred solution of 3-hydroxyphenylacetic acid methyl ester (22.6 g, 136 mmol) and 2-chloroethyl p-toluenesulfonate (40 g, 171 mmol) in 900 mL of acetone was added Cs$_2$CO$_3$ (88.8 g, 272 mmol) and the mixture was headed at reflux for 3 h. The reaction mixture was then cooled, filtered, and concentrated in vacuo. The residue was purified by flash chromatography on silica gel eluting with a gradient of 0-7% EtOAc in hexanes to yield 28.9 g (90% yield) of [3-(2-chloroethoxy)phenyl]-acetic acid methyl ester as a colorless oil.

To a 1.0 L three-necked round-bottomed flask was added 150 mL of anhydrous THF and cooled to −78° C. n-Butyl lithium (2.5 M in hexane, 52.5 mL, 131 mmol) was added dropwise. Anhydrous CH$_3$CN (7.2 mL, 138 mmol) in 150 mL of anhydrous THF was subsequently added dropwise to the flask amidst stirring and cooling. After 1 h of stirring, [3-(2-chloroethoxy)phenyl]-acetic acid methyl ester (15 g, 66 mmol) in 20 mL of anhydrous THF was added dropwise to the resulting white colloidal mixture in the flask. The reaction mixture was stirred for an additional 2 h, followed by the addition of 4:1 mixture of MeOH: acetic acid (AcOH) at −78° C. The solution was diluted with 500 mL water and extracted with EtOAc (4×150 mL). The organic layer was separated, dried with anhydrous MgSO$_4$, filtered, and concentrated in vacuo. Residual AcOH was removed by concentrating in vacuo with toluene. The residue was passed through silica gel eluting with CH$_2$Cl$_2$ to yield 4-[3-(2-chloroethoxy)phenyl]-3-oxo-butyronitrile as an off-white solid, 16.0 g (99% yield).

To a stirred solution of 4-[3-(2-chloroethoxy)phenyl]-3-oxo-butyronitrile (16.0 g, 67.0 mmol) in 100 mL anhydrous DMF was added DMF-DMA (19.7 mL, 148 mmol) and TEA (9.4 mL, 67.0 mmol), and the solution was heated at 100° C. for 2.5 h. The reaction mixture was concentrated in vacuo and the residue was dissolved in CH$_2$Cl$_2$, passed through Magnesol® and concentrated. The crude material was then stirred with 3,4-dimethoxybenzylamine (11 mL, 74 mmol) in 100 mL of anhydrous toluene at reflux for 2 h. The reaction was cooled, concentrated in vacuo, and purified by flash chromatography on silica gel eluting with EtOAc to yield 11.8 g (41% yield) of 5-[3-(2-chloroethoxy)phenyl]-1-(3,4-dimethoxybenzyl)-4-oxo-1,4-dihydro-pyridine-3-carbonitrile as an off-white solid.

A solution of 5-[3-(2-chloroethoxy)-phenyl]-1-(3,4-dimethoxybenzyl)-4-oxo-1,4-dihydro-pyridine-3-carbonitrile (2.5 g, 5.9 mmol) and LiCl (2.3 g, 53 mmol) in 22 mL of POCl$_3$ was heated at reflux for 2.5 h. The excess POCl$_3$ was removed by concentrating in vacuo. The residue was dissolved in 100 mL CH$_2$Cl$_2$ and washed with ice-cold 3 N NaOH. The organic layer was separated, dried over anhydrous MgSO$_4$, filtered, concentrated in vacuo, and purified by flash chromatography on silica gel eluting with 30% EtOAc in hexanes to yield 1.3 g (75% yield) of 4-chloro-5-[3-(2-chloroethoxy)phenyl]nicotinonitrile as an off-white solid.

To a stirred solution of 4-chloro-5-[3-(2-chloroethoxy) phenyl]-nicotinonitrile (200 mg, 0.68 mmol), 4-aminoindole (135 mg, 1 mmol), DavePhos (80 mg, 0.20 mmol), and K$_3$PO$_4$ (216 mg, 1 mmol) in 4 mL anhydrous ethylene glycol dimethyl ether was added Pd$_2$(dba)$_3$ (62 mg, 0.07 mmol). The mixture was heated at 90° C. for 2 h then cooled, filtered through celite, concentrated in vacuo, and purified by flash chromatography on silica gel eluting with a gradient of 5-50% MeOH in CH$_2$Cl$_2$ to yield 155 mg (59% yield) of 5-[3-(2-chloroethoxy)phenyl]-4-(1H-indol-4-ylamino)-nicotinonitrile 165 as a tan solid. MS: 389.1 (M+H), HPLC retention time: 9.60 min.$^{(a)}$ Following procedures analogous to those described for preparing compound 165, compounds 166 and 167 in Table 6 were prepared from 4-chloro-5-[3-(2-chloroethoxy)phenyl]-nicotinonitrile.

TABLE 6

| Compound | Compound Name | HPLC Retention Time (min) | Observed Ion m/e [M + H] |
|---|---|---|---|
| 166 | 5-[3-(2-chloroethoxy)phenyl]-4-(1H-indol-6-yl amino)nicotinonitrile | 9.91$^{(a)}$ | 389.1 |
| 167 | 5-[3-(2-chloroethoxy)phenyl]-4-(1H-indol-5-yl amino)nicotinonitrile | 9.45$^{(a)}$ | 389.1 |

Example 14

Preparation of 4-(1H-indol-4-ylamino)-5-{3-[2-(4-methyl-piperazin-1-yl)-ethoxy]-phenyl}-nicotinonitrile 168

Method A: A stirred solution of 5-[3-(2-chloroethoxy)phenyl]-4-(1H-indol-4-ylamino)-nicotinonitrile 165 (100 mg, 0.26 mmol) and N-methylpiperazine (262 mg, 2.6 mmol) in 2.5 mL of EtOH was heated to 105° C. for 7 h. The reaction was cooled, poured into 25 mL of water, and chilled to 0° C. The solid was filtered and dried in vacuo at 50° C. overnight to yield 40 mg (34% yield) of the title compound as a brown solid.

Method B: A mixture of 5-[3-(2-chloroethoxy)phenyl]-4-(1H-indol-4-ylamino)-nicotinonitrile 165 (150 mg, 0.39 mmol), N-methylpiperazine (390 mg, 3.9 mmol) and NaI (catalytic amount) in DME (2.0 mL) was heated at reflux for overnight. The reaction mixture was partitioned between saturated NaHCO$_3$ and CH$_2$Cl$_2$. The combined organics were dried over Na$_2$SO$_4$, concentrated and purified by flash chromatography on silica gel eluting with a gradient of 2-15% MeOH in CH$_2$Cl$_2$ to give 141 mg (79% yield) of the title compound as an off-white solid.

Following procedures analogous to those described in Method A for preparing compound 168, compounds 169-171 in Table 7 were prepared from 5-[3-(2-chloroethoxy)phenyl]-4-(1H-indol-4-ylamino)nicotinonitrile 165; compounds 172 and 173 were prepared from 5-[3-(2-chloroethoxy)phenyl]-4-(1H-indol-6-ylamino)nicotinonitrile 166; and compounds 174 and 175 were prepared from 5-[3-(2-chloroethoxy)phenyl]-4-(1H-indol-5-ylamino)nicotinonitrile 167. Following procedures analogous to those described in Method B for preparing compound 168, compounds 176 to 177 in Table 7 were prepared from 5-[3-(2-chloroethoxy)phenyl]-4-(1H-indol-5-ylamino)nicotinonitrile 167.

TABLE 7

| Compound | Compound Name | HPLC Retention Time (min.) | Observed Ion m/e [M + H] |
|---|---|---|---|
| 168 | 4-(1H-indol-4-ylamino)-5-{3-[2-(4-methyl-piperazin-1-yl)ethoxy]phenyl}nicotinonitrile | 5.01$^{(a)}$ | 453.2 |
| 169 | 4-(1H-indol-4-ylamino)-5-[3-(2-pyrrolidin-1-yl ethoxy)phenyl]nicotinonitrile | 5.40$^{(a)}$ | 424.2 |
| 170 | 4-(1H-indol-4-ylamino)-5-[3-(2-morpholin-4-yl ethoxy)phenyl]nicotinonitrile | 5.20$^{(a)}$ | 440.2 |
| 171 | 4-(1H-indol-4-ylamino)-5-[3-(2-piperidin-1-yl ethoxy)phenyl]nicotinonitrile | 3.91$^{(a)}$ | 438.2 |

TABLE 7-continued

| Compound | Compound Name | HPLC Retention Time (min.) | Observed Ion m/e [M + H] |
|---|---|---|---|
| 172 | 4-(1H-indol-6-ylamino)-5-[3-(2-pyrrolidin-1-yl ethoxy)phenyl]nicotinonitrile | 5.97[a] | 424.2 |
| 173 | 4-(1H-indol-6-ylamino)-5-[3-(2-morpholin-4-yl ethoxy)phenyl]nicotinonitrile | 5.52[a] | 440.2 |
| 174 | 4-(1H-indol-5-ylamino)-5-[3-(2-pyrrolidin-1-yl ethoxy)phenyl]nicotinonitrile | 5.14[a] | 424.2 |
| 175 | 4-(1H-indol-5-ylamino)-5-[3-(2-morpholin-4-yl ethoxy)phenyl]nicotinonitrile | 5.33[a] | 440.2 |
| 176 | 5-(3-{2-[(2-hydroxyethyl)amino]ethoxy}phenyl)-4-(1H-indol-5-ylamino)nicotinonitrile | 1.35[c] | 414.4 |
| 177 | 4-(1H-indol-5-ylamino)-5-(3-{2-[(2-pyrrolidin-1-ylethyl)amino]ethoxy}phenyl)nicotinonitrile | 0.67[c] | 467.5 |

Example 15

Preparation of 5-[3-(2-chloroethoxy)-4-methoxyphenyl]-4-(1H-indol-5-ylamino)nicotinonitrile 178

Following procedures analogous to those described in Example 12, 4-chloro-5-[3-(2-chloroethoxy)-4-methoxyphenyl]nicotinonitrile was prepared from methyl(3-hydroxy-4-methoxyphenyl)acetate. Following procedures analogous to those described for preparing compound 113 (Example 2, Method B), 5-[3-(2-chloroethoxy)-4-methoxyphenyl]-4-(1H-indol-5-ylamino)nicotinonitrile 178 was prepared from 4-chloro-5-[3-(2-chloroethoxy)-4-methoxyphenyl]-nicotinonitrile. MS: 419.1 (M+H); melting range: 153-155° C.

Following procedures for preparing compound 168 (Example 13, Method A), compounds 179-183 in Table 8 were prepared from 5-[3-(2-chloroethoxy)-4-methoxyphenyl]-4-(1H-indol-5-ylamino)nicotinonitrile 178.

TABLE 8

| Compound | Compound Name | HPLC Retention Time (min.) | Observed Ion m/e [M + H] |
|---|---|---|---|
| 179 | 5-{3-[2-(diethylamino)ethoxy]-4-methoxyphenyl}-4-(1H-indol-5-ylamino)nicotinonitrile | 0.613[c] | 456.2 |
| 180 | 5-{3-[2-(diisopropylamino)ethoxy]-4-methoxy phenyl}-4-(1H-indol-5-ylamino)nicotinonitrile | 0.597[c] | 484.2 |
| 181 | 5-{3-[2-(benzylamino)ethoxy]-4-methoxyphenyl}-4-(1H-indol-5-ylamino)nicotinonitrile | 1.038[c] | 490.2 |
| 182 | 4-(1H-indol-5-ylamino)-5-(4-methoxy-3-{2-[(2-methoxyethyl)amino]ethoxy}phenyl)nicotinonitrile | 0.456[c] | 458.2 |
| 183 | 4-(1H-indol-5-ylamino)-5-(4-methoxy-3-{2-[(5-methyl-1,3,4-thiadiazol-2-yl)amino]ethoxy} phenyl)nicotinonitrile | 0.533[c] | 498.1 |

Following procedures analogous to those described for the preparation of compound 168 (Example 13, Method B), compounds in Table 9 were prepared.

TABLE 9

| Compound | Compound Name | HPLC Retention Time (min.) | Observed Ion m/e [M + H] | Observed HRMS [M + H] | Melting Range (° C.) |
|---|---|---|---|---|---|
| 345 | 5-{4-[2-(dimethylamino)ethoxy]-3-methoxyphenyl}-4-[(4-methyl-1H-indol-5-yl)amino]nicotinonitrile | 7.7[g] | 442.2 | 442.22426 | 186-188 |
| 414 | 5-(4-{2-[(2-hydroxyethyl)amino]ethoxy} phenyl)-4-[(4-methyl-1H-indol-5-yl)amino]nicotinonitrile | 1.41[e] | 428.2 | N/A | N/A |
| 415 | 5-(4-{2-[(3-hydroxypropyl)amino]ethoxy} | 1.43[e] | 442.2 | N/A | N/A |

TABLE 9-continued

| Compound | Compound Name | HPLC Retention Time (min.) | Observed Ion m/e [M + H] | Observed HRMS [M + H] | Melting Range (° C.) |
|---|---|---|---|---|---|
| | phenyl)-4-[(4-methyl-1H-indol-5-yl)amino]nicotinonitrile | | | | |
| 416 | 5-(4-{2-[(2-ethoxyethyl)amino]ethoxy}phenyl)-4-[(4-methyl-1H-indol-5-yl)amino]nicotinonitrile | 1.51$^{(e)}$ | 456.2 | N/A | N/A |
| 417 | 5-[4-(2-{[2-(dimethylamino)ethyl]amino}ethoxy)phenyl]-4-[(4-methyl-1H-indol-5-yl)amino]nicotinonitrile | 1.32$^{(e)}$ | 455.2 | N/A | N/A |
| 418 | 4-[(4-methyl-1H-indol-5-yl)amino]-5-[4-(2-pyrrolidin-1-ylethoxy)phenyl]nicotinonitrile | 1.48$^{(e)}$ | 438.2 | N/A | N/A |
| 419 | 5-{4-[2-(benzylamino)ethoxy]phenyl}-4-[(4-methyl-1H-indol-5-yl)amino]nicotinonitrile | 1.62$^{(e)}$ | 474.2 | N/A | N/A |
| 420 | 4-[(4-methyl-1H-indol-5-yl)amino]-5-(4-{2-[(1-methylpiperidin-4-yl)amino]ethoxy}phenyl)nicotinonitrile | 1.31$^{(e)}$ | 481.3 | N/A | N/A |
| 421 | 4-[(4-methyl-1H-indol-5-yl)amino]-5-[4-(2-{[(1-methylpiperidin-4-yl)methyl]amino}ethoxy)phenyl]nicotinonitrile | 1.35$^{(e)}$ | 493.3 | N/A | N/A |
| 422 | 5-(4-{2-[4-(hydroxymethyl)piperidin-1-yl]ethoxy}phenyl)-4-[(4-methyl-1H-indol-5-yl)amino]nicotinonitrile | 1.47$^{(e)}$ | 482.2 | N/A | N/A |
| 423 | 4-[(4-methyl-1H-indol-5-yl)amino]-5-{4-[2-(4-pyrrolidin-1-ylpiperidin-1-yl)ethoxy]phenyl}nicotinonitrile | 1.36$^{(e)}$ | 521.3 | N/A | N/A |
| 424 | 4-[(4-methyl-1H-indol-5-yl)amino]-5-{4-[2-(4-morpholin-4-ylpiperidin-1-yl)ethoxy]phenyl}nicotinonitrile | 1.36$^{(e)}$ | 535.3 | N/A | N/A |
| 425 | 5-{4-[2-(4-ethylpiperazin-1-yl)ethoxy]phenyl}-4-[(4-methyl-1H-indol-5-yl)amino] nicotinonitrile | 1.50$^{(e)}$ | 481.3 | N/A | N/A |
| 426 | 5-{4-[2-(4-methyl-1,4-diazepan-1-yl)ethoxy]phenyl}-4-[(4-methyl-1H-indol-5-yl)amino]nicotinonitrile | 1.36$^{(e)}$ | 481.3 | N/A | N/A |
| 427 | 5-(4-{2-[4-(2-hydroxyethyl)piperazin-1-yl]ethoxy}phenyl)-4-[(4-methyl-1H-indol-5-yl)amino]nicotinonitrile | 1.36$^{(e)}$ | 497.3 | N/A | N/A |
| 428 | 5-[4-(2-{4-2-(dimethylamino)ethyl]piperazin-1-yl}ethoxy)phenyl]-4-[(4-methyl-1H-indol-5-yl)amino]nicotinonitrile | 1.36$^{(e)}$ | 524.3 | N/A | N/A |
| 429 | 5-[4-(2-{[3-(1H-imidazol-1-yl)propyl]amino}ethoxy)phenyl]-4-[(4-methyl-1H-indol-5-yl)amino]nicotinonitrile | 1.34$^{(e)}$ | 492.2 | N/A | N/A |
| 430 | 4-[(4-methyl-1H-indol-5-yl)amino]-5-{4-[2-(4-pyridin-2-ylpiperazin-1-yl)ethoxy]phenyl}nicotinonitrile | 1.53$^{(e)}$ | 530.3 | N/A | N/A |
| 431 | 4-[(4-methyl-1H-indol-5-yl)amino]-5-{4-[2-(4-pyridin-4-ylpiperazin-1-yl)ethoxy]phenyl}nicotinonitrile | 1.40$^{(e)}$ | 530.3 | N/A | N/A |
| 432 | 4-[(4-methyl-1H-indol-5-yl)amino]-5-(4-{2-[(pyridin-2-ylmethyl)amino]ethoxy}phenyl)nicotinonitrile | 1.55$^{(e)}$ | 475.2 | N/A | N/A |
| 433 | 4-[(4-methyl-1H-indol-5-yl)amino]-5-(4-{2-[(pyridin-3-ylmethyl)amino]ethoxy}phenyl)nicotinonitrile | 1.47$^{(e)}$ | 475.2 | N/A | N/A |
| 434 | 4-[(4-methyl-1H-indol-5-yl)amino]-5-(4-{2-[(pyridin-4-ylmethyl)amino]ethoxy}phenyl)nicotinonitrile | 1.44$^{(e)}$ | 475.2 | N/A | N/A |
| 435 | 4-[(4-methyl-1H-indol-5-yl)amino]-5-{4-[2-(4-phenylpiperidin-1-yl)ethoxy]phenyl} nicotinonitrile | 1.76$^{(e)}$ | 528.3 | N/A | N/A |

TABLE 9-continued

| Compound | Compound Name | HPLC Retention Time (min.) | Observed Ion m/e [M + H] | Observed HRMS [M + H] | Melting Range (° C.) |
|---|---|---|---|---|---|
| 438 | 4-[(4-methyl-1H-indol-5-yl)amino]-5-{5-[2-(4-methylpiperazin-1-yl)ethoxy]-1-benzofuran-2-yl}nicotinonitrile | 1.312(f) | 507.1 | N/A | N/A |
| 472 | 4-[(4-methyl-1H-indol-5-yl)amino]-5-{4-[3-(4-methylpiperazin-1-yl)propoxy]phenyl}nicotinonitrile | 4.6(g) | 481.3 | 481.2715 | 168-169 |
| 473 | 4-[(4-methyl-1H-indol-5-yl)amino]-5-[4-(3-morpholin-4-ylpropoxy)phenyl]nicotinonitrile | 5.1(g) | 468.3 | N/A | 176-177 |
| 474 | 4-[(4-methyl-1H-indol-5-yl)amino]-5-[4-(3-piperidin-1-ylpropoxy)phenyl]nicotinonitrile | 5.7(g) | 466.3 | 466.2608 | 169-170 |
| 475 | 5-{4-[3-(dimethylamino)propoxy]phenyl}-4-[(4-methyl-1H-indol-5-yl)amino]nicotinonitrile | 5.0(g) | 426.3 | 426.22905 | 180-181 |
| 491 | 4-[(4-methyl-1H-indol-5-yl)amino]-5-{4-[4-(4-methylpiperazin-1-yl)butoxy]phenyl} nicotinonitrile | 4.8(g) | 495.4 | 495.28638 | 149-151 |
| 496 | 4-[(6-methyl-1H-indol-5-yl)amino]-5-{4-[2-(4-methylpiperazin-1-yl)ethoxy]phenyl} nicotinonitrile | 4.4(g) | 467.4 | 467.25576 | 167-168 |
| 502 | 4-[(4-methyl-1H-indol-5-yl)amino]-5-{3-[4-(4-methylpiperazin-1-yl)butoxy]phenyl} nicotinonitrile | 0.7(g) | 495.4 | 495.28504 | 204-207 |
| 504 | 4-[(6-methyl-1H-indol-5-yl)amino]-5-[4-(2-piperidin-1-ylethoxy)phenyl]nicotinonitrile | 7.1(h) | 452.2 | 452.246 | 96.9-98.6 |
| 505 | 5-{4-[2-(4-hydroxypiperidin-1-yl)ethoxy]phenyl}-4-[(6-methyl-1H-indol-5-yl)amino]nicotinonitrile | 5.9(h) | 468.2 | 468.23924 | 96.0-97.2 |
| 506 | 4-[(6-methyl-1H-indol-5-yl)amino]-5-{4-[2-(4-pyrrolidin-1-ylpiperidin-1-yl)ethoxy]phenyl}nicotinonitrile | 4.7(h) | 521.3 | 521.30196 | 187-190 |
| 520 | 4-(1H-indol-5-ylamino)-5-{4-[2-(4-methylpiperazin-1-yl)ethoxy]phenyl}nicotinonitrile | 6.5(h) | N/A | 453.24093 | 125-128 (decom.) |

Example 16

Preparation of 4-(1H-indol-5-ylamino)-5-(3-{5-[(4-methyl piperazin-1-yl)methyl]-2-thienyl}phenyl) nicotinonitrile 184

To 5-[3-(5-formyl-2-thienyl)phenyl]-4-(1H-indol-5-ylamino)nicotinonitrile 150 (100 mg, 0.238 mmol) in CH$_2$Cl$_2$ (5 mL) and NMP (0.5 mL), cooled with ice-water bath, was added Na(OAc)$_3$BH (264 mg, 1.2 mmol) and N-methylpiperazine (133 µL, 1.2 mmol). The resulting mixture was stirred at r.t. overnight and partitioned between CH$_2$Cl$_2$ and aq. NaHCO$_3$. The combined organics were dried over Na$_2$SO$_4$, concentrated and purified by preparative TLC eluting with 10% MeOH/CH$_2$Cl$_2$ to give 63 mg (53% yield) of the title compound as a light yellow solid. MS: 505.2 (M+H); melting range: 120-123° C.

Following procedures analogous to those described for preparing compound 184, compounds 185-187 in Table 10 were prepared from 5-[3-(5-formyl-2-thienyl)phenyl]-4-(1H-indols-5-ylamino)nicotinonitrile 150.

TABLE 10

| Compound | Compound Name | Observed Ion m/e [M + H] | Melting Range (° C.) |
|---|---|---|---|
| 185 | 4-(1H-indol-5-ylamino)-5-{3-[5-(morpholin-4-yl methyl)-2-thienyl]phenyl}nicotinonitrile | 492.1 | 103-107 (decom.) |
| 186 | 4-(1H-indol-5-ylamino)-5-{3-[5-(piperidin-1-ylmethyl)-2-thienyl]phenyl}nicotinonitrile | 490.2 | 135-137 |
| 187 | 5-(3-{5-[(dimethylamino)methyl]-2-thienyl} phenyl)-4-(1H-indol-5-ylamino)nicotinonitrile | 450.1 | 102-107 (decom.) |

Example 17

Preparation of 5-(3-bromo-4-methoxyphenyl)-4-(1H-indol-5-ylamino)nicotinonitrile 188

Following procedures analogous to those described in Example 1, 5-(3-bromo-4-methoxyphenyl)-4-chloronicotinonitrile was prepared from methyl(3-bromo-4-methoxyphenyl)acetate. Following procedures analogous to those described above for preparing compound 101 (Example 1), 5-(3-bromo-4-methoxyphenyl)-4-chloronicotinonitrile was treated with 5-aminoindole to produce 5-(3-bromo-4-methoxyphenyl)-4-(1H-indol-5-ylamino)nicotinonitrile 188. MS: 419.2 (M+H); melting range: 148-150° C.

Compounds 189-193 in Table 11 were prepared from 5-(3-bromo-4-methoxyphenyl)-4-(1H-indol-5-ylamino)nicotinonitrile 188 and the appropriate boronic acid following procedures analogous to those described for preparing compound 114 (Example 6).

Example 18

Preparation of 5-[3-benzyloxyphenyl]-4-(1H-indol-5-ylamino)nicotinonitrile 194

Following procedures analogous to those described in Example 1, 5-(3-bezyloxyphenyl)-4-chloronicotinonitrile was prepared from methyl(3-benzyloxyphenyl)acetate. Following procedures analogous to those described for preparing compound 113 (Example 2, Method B), 5-[3-benzyloxyphenyl]-4-(1H-indol-5-ylamino)nicotinonitrile 194 was prepared from 5-(3-(benzyloxy)phenyl)-4-chloronicotinonitrile. MS: 417.3 (M+H); melting range: 165-166° C.

Example 19

Preparation of 5-[4-benzyloxyphenyl]-4-(1H-indol-5-ylamino)nicotinonitrile 195

Following procedures analogous to those described in Example 1, 5-(4-benzyloxyphenyl)-4-chloronicotinonitrile was prepared from methyl(4-benzyloxyphenyl)acetate. Following procedures analogous to those described for preparing compound 113 (Example 2, Method B), 5-[4-benzyloxyphenyl]-4-(1H-indol-5-ylamino)nicotinonitrile 195 was prepared from 5-(4-benzyloxyphenyl)-4-chloronicotinonitrile. MS: 417.1; melting range: 163-165° C.

Example 20

Preparation of 3'-[5-cyano-4-(1H-indol-5-ylamino)pyridin-3-yl]-N-methylbiphenyl-4-carboxamide 196

To a solution of 3'-[5-cyano-4-(1H-indol-5-ylamino)pyridin-3-yl]biphenyl-4-carboxylic acid 134 (40 mg, 0.09 mmol) and BOP (41 mg, 0.09 mmol) in DMF (1 mL) was added methylamine solution in MeOH (2M, 47 uL, 0.09 mmol) followed by TEA (19 uL, 0.14 mmol). The reaction mixture was stirred for 12 h at r.t. The crude reaction mixture was then dissolved in dimethylsulfoxide (DMSO, 1 mL) and purified by reversed phase HPLC to give 16 mg 3'-[5-cyano-4-(1H-indol-5-ylamino)pyridin-3-yl]-N-methyl biphenyl-4-carboxamide 196 (39%). MS: 44.2 (M+H); HPLC retention time: 2.10 min.[a].

Compounds 197-214 in Table 12 were prepared from 3'-[5-cyano-4-(1H-indol-5-ylamino)pyridin-3-yl]biphenyl-4-carboxylic acid 134 using a procedure analogous to the one described above. Similarly, compounds 215 and 216 in Table 12 were prepared from 3'-[5-cyano-4(1H-indol-4-ylamino)pyridin-3-yl]biphenyl-4-carboxylic acid 135 using a procedure analogous to the one described above.

TABLE 11

| Compound | Compound Name | Observed Ion m/e [M + H] | Melting Range (° C.) |
|---|---|---|---|
| 189 | 4-(1H-indol-5-ylamino)-5-[4-methoxy-3-(2-thienyl)phenyl]nicotinonitrile | 423.1 | 122-124 |
| 190 | 5-(4'-chloro-6-methoxybiphenyl-3-yl)-4-(1H-indol-5-ylamino)nicotinonitrile | 451.1 | 140-142 |
| 191 | 5-(3'-chloro-6-methoxybiphenyl-3-yl)-4-(1H-indol-5-ylamino)nicotinonitrile | 451.1 | 134-136 |
| 192 | 5'-[5-cyano-4-(1H-indol-5-ylamino)pyridin-3-yl]-N-cyclopentyl-2'-methoxybiphenyl-4-carboxamide | 528.2 | 155-157 |
| 193 | 5-(2'-chloro-6-methoxybiphenyl-3-yl)-4-(1H-indol-5-ylamino)nicotinonitrile | 451.1 | 158-160 |

TABLE 12

| Compound | Compound Name | HPLC Retention Time (min.) | Observed Ion m/e [M + H] |
|---|---|---|---|
| 197 | N-butyl-3'-[5-cyano-4-(1H-indol-5-ylamino) pyridin-3-yl] biphenyl-4-carboxamide | 2.28[a] | 486.2 |
| 198 | 3'-[5-cyano-4-(1H-indol-5-ylamino)pyridin-3-yl]-N-(1-ethyl propyl) biphenyl-4-carboxamide | 2.30[a] | 500.2 |
| 199 | 3'-[5-cyano-4-(1H-indol-5-ylamino)pyridin-3-yl]-N-(2-hydroxyethyl) biphenyl-4-carboxamide | 1.99[a] | 474.2 |
| 200 | 3'-[5-cyano-4-(1H-indol-5-ylamino)pyridin-3-yl]-N-(2-methoxyethyl) biphenyl-4-carboxamide | 2.11[a] | 488.2 |
| 201 | 3'-[5-cyano-4-(1H-indol-5-ylamino)pyridin-3-yl]-N-cyclopropylbiphenyl-4-carboxamide | 2.14[a] | 470.2 |
| 202 | 3'-[5-cyano-4-(1H-indol-5-ylamino)pyridin-3-yl]-N-cyclohexylbiphenyl-4-carboxamide | 2.35[a] | 512.2 |
| 203 | 3'-[5-cyano-4-(1H-indol-5-ylamino)pyridin-3-yl]-N-(2-pyrrolidin-1-ylethyl)biphenyl-4-carboxamide | 2.04[a] | 527.2 |
| 204 | N-benzyl-3'-[5-cyano-4-(1H-indol-5-ylamino)pyridin-3-yl] biphenyl-4-carboxamide | 2.29[a] | 520.2 |
| 205 | 4-(1H-indol-5-ylamino)-5-[4'-(pyrrolidin-1-ylcarbonyl) biphenyl-3-yl]nicotinonitrile | 2.23[a] | 484.2 |
| 206 | 4-(1H-indol-5-ylamino)-5-[4'-(morpholin-4-ylcarbonyl) biphenyl-3-yl]nicotinonitrile | 2.12[a] | 500.2 |
| 207 | 4-(1H-indol-5-ylamino)-5-{4'-[(4-methylpiperazin-1-yl) carbonyl]biphenyl-3-yl}nicotinonitrile | 1.97[a] | 513.2 |
| 208 | 3'-[5-cyano-4-(1H-indol-5-ylamino)pyridin-3-yl]-N-cyclopentylbiphenyl-3-carboxamide | N/A | 498.4 |
| 209 | 3'-[5-cyano-4-(1H-indol-5-ylamino)pyridin-3-yl]-N-(4-hydroxybutyl)biphenyl-4-carboxamide | 2.05[a] | 502.2 |
| 210 | 3'-[5-cyano-4-(1H-indol-5-ylamino)pyridin-3-yl]-N-(3-hydroxypropyl)biphenyl-4-carboxamide | 2.03[a] | 488.2 |
| 211 | 3'-[5-cyano-4-(1H-indol-5-ylamino)pyridin-3-yl]-N-[2-(methylamino)ethyl]biphenyl-4-carboxamide | 1.94[a] | 487.2 |
| 212 | 3'-[5-cyano-4-(1H-indol-5-ylamino)pyridin-3-yl]-N-(pyridin-2-ylmethyl)biphenyl-4-carboxamide | 2.17[a] | 521.2 |
| 213 | 3'-[5-cyano-4-(1H-indol-5-ylamino)pyridin-3-yl]-N-(pyridin-3-ylmethyl)biphenyl-4-carboxamide | 2.15[a] | 521.2 |
| 214 | 3'-[5-cyano-4-(1H-indol-5-ylamino)pyridin-3-yl]-N-(pyridin-4-ylmethyl)biphenyl-4-carboxamide | 2.12[a] | 521.1 |
| 215 | N-butyl-3'-[5-cyano-4-(1H-indol-4-ylamino)pyridin-3-yl] biphenyl-4-carboxamide | 2.26[a] | 486.2 |
| 216 | 3'-[5-cyano-4-(1H-indol-4-ylamino)pyridin-3-yl]-N-(2-hydroxyethyl)biphenyl-4-carboxamide | 1.99[a] | 474.2 |

Example 21

Preparation of 5-(3,4-dimethoxyphenyl)-4-[(7-methyl-1H-indol-5-yl)amino]nicotinonitrile 217

Following procedures analogous to those described for preparing compound 113 (Example 2, Method B), the title compound was prepared from 4-chloro-5-(3,4-dimethoxyphenyl)nicotinonitrile and 5-amino-7-methylindole. MS: 385.3 (M+H).

Example 22

Preparation of 5-(3,4-dimethoxyphenyl)-4-[(4-methyl-1H-indol-5-yl)amino]nicotinonitrile 218

Following procedures analogous to those described for preparing compound 113 (Example 2, Method B), 5-(3,4-dimethoxyphenyl)-4-[(4-methyl-1H-indol-5-yl)amino]nicotinonitrile 218 was prepared from 4-chloro-5-(3,4-dimethoxyphenyl)nicotinonitrile and 5-amino-4-methylindole. MS: 385.2 (M+H); melting range: 130-133° C.

Example 23

Preparation of 5-(3,4-dimethoxyphenyl)-4-[1H-indol-5-yl (methyl)amino]nicotinonitrile 219

Following procedures analogous to those described for preparing compound 113 (Example 2, Method B), 5-(3,4-dimethoxyphenyl)-4-[1H-indol-5-yl(methyl)amino]nicotinonitrile 219 was prepared from 4-chloro-5-(3,4-dimethoxyphenyl)nicotinonitrile and (1H-indol-5-yl)-methylamine. MS: 385.1; melting range: 224-226° C. (decom.).

Example 24

Preparation of 5-(3,4-dimethoxyphenyl)-4-(1H-indol-5-yloxy)nicotinonitrile

A mixture of 4-chloro-5-(3,4-dimethoxyphenyl)nicotinonitrile (120 mg, 0.44 mmol), 5-hydroxyindole (71 mg, 0.53 mmol) and $K_2CO_3$ (91 mg, 0.66 mmol) in $CH_3CN$ (4.0 mL) was heated at 80° C. for 4 h. After cooling to r.t., the reaction mixture was diluted with water (20 mL) and the precipitate was collected by filtration and washed with ether containing

Example 25

Preparation of 5-(3,4-dimethoxyphenyl)-4-(1H-indol-5-yl)nicotinonitrile 221

A mixture of 4-chloro-5-(3,4-dimethoxyphenyl)nicotinonitrile (120 mg, 0.44 mmol), indole-5-boronic acid (77 mg, 0.48 mmol), Pd(PPh$_3$)$_4$ (25 mg, 0.022 mmol) and aqueous saturated NaHCO$_3$ (3 mL) in DME (4.0 mL) was heated at reflux for 5 h. The reaction mixture was partitioned between water and EtOAc. The combined organics were dried over Na$_2$SO$_4$ and concentrated to give a brown syrup, which was purified by preparative thin-layer chromatography eluting with 3% MeOH/CH$_2$Cl$_2$ to give 94 mg (61%) of 5-(3,4-dimethoxyphenyl)-4-(1H-indol-5-yl)nicotinonitrile 221 as an off-white solid. MS: 356.2 (M+H); melting range: 215-217° C.

Example 26

Preparation of 5-(1-benzofuran-2-yl)-4-[(4-methyl-1H-indol-5-yl)amino]nicotinonitrile 222

A mixture of 3-aminobut-3-enenitrile (100 g, 1.22 mol) and conc. HCl (125 mL) in water (125 mL) was heated at 80° C. for 2 h, cooled to r.t. and filtered to remove the solid. The filtrate was extracted with EtOAc and the combined extracts were dried over Na$_2$SO$_4$ and concentrated to give a semi-solid residue which was distilled under vacuum to give 77.4 g (76%) of acetoacetonitrile (73-77° C./3-5 mmHg).

A mixture of acetoacetonitrile (41 g, 493 mmol), t-butoxybis(dimethyl amino)methane (86 g, 493 mmol) and DMF-DMA (263 mL, 1.97 mol) was heated at 100° C. overnight and evaporated to remove the volatiles. The residue was triturated with hexanes/ether (1:1) and the solids were collected by filtration and washed with hexanes/ether (1:1) and a minimum amount of EtOAc to give 64.3 g (67%) of 5-(dimethylamino)-2-[(dimethylamino)methylene]-3-oxopent-4-enenitrile as a light yellow solid, which was used for the next step without further purification.

A mixture of 5-(dimethylamino)-2-[(dimethylamino)methylene]-3-oxopent-4-enenitrile (64.3 g, 333 mmol) and ammonium acetate (126 g, 1.66 mol) in EtOH (1.8 L) was heated at reflux for 60 h and concentrated to remove solvent. The resultant semi-solid residue was diluted with EtOAc, filtered and washed with EtOAc followed by CH$_2$Cl$_2$. The filtrate was evaporated to a reduced volume. The precipitated solids were collected by filtration, washed with EtOAc and a minimum amount of EtOH. The process of evaporation and crystallization was repeated to obtain more solid product from the mother liquor. The combined off-white solids provided 20.9 g of 4-hydroxynicotinonitrile (53%); melting range: 234-236° C.

Alternatively, 4-hydroxynicotinonitrile may be synthesized according to the methods described in Broekman, F. W. et al., *Recueil des Travaux Chimiques des Pays-Bas*, 81: 792-796 (1962).

A mixture of 4-hydroxynicotinonitrile (45.7 g, 381 mmol), iodine (96.6 g, 381 mmol) and NaOH (19.8 g, 825 mmol) in water (600 mL) was heated at 85° C. overnight, cooled to r.t. and diluted with water. The precipitate was collected by filtration and washed with water to give 57.5 g (61%) of 4-hydroxy-5-iodonicotinonitrile as a tan solid. Mp>245° C.

A mixture of 4-hydroxy-5-iodonicotinonitrile (57.5 g, 234 mmol) and POCl$_3$ (200 mL) was heated at 100° C. for 2 hours, cooled to room temperature and evaporated to remove excess POCl$_3$. The residue was cooled in an ice-water bath, adjusted to pH 8-9 with aqueous 10 N NaOH and extracted with ethyl acetate. The combined organics were washed with water and brine, dried over magnesium sulfate and concentrated. The resulting solid residue was washed with a minimum amount of methanol and methylene chloride to give 46.5 g (75%) of 4-chloro-5-iodonicotinonitrile as a tan solid. Melting range: 120-122° C.

A mixture of 4-chloro-5-iodonicotinonitrile (5.0 g, 18.9 mmol) and 5-amino-4-methylindole (3.0 g, 20.8 mmol) in EtOH (100 mL) was heated at reflux for 3 days, cooled to r.t. and diluted with saturated aq. Na$_2$SO$_4$ (300 mL). The precipitated solids were collected by filtration, washed with water and dried to give 5.3 g (75%) of 5-iodo-4-[(4-methyl-1H-indol-5-yl)amino]nicotinonitrile as a grey solid. Melting range: 192-194° C.; MS (M+H$^+$): 375.1.

To a mixture of 5-iodo-4-[(4-methyl-1H-indol-5-yl)amino]nicotinonitrile (200 mg, 0.53 mmol), 2-benzofuranboronic acid (173 mg, 1.07 mmol) and Pd(PPh$_3$)$_4$ (31 mg, 0.027 mmol) in DME (4.0 mL) was added 2.0 M aqueous Na$_2$CO$_3$ (0.8 mL). The resulting mixture was heated at 80° C. for 2 h, cooled to r.t. and filtered. The filtrate was concentrated and purified by HPLC to give 35 mg of 5-(1-benzofuran-2-yl)-4-[(4-methyl-1H-indol-5-yl)amino]nicotinonitrile 222 as a yellow solid. MS: 365.2 (M+H); HPLC retention time: 11.4 min.[a].

Following procedures analogous to those described for the preparation of 5-(1-benzofuran-2-yl)-4-[(4-methyl-1H-indol-5-yl)amino]nicotinonitrile 222, compounds in Table 13 were prepared.

TABLE 13

| Compound | Compound Name | Melting range (° C.) | HPLC Retention Time (min.) | Observed ion m/e [M + H]$^+$ | Observed HRMS [M + H]$^+$ |
|---|---|---|---|---|---|
| 412 | 5-(3,4-dimethoxyphenyl)-4-[(6-methyl-1H-indol-5-yl)amino]nicotinonitrile | N/A | 1.72[e] | 385.2 | N/A |
| 413 | 5-(1-benzofuran-2-yl)-4-[(6-methyl-1H-indol-5-yl)amino]nicotinonitrile | N/A | 3.7[i] | 365.4 | N/A |
| 453 | 4-[(4-methyl-1H-indol-5-yl)amino]-2'-(morpholin-4-ylmethyl)-3,4'-bipyridine-5-carbonitrile | N/A | 0.339[f] | 425.0 | N/A |
| 460 | 5-[4-(3-chloropropoxy)phenyl]-4-[(4-methyl-1H-indol-5-yl)amino]nicotinonitrile | 151-153 | 10.3[g] | N/A | 417.14818 |

TABLE 13-continued

| Compound | Compound Name | Melting range (° C.) | HPLC Retention Time (min.) | Observed ion m/e [M + H]+ | Observed HRMS [M + H]+ |
|---|---|---|---|---|---|
| 463 | 5-(5-formyl-2-thienyl)-4-[(4-methyl-1H-indol-5-yl)amino]nicotinonitrile | 190-192 | 8.3(g) | 359.2 | 359.09612 |
| 466 | 5-(3-methyl-1-benzofuran-2-yl)-4-[(4-methyl-1H-indol-5-yl)amino]nicotinonitrile | 224-226 | 11.4(g) | 379.3 | 379.15464 |
| 467 | 4-[(4-methyl-1H-indol-5-yl)amino]-3,4'-bipyridine-5-carbonitrile | 250 (decom.) | 4.9(g) | 326.2 | 326.13969 |
| 469 | 2'-chloro-4-[(4-methyl-1H-indol-5-yl)amino]-3,4'-bipyridine-5-carbonitrile | 134-135 | 8.3(g) | 360.2 | 360.10099 |
| 470 | 5-{2-chloro-4-[2-(4-methylpiperazin-1-yl)ethoxy]phenyl}-4-[(4-methyl-1H-indol-5-yl)amino]nicotinonitrile | N/A | N/A | 501.4 | 501.21649 |
| 471 | 2'-chloro-4-[(4-methyl-1H-indol-5-yl)amino]-3,3'-bipyridine-5-carbonitrile | N/A | 7.2(g) | 360.2 | 360.10091 |
| 477 | 5-[3,4-bis(2-methoxyethoxy)phenyl]-4-[(4-methyl-1H-indol-5-yl)amino]nicotinonitrile | N/A | 8.6(g) | N/A | 529.18902 |
| 488 | 5-(3,4-dimethoxyphenyl)-4-(1H-pyrrolo[2,3-b]pyridin-5-ylamino)nicotinonitrile | 235-236 | 6.2(g) | 372.3 | 372.14654 |
| 489 | 5-(5-formyl-2-furyl)-4-[(4-methyl-1H-indol-5-yl)amino]nicotinonitrile | 225-227 (decom.) | N/A | 343.2 | 343.11964 |
| 494 | 5-[4-(2-chloroethoxy)phenyl]-4-[(6-methyl-1H-indol-5-yl)amino]nicotinonitrile | N/A | 9.6(g) | 403.2 | N/A |
| 498 | 4-[(7-chloro-4-methyl-1H-indol-5-yl)amino]-5-(3,4-dimethoxyphenyl)nicotinonitrile | N/A | 8.8(g) | 419.2 | 419.12665 |
| 507 | 4-[(4-methyl-1H-indol-5-yl)amino]-6'-morpholin-4-yl-3,3'-bipyridine-5-carbonitrile | >245 | 5.6(g) | N/A | 411.19329 |
| 508 | 4-[(4-methyl-1H-indol-5-yl)amino]-6'-piperidin-1-yl-3,3'-bipyridine-5-carbonitrile | >245 | 6.0(g) | N/A | 409.21414 |
| 509 | 4-[(4-methyl-1H-indol-5-yl)amino]-5-pyrimidin-5-ylnicotinonitrile | >245 | 5.5(g) | N/A | 327.13563 |
| 510 | 4-[(4-methyl-1H-indol-5-yl)amino]-5-(2-piperidin-1-ylpyrimidin-5-yl)nicotinonitrile | >245 | 9.3(g) | N/A | 410.20928 |
| 511 | 4-[(4-methyl-1H-indol-5-yl)amino]-5-(2-morpholin-4-ylpyrimidin-5-yl)nicotinonitrile | >245 | 7.1(g) | 412.3 | 412.18835 |
| 512 | 4-[(4-methyl-1H-indol-5-yl)amino]-5-(2-pyrrolidin-1-ylpyrimidin-5-yl)nicotinonitrile | >245 | 6.9(g) | 396.3 | 396.19427 |
| 513 | 5-[2-(dimethylamino)pyrimidin-5-yl]-4-[(4-methyl-1H-indol-5-yl)amino]nicotinonitrile | >245 | 6.7(g) | 370.3 | 370.17834 |
| 514 | 5-(1-benzothien-2-yl)-4-[(4-methyl-1H-indol-5-yl)amino]nicotinonitrile | >245 | 11.3(g) | N/A | 381.11811 |
| 515 | 5-[4-(2-chloroethoxy)phenyl]-4-(1H-indol-5-ylamino)nicotinonitrile | N/A | N/A | N/A | 389.11768 |
| 516 | 5-(5-formyl-3-thienyl)-4-[(4-methyl-1H-indol-5-yl)amino]nicotinonitrile | 241-244 (decom.) | 7.4(g) | 359.3 | N/A |
| 517 | 5-(4-formyl-2-furyl)-4-[(4-methyl-1H-indol-5-yl)amino]nicotinonitrile | 240-242 (decom.) | 8.0(g) | 343.3 | N/A |
| 519 | 4-[(4-methyl-1H-indol-5-yl)amino]-3,3'-bipyridine-5-carbonitrile | >245 | 5.1(g) | 326.2 | 326.14049 |
| 523 | 5-(3,4-dimethoxyphenyl)-4-(1H-indol-5-ylamino)nicotinonitrile 1-oxide | N/A | 8.5(g) | 387.3 | 387.14545 |
| 525 | 1-butyl-3-(4-{5-cyano-4-[(4-methyl-1H-indol-5-yl)amino]pyridin-3-yl}phenyl)urea | 142.7-147.2 | 8.9(g) | 439.1 | 439.2241 |
| 526 | methyl (4-{5-cyano-4-[(4-methyl-1H-indol-5-yl)amino]pyridin-3-yl}phenyl)carbamate | 216.4-219.2 | 7.8(g) | 398.3 | 398.1611 |

TABLE 13-continued

| Compound | Compound Name | Melting range (° C.) | HPLC Retention Time (min.) | Observed ion m/e [M + H]+ | Observed HRMS [M + H]+ |
|---|---|---|---|---|---|
| 527 | benzyl (4-{5-cyano-4-[(4-methyl-1H-indol-5-yl)amino]pyridin-3-yl}-2-fluorophenyl)carbamate | 200.9-203 | 10.9(g) | 492.3 | 492.1830 |
| 528 | 4-methoxybenzyl (4-{5-cyano-4-[(4-methyl-1H-indol-5-yl)amino]pyridin-3-yl}-2-fluorophenyl)carbamate | 115-116 | 11.2(g) | 522.3 | 522.1946 |
| 545 | 5-(3,4-dimethoxyphenyl)-4-[(4-methoxy-1H-indol-5-yl)amino]nicotinonitrile | N/A | 7.5(g) | 401.2 | 401.1613 |
| 546 | 5-(3,4-dimethoxyphenyl)-4-[(4-fluoro-1H-indol-5-yl)amino]nicotinonitrile | N/A | 8.2(g) | 389.2 | 389.1410 |
| 549 | 5-(3,4-dimethoxyphenyl)-4-[(2,4-dimethyl-1H-indol-5-yl)amino]nicotinonitrile | N/A | 8.8(g) | 399.2 | 399.1819 |
| 550 | 5-{2-[(dimethylamino)methyl]phenyl}-4-[(4-methyl-1H-indol-5-yl)amino]nicotinonitrile | 200-202 (decom.) | N/A | 382.3 | N/A |
| 551 | 5-(5-formyl-2-methoxyphenyl)-4-[(4-methyl-1H-indol-5-yl)amino]nicotinonitrile | N/A | 7.3(g) | 383.3 | N/A |
| 555 | 5-(3,4-dimethoxyphenyl)-4-[(1,4-dimethyl-1H-indol-5-yl)amino]nicotinonitrile | 233-234 (decom.) | 8.9(g) | 399.3 | N/A |
| 556 | 3-{5-cyano-4-[(4-methyl-1H-indol-5-yl)amino]pyridin-3-yl}benzoic acid | >250 | 7.0(g) | 369.3 | N/A |
| 557 | 5-(2-methoxyphenyl)-4-[(4-methyl-1H-indol-5-yl)amino]nicotinonitrile | N/A | 6.7(g) | 355.3 | N/A |
| 558 | 5-(3-methoxyphenyl)-4-[(4-methyl-1H-indol-5-yl)amino]nicotinonitrile | N/A | 8.4(g) | 355.3 | N/A |
| 559 | 5-(4-methoxyphenyl)-4-[(4-methyl-1H-indol-5-yl)amino]nicotinonitrile | N/A | 8.3(g) | 355.3 | N/A |
| 560 | 4-[(4-methyl-1H-indol-5-yl)amino]-5-phenylnicotinonitrile | N/A | 8.0(g) | 325.3 | N/A |
| 561 | 4-[(4-methyl-1H-indol-5-yl)amino]-5-(2-thienyl)nicotinonitrile | N/A | 8.2(g) | 331.2 | N/A |
| 562 | 4-[(4-methyl-1H-indol-5-yl)amino]-5-(3-thienyl)nicotinonitrile | N/A | 7.7(g) | 331.2 | N/A |
| 563 | 5-(3-furyl)-4-[(4-methyl-1H-indol-5-yl)amino]nicotinonitrile | N/A | 7.0(g) | 315.3 | N/A |
| 566 | 1-(4-{5-cyano-4-[(4-methyl-1H-indol-5-yl)amino]pyridin-3-yl}phenyl)-3-cyclopropylurea | N/A | 7.2(g) | 423.4 | N/A |
| 567 | 1-(4-{5-cyano-4-[(4-methyl-1H-indol-5-yl)amino]pyridin-3-yl}phenyl)-3-methylurea | N/A | 6.4(g) | 397.4 | N/A |
| 568 | 3-(4-{5-cyano-4-[(4-methyl-1H-indol-5-yl)amino]pyridin-3-yl}phenyl)-1,1-dimethylurea | N/A | 6.9(g) | 411.4 | N/A |
| 569 | N-(4-{5-cyano-4-[(4-methyl-1H-indol-5-yl)amino]pyridin-3-yl}phenyl)morpholine-4-carboxamide | N/A | 6.8(g) | 453.4 | N/A |
| 570 | 4-[(4-methyl-1H-indol-5-yl)amino]-5-(4-nitrophenyl)nicotinonitrile | N/A | 9.0(g) | 370.2 | N/A |
| 571 | 5-(4-aminophenyl)-4-[(4-methyl-1H-indol-5-yl)amino]nicotinonitrile | N/A | 5.8(g) | 340.2 | N/A |
| 572 | 5-(3-aminophenyl)-4-[(4-methyl-1H-indol-5-yl)amino]nicotinonitrile | N/A | 6.1(g) | 340.2 | N/A |
| 573 | 5-(2-aminophenyl)-4-[(4-methyl-1H-indol-5-yl)amino]nicotinonitrile | N/A | 7.7(g) | 340.2 | N/A |
| 574 | 5-[4-(dimethylamino)phenyl]-4-[(4-methyl-1H-indol-5-yl)amino]nicotinonitrile | N/A | 8.1(g) | 368.3 | N/A |
| 575 | 5-[3-(dimethylamino)phenyl]-4-[(4-methyl-1H-indol-5-yl)amino]nicotinonitrile | N/A | 8.0(g) | 368.3 | N/A |
| 576 | N-(4-{5-cyano-4-[(4-methyl-1H-indol-5-yl)amino]pyridin-3-yl}phenyl)acetamide | N/A | 6.6(g) | 382.3 | N/A |

TABLE 13-continued

| Compound | Compound Name | Melting range (° C.) | HPLC Retention Time (min.) | Observed ion m/e [M + H]+ | Observed HRMS [M + H]+ |
|---|---|---|---|---|---|
| 577 | N-(2-{5-cyano-4-[(4-methyl-1H-indol-5-yl)amino]pyridin-3-yl}phenyl)acetamide | N/A | 9.3(g) | 382.3 | N/A |
| 578 | N-(3-{5-cyano-4-[(4-methyl-1H-indol-5-yl)amino]pyridin-3-yl}phenyl)acetamide | N/A | 6.6(g) | 382.3 | N/A |
| 579 | N-(4-{5-cyano-4-[(4-methyl-1H-indol-5-yl)amino]pyridin-3-yl}phenyl)-2-methylpropanamide | N/A | 8.2(g) | 410.4 | N/A |
| 580 | 4-{5-cyano-4-[(4-methyl-1H-indol-5-yl)amino]pyridin-3-yl}-N-methylbenzamide | N/A | 6.1(g) | 382.3 | N/A |

Example 27

Preparation of 5-{5-[(dimethylamino)methyl]-1-benzothien-2-yl}-4-(1H-indol-4-ylamino)nicotinonitrile 224

Following procedures analogous to those described in Example 25, 5-(5-formyl-1-benzothien-2-yl)-4-(1H-indol-4-ylamino)nicotinonitrile 223 was prepared from 5-iodo-4-[(1H-indol-4-yl)amino]nicotinonitrile, MS: 395.1 (M+H); melting range: 206-208° C. (decom.).

To 5-(5-formyl-1-benzothien-2-yl)-4-(1H-indol-4-ylamino)nicotinonitrile 223 (166 mg, 0.38 mmol) in THF (7 mL) was added dimethylamine in THF (2.0 M, 0.58 mL, 1.15 mmol) followed by acetic acid (126 mg, 2.09 mmol). The resulting mixture was stirred at r.t. for 1 h and additional dimethylamine (1.2 mL, 2.30 mmol) was added. After stirring at r.t. for an additional hour, Na(OAc)$_3$BH (242 mg, 1.15 mmol) was added. The reaction mixture was stirred at r.t. for 2 h and was partitioned between diluted HCl and EtOAc. The combined aqueous extracts were basified with aqueous NaHCO$_3$ and extracted with EtOAc. The combined organics were dried over Na$_2$SO$_4$, concentrated and purified by flash column chromatography to give 115 mg (65%) of 5-{5-[(dimethylamino)methyl]-1-benzothien-2-yl}-4-(1H-indol-4-ylamino)nicotinonitrile 224 as a pale yellow solid. MS: 424.2 (M+H); HPLC retention time: 2.1 min.(a).

Following procedures analogous to those described for the preparation of 5-(1-benzofuran-2-yl)-4-[(4-methyl-1H-indol-5-yl)amino]nicotinonitrile 224, compounds in Table 14 were prepared.

TABLE 14

| Compound | Compound Name | Melting range (° C.) | HPLC retention time (min.) | Observed ion m/e [M + H]+ | Observed HRMS [M + H]+ |
|---|---|---|---|---|---|
| 382 | 5-{5-[(dimethylamino)methyl]-1-benzofuran-2-yl}-4-[(4-methyl-1H-indol-5-yl)amino]nicotinonitrile | N/A | 1.75(e) | 422.2 | N/A |
| 383 | 5-(5-{[(2-hydroxyethyl)amino]methyl}-1-benzofuran-2-yl)-4-[(4-methyl-1H-indol-5-yl)amino]nicotinonitrile | N/A | 1.69(e) | 438.2 | N/A |
| 384 | 5-(5-{[(3-hydroxypropyl)amino]methyl}-1-benzofuran-2-yl)-4-[(4-methyl-1H-indol-5-yl)amino]nicotinonitrile | N/A | 1.71(e) | 452.2 | N/A |
| 385 | 5-(5-{[(2,3-dihydroxypropyl)amino]methyl}-1-benzofuran-2-yl)-4-[(4-methyl-1H-indol-5-yl)amino]nicotinonitrile | N/A | 1.71(e) | 468.2 | N/A |
| 386 | 5-(5-{[(2,3-dihydroxypropyl)(methyl)amino]methyl}-1-benzofuran-2-yl)-4-[(4-methyl-1H-indol-5-yl)amino]nicotinonitrile | N/A | 1.69(e) | 482.2 | N/A |
| 387 | 5-{5-[(cyclohexylamino)methyl]-1-benzofuran-2-yl}-4-[(4-methyl-1H-indol-5-yl)amino]nicotinonitrile | N/A | 2.04(e) | 478.6 | N/A |
| 388 | 4-[(4-methyl-1H-indol-5-yl)amino]-5-[5-(morpholin-4-ylmethyl)-1-benzofuran-2-yl]nicotinonitrile | N/A | 1.76(e) | 464.2 | N/A |
| 389 | 4-[(4-methyl-1H-indol-5-yl)amino]-5-[5-(pyrrolidin-1-ylmethyl)-1-benzofuran-2-yl]nicotinonitrile | N/A | 1.81(e) | 448.2 | N/A |
| 391 | 4-[(4-methyl-1H-indol-5-yl)amino]-5-[5-({[(1-methylpiperidin-4-yl)methyl]amino}methyl)-1-benzofuran-2-yl]nicotinonitrile | 196-199 | 1.58(e) | 505.3 | N/A |

TABLE 14-continued

| Compound | Compound Name | Melting range (° C.) | HPLC retention time (min.) | Observed ion m/e [M + H]+ | Observed HRMS [M + H]+ |
|---|---|---|---|---|---|
| 392 | 5-(5-{[4-(hydroxymethyl)piperidin-1-yl]methyl}-1-benzofuran-2-yl)-4-[(4-methyl-1H-indol-5-yl)amino]nicotinonitrile | N/A | 1.77(e) | 492.2 | N/A |
| 393 | 4-[(4-methyl-1H-indol-5-yl)amino]-5-{5-[(4-pyrrolidin-1-ylpiperidin-1-yl)methyl]-1-benzofuran-2-yl}nicotinonitrile | N/A | 1.59(e) | 531.3 | N/A |
| 394 | 5-[5-(1,4'-bipiperidin-1'-ylmethyl)-1-benzofuran-2-yl]-4-[(4-methyl-1H-indol-5-yl)amino]nicotinonitrile | N/A | 1.61(e) | 545.3 | N/A |
| 395 | 4-[(4-methyl-1H-indol-5-yl)amino]-5-{5-[(4-morpholin-4-ylpiperidin-1-yl)methyl]-1-benzofuran-2-yl}nicotinonitrile | N/A | 1.58(e) | 547.3 | N/A |
| 396 | 5-[5-({4-[2-(dimethylamino)ethyl]piperazin-1-yl}methyl)-1-benzofuran-2-yl]-4-[(4-methyl-1H-indol-5-yl)amino]nicotinonitrile | N/A | 1.58(e) | 534.3 | N/A |
| 397 | 4-[(4-methyl-1H-indol-5-yl)amino]-5-{5-[(4-pyridin-2-ylpiperazin-1-yl)methyl]-1-benzofuran-2-yl}nicotinonitrile | N/A | 1.83(e) | 540.2 | N/A |
| 398 | 4-[(4-methyl-1H-indol-5-yl)amino]-5-(5-{[(pyridin-2-ylmethyl)amino]methyl}-1-benzofuran-2-yl)nicotinonitrile | N/A | 1.85(e) | 485.2 | N/A |
| 399 | 4-[(4-methyl-1H-indol-5-yl)amino]-5-(5-{[(pyridin-3-ylmethyl)amino]methyl}-1-benzofuran-2-yl)nicotinonitrile | N/A | 1.75(e) | 485.2 | N/A |
| 400 | 4-[(4-methyl-1H-indol-5-yl)amino]-5-(5-{[(pyridin-4-ylmethyl)amino]methyl}-1-benzofuran-2-yl)nicotinonitrile | N/A | 1.71(e) | 485.2 | N/A |
| 401 | 4-[(4-methyl-1H-indol-5-yl)amino]-5-[5-(morpholin-4-ylmethyl)-2-furyl]nicotinonitrile | N/A | 0.914(f) | 414.0 | N/A |
| 402 | 4-[(4-methyl-1H-indol-5-yl)amino]-5-[5-(piperidin-1-ylmethyl)-2-furyl]nicotinonitrile | N/A | 0.388(f) | 412.0 | N/A |
| 403 | 5-[5-(1,4'-bipiperidin-1'-ylmethyl)-2-furyl]-4-[(4-methyl-1H-indol-5-yl)amino]nicotinonitrile | N/A | 0.322(f) | 495.1 | N/A |
| 404 | 4-[(4-methyl-1H-indol-5-yl)amino]-5-{5-[(4-pyrrolidin-1-ylpiperidin-1-yl)methyl]-2-furyl}nicotinonitrile | N/A | 0.288(f) | 481.1 | N/A |
| 405 | 4-[(4-methyl-1H-indol-5-yl)amino]-5-{5-[(4-morpholin-4-ylpiperidin-1-yl)methyl]-2-furyl}nicotinonitrile | N/A | 0.324(f) | 497.1 | N/A |
| 406 | 5-{5-[(diethylamino)methyl]-2-furyl}-4-[(4-methyl-1H-indol-5-yl)amino]nicotinonitrile | N/A | 0.356(f) | 400.0 | N/A |
| 407 | 5-{5-[(dibutylamino)methyl]-2-furyl}-4-[(4-methyl-1H-indol-5-yl)amino]nicotinonitrile | N/A | 1.497(f) | 456.1 | N/A |
| 408 | 5-{5-[(benzylamino)methyl]-2-furyl}-4-[(4-methyl-1H-indol-5-yl)amino]nicotinonitrile | N/A | 0.819(f) | 433.9 | N/A |
| 409 | 4-[(4-methyl-1H-indol-5-yl)amino]-5-(5-{[(3-phenylpropyl)amino]methyl}-2-furyl)nicotinonitrile | N/A | 0.316(f) | 398.0 | N/A |
| 410 | 4-[(4-methyl-1H-indol-5-yl)amino]-5-[5-(pyrrolidin-1-ylmethyl)-2-furyl]nicotinonitrile | N/A | 0.873(f) | 430.0 | N/A |
| 411 | 4-[(4-methyl-1H-indol-5-yl)amino]-5-[5-(thiomorpholin-4-ylmethyl)-2-furyl]nicotinonitrile | N/A | 1.381(f) | 462.0 | N/A |
| 436 | 5-(5-{[4-(dimethylamino)piperidin-1-yl]methyl}-2-furyl)-4-[(4-methyl-1H-indol-5-yl)amino]nicotinonitrile | N/A | 0.280(f) | 455.0 | N/A |
| 437 | 5-{5-[(4-isopropylpiperazin-1-yl)methyl]-2-furyl}-4-[(4-methyl-1H-indol-5-yl)amino]nicotinonitrile | N/A | 0.407(f) | 455.0 | N/A |
| 449 | 4-[(4-methyl-1H-indol-5-yl)amino]-5-{4-[(4-methylpiperazin-1-yl)methyl]phenyl}nicotinonitrile | N/A | 0.314(f) | 437.0 | N/A |
| 450 | 4-[(4-methyl-1H-indol-5-yl)amino]-5-[4-(pyrrolidin-1-ylmethyl)phenyl]nicotinonitrile | N/A | 0.298(f) | 408.0 | N/A |
| 451 | 4-[(4-methyl-1H-indol-5-yl)amino]-5-[4-(morpholin-4-ylmethyl)phenyl]nicotinonitrile | N/A | 0.381(f) | 424.0 | N/A |

TABLE 14-continued

| Compound | Compound Name | Melting range (° C.) | HPLC retention time (min.) | Observed ion m/e [M + H]+ | Observed HRMS [M + H]+ |
|---|---|---|---|---|---|
| 452 | 5-{4-[(dimethylamino)methyl]phenyl}-4-[(4-methyl-1H-indol-5-yl)amino]nicotinonitrile | N/A | 0.263(f) | 381.9 | N/A |
| 454 | 4-[(4-methyl-1H-indol-5-yl)amino]-5-{3-[(4-methylpiperazin-1-yl)methyl]phenyl}nicotinonitrile | N/A | 0.355(f) | 437.0 | N/A |
| 455 | 4-[(4-methyl-1H-indol-5-yl)amino]-5-[3-(pyrrolidin-1-ylmethyl)phenyl]nicotinonitrile | N/A | 0.320(f) | 408.0 | N/A |
| 456 | 4-[(4-methyl-1H-indol-5-yl)amino]-5-[3-(morpholin-4-ylmethyl)phenyl]nicotinonitrile | N/A | 0.425(f) | 424.0 | N/A |
| 457 | 5-{3-[(dimethylamino)methyl]phenyl}-4-[(4-methyl-1H-indol-5-yl)amino]nicotinonitrile | N/A | 0.678(f) | 382.0 | N/A |
| 459 | 5-{2-fluoro-4-[(4-methylpiperazin-1-yl)methyl]phenyl}-4-[(4-methyl-1H-indol-5-yl)amino]nicotinonitrile | N/A | 5.0(g) | 455.4 | 455.23501 |
| 461 | 4-[(4-methyl-1H-indol-5-yl)amino]-5-[5-(piperidin-1-ylmethyl)-1-benzofuran-2-yl]nicotinonitrile | 212-214 | 6.9(g) | N/A | 462.22967 |
| 486 | 5-{5-[(4-cyclopentylpiperazin-1-yl)methyl]-2-furyl}-4-[(4-methyl-1H-indol-5-yl)amino]nicotinonitrile | 174-176 (decom.) | 5.9(g) | 481.4 | 481.26968 |
| 487 | 5-{5-[(1,1-dioxidothiomorpholin-4-yl)methyl]-2-furyl}-4-[(4-methyl-1H-indol-5-yl)amino]nicotinonitrile | 170-172 (decom.) | 7.2(g) | 462.3 | 462.15913 |
| 521 | 4-[(4-methyl-1H-indol-5-yl)amino]-5-{5-[(4-methylpiperazin-1-yl)methyl]-1-benzothien-2-yl}nicotinonitrile | 171-172 | 10.7(h) | N/A | 493.21682 |

Example 28

Preparation of 5-(4-{[(2S)-2-amino-3-phenylpropyl]oxy}phenyl)-4-(1H-indol-4-ylamino)nicotinonitrile 226

Following procedures analogous to those described in Example 25, 5-(4-hydroxyphenyl)-4-(1H-indol-4-ylamino)nicotinonitrile 225 was prepared from 5-iodo-4-[(1H-indol-4-yl)amino]nicotinonitrile. MS: 327.1 (M+H); melting range: 235-237° C.

To a suspension of 5-(4-hydroxyphenyl)-4-(1H-indol-4-ylamino)nicotinonitrile 225 (100 mg, 0.31 mmol), tert-butyl (1S)-1-benzyl-2-hydroxyethylcarbamate (77 mg, 0.31 mmol), and Ph₃P (97 mg, 0.37 mmol) in THF (2.0 mL) was added diethyl azodicarboxylate (64 mg, 0.37 mmol) via a syringe over 6 min. The resulting mixture was stirred at r.t. for 21 h and treated with concentrated HCl (~200 mg). After heating at 60° C. for one h, the reaction mixture was partitioned between saturated NaHCO₃ and CH₂Cl₂. The combined organics were dried over Na₂SO₄, concentrated and purified by silica gel flash column chromatography (eluting with 4% MeOH/CH₂Cl₂) to give 42 mg (30%) of 5-(4-{[(2S)-2-amino-3-phenylpropyl]oxy}phenyl)-4-(1H-indol-4-ylamino)nicotinonitrile 226 as a white solid. MS: 460.4 (M+H); melting range: 83-85° C.

Following procedures analogous to those described for the preparation of 5-(4-{[(2S)-2-amino-3-phenylpropyl]oxy}phenyl)-4-(1H-indol-4-ylamino)nicotinonitrile 226, 5-(4-{[(2R)-2-amino-3-phenylpropyl]oxy}phenyl)-4-(1H-indol-4-ylamino)nicotinonitrile 458 was prepared. HPLC retention time: 6.2 min.(g); MS: 460.2 (M+H); melting point: 95-96° C.; and HRMS: 460.21519.

Example 29

Preparation of 4-[(4-methyl-1H-indol-5-yl)amino]-5-[5-(piperidin-1-ylmethyl)-1-benzothien-2-yl]nicotinonitrile 228 and 5-[5-(hydroxymethyl)-1-benzothien-2-yl]-4-[(4-methyl-1H-indol-5-yl)amino]nicotinonitrile 229

Following procedures analogous to those described in Example 25, 5-(5-formyl-1-benzothien-2-yl)-4-[(4-methyl-1H-indol-5-yl)amino]nicotinonitrile 227 was prepared from 5-iodo-4-[(4-methyl-1H-indol-5-yl)amino]nicotinonitrile. MS: 409.2 (M+H); melting range: 185-187° C.

Sodium cyanoborohydride (8.0 mg, 0.13 mmol) was added in portions to a stirred mixture of 5-(5-formyl-1-benzothien-2-yl)-4-[(4-methyl-1H-indol-5-yl)amino]nicotinonitrile 227 (40 mg, 0.098 mmol), piperidine (10 mg, 0.12 mmol) and acetic acid (7.0 mg, 0.12 mmol) in EtOH (3.0 mL). The resulting mixture was stirred at r.t. overnight and diluted with CH₂Cl₂ (30 mL). Silica gel and potassium bicarbonate (20 mg) were added and the mixture was concentrated to give a solid residue which was purified by silica gel flash column chromatography (eluting with 3% MeOH in CH₂Cl₂) to give 26 mg (57%) of 4-[(4-methyl-1H-indol-5-yl)amino]-5-[5-(piperidin-1-ylmethyl)-1-benzothien-2-yl]nicotinonitrile 228 as an off-white solid (MS: 478.3 (M+H); melting range: 180-182° C.; HPLC retention time: 7.1 min.), and 7 mg (18%) of 5-[5-(hydroxymethyl)-1-benzothien-2-yl]-4-[(4-methyl-1H-indol-5-yl)amino]nicotinonitrile 229 as an off-white solid (MS: 411.3 (M+H); melting range: 174-175° C., HPLC retention time: 8.6 min.(a)).

Following procedures analogous to those described for the preparation of 4-[(4-methyl-1H-indol-5-yl)amino]-5-[5-(piperidin-1-ylmethyl)-1-benzothien-2-yl]nicotinonitrile 228, the following compounds were prepared:

4-[(4-Methyl-1H-indol-5-yl)amino]-5-{5-[(4-methylpiperazin-1-yl)methyl]-2-thienyl}nicotinonitrile 464. HPLC retention time: 4.9 min.(g); MS: 443.4 (M+H); melting point: 255° C. (decom.); and HRMS: 443.20223; and 4-[(4-Methyl-1H-indol-5-yl)amino]-5-{5-[(4-methylpiperazin-1-yl)methyl]-2-furyl}nicotinonitrile 468. HPLC retention time: 5.2 min.(g); MS: 427.3 (M+H); melting point: 245° C. (decom.); and HRMS: 427.22449.

Example 30

Preparation of 4-chloro-5-iodo-1-oxy-nicotinonitrile

To a solution of 4-chloro-5-iodo-nicotinonitrile (529 mg, 2.0 mmol) in TFA (5 mL) was added $H_2O_2$ (30 wt % in $H_2O$, 5 mL). The reaction mixture was stirred at room temperature overnight, heated to 50° C. for 8 h, and concentrated. To the residue was added saturated aqueous $NaHCO_3$ (10 mL) followed by extraction with EtOAc/THF. The organic layers were combined, washed with $H_2O$, dried over $Na_2SO_4$, filtered, and concentrated. The residue was purified by a flash chromatography ($CH_2Cl_2$-THF=10:1) to give 202 mg (36%) of 4-chloro-5-iodo-1-oxy-nicotinonitrile as a pale-yellow solid.

Example 31

Preparation of 4-fluoro-5-[3-methoxy-4-(2-methoxyethoxy)phenyl]nicotinonitrile

4-Chloro-5-(3,4-dimethoxyphenyl)nicotinonitrile (2.0 g, 7.3 mmol) was dissolved in DMF (70 mL) and treated with CsF (2.2 g, 14.6 mmol). After the resulting solution was heated at 80° C. for 2 h, additional CsF (1 g, 7 mmol) was added and the heating was continued overnight. The crude product was purified by chromatography (EtOAc/Hex) to give 300 mg of 4-fluoro-5-[3-methoxy-4-(2-methoxyethoxy) phenyl]nicotinonitrile.

Example 32

Preparation of 5-amino-6-methylindole

3-Methyl-4-nitroaniline was treated with iodine and silver sulfate to give 2-iodo-5-methyl-4-nitroaniline. Treatment of the nitroaniline with 2-(trimethylsilyl)acetylene under the typical Sonogashira conditions gave 5-methyl-4-nitro-2-[(trimethylsilyl)ethynyl]aniline, which was treated with a base in an aqueous methanolic solution to give 2-ethynyl-5-methyl-4-nitroaniline. A subsequent base-induced cyclization at an elevated temperature gave 5-nitro-6-methylindole, which was treated under a high pressure hydrogenation condition to provide 5-amino-6-methylindole.

Example 33

Preparation of 5-amino-4-fluoroindole

Treatment of 1-(4-fluoro-2,3-dihydro-indol-1-yl)-ethanone, prepared from 4-fluoroindole (See e.g., EP 0645385A1), with concentrated $H_2SO_4$ and fuming $HNO_3$ in glacial acetic acid gave 1-(4-fluoro-5-nitro-2,3-dihydro-indol-1-yl)-ethanone. Deprotection of the acetyl group with $Na_2S$ in aqueous ethanol provided 4-fluoro-5-nitro-2,3-dihydro-1H-indole, which was treated with 2,3-dicyano-5,6-dichloro-parabenzoquinone (DDQ) to provide 4-fluoro-5-nitroindole. A subsequent hydrogenation over Pd/C gave 5-amino-4-fluoroindole.

Example 34

Preparation of 5-amino-4-methoxyindole

Treatment of 1-(4-fluoro-5-nitro-2,3-dihydro-indol-1-yl)-ethanone with Claisen's alkali in $CH_3OH$ gave 4-methoxy-5-nitro-2,3-dihydro-1H-indole, which was treated with DDQ followed by a hydrogenation over Pd/C to produce 5-amino-4-methoxyindole.

Example 35

Preparation of 5-amino-2,4-dimethylindole

Addition of MeMgBr to 2-methyl-5-nitroindole followed by hydrogenation over Pd/C provided 5-amino-2,4-dimethylindole.

Example 36

Preparation of 5-amino-4-ethylindole

Addition of EtMgBr to 5-nitroindole followed by hydrogenation over Pd/C provided 5-amino-4-ethylindole.

Example 37

Preparation of 5-amino-7-chloro-4-methylindole

5-Chloro-2-methyl-4-nitroaniline was treated with acetic anhydride in the presence of 4-dimethylaminopyridine (DMAP) in $CH_2Cl_2$ to provide N-(5-chloro-2-methyl-4-nitrophenyl)acetamide, which was reacted with vinyl magnesium bromide at −40° C. to room temperature to give N-(7-chloro-4-methyl-1H-indol-5-yl)acetamide. Deprotection of the acetyl group by heating in an aqueous HCl solution at the reflux temperature provided 5-amino-7-chloro-4-methylindole.

Example 38

Preparation of diisopropyl 2-chloro-4-(2-(4-methylpiperazin-1-yl)ethoxy)phenylboronate 4-Bromo-3-chlorophenol was reacted with 1-methyl-4-(2-hydroxyethyl)piperazine under the Mitsunobu conditions to provide 1-[2-(4-bromo-3-chlorophenoxy)ethyl]-4-methylpiperazine.

1-[2-(4-Bromo-3-chlorophenoxy)ethyl]-4-methyl-piperazine was reacted with n-BuLi at 0° C. in the presence of triisopropyl borate to give diisopropyl 2-chloro-4-(2-(4-methylpiperazin-1-yl)ethoxy)phenylboronate upon warming to room temperature.

Example 39

Preparation of tributyl (5-(2-chloroethoxy)benzofuran-2-yl)stannane

5-Methoxybenzofuran was treated with 2,4,5-collidine and LiI at 170° C. to provide benzofuran-5-ol, which was reacted with 2-chloroethyl-p-toluenesulfonate and Cs$_2$CO$_3$ to give 5-(2-chloroethoxy)-1-benzofuran.

Treatment of 5-(2-chloroethoxy)-1-benzofuran with n-BuLi for 16 h followed by the addition of tributyltin chloride at −50° C. gave tributyl (5-(2-chloroethoxy)benzofuran-2-yl)stannane upon warming to room temperature.

Example 40

Preparation of diisopropyl 4-(3-chloropropoxy)phenylboronate

4-Bromophenol was reacted with 2-chloropropyl-p-toluenesulfonate and Cs$_2$CO$_3$ to give 1-bromo-4-(3-chloropropoxy)benzene.

Treatment of 1-bromo-4-(3-chloropropoxy)benzene with n-BuLi at 0° C. in the presence of triisopropyl borate gave diisopropyl 4-(3-chloropropoxy)phenylboronate upon warming to room temperature.

Example 41

Preparation of diisopropyl 4-(2-chloroethoxy)-3-methoxyphenylboronate

4-Bromo-2-methoxyphenol was reacted with 2-chloroethyl-p-toluenesulfonate and Cs$_2$CO$_3$ at 50° C. for 4 h to give 1-bromo-4-(2-chloroethoxy)-3-methoxybenzene.

Treatment of 1-bromo-4-(2-chloroethoxy)-3-methoxybenzene with n-BuLi at 0° C. in the presence of triisopropyl borate gave diisopropyl 4-(2-chloroethoxy)-3-methoxyphenylboronate upon warming to room temperature.

Example 42

Preparation of 4-((4-(tributylstannyl)pyridin-2-yl)methyl)morpholine

4-Chloro-2-picolene (10.00 g, 78.74 mmol) in 2-butanone (100 ml) was treated with sodium iodide (50.00 g, 335.82 mmol) and hydriodic acid (12 ml, 57%) and the resulting mixture was heated at the reflux temperature for 18 h. The reaction was cooled to room temperature and the solvent was removed under reduced pressure. The residue was partitioned between ethyl acetate and saturated aqueous sodium bicarbonate. The organic layer was dried over MgSO$_4$ and concentrated to give a dark brown syrup, which was purified by column chromatography (25% ethyl acetate in hexanes) to give 4-iodo-2-picolene as an orange syrup which later crystallized to a red solid (12.3 g, 71% yield).

4-Iodo-2-picolene (10.00 g, 45.66 mmol) in dry carbon tetrachloride (200 ml) was treated with NBS (9.75 g, 54.78 mmol) and benzoyl peroxide (550 mg, 2.27 mmol) under nitrogen and the resulting mixture was heated at reflux for 24 h. After cooled to room temperature, the reaction mixture was filtered and the solid was washed with dichloromethane, which was combined with the filtrate. The combined organic solution was concentrated to give the crude product, which was purified by column chromatography (20% ethyl acetate in hexanes) to give 2-(bromomethyl)-4-iodopyridine as a yellow solid (4.00 g).

2-(Bromomethyl)-4-iodopyridine (500 mg, 1.68 mmol) in 1,2-dimethoxyethane (15 ml) was treated with morpholine (1.00 g, 11.48 mmol) and sodium iodide (13 mg, 0.09 mmol) and the resulting solution was heated at 90° C. for 5 h. After cooled to room temperature, the reaction mixture was partitioned between dichloromethane and saturated aqueous sodium bicarbonate. The organic layer was dried over MgSO$_4$ and concentrated to give 4-[(4-iodo-2-pyridinyl)methyl]morpholine as a brown solid (315 mg, 62% yield).

Treatment of 4-[(4-iodo-2-pyridinyl)methyl]morpholine with n-BuLi at 0° C. and tributyltin chloride provided 4-((4-(tributylstannyl)pyridin-2-yl)methyl)morpholine.

Example 43

Preparation of 2-(3,4-bis(2-methoxyethoxy)phenyl)-4,4,5,5-tetramethyl-1,3,2-dioxaborolane Step 1: Preparation of 1,2-bis(2-methoxyethoxy)benzene Ortho-catechol (4.75 g, 43 mmol), 2-bromo-1-methoxyethane (15 g, 108 mmol), and potassium carbonate (18 g, 129 mmol) were stirred in 200 mL DMF at 80° C. overnight. The suspension was partitioned between water and EtOAc. The organic layer was washed with water 4 times, dried over magnesium sulfate, and concentrated to give 9.9 g of 1,2-bis(2-methoxyethoxy)benzene.

Step 2: Preparation of 4-bromo-1,2-bis(2-methoxyethoxy)benzene 1,2-Bis(2-methoxyethoxy)benzene (8.1 g, 31.9 mmol) and N-bromosuccinimide (6.2 g, 35 mmol) were stirred in 50 mL DMF at room temperature overnight. The reaction was diluted with 200 mL EtOAc and washed with 1N NaOH and water. The organic layer was dried over magnesium sulfate and concentrated to give 9.7 g (92%) of 4-bromo-1,2-bis(2-methoxyethoxy)benzene.

Step 3: 2-(3,4-bis(2-methoxyethoxy)phenyl)-4,4,5,5-tetramethyl-1,32-dioxaborolane 4-Bromo-1,2-bis(2-methoxyethoxy)benzene (4 g, 12 mmol), bis(pinacolato)diboron (3.5 g, 13.8 mmol), KOAc (3.5 g, 36 mmol), and Pd(dppf)$_2$Cl$_2$ (490 mg, 0.6 mmol) were mixed in 50 mL DMSO and the resulting suspension was heated at 80° C. overnight. The reaction was diluted with EtOAc and washed 4 times with water. The organic layer was concentrated to provide the crude product, which was purified by silica gel chromatography (EtOAc/Hex) to give 4.8 g of 2-(3,4-bis(2-methoxyethoxy)phenyl)-4,4,5,5-tetramethyl-1,3,2-dioxaborolane.

Example 44

Preparation of 2-[4-(2-methoxyethoxy)phenyl]-4,4,5,5-tetramethyl-1,3,2-dioxaborolane To a solution of 4-(4,4,5,5-tetramethyl-1,3,2-dioxaboralan-2-yl)phenol (1 g, 4.5 mmol), 2-methoxyethanol (450 mg, 5.9 mmol), and triphenylphosphine (1.6 g, 5.9 mmol) in THF (35 mL) was added dropwise diethyl azodicarboxylate (2.7 ml, 5.9-mmol, 40% in toluene) at 0-5° C. The resulting mixture was stirred at room temperature for 18 h and partitioned between ethyl acetate and water. The organic phase was dried over Na$_2$SO$_4$, filtered, and concentrated in vacuo. The residue was purified by flash column chromatography (ethyl acetate/hexane, 5% to 20%) to provide 989 mg (79%) of 2-[4-(2-methoxyethoxy)phenyl]-4,4,5,5-tetramethyl-1,3,2-dioxaborolane as a white solid.

Following procedures analogous to those described above, the following boronic esters were prepared: 2-[3-(2-methoxyethoxy)phenyl]-4,4,5,5-tetramethyl-1,3,2-dioxaborolane, 2-[4-(4-chlorobutoxy)phenyl]-4,4,5,5-tetramethyl-1,3,2-dioxaborolane, and 2-[3-(4-chlorobutoxy)phenyl]-4,4,5,5-tetramethyl-1,3,2-dioxaborolane.

Example 45

Preparation of 1-benzofuran-5-carbaldehyde

To a solution of 1-benzofuran-5-carbonitrile (5.0 g, 34.9 mmol) in $CH_2Cl_2$ under nitrogen at −15 to −20° C. was added DIBAL-H (41.9 mL, 41.9 mmol, 1 M/heptane), maintaining the reaction temperature below −15° C., and the reaction mixture was stirred at −15 to −20° C. for additional 10 min. The reaction mixture was then quenched via dropwise addition of aqueous 2N HCl, maintaining the temperature below room temperature. The organic layer was separated, washed with water, dried over sodium sulfate, and concentrated to give 4.0 g (78%) of 1-benzofuran-5-carbaldehyde as a yellow oil.

Example 46

Preparation of 2-(tributylstannyl)-1-benzofuran-5-carbaldehyde

To a solution of N-methylpiperazine (0.75 g, 7.5 mmol) in hexane (15 mL) at 0° C. under nitrogen was added dropwise a solution of n-BuLi (3 mL, 7.43 mmol, 2.5M/hexanes), and the reaction mixture was stirred at 0° C. for 40 min. 1-Benzofuran-5-carbaldehyde (1.0 g, 6.8 mmol) was added dropwise to the reaction mixture at 0° C. and the resulting mixture was stirred at 0° C. for 15 min. After addition of tetramethylethylenediamine (TMEDA) (1.7 g, 14.96 mmol), a solution of n-BuLi (6.0 mL, 14.86 mmol, 2.5M/hexanes) was added dropwise to the reaction mixture at 0° C. and the reaction mixture was allowed to warm up to room temperature and stirred for a total of 18 h. After the reaction mixture was cooled to 0° C. and THF (30 mL) was added, the reaction mixture was cooled to −50° C., tributyltin chloride (4.87 g, 14.96 mmol) was added dropwise, and the reaction mixture was stirred at −50° C. for 15 min. and at room temperature for 5-6 h. The reaction mixture was quenched with saturated aqueous $NaHCO_3$ and extracted into diethyl ether. The organic layer was dried over sodium sulfate and concentrated and the crude product was purified by column chromatography (ethyl acetate/hexane, 2%) to give 1.0 g (34%) of 2-(tributylstannyl)-1-benzofuran-5-carbaldehyde as a yellow oil.

Example 47

Preparation of dimethyl 5-(piperidin-1-ylmethyl)benzofuran-2-ylboronate

1-Benzofuran-5-carbaldehyde was treated with piperidine and sodium triacetoxyborohydride under the standard reductive amination protocol to provide 1-(5-benzofuranylmethyl)piperidine.

Treatment of 1-(5-benzofuranylmethyl)piperidine with butyl lithium and trimethylborate at low temperature provided dimethyl 5-(piperidin-1-ylmethyl)benzofuran-2-ylboronate.

Example 48

Preparation of 5-(5-formyl-1-benzofuran-2-yl)-4-[(4-methyl-1H-indol-5-yl)amino]nicotinonitrile 465

A mixture of 5-iodo-4-[(4-methyl-1H-indol-5-yl)amino]nicotinonitrile (2.5 g, 6.7 mmol), 2-(tributylstannyl)-1-benzofuran-5-carbaldehyde (4.35 g, 10 mmol), and tetrakis(triphenylphosphine)palladium(0) (0.38 g, 0.34 mmol) in DMF (25 mL) was heated at 120° C. for 1 h. The reaction mixture was cooled to room temperature and partitioned between ethyl acetate and water, resulting in a suspension. The insoluble material was removed by filtration and the residue was washed thoroughly with ethyl acetate. The organic layer (from filtrate) was washed with water twice and brine, dried over sodium sulfate, and concentrated and the residue was purified by column chromatography (ethyl acetate/hexane, 1:1) to give 2.0 g (76%) of 5-(5-formyl-1-benzofuran-2-yl)-4-[(4-methyl-1H-indol-5-yl)amino]nicotinonitrile as a yellow solid. HPLC retention time: 10.7 min.[(h)]; MS: 393.2 (M+H); melting point: 235-237° C.; and HRMS: 393.13484.

Following procedures analogous to those described for the preparation of 5-(5-formyl-1-benzofuran-2-yl)-4-[(4-methyl-1H-indol-5-yl)amino]nicotinonitrile 465, compounds in Table 15 were prepared.

TABLE 15

| Compound | Compound Name | HPLC retention time (min.) | Observed Ion m/e [M + H] |
|---|---|---|---|
| 484 | 5-(5-formyl-1-benzofuran-2-yl)-4-(1H-indol-5-ylamino)nicotinonitrile | 10.5[(g)] | 379.2 |
| 495 | 5-(5-formyl-1-benzofuran-2-yl)-4-[(6-methyl-1H-indol-5-yl)amino]nicotinonitrile | N/A | 393.2 |

Example 49

Preparation of 4-[(4-methyl-1H-indol-5-yl)amino]-5-{5-[(4-methylpiperazin-1-yl)methyl]-1-benzofuran-2-yl}nicotinonitrile 462

To a solution of 5-(5-formyl-1-benzofuran-2-yl)-4-[(4-methyl-1H-indol-5-yl)amino]nicotinonitrile (800 mg, 2.04 mmol) in a mixture of $CH_2Cl_2$ (40 mL) and NMP (5 mL) at room temperature under nitrogen was added N-methylpiperazine (613 mg, 6.12 mmol) followed by glacial acetic acid (674 mg, 11.22 mmol) and the reaction mixture was stirred at room temperature for 1 h. Sodium triacetoxyborohydride (2.38 g, 11.22 mmol) was added to the reaction mixture and the reaction was stirred at room temperature for 5 h. The reaction mixture was partitioned between $CH_2Cl_2$ and aqueous 1N HCl. The aqueous layer was washed with $CH_2Cl_2$ and treated with aqueous 1N NaOH whereupon solids precipitated. The solids were collected and dissolved in $CH_2Cl_2$. The solution was washed with water thrice and brine, dried over sodium sulfate, and concentrated and the residue was purified by column chromatography (MeOH/$CH_2Cl_2$, 6% to 7.5%) to give 560 mg (58%) of 4-[(4-methyl-1H-indol-5-yl)amino]-5-

{5-[(4-methylpiperazin-1-yl)methyl]-1-benzofuran-2-yl}nicotinonitrile as a yellow solid. HPLC retention time: 5.9 min.[g]; melting range: 162-165° C. (decom.); and HRMS: 477.24093.

Example 50

Preparation of 5-(5-{[4-(hydroxymethyl)piperidin-1-yl]methyl}-1-benzofuran-2-yl)-4-[(4-methyl-1H-indol-5-yl)amino]nicotinonitrile 392 and 5-[5-(hydroxymethyl)-1-benzofuran-2-yl]-4-[(4-methyl-1H-indol-5-yl)amino]nicotinonitrile 481

An alternative procedure for preparing 5-(5-{[4-(hydroxymethyl)piperidin-1-yl]methyl}-1-benzofuran-2-yl)-4-[(4-methyl-1H-indol-5-yl)amino]nicotinonitrile 392 is described below (compare Example 27).

To a suspension of 5-(5-formyl-1-benzofuran-2-yl)-4-[(4-methyl-1H-indol-5-yl)amino]nicotinonitrile (200 mg, 0.51 mmol) in a mixture of $CH_2Cl_2$ (10 mL) and NMP (1 mL) at room temperature under nitrogen was added 4-(hydroxymethyl)piperidine (176 mg, 1.53 mmol) followed by glacial acetic acid (153 mg, 2.55 mmol) and the reaction mixture was stirred at room temperature for 0.5 h. Sodium triacetoxyborohydride (540 mg, 2.55 mmol) was added in portions at 0° C. and the resulting mixture was stirred at room temperature overnight. The reaction mixture was partitioned between $CH_2Cl_2$ and saturated aqueous sodium bicarbonate, and the aqueous layer was extracted with $CH_2Cl_2$. The combined organic phases were washed with water and brine, dried over sodium sulfate, filtered, and concentrated in vacuo. The residue was purified by flash column chromatography (MeOH/$CH_2Cl_2$, 3% to 20%) to give 128 mg (51%) of 5-(5-{[4-(hydroxymethyl)piperidin-1-yl]methyl}-1-benzofuran-2-yl)-4-[(4-methyl-1H-indol-5-yl)amino]nicotinonitrile 392 as a yellow solid and 23.8 mg of 5-[5-(hydroxymethyl)-1-benzofuran-2-yl]-4-[(4-methyl-1H-indol-5-yl)amino]nicotinonitrile 481 as a yellow solid. Compound 392: HPLC retention time: 6.4 min.[g]; melting range: 196-199° C.; and HRMS: 395.15023. Compound 481: HPLC retention time: 8.9 min.[g]; MS: 395.3 (M+H); melting range: 232-234° C.; and HRMS: 395.15023.

Following procedures analogous to those described for the preparation of 5-(5-{[4-(hydroxymethyl)piperidin-1-yl]methyl}-1-benzofuran-2-yl)-4-[(4-methyl-1H-indol-5-yl)amino]nicotinonitrile 392 and 5-[5-(hydroxymethyl)-1-benzofuran-2-yl]-4-[(4-methyl-1H-indol-5-yl)amino]nicotinonitrile 481, the compounds in Table 16 were prepared.

TABLE 16

| Compound | Compound Name | Melting range (° C.) | HPLC retention time (min.) | Observed ion m/e [M + H] | Observed HRMS [M + H] |
|---|---|---|---|---|---|
| 390 | 4-[(4-methyl-1H-indol-5-yl)amino]-5-(5-{[(2-pyrrolidin-1-ylethyl)amino]methyl}-1-benzofuran-2-yl)nicotinonitrile | 125 (decom.) | 5.3[g] | 491.4 | 491.25451 |
| 485 | 4-(1H-indol-5-ylamino)-5-{5-[(4-methylpiperazin-1-yl)methyl]-1-benzofuran-2-yl}nicotinonitrile | 192-194 | 5.8[g] | 463.4 | 463.22532 |
| 497 | 4-[(6-methyl-1H-indol-5-yl)amino]-5-{5-[(4-methylpiperazin-1-yl)methyl]-1-benzofuran-2-yl}nicotinonitrile | 202.4-205.2 | 6.0[g] | 477.4 | 477.2395 |
| 499 | 5-[5-(hydroxymethyl)-1-benzofuran-2-yl]-4-[(6-methyl-1H-indol-5-yl)amino]nicotinonitrile | N/A | 9.0[g] | 395.3 | 395.14956 |
| 500 | 5-{5-[(diethylamino)methyl]-1-benzofuran-2-yl}-4-[(6-methyl-1H-indol-5-yl)amino]nicotinonitrile | N/A | 6.9[g] | 450.3 | 450.2296 |
| 518 | 4-[(4-methyl-1H-indol-5-yl)amino]-5-{5-[(4-methylpiperazin-1-yl)methyl]-3-thienyl}nicotinonitrile | 185-187 | N/A | 443.4 | 443.20262 |
| 536 | tert-butyl 4-[(2-{5-cyano-4-[(4-methyl-1H-indol-5-yl)amino]pyridin-3-yl}-1-benzofuran-5-yl)methyl]piperazine-1-carboxylate | 183-185 | N/A | 563.4 | 563.2768 |

TABLE 16-continued

| Compound | Compound Name | Melting range (° C.) | HPLC retention time (min.) | Observed ion m/e [M + H] | Observed HRMS [M + H} |
|---|---|---|---|---|---|
| 538 | 4-[(4-methyl-1H-indol-5-yl)amino]-5-(5-{[4-(methylsulfonyl)piperazin-1-yl]methyl}-1-benzofuran-2-yl)nicotinonitrile | 239-241 | N/A | 541.3 | 541.2011 |
| 539 | 4-[(4-methyl-1H-indol-5-yl)amino]-5-{1-methyl-2-[(4-methylpiperazin-1-yl)methyl]-1H-imidazol-5-yl}nicotinonitrile | 165-168 | 3.4$^{(g)}$ | 441.3 | 441.2510 |
| 552 | 5-{2-methoxy-5-[(4-methylpiperazin-1-yl)methyl]phenyl}-4-[(4-methyl-1H-indol-5-yl)amino]nicotinonitrile | N/A | 4.8$^{(g)}$ | 467.4 | N/A |
| 553 | 5-{5-[(4-ethylpiperazin-1-yl)methyl]-1-benzofuran-2-yl}-4-[(4-methyl-1H-indol-5-yl)amino]nicotinonitrile | 129-132 | 7.8$^{(j)}$ | N/A | N/A |
| 554 | 4-[(4-methyl-1H-indol-5-yl)amino]-5-{5-[(4-methyl-4-oxidopiperazin-1-yl)methyl]-1-benzofuran-2-yl}nicotinonitrile | 120 (decom.) | 6.7$^{(g)}$ | 493.5 | N/A |

Example 51

Preparation of the trifluoroacetic salt of 4-[(4-methyl-1H-indol-5-yl)amino]-5-[5-(piperazin-1-ylmethyl)-1-benzofuran-2-yl]nicotinonitrile 540

A mixture of tert-butyl 4-[(2-{5-cyano-4-[(4-methyl-1H-indol-5-yl)amino]pyridin-3-yl}-1-benzofuran-5-yl)methyl]piperazine-1-carboxylate (63 mg, 0.11 mmol) in 10% trifluoroacetic acid/$CH_2Cl_2$ was stirred at room temperature for 4 h, concentrated in vacuo, and the residue was purified by preparative HPLC (column: Prodigy ODS3, 4.6×150 mm, from Phenomenex (Torrance, Calif.); mobile phase A: 0.02% trifluoroacetic acid (TFA) in water; mobile phase B: 0.02% TFA in $CH_3CN$, 10-95% B in 25 minutes (min.); flow rate: 1.0 mL/min; column temperature: 40° C.; detection wavelength: 254 and 215 nm) to provide 46 mg (50%) of the trifluoroacetic salt of 4-[(4-methyl-1H-indol-5-yl)amino]-5-[5-(piperazin-1-ylmethyl)-1-benzofuran-2-yl]nicotinonitrile 540 as an orange solid. HPLC retention time: 5.8 min.$^{(g)}$; MS: 463.3 (M+H); melting point: 113-115° C.; and HRMS: 463.2234.

Example 52

Preparation of 5-(3,4-dimethoxyphenyl)-4-[(4-methyl-1H-indol-7-yl)amino]nicotinonitrile 530

A solution of 5-(3,4-dimethoxyphenyl)-4-chloronicotinonitrile (120 mg, 0.44 mmol) and 4-methyl-7-aminoindole (77.8 mg, 0.52 mmol) in ethanol (2.5 mL) was heated at the reflux temperature for 24 h and cooled to room temperature. The reaction mixture was treated with aqueous $NH_4OH$ and concentrated in vacuo, and the residue was purified by flash column chromatography (ethyl acetate/$CH_2Cl_2$ 5% to 25%) to provide a 48 mg (29%) of 5-(3,4-dimethoxyphenyl)-4-[(4-methyl-1H-indol-7-yl)amino]nicotinonitrile 530 as an off white solid. HPLC retention time: 9.0 min.$^{(g)}$; MS: 385.3 (M+H); and HRMS: 385.1659.

Following procedures analogous to those described for the preparation of 5-(3,4-dimethoxyphenyl)-4-[(4-methyl-1H-indol-7-yl)amino]nicotinonitrile 530, 5-(3,4-dimethoxyphenyl)-4-(1H-indol-7-ylamino)nicotinonitrile 544 was prepared. HPLC retention time: 8.6 min.$^{(g)}$; HRMS: 371.1498; melting range: 205-207° C.

Example 53

Preparation of 5-(2-formyl-1-methyl-1H-imidazol-5-yl)-4-[(4-methyl-1H-indol-5-yl)amino]nicotinonitrile 537

A mixture of 5-iodo-4[(4-methyl-1H-indol-5-yl)amino] nicotinonitrile (250 mg, 0.67 mmol), 1-methyl-5-(tributylstannyl)-1H-imidazole-2-carbaldehyde (see e.g., U.S. Pat. No. 6,521,618) (401 mg, 1.0 mmol), dichlorobis(triphenylphosphine)palladium(II) (24 mg, 0.034 mmol), and triethylamine (74.9 mg, 0.74 mmol) in dioxane (6 mL) was heated at the reflux temperature for 22 h, cooled to room temperature, and concentrated in vacuo. The residue was suspended in $CH_2Cl_2$ and filtered and the solid was washed with $CH_2Cl_2$. The combined filtrate and washings were concentrated in vacuo and the residue was purified by column chromatography (ethyl acetate/$CH_2Cl_2$, 20% to 90%; MeOH/ethyl acetate, 5%) to provide 103 mg (43%) of 5-(2-formyl-1-methyl-1H-imidazol-5-yl)-4-[(4-methyl-1H-indol-5-yl)amino]nicotinonitrile 537 as a dark yellow solid. MS: 355.2 (M+H); melting range: 200-202° C.; and HRMS: 357.1458.

Following procedures analogous to those described for the preparation of 5-(2-formyl-1-methyl-1H-imidazol-5-yl)-4-[(4-methyl-1H-indol-5-yl)amino]nicotinonitrile 537, compounds in Table 17 were prepared.

TABLE 17

| Compound | Compound Name | Melting range (° C.) | HPLC retention time (min.) | Observed ion m/e [M + H] | Observed HRMS [M + H] |
|---|---|---|---|---|---|
| 542 | 5-(1-methyl-1H-imidazol-2-yl)-4-[(4-methyl-1H-indol-5-yl)amino]nicotinonitrile | 239-241 | 4.2[g] | 329.2 | 329.1510; |
| 564 | 5-(1-methyl-1H-imidazol-5-yl)-4-[(4-methyl-1H-indol-5-yl)amino]nicotinonitrile | N/A | 4.4[g] | 329.3 | N/A |
| 565 | 4'-[(4-methyl-1H-indol-5-yl)amino]-2,3'-bipyridine-5'-carbonitrile | N/A | 8.1[g] | 326.3 | N/A |

Example 54

Preparation of 4-[(4-methyl-1H-indol-5-yl)amino]-5-(1,3-thiazol-2-yl)nicotinonitrile 541

A mixture of 5-iodo-4[(4-methyl-1H-indol-5-yl)amino]nicotinonitrile (120 mg, 0.32 mmol), 2-(tributylstannyl)-1,3-thiazole (340 mg, 0.91 mmol), dichlorobis(triphenylphosphine)palladium(II) (28 mg, 0.04 mmol), and triethylamine (36 mg, 0.35 mmol) in dioxane (4 mL) was heated at reflux for 24 h. 4-[(4-Methyl-1H-indol-5-yl)amino]-5-(1,3-thiazol-2-yl)nicotinonitrile was obtained following the work-up and purification procedures as described for the preparation of 5-(2-formyl-1-methyl-1H-imidazol-5-yl)-4-[(4-methyl-1H-indol-5-yl)amino]nicotinonitrile 541. HPLC retention time: 10.1 min.[g]; MS: 332.2 (M+H); melting range: 245-247° C.; and HRMS: 332.0964.

Following procedures analogous to those described for the preparation of 5-(2-formyl-1-methyl-1H-imidazol-5-yl)-4-[(4-methyl-1H-indol-5-yl)amino]nicotinonitrile 541, 4-[(4-methyl-1H-indol-5-yl)amino]-5-(1,3-thiazol-4-yl)nicotinonitrile 543 was prepared. HPLC retention time: 7.7 min.[g]; MS: 332.2 (M+H); melting range: 245-247° C.; and HRMS: 332.0966.

Example 55

Preparation of 5-[4-(2-methoxyethoxy)phenyl]-4-[(4-methyl-1H-indol-5-yl)amino]nicotinonitrile 482

A mixture of 5-iodo-4[(4-methyl-1H-indol-5-yl)amino]nicotinonitrile (100 mg, 0.27 mmol), 2-[4-(2-methoxyethoxy)phenyl]-4,4,5,5-tetramethyl-1,3,2-dioxaborolane (98 mg, 0.35 mmol), and tetrakis(triphenylphosphine)palladium (0) (16 mg, 0.014 mmol) in DME (6 mL) and saturated aqueous NaHCO₃ (4 mL) was heated at 95° C. for 3 h, cooled to room temperature, and treated with water. The precipitate was filtered, washed with water, dried in vacuo, and purified by flash column chromatography (MeOH/CH₂Cl₂, 2% to 4%) to provide 75 mg (70%) of 5-[4-(2-methoxyethoxy)phenyl]-4-[(4-methyl-1H-indol-5-yl)amino]nicotinonitrile as a tan solid. HPLC retention time: 8.2 min.[g]; MS: 399.3 (M+H); melting range: 208-210° C.; and HRMS: 399.18056.

Example 56

Preparation of 5-[3-(2-methoxyethoxy)phenyl]-4-[(4-methyl-1H-indol-5-yl)amino]nicotinonitrile 483

A mixture of 5-iodo-4[(4-methyl-1H-indol-5-yl)amino]nicotinonitrile (100 mg, 0.27 mmol), 2-[3-(2-methoxyethoxy)phenyl]-4,4,5,5-tetramethyl-1,3,2-dioxaborolane (98 mg, 0.35 mmol) and tetrakis(triphenylphosphine)palladium (0) (16 mg, 0.014 mmol) in DME (6 mL) and saturated aqueous NaHCO₃ (4 mL) was heated at 95° C. for 2 h, cooled to room temperature and partitioned between dichloromethane and water. The organic phase was dried over Na₂SO₄, filtered, and concentrated in vacuo, and the residue was purified by flash column chromatography (MeOH/CH₂Cl₂, 1% to 5%) to provide 71 mg (66%) of 5-[3-(2-methoxyethoxy)phenyl]-4-[(4-methyl-1H-indol-5-yl)amino]nicotinonitrile as a tan solid. HPLC retention time: 8.3 min.[g]; MS: 399.3 (M+H); melting range: 158-160° C.; and HRMS: 399.18291.

Following procedures analogous to those described for the preparation of 5-[3-(2-methoxyethoxy)phenyl]-4-[(4-methyl-1H-indol-5-yl)amino]nicotinonitrile 483, 5-[4-(4-chlorobutoxy)phenyl]-4-[(4-methyl-1H-indol-5-yl)amino]nicotinonitrile 490 and 5-[3-(4-chlorobutoxy)phenyl]-4-[(4-methyl-1H-indol-5-yl)amino]nicotinonitrile 501 were prepared. Compound 490: HPLC retention time: 11.1 min.[g]; MS: 431.3 (M+H); melting point: 157-159° C.; and HRMS: 431.16279; and compound 501: HPLC retention time: 11.2 min.[g]; MS: 431.3 (M+H); melting point: 151-153° C.; and HRMS: 431.16345.

Example 57

Preparation of 4-[(4-methyl-1H-indol-5-yl)amino]-5-{5-[(4-methylpiperazin-1-yl)methyl]-3-furyl}nicotinonitrile 503

To a solution of 1-[4-bromo-2-furyl)methyl]-4-methylpiperazine (see e.g., J. Med. Chem., 49, 7868, (2006)) (145 mg, 0.56 mmol), and triisopropylborate (132 mg, 0.16 mL, 0.7 mmol) in THF was added dropwise n-BuLi (0.3 ml, 0.76 mmol, 2.5M/hexane) at −78° C. and the reaction mixture was stirred at −78° C. for 3 h and warmed to room temperature in 1 h. A few drops of water were added and the mixture was concentrated in vacuo. To the residue was added 5-iodo-4[(4-methyl-1H-indol-5-yl)amino]nicotinonitrile (100 mg, 0.27 mmol), [1,1'-bis(diphenylphosphino)ferrocene]dichloropalladium(II)-CH₂Cl₂ ((dppf)₂PdCl₂, 12 mg, 0.014 mmol), DME (6 mL) and saturated aqueous Na₂CO₃ (4 mL) and the resulting mixture was heated at 85° C. for 1.5 h and cooled to room temperature. The mixture was partitioned between dichloromethane and water, and the organic phase was dried over Na₂SO₄, filtered and concentrated in vacuo. The residue was purified by flash column chromatography (MeOH/CH₂Cl₂, 5% to 20%) to provide 68 mg (57%) of 4-[(4-methyl-1H-indol-5-yl)amino]-5-{5-[(4-methylpiperazin-1-yl)me-

Example 58

Preparation of 4-[(7-chloro-4-methyl-1H-indol-5-yl)amino]-5-(5-formyl-1-benzofuran-2-yl)nicotinonitrile 532

To a stirred solution of 4-[(7-chloro-4-methyl-1H-indol-5-yl)amino]-5-iodonicotinonitrile (405 mg, 1 mmol) in DMF (7 mL) was added 2-(tributylstannyl)-1-benzofuran-5-carbaldehyde (609 mg, 1.4 mmol) and tetrakis(triphenylphosphine)palladium(0) (110 mg, 0.1 mmol) under nitrogen atmosphere, the reaction mixture was heated at 110° C. for 1.5 h and cooled to room temperature and ethyl acetate was added to the resulting mixture. The organic phase was washed with water, saturated aqueous sodium chloride, dried over magnesium sulfate and concentrated and the residue was purified by flash column chromatography (ethyl acetate/hexane) to give 4-[(7-chloro-4-methyl-1H-indol-5-yl)amino]-5-(5-formyl-1-benzofuran-2-yl)nicotinonitrile as a yellow solid (351 mg, 82%). HPLC retention time: 12.4 min.$^{(g)}$; and MS: 427.3 (M+H).

Example 59

Preparation of 4-[(7-chloro-4-methyl-1H-indol-5-yl)amino]-5-{5-[(4-methylpiperazin-1-yl)methyl]-1-benzofuran-2-yl}nicotinonitrile 529

To a stirred solution of 4-[(7-chloro-4-methyl-1H-indol-5-yl)amino]-5-(5-formyl-1-benzofuran-2-yl)nicotinonitrile (106 mg, 0.25 mmol) in THF (3 mL) and EtOH (1 mL) was added 1-methylpiperazine (75 mg, 0.75 mmol) and acetic acid (75 mg, 1.2 mmol) and the reaction mixture was stirred at room temperature for 1 h. Sodium triacetoxyborohydride (159 mg, 0.75 mmol) was added to the reaction mixture and the solution was stirred at room temperature overnight, and concentrated. Aqueous 1N HCl was added and the aqueous phase was extracted with ethyl acetate, basified to pH of 10 by adding sodium carbonate, and extracted with ethyl acetate. The combined organic phases were washed with water and brine, dried over magnesium sulfate, and concentrated to give 4-[(7-chloro-4-methyl-1H-indol-5-yl)amino]-5-{5-[(4-methylpiperazin-1-yl)methyl]-1-benzofuran-2-yl}nicotinonitrile as a yellow solid (68 mg, 53%). HPLC retention time: 7.0 min.$^{(g)}$; and MS: 511.5 (M+H).

Example 60

Preparation of tert-butyl 4-[(2-{4-[(7-chloro-4-methyl-1H-indol-5-yl)amino]-5-cyanopyridin-3-yl}-1-benzofuran-5-yl)methyl]piperazine-1-carboxylate 548

To a stirred solution of 4-[(7-chloro-4-methyl-1H-indol-5-yl)amino]-5-(5-formyl-1-benzofuran-2-yl)nicotinonitrile (200 mg, 0.47 mmol) in THF (5 mL) and EtOH (2 mL) was added tert-butyl 1-piperazinecarboxylate (262 mg, 1.41 mmol) and acetic acid (54 mg, 0.9 mmol) and the reaction mixture was stirred at room temperature for 1 h. Sodium triacetoxyborohydride (398 mg, 1.88 mmol) was added to the reaction mixture and the resulting solution was stirred at room temperature overnight. After the reaction was concentrated, ethyl acetate was added; and the organic phase was washed with saturated aqueous sodium bicarbonate solution and saturated aqueous sodium chloride solution, dried over magnesium sulfate, and concentrated. The residue was purified by flash column chromatography (ethyl acetate/hexane) to give tert-butyl 4-[(2-{4-[(7-chloro-4-methyl-1H-indol-5-yl)amino]-5-cyanopyridin-3-yl}-1-benzofuran-5-yl)methyl]piperazine-1-carboxylate as a yellow solid (203 mg, 73%). HPLC retention time: 9.5 min.$^{(g)}$; MS: 597.4 (M+H); and HRMS: 597.2378.

Example 61

Preparation of 4-[(7-chloro-4-methyl-1H-indol-5-yl)amino]-5-[5-(piperazin-1-ylmethyl)-1-benzofuran-2-yl]nicotinonitrile 547

A solution of tert-butyl 4-[(2-{4-[(7-chloro-4-methyl-1H-indol-5-yl)amino]-5-cyanopyridin-3-yl}-1-benzofuran-5-yl)methyl]piperazine-1-carboxylate (176 mg, 0.29 mmol) in CH$_2$Cl$_2$ (4 mL) and trifluoroacetic acid (2 mL) was stirred at room temperature for 4 h and concentrated to provide 4-[(7-chloro-4-methyl-1H-indol-5-yl)amino]-5-[5-(piperazin-1-ylmethyl)-1-benzofuran-2-yl]nicotinonitrile as a yellow solid in quantitative yield (182 mg). HPLC retention time: 6.5 min.$^{(g)}$; MS: 497.3 (M+H); and HRMS: 497.1851.

Example 62

Preparation of 5-(1-benzofuran-2-yl)-4-[(7-chloro-4-methyl-1H-indol-5-yl)amino]nicotinonitrile 531

To a stirred solution of 4-[(7-chloro-4-methyl-1H-indol-5-yl)amino]-5-iodonicotinonitrile (122 mg, 0.3 mmol) in DMF (4 mL) was added 2-benzofuranboronic acid (162 mg, 0.4 mmol) and tetrakis(triphenylphosphine)palladium(0) (34 mg, 0.03 mmol) under nitrogen atmosphere and the reaction mixture was heated at 60° C. overnight. After the solution was cooled to room temperature, ethyl acetate was added, and the organic phase was washed with water and saturated aqueous sodium chloride, dried over magnesium sulfate and concentrated. The residue was purified by flash column chromatography (ethyl acetate/hexane) to give 5-(1-benzofuran-2-yl)-4-[(7-chloro-4-methyl-1H-indol-5-yl)amino]nicotinonitrile (18 mg, 15%). HPLC retention time: 13.4 min.$^{(g)}$; MS: 399.3 (M+H); and HRMS: 399.1009.

Example 63

Preparation of 5-[4-(2-chloroethoxy)phenyl]-4-[(7-chloro-4-methyl-1H-indol-5-yl)amino]nicotinonitrile 533

To a stirred solution of 4-[(7-chloro-4-methyl-1H-indol-5-yl)amino]-5-iodonicotinonitrile (534 mg, 1.3 mmol) in DME (30 mL) was added diisopropyl 4-(2-chloroethoxy)phenylboronate (754 mg, 2.6 mmol), sodium carbonate solution (2.7 mL of 2M solution, 5.4 mmol) and tetrakis(triphenylphosphine)palladium(0) (150 mg, 0.15 mmol) under nitrogen atmosphere and the reaction mixture was heated at 80° C. for 6 h and cooled to room temperature. Ethyl acetate was added and the organic phase was washed with saturated sodium bicarbonate solution and saturated sodium chloride solution, dried over magnesium sulfate, and concentrated. The residue was purified by flash column chromatography (ethyl acetate/hexane) to give 5-[4-(2-chloroethoxy)phenyl]-4-[(7-chloro-4-methyl-1H-indol-5-yl)amino]nicotinonitrile as a yellow solid (482 mg, 84%). HPLC retention time: 10.7 min.$^{(g)}$ and MS: 437.2 (M+H).

Example 64

Preparation of 4-[(7-chloro-4-methyl-1H-indol-5-yl)amino]-5-{4-[2-(4-methylpiperazin-1-yl)ethoxy]phenyl}nicotinonitrile 535

A solution of 5-[4-(2-chloroethoxy)phenyl]-4-[(7-chloro-4-methyl-1H-indol-5-yl)amino]nicotinonitrile (144 mg, 0.3 mmol) and 1-methylpiperazine (330 mg, 3.3 mmol) in DME (3 mL) was stirred at 110° C. for 48 h. After the solution was concentrated, 1 N HCl was added and the aqueous phase was extracted with ethyl acetate, adjusted to pH of 10 by adding sodium carbonate, and extracted with ethyl acetate. The combined organic phases were washed with water and brine, dried over magnesium sulfate, and concentrated to give 4-[(7-chloro-4-methyl-1H-indol-5-yl)amino]-5-{4-[2-(4-methylpiperazin-1-yl)ethoxy]phenyl}nicotinonitrile as a yellow solid (140 mg, 84% yield). HPLC retention time: 5.1 min.$^{(g)}$; MS: 501.3 (M+H); and HRMS: 501.2159.

Example 65

Preparation of 4-[(7-chloro-4-methyl-1H-indol-5-yl)amino]-5-{4-[2-(dimethylamino)ethoxy]phenyl}nicotinonitrile 534

A solution of 5-[4-(2-chloroethoxy)phenyl]-4-[(7-chloro-4-methyl-1H-indol-5-yl)amino]nicotinonitrile (144 mg, 0.3 mmol) and dimethyl amine (1.7 mL of a 2.0 M solution in THF, 3.4 mmol) in DME (3 mL) in a sealed tube was stirred at 110° C. for 48 h and cooled to room temperature. After the resulting solution was concentrated, 1 N aqueous HCl was added and the aqueous phase was extracted with ethyl acetate and the aqueous solution was adjusted to pH of 10 by adding sodium carbonate and extracted with ethyl acetate. The combined organic phases were washed with water and brine, dried over magnesium sulfate, and concentrated to give 4-[(7-chloro-4-methyl-1H-indol-5-yl)amino]-5-{4-[2-(dimethylamino)ethoxy]phenyl}nicotinonitrile as a yellow solid (109 mg, 74%). HPLC retention time: 5.1 min.$^{(g)}$; MS: 446.3 (M+H); and HRMS: 446.1743.

Example 66

Preparation of 5-(3,4-dimethoxyphenyl)-4-{[2-(4-methylpiperazin-1-yl)ethyl]amino}nicotinonitrile 439

A mixture of 4-chloro-5-(3,4-dimethoxyphenyl)nicotinonitrile (74 mg, 0.27 mmol), 2-(4-methylpiperazin-1-yl)ethanamine (58 mg, 0.40 mmol) and triethylamine (40 mg, 0.40 mmol) in 3 mL DMF was heated at 60° C. overnight, cooled to room temperature, and concentrated to dryness. The residue was dissolved in 3 mL DMSO, filtered, and purified by a preparative HPLC to give 5-(3,4-dimethoxyphenyl)-4-{[2-(4-methylpiperazin-1-yl)ethyl]amino}nicotinonitrile as a TFA salt (67 mg). HPLC retention time: 1.24 min.$^{(k)}$; MS: 382.2 (M+H).

Following procedures analogous to those described for the preparation of 5-(3,4-dimethoxyphenyl)-4-{[2-(4-methylpiperazin-1-yl)ethyl]amino}nicotinonitrile 439, the compounds in Table 18 were prepared.

TABLE 18

| Compound | Compound Name | HPLC retention time (min.) | Observed Ion m/e [M + H] |
|---|---|---|---|
| 440 | 5-(3,4-dimethoxyphenyl)-4-{[3-(4-methylpiperazin-1-yl)propyl]amino}nicotinonitrile | 1.24$^{(k)}$ | 396.2 |
| 446 | 4-[(cis-4-aminocyclohexyl)amino]-5-(3,4-dimethoxyphenyl)nicotinonitrile | 1.27$^{(k)}$ | 353.2 |
| 447 | 5-(3,4-dimethoxyphenyl)-4-{[2-(1-methylpiperidin-4-yl)ethyl]amino}nicotinonitrile | 1.3$^{(k)}$ | 381.2 |
| 448 | 5-(3,4-dimethoxyphenyl)-4-{[(1-methylpiperidin-4-yl)methyl]amino}nicotinonitrile | 1.25$^{(k)}$ | 367.2 |
| 524 | 4-[(trans-4-aminocyclohexyl)amino]-5-(3,4-dimethoxyphenyl)nicotinonitrile | 5.4$^{(h)}$ | 353.2; |

Example 67

Preparation of 4-({[trans-4-(aminomethyl)cyclohexyl]methyl}amino)-5-(3,4-dimethoxyphenyl)nicotinonitrile 441

A solution of 4-chloro-5-(3,4-dimethoxyphenyl)nicotinonitrile (0.27 mmol, 74 mg), trans-tert-butyl (4-(aminomethyl)cyclohexyl)methylcarbamate (0.40 mmol, 97 mg), and triethylamine (0.40 mmol, 40 mg) in 3 mL DMF was heated at 60° C. overnight, cooled to room temperature, and concentrated to dryness. A mixture of dichloromethane (2 mL) and trifluoroacetic acid (2 mL) were added to the residue, and, after standing for 1 h at r.t., the solution was concentrated to dryness, redissolved in 3 mL DMSO, filtered, and purified by a preparation HPLC to give 4-({[trans-4-(aminomethyl)cyclohexyl]methyl}amino)-5-(3,4-dimethyloxyphenyl)nicotinonitrile as a TFA salt (92 mg). HPLC retention time: 1.33 min.$^{(k)}$ and MS: 381.2 (M+H).

Following procedures analogous to those described for the preparation of 4-({[trans-4(aminomethyl)cyclohexyl]methyl}amino)-5-(3,4-dimethoxyphenyl)nicotinonitrile 441, compounds in Table 19 were prepared.

TABLE 19

| Compound | Compound Name | HPLC retention time (min.) | Observed Ion m/e [M + H] |
|---|---|---|---|
| 442 | 4-{[(trans-4-aminocyclohexyl)methyl]amino}-5-(3,4-dimethoxyphenyl)nicotinonitrile | 1.27$^{(k)}$ | 367.2 |
| 443 | 4-({[cis-3-(aminomethyl)cyclohexyl]methyl}amino)-5-(3,4-dimethoxyphenyl)nicotinonitrile | 1.37$^{(k)}$ | 381.2 |
| 444 | 5-(3,4-dimethoxyphenyl)-4-[(2-piperidin-4-ylethyl)amino]nicotinonitrile | 1.28$^{(k)}$ | 367.2 |

TABLE 19-continued

| Compound | Compound Name | HPLC retention time (min.) | Observed Ion m/e [M + H] |
|---|---|---|---|
| 445 | 5-(3,4-dimethoxyphenyl)-4-[(piperidin-4-ylmethyl)amino]nicotinonitrile | 1.22[k] | 353.2 |

Example 68

Preparation of 4-[(4-chloro-1H-pyrrolo[2,3-b]pyridin-5-yl)amino]-5-(3,4-dimethoxyphenyl)nicotinonitrile 522

A mixture of 4-chloro-1H-pyrrolo[2,3-b]pyridin-5-amine (see e.g., Tetrahedron Lett., 45(11), 2317-2319 (2004)) (0.30 mmol, 51 mg) and 4-fluoro-5-[3-methoxy-4-(2-methoxyethoxy)phenyl]nicotinonitrile (0.23 mmol, 60 mg) in 2 mL DMSO was heated to 100° C. overnight. The product was purified by a preparative HPLC followed by silica gel chromatography (CH$_2$Cl$_2$/MeOH) to give 4-[(4-chloro-1H-pyrrolo[2,3-b]pyridin-5-yl)amino]-5-(3,4-dimethoxyphenyl) nicotinonitrile (23 mg). HPLC retention time: 7.9 min.[g] and MS: 406.2 (M+H) and HRMS: 406.10747.

Following procedures analogous to those described for the preparation of 4-[(4-chloro-1H-pyrrolo[2,3-b]pyridin-5-yl) amino]-5-(3,4-dimethoxyphenyl)nicotinonitrile 522, 4-[(4-chloro-1H-pyrrolo[2,3-b]pyridin-5-yl)amino]-5-[3-methoxy-4-(2-methoxyethoxy)phenyl]nicotinonitrile 492 was prepared. HPLC retention time: 8.5 min.[g] and HRMS: 450.13144.

Additional compounds in Table 20 were prepared in accordance with the procedures outlined in the schemes above and/or by standard synthetic methods and procedures known to those skilled in the art.

TABLE 20

| Compound | Compound Name | HPLC Retention Time (min.) | Observed Ion m/e [M + H] | Melting Range (° C.) |
|---|---|---|---|---|
| 230 | 4-(1H-indol-5-ylamino)-5-[4-methoxy-3-(2-morpholin-4-ylethoxy)phenyl]nicotinonitrile | 4.1[e] | 469.2 | N/A |
| 231 | 4-(1H-indol-5-ylamino)-5-{4-methoxy-3-[2-(4-methylpiperazin-1-yl)ethoxy]phenyl}nicotinonitrile | 4.0[e] | 482.3 | N/A |
| 232 | 4-(1H-indol-5-ylamino)-5-[4-methoxy-3-(2-piperazin-1-ylethoxy)phenyl]nicotinonitrile | 3.8[e] | 468.2 | N/A |
| 233 | 4-(1H-indol-5-ylamino)-5-[4-methoxy-3-(2-thiomorpholin-4-ylethoxy)phenyl]nicotinonitrile | 4.4[e] | 485.2 | N/A |
| 234 | 5-{3-[2-(4-ethylpiperazin-1-yl)ethoxy]-4-methoxyphenyl}-4-(1H-indol-5-ylamino) nicotinonitrile | 4.0[e] | 496.3 | N/A |
| 235 | 4-(1H-indol-5-ylamino)-5-[4-methoxy-3-(2-piperidin-1-ylethoxy)phenyl]nicotinonitrile | 4.5[e] | 467.2 | N/A |
| 236 | 5-{3-[2-(dimethylamino)ethoxy]-4-methoxy phenyl}-4-(1H-indol-5-ylamino)nicotinonitrile | 4.0[e] | 427.2 | N/A |
| 237 | 5-(3-{2-[bis(2-hydroxyethyl)amino]ethoxy}-4-methoxyphenyl)-4-(1H-indol-5-ylamino) nicotinonitrile | 3.8[e] | 487.2 | N/A |
| 238 | 5-{3-[2-(4-hydroxypiperidin-1-yl)ethoxy]-4-methoxyphenyl}-4-(1H-indol-5-ylamino) nicotinonitrile | 4.1[e] | 483.2 | N/A |
| 239 | 4-(1H-indol-5-ylamino)-5-(4-methoxy-3-{2-[(pyridin-3-ylmethyl)amino]ethoxy}phenyl) nicotinonitrile | 4.0[e] | 490.2 | N/A |
| 240 | 4-(1H-indol-5-ylamino)-5-(4-methoxy-3-{2-[(pyridin-4-ylmethyl)amino]ethoxy}phenyl) nicotinonitrile | 3.9[e] | 490.2 | N/A |
| 241 | 4-(1H-indol-5-ylamino)-5-(4-methoxy-3-{2-[(pyridin-2-ylmethyl)amino]ethoxy}phenyl) nicotinonitrile | 4.5[e] | 490.2 | N/A |
| 242 | 4-(1H-indol-5-ylamino)-5-(4-methoxy-3-{2-[(2-phenylethyl)amino]ethoxy}phenyl)nicotinonitrile | 5.2[e] | 503.2 | N/A |
| 243 | 5-{3-[2-(cyclopentylamino)ethoxy]-4-methoxyphenyl}-4-(1H-indol-5-ylamino) nicotinonitrile | 4.7[e] | 467.3 | N/A |
| 244 | 5-{3-[2-(cyclohexylamino)ethoxy]-4-methoxyphenyl}-4-(1H-indol-5-ylamino) nicotinonitrile | 5.0[e] | 481.3 | N/A |
| 245 | 5-(3-{2-[(2-furylmethyl)amino]ethoxy}-4-methoxyphenyl)-4-(1H-indol-5-ylamino) nicotinonitrile | 4.6[e] | 479.2 | N/A |

TABLE 20-continued

| Compound | Compound Name | HPLC Retention Time (min.) | Observed Ion m/e [M + H] | Melting Range (° C.) |
|---|---|---|---|---|
| 246 | 5-(2-bromo-4,5-dimethoxyphenyl)-4-(1H-indol-5-ylamino)nicotinonitrile | 2.5$^{(c)}$ | 449.1 | N/A |
| 247 | 5-(2-bromo-4,5-dimethoxyphenyl)-4-[(4-methyl-1H-indol-5-yl)amino]nicotinonitrile | 2.6$^{(c)}$ | 462.2 | N/A |
| 248 | 4-(1H-indol-4-ylamino)-5-[4-methoxy-3-(2-piperidin-1-ylethoxy)phenyl]nicotinonitrile | 2.5$^{(c)}$ | 467.2 | N/A |
| 249 | 5-(3-{2-[(2-hydroxyethyl)amino]ethoxy}-4-methoxyphenyl)-4-(1H-indol-4-ylamino)nicotinonitrile | 1.9$^{(c)}$ | 443.2 | N/A |
| 250 | 4-(1H-indol-5-ylamino)-5-(4-methoxy-3-{2-[(3-phenylpropyl)amino]ethoxy}phenyl)nicotinonitrile | 2.8$^{(c)}$ | 517.2 | N/A |
| 251 | 4-(1H-indol-5-ylamino)-5-(4-methoxy-3-{2-[(2-pyridin-2-ylethyl)amino]ethoxy}phenyl)nicotinonitrile | 2.3$^{(c)}$ | 50.42 | N/A |
| 252 | 4-(1H-indol-5-ylamino)-5-(4-methoxy-3-{2-[(2-pyridin-3-ylethyl)amino]ethoxy}phenyl)nicotinonitrile | 2.3$^{(c)}$ | 504.2 | N/A |
| 253 | 4-(1H-indol-5-ylamino)-5-(4-methoxy-3-{2-[(2-pyridin-4-ylethyl)amino]ethoxy}phenyl)nicotinonitrile | 2.2$^{(c)}$ | 504.2 | N/A |
| 254 | 5-[3-(dimethylamino)phenyl]-4-(1H-indol-4-ylamino)nicotinonitrile | 1.8$^{(c)}$ | 354.2 | N/A |
| 255 | 4-(1H-indol-4-ylamino)-5-[3-(methylsulfonyl)phenyl]nicotinonitrile | 1.7$^{(c)}$ | 389.7 | N/A |
| 256 | N-{3-[5-cyano-4-(1H-indol-4-ylamino)pyridin-3-yl]phenyl}methanesulfonamide | 1.7$^{(c)}$ | 404.1 | N/A |
| 257 | 4-(1H-indol-5-ylamino)-5-phenylnicotinonitrile | 2.4$^{(c)}$ | 310.1 | N/A |
| 258 | 4-(1H-indol-5-ylamino)-5-(3-thienyl)nicotinonitrile | 2.3$^{(c)}$ | 316.1 | N/A |
| 259 | 4-(1H-indol-5-ylamino)-3,3'-bipyridine-5-carbonitrile | 1.8$^{(c)}$ | 311.1 | N/A |
| 260 | 5-(1,3-benzodioxol-5-yl)-4-(1H-indol-5-ylamino)nicotinonitrile | 2.4$^{(c)}$ | 354.1 | N/A |
| 261 | 4-(1H-indol-5-ylamino)-3,4'-bipyridine-5-carbonitrile | 1.8$^{(c)}$ | 311.1 | N/A |
| 262 | 5-(3-furyl)-4-(1H-indol-5-ylamino)nicotinonitrile | 2.2$^{(c)}$ | 300.1 | N/A |
| 263 | 5-(1H-indol-5-yl)-4-(1H-indol-5-ylamino)nicotinonitrile | 2.3$^{(c)}$ | 349.1 | N/A |
| 264 | 5-(2,3-dihydro-1,4-benzodioxin-6-yl)-4-(1H-indol-5-ylamino)nicotinonitrile | 2.4$^{(c)}$ | 368.1 | N/A |
| 265 | 4-(1H-indol-5-ylamino)-5-pyrimidin-5-ylnicotinonitrile | 1.4$^{(c)}$ | 312.1 | N/A |
| 266 | 4-(1H-indol-5-ylamino)-5-(2-methoxypyrimidin-5-yl)nicotinonitrile | 1.8$^{(c)}$ | 342.1 | N/A |
| 267 | 4-(1H-indol-5-ylamino)-5-(2-thienyl)nicotinonitrile | 2.3$^{(c)}$ | 316.1 | N/A |
| 268 | 5-(1-benzofuran-2-yl)-4-(1H-indol-5-ylamino)nicotinonitrile | 2.7$^{(c)}$ | 350.1 | N/A |
| 269 | 5-(3,5-dimethylisoxazol-4-yl)-4-(1H-indol-5-ylamino)nicotinonitrile | 2.3$^{(c)}$ | 329.2 | N/A |
| 270 | 5-[3-(hydroxymethyl)phenyl]-4-(1H-indol-4-ylamino)nicotinonitrile | 1.6$^{(c)}$ | 341.1 | N/A |
| 271 | 5-{3-[(dimethylamino)methyl]phenyl}-4-(1H-indol-4-ylamino)nicotinonitrile | 1.4$^{(c)}$ | 368.2 | N/A |
| 272 | 4-(1H-indol-4-ylamino)-5-{5-[(prop-2-yn-1-ylamino)methyl]-1-benzothien-2-yl}nicotinonitrile | 2.2$^{(c)}$ | 434.2 | N/A |
| 273 | 5-{5-[(butylamino)methyl]-1-benzothien-2-yl}-4-(1H-indol-4-ylamino)nicotinonitrile | 2.3$^{(c)}$ | 452.3 | N/A |
| 274 | 5-(5-{[(2-hydroxyethyl)amino]methyl}-1-benzothien-2-yl)-4-(1H-indol-4-ylamino)nicotinonitrile | 2.1$^{(c)}$ | 440.2 | N/A |
| 275 | 5-(5-{[(3-hydroxypropyl)amino]methyl}-1-benzothien-2-yl)-4-(1H-indol-4-ylamino)nicotinonitrile | 2.1$^{(c)}$ | 454.3 | N/A |
| 276 | 4-(1H-indol-4-ylamino)-5-(5-{[(3-methoxypropyl)amino]methyl}-1-benzothien-2-yl)nicotinonitrile | 2.2$^{(c)}$ | 468.3 | N/A |
| 277 | 5-(5-{[(4-hydroxybutyl)amino]methyl}-1-benzothien-2-yl)-4-(1H-indol-4-ylamino)nicotinonitrile | 2.2$^{(c)}$ | 468.3 | N/A |
| 278 | 5-{5-[(cyclopropylamino)methyl]-1-benzothien-2-yl}-4-(1H-indol-4-ylamino) nicotinonitrile | 2.2$^{(c)}$ | 436.2 | N/A |

TABLE 20-continued

| Compound | Compound Name | HPLC Retention Time (min.) | Observed Ion m/e [M + H] | Melting Range (° C.) |
|---|---|---|---|---|
| 279 | 5-(5-{[(cyclopropylmethyl)amino]methyl}-1-benzothien-2-yl)-4-(1H-indol-4-ylamino)nicotinonitrile | 2.3(c) | 450.3 | N/A |
| 280 | 4-(1H-indol-4-ylamino)-5-[5-(pyrrolidin-1-ylmethyl)-1-benzothien-2-yl] nicotinonitrile | 2.2(c) | 450.3 | N/A |
| 281 | 4-(1H-indol-4-ylamino)-5-[5-(morpholin-4-ylmethyl)-1-benzothien-2-yl] nicotinonitrile | 2.2(c) | 466.3 | N/A |
| 282 | 4-(1H-indol-4-ylamino)-5-(5-{[(2-morpholin-4-yl ethyl)amino]methyl}-1-benzothien-2-yl) nicotinonitrile | 2.1(c) | 509.3 | N/A |
| 283 | 4-(1H-indol-4-ylamino)-5-[5-(piperidin-1-yl methyl)-1-benzothien-2-yl]nicotinonitrile | 2.3(c) | 464.3 | N/A |
| 284 | 5-(5-{[4-(hydroxymethyl)piperidin-1-yl]methyl}-1-benzothien-2-yl)-4-(1H-indol-4-ylamino)nicotinonitrile | 2.2(c) | 494.3 | N/A |
| 285 | 5-[5-(hydroxymethyl)-1-benzothien-2-yl]-4-(1H-indol-4-ylamino)nicotinonitrile | 3.0(c) | 397.2 | N/A |
| 286 | 5-{5-[(benzylamino)methyl]-1-benzothien-2-yl}-4-(1H-indol-4-ylamino)nicotinonitrile | 2.4(c) | 486.3 | N/A |
| 287 | 4-(1H-indol-4-ylamino)-5-(5-{[(2-phenylethyl)amino]methyl}-1-benzothien-2-yl)nicotinonitrile | 2.5(c) | 500.3 | N/A |
| 288 | 4-(1H-indol-4-ylamino)-5-(5-{[(pyridin-2-yl methyl)amino]methyl}-1-benzothien-2-yl)nicotinonitrile | 2.3(c) | 487.3 | N/A |
| 289 | 4-(1H-indol-4-ylamino)-5-(5-{[(pyridin-3-yl methyl)amino]methyl}-1-benzothien-2-yl)nicotinonitrile | 2.2(c) | 487.3 | N/A |
| 290 | 4-(1H-indol-4-ylamino)-5-(5-{[(pyridin-4-yl methyl)amino]methyl}-1-benzothien-2-yl)nicotinonitrile | 2.2(c) | 487.3 | N/A |
| 291 | 5-[4-(dimethylamino)phenyl]-4-(pyridin-3-yl amino)nicotinonitrile | 2.1(d) | 316.1 | N/A |
| 292 | 5-[4-(dimethylamino)phenyl]-4-(1H-indazol-5-ylamino)nicotinonitrile | 2.4(d) | 355.4 | N/A |
| 293 | 5-[4-(dimethylamino)phenyl]-4-(1H-indazol-6-ylamino)nicotinonitrile | 2.7(d) | 355.4 | N/A |
| 294 | 5-[4-(dimethylamino)phenyl]-4-[(5-hydroxy-1H-pyrazol-3-yl)amino]nicotinonitrile | 2.4(d) | 320.8 | N/A |
| 295 | 4-(1H-indazol-5-ylamino)-5-(3-methoxyphenyl)nicotinonitrile | 2.7(d) | 342.4 | N/A |
| 296 | 4-(1H-indazol-6-ylamino)-5-(3-methoxyphenyl)nicotinonitrile | 2.8(d) | 341.7 | N/A |
| 297 | 4-[(5-hydroxy-1H-pyrazol-3-yl)amino]-5-(3-methoxyphenyl)nicotinonitrile | 2.5(d) | 413.7 | N/A |
| 298 | 5-(3-bromophenyl)-4-[(4-methyl-1H-indol-5-yl)amino]nicotinonitrile | N/A | 403.2 | N/A |
| 299 | 4-(1H-indol-4-ylamino)-5-[4-methoxy-3-(2-morpholin-4-ylethoxy)phenyl]nicotinonitrile | 5.1(a) | 470.3 | 172-174 |
| 300 | 4-(1H-indol-4-ylamino)-5-{4-methoxy-3-[2-(4-methylpiperazin-1-yl)ethoxy]phenyl} nicotinonitrile | N/A | 483.2 | 99-102 (decom.) |
| 301 | 5-{3-[2-(dimethylamino)ethoxy]-4-methoxy phenyl}-4-(1H-indol-4-ylamino)nicotinonitrile | N/A | 428.2 | 179-181 (decom.) |
| 302 | 5-{3-[2-(4-hydroxypiperidin-1-yl)ethoxy]-4-methoxyphenyl}-4-(1H-indol-4-ylamino) nicotinonitrile | N/A | 484.2 | 107-110 (decom.) |
| 303 | 5-[3-(2-chloroethoxy)-4-methoxyphenyl]-4-(1H-indol-4-ylamino)nicotinonitrile | N/A | 419.2 | 171-173 |
| 304 | 4-[(4-methyl-1H-indol-5-yl)amino]-5-[3-(2-thienyl) phenyl]nicotinonitrile | 3.6(c) | 407.2 | N/A |
| 305 | 5-(3,4-dimethoxyphenyl)-4-[(4-ethyl-1H-indol-5-yl)amino]nicotinonitrile | N/A | 399.2 | 190-192 |
| 306 | 5-[3-(5-formyl-2-thienyl)phenyl]-4-[(4-methyl-1H-indol-5-yl)amino]nicotinonitrile | 9.4(a) | 435.2 | N/A |
| 307 | 5-(3-{5-[(dimethylamino)methyl]-2-thienyl} phenyl)-4-[(4-methyl-1H-indol-5-yl)amino] nicotinonitrile | 6.9(a) | 464.2 | N/A |
| 308 | 3'-[5-cyano-4-(1H-indol-4-ylamino)pyridin-3-yl]-N-(4-hydroxybutyl)biphenyl-4-carboxamide | 7.9(a) | 502.2 | N/A |
| 309 | 3'-{5-cyano-4-[(4-methyl-1H-indol-5-yl)amino] pyridin-3-yl}-N-(4-hydroxybutyl)biphenyl-4-carboxamide | 8.0(a) | 516.3 | N/A |
| 310 | 4-(1H-indol-4-ylamino)-5-[3-(trifluoromethyl) phenyl]nicotinonitrile | 10.8(a) | 379.1 | N/A |

TABLE 20-continued

| Compound | Compound Name | HPLC Retention Time (min.) | Observed Ion m/e [M + H] | Melting Range (° C.) |
|---|---|---|---|---|
| 311 | 5-(3-cyanophenyl)-4-(1H-indol-4-ylamino)nicotinonitrile | 8.5[a] | 336.1 | N/A |
| 312 | 3-[5-cyano-4-(1H-indol-4-ylamino) pyridin-3-yl]-N,N-dimethylbenzamide | 6.9[a] | 382.2 | N/A |
| 313 | 3-[5-cyano-4-(1H-indol-4-ylamino)pyridin-3-yl]-N,N-dimethylbenzenesulfonamide | 9.0[a] | 418.2 | N/A |
| 314 | 3-[5-cyano-4-(1H-indol-4-ylamino) pyridin-3-yl]benzamide | 5.8[a] | 354.2 | N/A |
| 315 | 5-(3-{5-[(dimethylamino)methyl]-2-thienyl}phenyl)-4-(1H-indol-4-ylamino)nicotinonitrile | 6.1[a] | 450.3 | N/A |
| 316 | 2-[5-cyano-4-(1H-indol-4-ylamino)pyridin-3-yl]-N,N-dimethylbenzenesulfonamide | 6.6[a] | 418.2 | N/A |
| 317 | N-{4-[5-cyano-4-(1H-indol-4-ylamino)pyridin-3-yl]phenyl}methanesulfonamide | 5.9[a] | 404.2 | N/A |
| 318 | 5-(1-benzofuran-2-yl)-4-(1H-indol-4-ylamino)nicotinonitrile | 11.5[a] | 351.2 | N/A |
| 319 | 5-dibenzo[b,d]furan-4-yl-4-(1H-indol-4-ylamino)nicotinonitrile | 10.7[a] | 401.3 | N/A |
| 320 | 4-(1H-indol-4-ylamino)-5-{1-[(4-methylphenyl)sulfonyl]-1H-indol-3-yl}nicotinonitrile | 12.3[a] | 504.3 | N/A |
| 322 | 5-(1-benzothien-2-yl)-4-(1H-indol-4-ylamino)nicotinonitrile | N/A | 367.1 | >245 |
| 323 | 4-(1H-indol-4-ylamino)-5-(4-methoxyphenyl)nicotinonitrile | N/A | 341.2 | 204-206 (decom.) |
| 324 | 4-(1H-indol-4-ylamino)-5-(2-methoxyphenyl)nicotinonitrile | N/A | 341.2 | >245 |
| 325 | 5-(1H-indol-2-yl)-4-(1H-indol-4-ylamino)nicotinonitrile | N/A | 350.2 | 242-244 (decom.) |
| 326 | 4-[5-cyano-4-(1H-indol-4-ylamino)pyridin-3-yl]-N,N-dimethylbenzenesulfonamide | 8.4[a] | 418.3 | N/A |
| 327 | 3-[5-cyano-4-(1H-indol-4-ylamino)pyridin-3-yl]benzoic acid | 6.4[a] | 355.2 | N/A |
| 328 | 5-[3-(aminomethyl)phenyl]-4-(1H-indol-4-ylamino)nicotinonitrile | 4.0[a] | 340.2 | N/A |
| 329 | 5-(3,4-dimethoxyphenyl)-4-[(2-oxo-2,3-dihydro-1H-indol-4-yl)amino]nicotinonitrile | 6.1[a] | 387.2 | N/A |
| 330 | 4-[5-cyano-4-(1H-indol-4-ylamino)pyridin-3-yl]-N-(2-methoxyethyl)benzamide | 6.6[a] | 412.3 | N/A |
| 331 | 4-(1H-indol-4-ylamino)-5-(4-methoxy-3-{2-[(3-phenylpropyl)amino]ethoxy}phenyl)nicotinonitrile | N/A | 518.3 | 202-204 |
| 332 | 5-[4-(2-chloroethoxy)phenyl]-4-(1H-indol-4-ylamino)nicotinonitrile | N/A | 389.2 | 190-191 |
| 333 | 5-[3-(5-formyl-2-thienyl)phenyl]-4-(1H-indol-4-ylamino)nicotinonitrile | 3.2[a] | 421.2 | N/A |
| 334 | 4-(1H-indol-4-ylamino)-5-[4-(2-morpholin-4-ylethoxy)phenyl]nicotinonitrile | N/A | 440.3 | 130-132 |
| 335 | 4-(1H-indol-4-ylamino)-5-{4-[2-(4-methylpiperazin-1-yl)ethoxy]phenyl}nicotinonitrile | N/A | 453.3 | 114-115 |
| 336 | 5-(3,4-dimethoxyphenyl)-4-[(5-methyl-1H-indol-4-yl)amino]nicotinonitrile | N/A | 385.2 | 204-205 |
| 337 | 5-(2,4-dimethoxyphenyl)-4-(1H-indol-4-ylamino)nicotinonitrile | N/A | 374.9 | 192-193 |
| 338 | 4-(1H-indol-4-ylamino)-5-[4-methoxy-3-(2-{[3-(2-oxopyrrolidin-1-yl)propyl]amino}ethoxy)phenyl]nicotinonitrile | 0.7[c] | 525.1 | N/A |
| 339 | 5-[3-(2-{[2-(1H-imidazol-4-yl)ethyl]amino}ethoxy)-4-methoxyphenyl]-4-(1H-indol-4-ylamino)nicotinonitrile | 0.45[c] | 494.0 | N/A |
| 340 | 4-(1H-indol-4-ylamino)-5-(4-methoxy-3-{2-[(3-pyrrolidin-1-ylpropyl)amino]ethoxy}phenyl)nicotinonitrile | 0.43[c] | 571.1 | N/A |
| 341 | 4-(1H-indol-4-ylamino)-5-[4-methoxy-3-(2-{[2-(1-methylpyrrolidin-2-yl)ethyl]amino}ethoxy)phenyl]nicotinonitrile | 0.24[c] | 571.1 | N/A |
| 342 | 5-(4-methoxy-3-{2-[(3-phenylpropyl)amino]ethoxy}phenyl)-4-[(4-methyl-1H-indol-5-yl)amino]nicotinonitrile | 3.0[c] | 531.1 | N/A |
| 343 | 5-{4-methoxy-3-[2-(4-methylpiperazin-1-yl)ethoxy]phenyl}-4-[(4-methyl-1H-indol-5-yl)amino]nicotinonitrile | 2.4[c] | 495.1 | N/A |
| 344 | 5-(3-methoxy-4-{2-[(3-phenylpropyl)amino]ethoxy}phenyl)-4-[(4-methyl-1H-indol-5-yl)amino]nicotinonitrile | 1.6[c] | 532.1 | N/A |

TABLE 20-continued

| Compound | Compound Name | HPLC Retention Time (min.) | Observed Ion m/e [M + H] | Melting Range (° C.) |
|---|---|---|---|---|
| 346 | 5-(3-bromophenyl)-4-[(2-oxo-2,3-dihydro-1H-indol-4-yl)amino]nicotinonitrile | 8.4(a) | 405 | N/A |
| 347 | 4-(1H-indol-4-ylamino)-5-(4-{2-[(3-phenylpropyl)amino]ethoxy}phenyl)nicotinonitrile | N/A | 448.2 | 105-107 |
| 348 | 5-[4-(2-chloroethoxy)phenyl]-4-[(4-methyl-1H-indol-5-yl)amino]nicotinonitrile | N/A | 403.1 | 200-202 |
| 349 | 5-(3,4-dimethoxyphenyl)-4-[(2-methyl-1H-indol-4-yl)amino]nicotinonitrile | N/A | 385.1 | 112-115 |
| 350 | 4-[(4-methyl-1H-indol-5-yl)amino]-5-{4-[2-(4-methylpiperazin-1-yl)ethoxy]phenyl}nicotinonitrile | 4.60(a) | 467.2 | 215-217 (decom.) |
| 351 | 4-[(4-methyl-1H-indol-5-yl)amino]-5-[4-(2-morpholin-4-ylethoxy)phenyl]nicotinonitrile | N/A | 454.2 | 154-156 |
| 352 | 5-(1-benzofuran-3-yl)-4-(1H-indol-4-ylamino)nicotinonitrile | N/A | 357.2 | 238-240 |
| 353 | 4-(1H-indol-4-ylamino)-5-(4-methoxy-3-{2-[(2-phenylethyl)amino]ethoxy}phenyl)nicotinonitrile | N/A | 504.3 | 180-182 |
| 354 | 4-(1H-indol-4-ylamino)-5-(4-methoxy-3-{2-[(2-pyridin-3-ylethyl)amino]ethoxy}phenyl)nicotinonitrile | N/A | 505.4 | 170-172 |
| 355 | 4-[(4-methyl-1H-indol-5-yl)amino]-5-(4-{2-[(3-phenylpropyl)amino]ethoxy}phenyl)nicotinonitrile | N/A | 502.3 | 115-117 |
| 356 | 6'-[3-(dimethylamino)propoxy]-4-(1H-indol-4-ylamino)-3,3'-bipyridine-5-carbonitrile | N/A | 413.2 | 120-122 |
| 357 | 6'-[3-(dimethylamino)propoxy]-4-[(4-methyl-1H-indol-5-yl)amino]-3,3'-bipyridine-5-carbonitrile | N/A | 427.2 | 125-127 |
| 358 | 5-(3-hydroxyphenyl)-4-(1H-indol-4-ylamino)nicotinonitrile | N/A | 325.2 [M − H] | 268-270 |
| 359 | 4-(1H-indol-4-ylamino)-5-[5-(piperazin-1-ylmethyl)-1-benzothien-2-yl]nicotinonitrile | 5.4(a) | 465.1 | N/A |
| 360 | N-({2-[5-cyano-4-(1H-indol-4-ylamino)pyridin-3-yl]-1-benzothien-5-yl}methyl)-b-alaninamide | 5.6(a) | 467.3 | N/A |
| 361 | 4-(1H-indol-4-ylamino)-6'-[(2-morpholin-4-ylethyl)amino]-3,3'-bipyridine-5-carbonitrile | N/A | 440.4 | 148-150 |
| 362 | 4-[(4-methyl-1H-indol-5-yl)amino]-6'-[(2-morpholin-4-ylethyl)amino]-3,3'-bipyridine-5-carbonitrile | N/A | 445.4 | 173-175 |
| 363 | 5-{2-chloro-4-[2-(dimethylamino)ethoxy]phenyl}-4-[(4-methyl-1H-indol-5-yl)amino]nicotinonitrile | 5.2(a) | 446.2 | N/A |
| 364 | 4-(1H-indol-4-ylamino)-5-(4-methoxy-3-{2-[(3-morpholin-4-ylpropyl)amino]ethoxy}phenyl)nicotinonitrile | N/A | 527.4 | 71-74 |
| 365 | 5-[3-(2-{[3-(1H-imidazol-1-yl)propyl]amino}ethoxy)-4-methoxyphenyl]-4-(1H-indol-4-ylamino)nicotinonitrile | N/A | 508.4 | 100-104 |
| 366 | 5-(3-{[(2S)-2-amino-3-phenylpropyl]oxy}phenyl)-4-(1H-indol-4-ylamino)nicotinonitrile | N/A | 460.2 | 90-92 |
| 367 | 5-{5-[(benzylamino)methyl]-1-benzothien-2-yl}-4-[(4-methyl-1H-indol-5-yl)amino]nicotinonitrile | 7.9(a) | N/A | 145-147 |
| 368 | 5-{4-[2-(4-butylpiperazin-1-yl)ethoxy]phenyl}-4-[(4-methyl-1H-indol-5-yl)amino]nicotinonitrile | 5.70(a) | N/A | 158-160 |
| 369 | 5-[5-(1,3-dioxan-2-yl)-1-benzofuran-2-yl]-4-(1H-indol-4-ylamino)nicotinonitrile | N/A | 437.2 | 225-227 (decom.) |
| 370 | 5-[5-(1,3-dioxan-2-yl)-1-benzofuran-2-yl]-4-[(4-methyl-1H-indol-5-yl)amino]nicotinonitrile | N/A | 451.2 | 231-233 (decom.) |
| 371 | 5-(2-chloro-4-methoxyphenyl)-4-[(4-methyl-1H-indol-5-yl)amino]nicotinonitrile | 14.3(a) | 389.2 | N/A |
| 372 | 5-[4-(2-chloroethoxy)-3-methoxyphenyl]-4-[(4-methyl-1H-indol-5-yl)amino]nicotinonitrile | N/A | 433.3 | >245 |
| 373 | 5-(1-benzofuran-2-yl)-4-(1H-indazol-5-ylamino)nicotinonitrile | 10.0(a) | 352.2 | 190-192 |
| 374 | 5-(4-hydroxyphenyl)-4-[(4-methyl-1H-indol-5-yl)amino]nicotinonitrile | 6.5(a) | 341.2 | 240 (decom.) |
| 375 | 5-(2-chloro-6-methoxyphenyl)-4-[(4-methyl-1H-indol-5-yl)amino]nicotinonitrile | 8.8(a) | 389.2 | N/A |
| 376 | 5-[3-methoxy-4-(2-piperidin-1-ylethoxy)phenyl]-4-[(4-methyl-1H-indol-5-yl)amino]nicotinonitrile | N/A | 482.4 | 114-116 |
| 377 | 5-{3-methoxy-4-[2-(4-methylpiperazin-1-yl)ethoxy]phenyl}-4-[(4-methyl-1H-indol-5-yl)amino]nicotinonitrile | N/A | 497.5 | 107-109 |
| 378 | 5-[3-methoxy-4-(2-morpholin-4-ylethoxy)phenyl]-4-[(4-methyl-1H-indol-5-yl)amino]nicotinonitrile | N/A | 484.4 | 113-115 |
| 379 | 5-(3,4-dimethoxyphenyl)-4-(1H-indazol-5-ylamino)nicotinonitrile | N/A | 372.2 | 191-193 |

TABLE 20-continued

| Compound | Compound Name | HPLC Retention Time (min.) | Observed Ion m/e [M + H] | Melting Range (° C.) |
|---|---|---|---|---|
| 380 | 5-(2,3-dichlorophenyl)-4-[(4-methyl-1H-indol-5-yl)amino]nicotinonitrile | 10.1[a] | 393.2 | N/A |
| 381 | 5-(4-bromo-2-fluorophenyl)-4-[(4-methyl-1H-indol-5-yl)amino]nicotinonitrile | 10.2[a] | 421.1 | N/A |

Example 69

Pharmacological Testing

Evaluation of representative compounds of the present teachings in several standard pharmacological test procedures indicated that the compounds are inhibitors of PKCθ. Based on the activity shown in the standard pharmacological test procedures, the compounds of the present teachings are therefore useful as anti-inflammatory agents.

A Radioactive Kinase Assay for Inhibition of the Active Kinase Domain (KD) of PKCθ

This assay is based on the phosphorylation of a biotinylated substrate by a kinase utilizing radiolabeled ATP (ATP γ P33). The substrate was a biotinylated peptide with a sequence of biotin-FARKGSLRQ-C(O)NH$_2$. The enzyme was purified recombinant active kinase domain of full length PKC theta (amino acids 362-706). The assay buffer was composed of 100 mM Hepes, pH7.5, 2 mM MgCl$_2$, 20 mM β-glycerophosphate and 0.008% TritonX 100. A reaction mixture of ATP, ATP γ P33 (PerkinElmer), DTT, and the enzyme was prepared in the assay buffer and added to a 96-well polypropylene plate. The compound (diluted in DMSO in a separate 96-well polypropylene plate) was added to the reaction mixture and incubated at room temperature. Following the incubation, the peptide substrate was added to the reaction mixture to initiate the enzymatic reaction. The reaction was terminated with the addition of a stop solution (100 mM EDTA, 0.2% TritonX100, and 20 mM NaHPO$_4$) and transferred from the assay plate to a washed streptavidin-coated 96-well scintiplate (PerkinElmer). The scintiplate was incubated at room temperature, washed in PBS with 0.1% TritonX 100, and counted in the 1450 Microbeta Trilux (Wallac, Version 2.60). Counts were recorded for each well as corrected counts per minute (CCPM). The counts were considered corrected because they were adjusted according to a P33 normalization protocol, which corrects for efficiency and background differences between the instrument detectors (software version 4.40.01).

A Radioactive Kinase Assay for Inhibition of Full Length (FL) PKCθ Inhibitors

This assay differs from what was described above in that the enzyme used was purified recombinant full length PKC theta (Panvera, P2996).

PKCθ IMAP Assay

The materials used include the following: human PKCθ full length enzyme (Panvera Cat# P2996); substrate peptide: 5FAM-RFARKGSLRQKNV-OH (Molecular Devices, RP7032); ATP (Sigma Cat # A2383); DTT (Pierce, 20291); 5× kinase reaction buffer (Molecular Devices, R7209); 5× binding buffer A (Molecular Devices, R7282), 5× binding buffer B (Molecular Devices, R7209); IMAP Beads (Molecular Devices, R7284); and 384-well plates (Corning Costar, 3710).

The reaction buffer was prepared by diluting the 5× stock reaction buffer and adding DTT to obtain a concentration of 3.0 mM. The binding buffer was prepared by diluting the 5× binding buffer A. A master mix solution was prepared using a 90% dilution of the reaction buffer containing 2×ATP (12 uM) and 2× peptide (200 nm). Compounds were diluted in DMSO to 20× of the maximum concentration for the IC50 measurement. 27 μl of the master mix solution for each IC50 curve was added to the first column in a 384-well plate and 3 μl of 20× compound in DMSO was added to each well. The final concentration of compound was 2× and 10% DMSO. DMSO was added to the rest of the master mix to increase the concentration to 10%. 10 μl of the master mix containing 10% DMSO was added to the rest of the wells on the plate except the 2nd column. 20 μl was transferred from the first column to the 2nd column. The compounds were serially diluted in 2:1 ratio starting from the 2nd column. A 2× (2 mM) PKCθ solution was made in the reaction buffer. 10 μl of the PKCθ solution was added to every well to achieve these final concentrations: PKCθ—1 nM; ATP—6 μM; peptide—100 nM; DMSO—5%. Samples were incubated for 25 minutes at room temperature. The binding reagent was prepared by diluting the beads in 1× binding buffer to 800:1. 50 μl of the binding reagent was added to every well and incubated for 20 minutes. FP was measured using Envision2100 (PerkinElmer Life Sciences). Wells with no ATPs and wells with no enzymes were used as controls.

The results obtained are summarized in Table 21 below. Data presented represent the average value when one or more samples were tested.

TABLE 21

| Compound | IC$_{50}$ PKCθ IMAP (μM) | IC$_{50}$ PKCθ FL (μM) | IC$_{50}$ PKCθKD (μM) |
|---|---|---|---|
| 101 | 0.14 | 0.083 | 0.14 |
| 102 | N/A | N/A | 0.96 |
| 103 | N/A | N/A | 5.68 |
| 104 | N/A | N/A | 6.56 |
| 105 | N/A | N/A | 2.66 |
| 106 | N/A | N/A | 11.4 |
| 107 | 9.32 | N/A | N/A |
| 108 | 0.45 | 2.25 | 1.01 |
| 109 | 0.013 | 0.04 | 0.15 |
| 110 | 0.065 | N/A | N/A |
| 111 | 0.58 | N/A | N/A |
| 112 | 1.13 | N/A | N/A |
| 113 | 0.05 | N/A | N/A |
| 114 | 0.002 | N/A | N/A |
| 115 | 0.31 | N/A | N/A |
| 116 | 0.07 | N/A | N/A |
| 117 | N/A | 0.14 | N/A |
| 118 | N/A | 0.09 | N/A |
| 119 | 0.3 | N/A | N/A |

TABLE 21-continued

| Compound | IC$_{50}$ PKCθ IMAP (μM) | IC$_{50}$ PKCθ FL (μM) | IC$_{50}$ PKCθKD (μM) |
|---|---|---|---|
| 120 | 0.23 | 0.12 | N/A |
| 121 | N/A | 0.17 | N/A |
| 122 | N/A | 0.34 | N/A |
| 123 | 0.18 | N/A | N/A |
| 124 | 1.1 | N/A | N/A |
| 127 | N/A | 0.29 | N/A |
| 128 | 0.13 | N/A | N/A |
| 129 | 0.24 | 0.06 | N/A |
| 130 | 0.16 | 0.08 | N/A |
| 131 | 0.12 | 0.05 | N/A |
| 132 | 0.11 | N/A | N/A |
| 133 | N/A | 0.37 | N/A |
| 134 | N/A | 0.39 | N/A |
| 136 | 0.13 | N/A | N/A |
| 137 | N/A | 0.07 | N/A |
| 138 | 0.19 | 0.1 | N/A |
| 139 | 0.25 | N/A | N/A |
| 140 | 0.11 | N/A | N/A |
| 141 | N/A | 0.09 | N/A |
| 142 | 0.12 | N/A | N/A |
| 143 | N/A | 0.91 | N/A |
| 144 | N/A | 0.91 | N/A |
| 145 | N/A | 1.92 | N/A |
| 146 | N/A | 1.33 | N/A |
| 147 | 0.02 | N/A | N/A |
| 148 | 0.04 | N/A | N/A |
| 149 | 0.07 | N/A | N/A |
| 150 | 0.12 | N/A | N/A |
| 152 | N/A | 1.94 | N/A |
| 153 | N/A | 0.04 | N/A |
| 154 | 0.32 | 0.36 | N/A |
| 155 | N/A | 7.8 | N/A |
| 156 | N/A | >20 | N/A |
| 157 | N/A | 0.55 | N/A |
| 158 | N/A | 37.4 | N/A |
| 159 | 0.016 | 0.06 | N/A |
| 160 | N/A | 0.14 | N/A |
| 161 | N/A | 5.5 | N/A |
| 162 | N/A | 15 | N/A |
| 163 | N/A | 0.32 | N/A |
| 164 | 0.03 | N/A | N/A |
| 165 | N/A | 0.02 | N/A |
| 166 | N/A | 3.83 | N/A |
| 167 | N/A | 0.11 | N/A |
| 168 | 0.02 | N/A | N/A |
| 169 | N/A | 0.03 | N/A |
| 170 | N/A | 0.02 | N/A |
| 171 | 0.05 | N/A | N/A |
| 172 | N/A | 2.59 | N/A |
| 173 | N/A | 2.63 | N/A |
| 174 | N/A | 0.07 | N/A |
| 175 | N/A | 0.1 | N/A |
| 176 | 0.03 | N/A | N/A |
| 177 | 0.02 | N/A | N/A |
| 178 | 0.11 | N/A | N/A |
| 179 | 0.41 | N/A | N/A |
| 180 | 0.69 | N/A | N/A |
| 181 | 0.039 | N/A | N/A |
| 182 | 0.12 | N/A | N/A |
| 183 | 0.07 | N/A | N/A |
| 184 | 0.26 | N/A | N/A |
| 185 | 0.5 | N/A | N/A |
| 186 | 0.14 | N/A | N/A |
| 187 | 0.11 | N/A | N/A |
| 188 | 0.01 | N/A | N/A |
| 189 | 0.03 | N/A | N/A |
| 190 | 0.18 | N/A | N/A |
| 191 | 0.32 | N/A | N/A |
| 192 | 0.28 | N/A | N/A |
| 193 | 0.25 | N/A | N/A |
| 194 | N/A | 0.05 | N/A |
| 195 | 0.25 | N/A | N/A |
| 196 | 0.46 | N/A | N/A |
| 197 | 0.19 | N/A | N/A |
| 198 | 0.33 | N/A | N/A |
| 199 | 1.3 | N/A | N/A |
| 200 | 0.19 | N/A | N/A |
| 201 | 0.3 | N/A | N/A |
| 202 | 0.34 | N/A | N/A |
| 203 | 0.29 | N/A | N/A |
| 204 | N/A | 0.19 | N/A |
| 205 | 0.51 | N/A | N/A |
| 206 | N/A | 1.14 | N/A |
| 207 | N/A | 0.53 | N/A |
| 208 | N/A | 0.39 | N/A |
| 209 | 0.28 | N/A | N/A |
| 210 | 2.58 | N/A | N/A |
| 211 | 0.33 | N/A | N/A |
| 212 | 0.59 | N/A | N/A |
| 213 | 0.27 | N/A | N/A |
| 214 | 0.25 | N/A | N/A |
| 215 | 0.06 | N/A | N/A |
| 216 | 0.05 | N/A | N/A |
| 217 | N/A | 0.36 | N/A |
| 218 | 0.006 | N/A | N/A |
| 219 | 0.27 | N/A | N/A |
| 220 | N/A | >20 | N/A |
| 221 | 1.75 | N/A | N/A |
| 222 | 0.001 | N/A | N/A |
| 223 | 0.006 | N/A | N/A |
| 224 | 0.004 | N/A | N/A |
| 225 | 0.005 | N/A | N/A |
| 226 | 0.003 | N/A | N/A |
| 227 | 0.001 | N/A | N/A |
| 228 | 0.002 | N/A | N/A |
| 229 | 0.008 | N/A | N/A |
| 230 | 0.33 | N/A | N/A |
| 231 | 0.25 | N/A | N/A |
| 232 | 0.2 | N/A | N/A |
| 233 | 0.18 | N/A | N/A |
| 234 | 0.19 | N/A | N/A |
| 235 | 0.24 | N/A | N/A |
| 236 | 0.2 | N/A | N/A |
| 237 | 4.32 | N/A | N/A |
| 238 | 0.21 | N/A | N/A |
| 239 | 0.08 | N/A | N/A |
| 240 | 0.08 | N/A | N/A |
| 241 | 0.08 | N/A | N/A |
| 242 | 0.02 | N/A | N/A |
| 243 | 0.23 | N/A | N/A |
| 244 | 0.17 | N/A | N/A |
| 245 | 0.27 | N/A | N/A |
| 246 | 0.16 | N/A | N/A |
| 247 | 0.1 | N/A | N/A |
| 248 | 0.05 | N/A | N/A |
| 249 | 0.03 | N/A | N/A |
| 250 | 0.02 | N/A | N/A |
| 251 | 0.04 | N/A | N/A |
| 252 | 0.03 | N/A | N/A |
| 253 | 0.05 | N/A | N/A |
| 254 | 0.08 | N/A | N/A |
| 255 | 0.08 | N/A | N/A |
| 256 | 0.02 | N/A | N/A |
| 257 | 0.1 | N/A | N/A |
| 258 | 0.1 | N/A | N/A |
| 259 | 1.37 | N/A | N/A |
| 260 | 0.07 | N/A | N/A |
| 261 | 0.08 | N/A | N/A |
| 262 | 0.12 | N/A | N/A |
| 263 | 0.05 | N/A | N/A |
| 264 | 0.06 | N/A | N/A |
| 265 | 3.86 | N/A | N/A |
| 266 | 1.45 | N/A | N/A |
| 267 | 0.1 | N/A | N/A |
| 268 | 0.01 | N/A | N/A |
| 269 | 10.9 | N/A | N/A |
| 270 | 0.02 | N/A | N/A |
| 271 | 0.1 | N/A | N/A |
| 272 | 0.004 | N/A | N/A |
| 273 | 0.002 | N/A | N/A |
| 274 | 0.002 | N/A | N/A |
| 275 | 0.002 | N/A | N/A |

TABLE 21-continued

| Compound | IC$_{50}$ PKCθ IMAP (μM) | IC$_{50}$ PKCθ FL (μM) | IC$_{50}$ PKCθKD (μM) |
|---|---|---|---|
| 276 | 0.002 | N/A | N/A |
| 277 | 0.003 | N/A | N/A |
| 278 | 0.002 | N/A | N/A |
| 279 | 0.001 | N/A | N/A |
| 280 | 0.004 | N/A | N/A |
| 281 | 0.01 | N/A | N/A |
| 282 | 0.003 | N/A | N/A |
| 283 | 0.002 | N/A | N/A |
| 284 | 0.004 | N/A | N/A |
| 285 | 0.004 | N/A | N/A |
| 286 | 0.001 | N/A | N/A |
| 287 | 0.003 | N/A | N/A |
| 288 | 0.003 | N/A | N/A |
| 289 | 0.004 | N/A | N/A |
| 290 | 0.004 | N/A | N/A |
| 291 | 4.86 | N/A | N/A |
| 292 | 13.2 | N/A | N/A |
| 293 | 36 | N/A | N/A |
| 294 | 33.4 | N/A | N/A |
| 295 | 2.95 | N/A | N/A |
| 296 | 16.2 | N/A | N/A |
| 298 | 0.004 | N/A | N/A |
| 299 | 0.03 | N/A | N/A |
| 300 | 0.02 | N/A | N/A |
| 301 | 0.05 | N/A | N/A |
| 302 | 0.03 | N/A | N/A |
| 303 | 0.04 | N/A | N/A |
| 304 | 0.11 | N/A | N/A |
| 305 | 0.06 | N/A | N/A |
| 306 | 0.06 | N/A | N/A |
| 308 | 0.03 | N/A | N/A |
| 309 | 0.12 | N/A | N/A |
| 310 | 0.02 | N/A | N/A |
| 311 | 0.02 | N/A | N/A |
| 312 | 0.6 | N/A | N/A |
| 313 | 0.02 | N/A | N/A |
| 314 | 0.1 | N/A | N/A |
| 315 | 0.01 | N/A | N/A |
| 316 | 1.35 | N/A | N/A |
| 317 | 0.02 | N/A | N/A |
| 318 | 0.01 | N/A | N/A |
| 319 | 0.06 | N/A | N/A |
| 320 | 0.03 | N/A | N/A |
| 322 | 0.02 | N/A | N/A |
| 323 | 0.02 | N/A | N/A |
| 324 | 0.02 | N/A | N/A |
| 325 | 0.06 | N/A | N/A |
| 326 | 0.19 | N/A | N/A |
| 327 | 0.12 | N/A | N/A |
| 328 | 0.02 | N/A | N/A |
| 329 | 8.21 | N/A | N/A |
| 330 | 0.13 | N/A | N/A |
| 332 | 0.008 | N/A | N/A |
| 334 | 0.03 | N/A | N/A |
| 335 | 0.01 | N/A | N/A |
| 336 | 0.2 | N/A | N/A |
| 337 | 0.1 | N/A | N/A |
| 338 | 0.008 | N/A | N/A |
| 339 | 0.01 | N/A | N/A |
| 340 | 0.008 | N/A | N/A |
| 341 | 0.003 | N/A | N/A |
| 342 | 0.001 | N/A | N/A |
| 343 | 0.01 | N/A | N/A |
| 344 | 0.008 | N/A | N/A |
| 345 | 0.007 | N/A | N/A |
| 346 | 0.54 | N/A | N/A |
| 347 | 0.004 | N/A | N/A |
| 348 | 0.004 | N/A | N/A |
| 349 | 0.13 | N/A | N/A |
| 350 | 0.008 | N/A | N/A |
| 351 | 0.02 | N/A | N/A |
| 352 | 0.02 | N/A | N/A |
| 353 | 0.001 | N/A | N/A |
| 354 | 0.004 | N/A | N/A |
| 355 | 0.003 | N/A | N/A |
| 356 | 0.04 | N/A | N/A |
| 357 | 0.03 | N/A | N/A |
| 358 | 0.01 | N/A | N/A |
| 359 | 0.02 | N/A | N/A |
| 360 | 0.002 | N/A | N/A |
| 361 | 0.04 | N/A | N/A |
| 362 | 0.05 | N/A | N/A |
| 363 | 0.02 | N/A | N/A |
| 364 | 0.01 | N/A | N/A |
| 365 | 0.004 | N/A | N/A |
| 366 | 0.02 | N/A | N/A |
| 367 | 0.003 | N/A | N/A |
| 368 | 0.01 | N/A | N/A |
| 369 | 0.04 | N/A | N/A |
| 370 | 0.004 | N/A | N/A |
| 371 | 0.03 | N/A | N/A |
| 372 | 0.007 | N/A | N/A |
| 373 | 1 | N/A | N/A |
| 374 | 0.02 | N/A | N/A |
| 375 | 0.15 | N/A | N/A |
| 376 | 0.02 | N/A | N/A |
| 377 | 0.01 | N/A | N/A |
| 378 | 0.03 | N/A | N/A |
| 379 | 2.53 | N/A | N/A |
| 380 | 0.05 | N/A | N/A |
| 381 | 0.02 | N/A | N/A |
| 382 | 0.006 | N/A | N/A |
| 383 | 0.002 | N/A | N/A |
| 384 | 0.002 | N/A | N/A |
| 385 | 0.002 | N/A | N/A |
| 386 | 0.005 | N/A | N/A |
| 387 | 0.001 | N/A | N/A |
| 388 | 0.013 | N/A | N/A |
| 389 | 0.003 | N/A | N/A |
| 390 | 0.001 | N/A | N/A |
| 391 | 0.001 | N/A | N/A |
| 392 | 0.005 | N/A | N/A |
| 393 | 0.001 | N/A | N/A |
| 394 | 0.001 | N/A | N/A |
| 395 | 0.004 | N/A | N/A |
| 396 | 0.002 | N/A | N/A |
| 397 | 0.013 | N/A | N/A |
| 398 | 0.003 | N/A | N/A |
| 399 | 0.002 | N/A | N/A |
| 400 | 0.002 | N/A | N/A |
| 401 | 0.008 | N/A | N/A |
| 402 | 0.041 | N/A | N/A |
| 403 | 0.005 | N/A | N/A |
| 404 | 0.004 | N/A | N/A |
| 405 | 0.009 | N/A | N/A |
| 406 | 0.042 | N/A | N/A |
| 407 | 0.020 | N/A | N/A |
| 408 | 0.011 | N/A | N/A |
| 409 | 0.027 | N/A | N/A |
| 410 | 0.035 | N/A | N/A |
| 411 | 0.008 | N/A | N/A |
| 412 | 0.010 | N/A | N/A |
| 413 | 0.055 | N/A | N/A |
| 414 | 0.004 | N/A | N/A |
| 415 | 0.005 | N/A | N/A |
| 416 | 0.006 | N/A | N/A |
| 417 | 0.006 | N/A | N/A |
| 418 | 0.004 | N/A | N/A |
| 419 | 0.004 | N/A | N/A |
| 420 | 0.003 | N/A | N/A |
| 421 | 0.003 | N/A | N/A |
| 422 | 0.008 | N/A | N/A |
| 423 | 0.011 | N/A | N/A |
| 424 | 0.004 | N/A | N/A |
| 425 | 0.009 | N/A | N/A |
| 426 | 0.013 | N/A | N/A |
| 427 | 0.014 | N/A | N/A |
| 428 | 0.015 | N/A | N/A |
| 429 | 0.005 | N/A | N/A |
| 430 | 0.017 | N/A | N/A |
| 431 | 0.005 | N/A | N/A |
| 432 | 0.009 | N/A | N/A |

TABLE 21-continued

| Compound | IC$_{50}$ PKCθ IMAP (μM) | IC$_{50}$ PKCθ FL (μM) | IC$_{50}$ PKCθKD (μM) |
|---|---|---|---|
| 433 | 0.010 | N/A | N/A |
| 434 | 0.014 | N/A | N/A |
| 435 | 0.049 | N/A | N/A |
| 436 | 0.001 | N/A | N/A |
| 437 | 0.002 | N/A | N/A |
| 438 | 0.004 | N/A | N/A |
| 439 | 5.845 | N/A | N/A |
| 440 | 14.321 | N/A | N/A |
| 441 | 0.529 | N/A | N/A |
| 442 | 1.765 | N/A | N/A |
| 443 | 1.125 | N/A | N/A |
| 444 | 2.458 | N/A | N/A |
| 445 | 20.423 | N/A | N/A |
| 446 | 4.880 | N/A | N/A |
| 447 | 1.934 | N/A | N/A |
| 448 | 14.064 | N/A | N/A |
| 449 | 0.005 | N/A | N/A |
| 450 | 0.016 | N/A | N/A |
| 451 | 0.009 | N/A | N/A |
| 452 | 0.008 | N/A | N/A |
| 453 | 0.060 | N/A | N/A |
| 454 | 0.003 | N/A | N/A |
| 455 | 0.007 | N/A | N/A |
| 456 | 0.023 | N/A | N/A |
| 457 | 0.007 | N/A | N/A |
| 458 | 0.014 | N/A | N/A |
| 459 | 0.006 | N/A | N/A |
| 461 | 0.001 | N/A | N/A |
| 462 | 0.0002 | N/A | N/A |
| 464 | 0.006 | N/A | N/A |
| 465 | 0.001 | N/A | N/A |
| 466 | 0.017 | N/A | N/A |
| 467 | 0.036 | N/A | N/A |
| 468 | 0.004 | N/A | N/A |
| 469 | 0.031 | N/A | N/A |
| 470 | 0.107 | N/A | N/A |
| 471 | 0.156 | N/A | N/A |
| 472 | 0.019 | N/A | N/A |
| 473 | 0.024 | N/A | N/A |
| 474 | 0.013 | N/A | N/A |
| 475 | 0.009 | N/A | N/A |
| 477 | 0.072 | N/A | N/A |
| 478 | 0.011 | N/A | N/A |
| 481 | 0.00021 | N/A | N/A |
| 482 | 0.011 | N/A | N/A |
| 483 | 0.036 | N/A | N/A |
| 485 | 0.005 | N/A | N/A |
| 486 | 0.004 | N/A | N/A |
| 487 | 0.016 | N/A | N/A |
| 488 | 2.023 | N/A | N/A |
| 490 | 0.051 | N/A | N/A |
| 491 | 0.015 | N/A | N/A |
| 492 | 0.061 | N/A | N/A |
| 496 | 0.033 | N/A | N/A |
| 497 | 0.007 | N/A | N/A |
| 498 | 0.016 | N/A | N/A |
| 499 | 0.003 | N/A | N/A |
| 500 | 0.005 | N/A | N/A |
| 501 | 0.089 | N/A | N/A |
| 502 | 0.021 | N/A | N/A |
| 503 | 0.012 | N/A | N/A |
| 504 | 0.084 | N/A | N/A |
| 505 | 0.076 | N/A | N/A |
| 506 | 0.083 | N/A | N/A |
| 507 | 0.030 | N/A | N/A |
| 508 | 0.078 | N/A | N/A |
| 509 | 0.261 | N/A | N/A |
| 510 | 0.300 | N/A | N/A |
| 511 | 0.083 | N/A | N/A |
| 512 | 0.215 | N/A | N/A |
| 513 | 0.125 | N/A | N/A |
| 514 | 0.023 | N/A | N/A |
| 516 | 0.005 | N/A | N/A |
| 517 | 0.008 | N/A | N/A |
| 518 | 0.005 | N/A | N/A |
| 519 | 0.036 | N/A | N/A |
| 520 | 0.073 | N/A | N/A |
| 521 | 0.001 | N/A | N/A |
| 522 | 0.020 | N/A | N/A |
| 523 | 0.737 | N/A | N/A |
| 524 | 4.095 | N/A | N/A |
| 525 | 0.007 | N/A | N/A |
| 526 | 0.010 | N/A | N/A |
| 527 | 0.027 | N/A | N/A |
| 528 | 0.040 | N/A | N/A |
| 529 | 0.002 | N/A | N/A |
| 530 | 0.179 | N/A | N/A |
| 531 | 0.020 | N/A | N/A |
| 533 | 0.051 | N/A | N/A |
| 534 | 0.017 | N/A | N/A |
| 535 | 0.038 | N/A | N/A |
| 536 | 0.058 | N/A | N/A |
| 537 | 0.023 | N/A | N/A |
| 538 | 0.015 | N/A | N/A |
| 539 | 0.036 | N/A | N/A |
| 540 | 0.005 | N/A | N/A |
| 541 | 0.007 | N/A | N/A |
| 542 | 0.042 | N/A | N/A |
| 543 | 0.008 | N/A | N/A |
| 544 | 0.737 | N/A | N/A |
| 545 | 0.011 | N/A | N/A |
| 546 | 0.005 | N/A | N/A |
| 547 | 0.004 | N/A | N/A |
| 548 | 0.406 | N/A | N/A |
| 549 | 0.010 | N/A | N/A |
| 550 | 0.205 | N/A | N/A |
| 551 | 0.028 | N/A | N/A |
| 552 | 0.084 | N/A | N/A |
| 553 | 0.00048 | N/A | N/A |
| 554 | 0.006 | N/A | N/A |
| 555 | 0.226 | N/A | N/A |
| 556 | 0.110 | | |
| 557 | 0.082 | N/A | N/A |
| 558 | 0.036 | N/A | N/A |
| 559 | 0.006 | N/A | N/A |
| 560 | 0.027 | N/A | N/A |
| 561 | 0.021 | N/A | N/A |
| 562 | 0.012 | N/A | N/A |
| 563 | 0.022 | N/A | N/A |
| 564 | 0.098 | N/A | N/A |
| 565 | 0.022 | N/A | N/A |
| 566 | 0.023 | N/A | N/A |
| 567 | 0.021 | N/A | N/A |
| 568 | 0.056 | N/A | N/A |
| 569 | 0.059 | N/A | N/A |
| 570 | 0.016 | N/A | N/A |
| 571 | 0.016 | N/A | N/A |
| 572 | 0.050 | N/A | N/A |
| 573 | 0.057 | N/A | N/A |
| 574 | 0.015 | N/A | N/A |
| 575 | 0.036 | N/A | N/A |
| 576 | 0.073 | N/A | N/A |
| 577 | 0.036 | N/A | N/A |
| 578 | 0.097 | N/A | N/A |
| 579 | 4.728 | N/A | N/A |
| 580 | 0.016 | N/A | N/A |
| 581 | 0.023 | N/A | N/A |
| 582 | 0.092 | N/A | N/A |
| 583 | 0.061 | N/A | N/A |
| 584 | 0.043 | N/A | N/A |
| 585 | 0.088 | N/A | N/A |
| 586 | 0.0087 | N/A | N/A |
| 587 | 0.036 | N/A | N/A |
| 588 | 0.057 | N/A | N/A |
| 589 | 0.1913 | N/A | N/A |
| 590 | 0.972 | N/A | N/A |
| 591 | 0.0197 | N/A | N/A |
| 592 | 0.0069 | N/A | N/A |
| 593 | 0.1205 | N/A | N/A |
| 594 | 0.038 | N/A | N/A |
| 595 | 0.046 | N/A | N/A |

Variations, modifications, and other implementations of what is described herein will occur to those of ordinary skill in the art without departing from the spirit and the essential characteristics of the present teachings. Accordingly, the scope of the present invention is to be defined not by the preceding illustrative description but instead by the following claims, and all changes that come within the meaning and range of equivalency of the claims are intended to be embraced therein.

What is claimed is:

1. A compound of formula I or formula I':

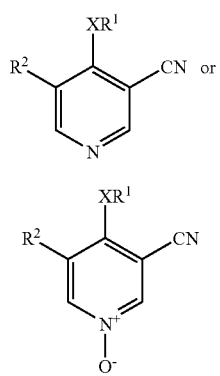

or a pharmaceutically acceptable salt, or ester thereof, wherein:

X is selected from $NR^3$—Y—, —O—Y and a covalent bond;

Y, at each occurrence, independently is selected from a divalent $C_{1-10}$ alkyl group and a covalent bond;

$R^1$ is an indolyl group, optionally substituted with 1-4 groups selected from halogen, oxo, —O—Y—$R^5$, —$NR^6$—Y—$R^7$, a $C_{1-10}$ alkyl group and a $C_{1-10}$ haloalkyl group;

$R^2$ is a $C_{6-14}$ aryl group or a 5-14-membered heteroaryl group selected from furyl, thienyl, benzothienyl, benzofuranyl, pyrazolyl, pyridyl, indolyl, quinolinyl, pyrimidinyl, imidazolyl, thiazolyl, isothiazolyl, oxazolyl, isoxazolyl, dibenzothienyl, dibenzofuranyl, benzodioxolyl and benzodioxanyl, wherein each group optionally is substituted with 1-4 groups independently selected from —Y—$R^4$ or —O—Y—$R^4$;

$R^3$ is H, or a $C_{1-10}$ alkyl group;

$R^4$, at each occurrence, independently is selected from a) halogen, b) —CN, c) —$NO_2$, d) oxo, e) —O—Y—$R^5$, f) —$NR^6$—Y—$R^7$, g) —N(O)$R^6$—Y—$R^7$, h) —S(O)$_m$—Y—$R^5$, i) —S(O)$_m$O—Y—$R^5$, j) —S(O)$_m$$NR^6$—Y—$R^7$, k) —C(O)—Y—$R^5$, l) —C(O)O—Y—$R^5$, m) —C(O)$NR^6$—Y—$R^7$, n) —C(S)$NR^6$—Y—$R^7$, o) a $C_{1-10}$ alkyl group, r) a $C_{1-10}$haloalkyl group, s) a $C_{3-14}$ cycloalkyl group, t) a $C_{6-14}$ aryl group, u) a 3-14 membered cycloheteroalkyl group, and v) a 5-14 membered heteroaryl group, wherein each of o)-v) optionally is substituted with 1-4-Y—$R^8$ groups;

$R^5$, at each occurrence, independently is selected from a) H, b) —C(O)$R^9$, c) —C(O)O$R^9$, d) a $C_{1-10}$ alkyl group, g) a $C_{1-10}$ haloalkyl group, h) a $C_{3-14}$ cycloalkyl group, i) a $C_{6-14}$ aryl group, j) a 3-14 membered cycloheteroalkyl group, and k) a 5-14 membered heteroaryl group, wherein each of d)-k) optionally is substituted with 1-4-Y—$R^8$ groups;

$R^6$ and $R^7$, at each occurrence, independently are selected from a) H, b) —O—Y—$R^9$, c) —S—(O)$_m$—Y—$R^9$, d) —S(O)$_m$O—Y—$R^9$, e) —C(O)—Y—$R^9$, f) —C(O)O—Y—$R^9$, g) —C(O)$NR^{10}$—Y—$R^{11}$, h) —C(S)$NR^{10}$—Y—$R^{11}$, i) a $C_{1-10}$ alkyl group, l) a $C_{1-10}$ haloalkyl group, m) a $C_{3-14}$ cycloalkyl group, n) a $C_{6-14}$ aryl group, o) a 3-14 membered cycloheteroalkyl group, and p) a 5-14 membered heteroaryl group; wherein each of i)-p) optionally is substituted with 1-4-Y—$R^8$ groups;

$R^8$, at each occurrence, independently is selected from a) halogen, b) —CN, c) —$NO_2$, d) oxo, e) —O—Y—$R^9$, f) —$NR^{10}$—Y—$R^{11}$, g) —N(O)$R^{10}$—Y—$R^{11}$, h) —S(O)$_m$—Y—$R^9$, i) —S(O)$_m$—Y—$R^9$, j) —S(O)$_m$$NR^{10}$—Y—$R^{11}$, k) —C(O)—Y—$R^9$, l) —C(O)O—Y—$R^9$, m) —C(O)$NR^{10}$—Y—$R^{11}$, n) —C(S)$NR^{10}$—Y—$R^{11}$, o) a $C_{1-10}$ alkyl group, r) a $C_{1-10}$ haloalkyl group, s) a $C_{3-14}$ cycloalkyl group, t) a $C_{6-14}$ aryl group, u) a 3-14 membered cycloheteroalkyl group, and v) a 5-14 membered heteroaryl group, wherein each of o)-v) optionally is substituted with 1-4-Y—$R^{12}$ groups;

$R^9$, at each occurrence, independently is selected from a) H, b) —C(O)—$C_{1-10}$ alkyl, c) —C(O)OH, d) —C(O)O—$C_{1-10}$ alkyl, e) a $C_{1-10}$ alkyl group, h) a $C_{1-10}$ haloalkyl group, i) a $C_{3-14}$ cycloalkyl group, j) a $C_{6-14}$ aryl group, k) a 3-14 membered cycloheteroalkyl group, and l) a 5-14 membered heteroaryl group, wherein each of the $C_{1-10}$ alkyl group, the $C_{1-10}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-4-Y—$R^{12}$ groups;

$R^{10}$ and $R^{11}$, at each occurrence, independently are selected from a) H, b) —OH, c) —SH, d) —$NH_2$, e) —NH—$C_{1-10}$ alkyl, f) —N($C_{1-10}$ alkyl)$_2$, g) —S(O)$_m$—$C_{1-10}$ alkyl, h) —S(O)$_2$OH, i) —S(O)$_m$—O$C_{1-10}$ alkyl, j) —C(O)—$C_{1-10}$ alkyl, k) —C(O)OH, l) —C(O)—O$C_{1-10}$ alkyl, m) —C(O)$NH_2$, n) —C(O)NH—$C_{1-10}$ alkyl, o) —C(O)N($C_{1-10}$ alkyl)$_2$, p) —C(S)$NH_2$, q) —C(S)NH—$C_{1-10}$ alkyl r) —C(S)N($C_{1-10}$ alkyl)$_2$, s) a $C_{1-10}$ alkyl group, v) a $C_{1-10}$ alkoxy group, w) a $C_{1-10}$ haloalkyl group, x) a $C_{3-14}$ cycloalkyl group, y) a $C_{6-14}$ aryl group, z) a 3-14 membered cycloheteroalkyl group, and aa) a 5-14 membered heteroaryl group, wherein each of the $C_{1-10}$ alkyl group, the $C_{1-10}$ alkoxy group, the $C_{1-10}$ haloalkyl group, the $C_{3-14}$ cycloalkyl group, the $C_{6-14}$ aryl group, the 3-14 membered cycloheteroalkyl group, and the 5-14 membered heteroaryl group optionally is substituted with 1-4-Y—$R^{12}$ groups;

$R^{12}$, at each occurrence, independently is selected from a) halogen, b) —CN, c) —$NO_2$, d) oxo, e) —OH, f) —$NH_2$, g) —NH($C_{1-10}$ alkyl), h) —N($C_{1-10}$ alkyl)$_2$, i) —SH, j) —S(O)$_m$—$C_{1-10}$ alkyl, k) —S(O)$_2$OH, l) —S(O)$_m$—O$C_{1-10}$ alkyl, m) —C(O)—$C_{1-10}$ alkyl, n) —C(O)OH, o) —C(O)—O$C_{1-10}$ alkyl, p) —C(O)$NH_2$, q) —C(O)NH—$C_{1-10}$ alkyl, r) —C(O)N($C_{1-10}$ alkyl)$_2$, s) —C(S)$NH_2$, t) —C(S)NH—$C_{1-10}$ alkyl, u) —C(S)N($C_{1-10}$ alkyl)$_2$, v) a $C_{1-10}$ alkyl group, y) a $C_{1-10}$ alkoxy group, z) a $C_{1-10}$ haloalkyl group, aa) a $C_{3-14}$ cycloalkyl group, ab) a $C_{6-14}$ aryl group, ac) a 3-14 membered cycloheteroalkyl group, and ad) a 5-14 membered heteroaryl group; and m is 0, 1, or 2.

2. The compound of claim 1 or a pharmaceutically acceptable salt, or ester thereof, wherein X is selected from —NH—, —N($CH_3$)—, —NH—$CH_2$—, —NH—$CH_2CH_2$—, —NH—$CH_2CH_2CH_2$, —O—, and a covalent bond.

3. The compound of claim 1 or 2 or a pharmaceutically acceptable salt, or ester thereof, wherein $R^1$ is an indolyl group, wherein each group optionally is substituted with 1-4 groups selected from halogen, oxo, —O—Y—$R^5$, $NR^6Y$—$R^7$, a $C_{1-10}$ alkyl group and a $C_{1-10}$ haloalkyl group.

4. The compound of claim 1 or 2 or a pharmaceutically acceptable salt, or ester thereof, wherein $R^1$ is an indolyl group, each of which optionally is substituted with 1-4 groups selected from halogen, —O—Y—$R^5$, $NR^6Y$—$R^7$, a $C_{1-10}$ alkyl group and a $C_{1-10}$ haloalkyl group.

5. The compound of claim 1 or 2 or a pharmaceutically acceptable salt, or ester thereof, wherein $R^1$ is a 1H-indol-4-yl group, a 1H-indol-5-yl group, a 1H-indol-6-yl group, or a 1H-indol-7-yl group, wherein each group optionally is substituted with 1-4 groups independently selected from a halogen, a $C_{1-4}$ alkyl group, and a $C_{1-4}$ alkoxy group.

6. The compound of claims 1 or 2 or a pharmaceutically acceptable salt, or ester thereof, wherein $R^2$ is a phenyl group, a naphthyl group or a tetrahydronaphthyl group, wherein each group optionally is substituted with 1-4 groups independently selected from —Y—$R^4$ and —O—Y—$R^4$.

7. The compound of claim 1 or 2 or a pharmaceutically acceptable salt, or ester thereof, wherein $R^2$ is:

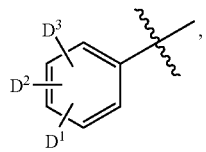

wherein $D^1$, $D^2$, and $D^3$ independently are H, a —Y—$R^4$ group, or an —O—Y—$R^4$ group.

8. The compound of claim 7 or a pharmaceutically acceptable salt, or ester thereof, wherein at least one of $D^1$, $D^2$, and $D^3$ is a —Y—$R^4$ group or an —O—Y—$R^4$ group, wherein Y, at each occurrence, independently is a divalent $C_{1-4}$ alkyl group or a covalent bond, and $R^4$, at each occurrence, independently is selected from a halogen, CN, $NO_2$, —O—Y—$R^5$, $NR^6$—Y—$R^7$, —S(O)$_2$—Y—$R^5$, —S(O)$_2NR^6$—Y—$R^7$, —C(O)—Y—$R^5$, —C(O)O—Y—$R^5$, —C(O)$NR^6$—Y—$R^7$, a $C_{1-10}$ alkyl group, a $C_{1-10}$ haloalkyl group, a $C_{3-14}$ cycloalkyl group, a $C_{6-14}$ aryl group, a 3-14 membered cycloheteroalkyl group, and a 5-14 membered heteroaryl group, wherein each of the $C_{1-10}$ alkyl group, the $C_{1-10}$ haloalkyl group, the $C_{3-14}$ cycloalkyl group, the $C_{6-14}$ aryl group, the 3-14 membered cycloheteroalkyl group, and the 5-14 membered heteroaryl group is optionally substituted with 1-4-Y—$R^8$ groups.

9. The compound of claim 8 or a pharmaceutically acceptable salt, or ester thereof, wherein the —Y—$R^4$ group and the —O—Y—$R^4$ group are selected from —O—(CH$_2$)$_n$NR$^6$—Y—$R^7$, —(CH$_2$)$_n$NR$^6$—Y—$R^7$, an —O—(CH$_2$)$_n$-3-14 membered cycloheteroalkyl group, and a —(CH$_2$)$_n$-3-14 membered cycloheteroalkyl group, wherein each of the 3-14 membered cycloheteroalkyl group optionally is substituted with 1-4-Y—$R^8$ groups, and n, at each occurrence, independently is 0, 1, 2, 3, or 4.

10. The compound of claim 9 or a pharmaceutically acceptable salt, or ester thereof, wherein the 3-14 membered cycloheteroalkyl group of the —O—(CH$_2$)$_n$-3-14 membered cycloheteroalkyl group and the (CH$_2$)$_n$-3-14 membered cycloheteroalkyl group is selected from a pyrrolidinyl group, a morpholinyl group, a piperazinyl group, a piperidinyl group, an azepanyl group, a diazepanyl group, and a thiomorpholinyl group.

11. The compound of claim 8 or a pharmaceutically acceptable salt, or ester thereof, wherein the —Y—$R^4$ group and the —O—Y—$R^4$ group are

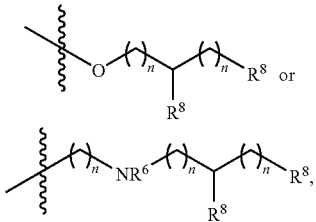

wherein $R^8$, at each occurrence, independently is selected from —O—Y—$R^9$, —$NR^{10}$—Y—$R^{11}$ aryl group, and a 5-14 membered heteroaryl group, wherein the $C_{6-14}$ aryl group and the 5-14 membered heteroaryl group optionally are substituted with 1-4-Y—$R^{12}$ groups, and n, at each occurrence, independently is 0, 1, 2, 3, or 4.

12. The compound of claim 8 or 9 or a pharmaceutically acceptable salt, or ester thereof, wherein at least one of $D^1$, $D^2$, and $D^3$ is selected from a halogen, —CN, —$NO_2$, —S(O)$_2$—Y—$R^5$, —S(O)$_2$$NR^8$—Y—$R^7$, —C(O)O—Y—$R^5$, —C(O)$NR^8$—Y—$R^7$, a $C_{1-10}$ alkyl group, and a $C_{1-10}$ haloalkyl group.

13. The compound of claim 8 or 9 or a pharmaceutically acceptable salt, or ester thereof, wherein at least one of $D^1$, $D^2$, and $D^3$ is a $C_{6-14}$ aryl group or a 5-14 membered heteroaryl group, wherein each group optionally is substituted with 1-4-Y—$R^8$ groups.

14. The compound of claim 13 or a pharmaceutically acceptable salt, or ester thereof, wherein at least one of $D^1$, $D^2$, and $D^3$ is selected from a benzothienyl group, a benzofuryl group, a furyl group, a pyridyl group, a pyrimidinyl group, a pyrrolyl group, and a thienyl group, wherein each group optionally is substituted with 1-4-Y—$R^8$ groups, Y, at each occurrence, is independently a $C_{1-4}$ alkyl group or a covalent bond, and $R^8$, at each occurrence, is independently selected from halogen, —CN, —$NO_2$, —O—Y—$R^9$, —C(O)$NR^{10}$—Y—$R^{11}$, —S(O)$_2$—Y—$R^9$, —S(O)$_2NR^{10}$—Y—$R^{11}$, and a 3-14 membered cycloheteroalkyl group optionally substituted with a $C_{1-4}$ alkyl group.

15. The compound of claim 1 or 2 or a pharmaceutically acceptable salt, or ester thereof, wherein $R^2$ is pyridyl group, a pyrimidyl group, a pyrazinyl group, a furyl group, a thienyl group, a thiazolyl group, an oxazolyl group, a benzofuranyl group, a benzothienyl group, an indolyl group, a benzodioxolyl group, a benzodioxanyl group, a dibenzofuranyl group, a dibenzothienyl group, an isothiazolyl group, a pyrazolyl group, an isoxazolyl group, a quinolinyl group or an imidazolyl group, wherein each group optionally is substituted with 1-4 groups independently selected from —Y—$R^4$ and —O—Y—$R^4$.

16. The compound of claim 15 or a pharmaceutically acceptable salt, or ester thereof, wherein each $R^2$ optionally is substituted with 1-4 groups independently selected from —(CH$_2$)$_n$—$R^4$ and —O—(CH$_2$)$_n$—$R^4$, wherein n, at each occurrence, independently is 0, 1, 2, 3, or 4, and $R^4$, at each occurrence, independently is —$NR^8$—Y—$R^7$ or a 3-14 membered cycloheteroalkyl group optionally substituted with a —Y—$R^8$ group.

17. A compound of claim 1 selected from the following compounds:

5-(3,4-dimethoxyphenyl)-4-(1H-indol-5-ylamino)nicotinonitrile, 5-(3,4-dimethoxyphenyl)-4-(1H-indol-6-ylamino)nicotinonitrile,
5-(3,4-dimethoxyphenyl)-4-(1H-indol-4-ylamino)nicotinonitrile,
5-(3,4-dimethoxyphenyl)-4-[(2-methyl-1H-indol-5-yl)amino]nicotinonitrile,
5-(3-bromophenyl)-4-(1H-indol-5-ylamino)nicotinonitrile,
5-(3-bromophenyl)-4-(1H-indol-4-ylamino)nicotinonitrile,
5-(2-bromophenyl)-4-(1H-indol-5-ylamino)nicotinonitrile,
5-(4-bromophenyl)-4-(1H-indol-5-ylamino)nicotinonitrile,
5-(3'-aminobiphenyl-3-yl)-4-(1H-indol-5-ylamino)nicotinonitrile,
5-(4'-cyanobiphenyl-3-yl)-4-(1H-indol-5-ylamino)nicotinonitrile,
5-(4'-aminobiphenyl-3-yl)-4-(1H-indol-5-ylamino)nicotinonitrile,
N-{3'-[5-cyano-4-(1H-indol-5-ylamino)pyridin-3-yl]biphenyl-4-yl}acetamide,
4-(1H-indol-5-ylamino)-5-(3-pyridin-4-ylphenyl)nicotinonitrile,
3'-[5-cyano-4-(1H-indol-5-ylamino)pyridin-3-yl]-N,N-dimethylbiphenyl-4-carboxamide,
3'-[5-cyano-4-(1H-indol-5-ylamino)pyridin-3-yl]-N-cyclopentylbiphenyl-4-carboxamide,
4-(1H-indol-5-ylamino)-5-[3-(1H-pyrrol-3-yl)phenyl]nicotinonitrile,
5-(2-bromophenyl)-4-[(7-methyl-1H-indol-5-yl)amino]nicotinonitrile,
5-(2-bromophenyl)-4-(1H-indol-4-ylamino)nicotinonitrile,
4-(1H-indol-5-ylamino)-5-(3'-methylbiphenyl-3-yl)nicotinonitrile,
4-(1H-indol-5-ylamino)-5-(4'-methylbiphenyl-3-yl)nicotinonitrile,
5-(2'-chlorobiphenyl-3-yl)-4-(1H-indol-5-ylamino)nicotinonitrile,
5-(3'-chlorobiphenyl-3-yl)-4-(1H-indol-5-ylamino)nicotinonitrile,
5-(4'-chlorobiphenyl-3-yl)-4-(1H-indol-5-ylamino)nicotinonitrile,
5-(3'-cyanobiphenyl-3-yl)-4-(1H-indol-5-ylamino)nicotinonitrile,
3'-[5-cyano-4-(1H-indol-5-ylamino)pyridin-3-yl]biphenyl-3-carboxylic acid,
3'-[5-cyano-4-(1H-indol-5-ylamino)pyridin-3-yl]biphenyl-4-carboxylic acid,
3'-[5-cyano-4-(1H-indol-4-ylamino)pyridin-3-yl]biphenyl-4-carboxylic acid,
4-(1H-indol-5-ylamino)-5-[3-(2-thienyl)phenyl]nicotinonitrile,
4-(1H-indol-5-ylamino)-5-(3-pyridin-3-ylphenyl)nicotinonitrile,
4-(1H-indol-5-ylamino)-5-(3-pyrimidin-2-ylphenyl)nicotinonitrile,
4-(1H-indol-5-ylamino)-5-[3-(4-methyl-2-thienyl)phenyl]nicotinonitrile,
5-[3-(5-acetyl-2-thienyl)phenyl]-4-(1H-indol-5-ylamino)nicotinonitrile,
4-(1H-indol-5-ylamino)-5-[3-(3-thienyl)phenyl]nicotinonitrile,
5-[3-(3-furyl)phenyl]-4-(1H-indol-5-ylamino)nicotinonitrile,
5-(2'-chlorobiphenyl-2-yl)-4-(1H-indol-5-ylamino)nicotinonitrile,
5-(3'-chlorobiphenyl-2-yl)-4-(1H-indol-5-ylamino)nicotinonitrile,
5-(4'-chlorobiphenyl-2-yl)-4-(1H-indol-5-ylamino)nicotinonitrile,
4-(1H-indol-5-ylamino)-5-[2-(3-thienyl)phenyl]nicotinonitrile,
4-(1H-indol-4-ylamino)-5-[3-(2-thienyl)phenyl]nicotinonitrile,
3'-[5-cyano-4-(1H-indol-4-ylamino)pyridin-3-yl]-N-cyclopentylbiphenyl-4-carboxamide,
4-(1H-indol-4-ylamino)-5-[4'-(pyrrolidin-1-ylcarbonyl)biphenyl-3-yl]nicotinonitrile,
5-[3-(5-formyl-2-thienyl)phenyl]-4-(1H-indol-5-ylamino)nicotinonitrile,
4-(1H-indol-5-ylamino)-5-(3-nitrophenyl)nicotinonitrile,
N-{3-[5-cyano-4-(1H-indol-5-ylamino)pyridin-3-yl]phenyl}acetamide,
4-(1H-indol-4-ylamino)-5-[4-methoxy-3-(2-methoxyethoxy)phenyl]nicotinonitrile,
4-(1H-indol-5-ylamino)-5-[4-methoxy-3-(2-methoxyethoxy)phenyl]nicotinonitrile,
4-(1H-indol-6-ylamino)-5-[4-methoxy-3-(2-methoxyethoxy)phenyl]nicotinonitrile,
5-[4-methoxy-3-(2-methoxyethoxy)phenyl]-4-[(2-methyl-1H-indol-5-yl)amino]nicotinonitrile,
4-(1H-indol-4-ylamino)-5-[3-methoxy-4-(2-methoxyethoxy)phenyl]nicotinonitrile,
4-(1H-indol-5-ylamino)-5-[3-methoxy-4-(2-methoxyethoxy)phenyl]nicotinonitrile,
4-(1H-indol-6-ylamino)-5-[3-methoxy-4-(2-methoxyethoxy)phenyl]nicotinonitrile,
5-[3-methoxy-4-(2-methoxyethoxy)phenyl]-4-[(2-methyl-1H-indol-5-yl)amino]nicotinonitrile,
4-(1H-indol-4-ylamino)-5-[3-(2-methoxyethoxy)phenyl]nicotinonitrile,
5-[3-(2-chloroethoxy)phenyl]-4-(1H-indol-4-ylamino)nicotinonitrile,
5-[3-(2-chloroethoxy)phenyl]-4-(1H-indol-6-ylamino)nicotinonitrile,
5-[3-(2-chloroethoxy)phenyl]-4-(1H-indol-5-ylamino)nicotinonitrile,
4-(1H-indol-4-ylamino)-5-{3-[2-(4-methylpiperazin-1-yl)ethoxy]phenyl}nicotinonitrile,
4-(1H-indol-4-ylamino)-5-[3-(2-pyrrolidin-1-ylethoxy)phenyl]nicotinonitrile,
4-(1H-indol-4-ylamino)-5-[3-(2-morpholin-4-ylethoxy)phenyl]nicotinonitrile,
4-(1H-indol-4-ylamino)-5-[3-(2-piperidin-1-ylethoxy)phenyl]nicotinonitrile,
4-(1H-indol-6-ylamino)-5-[3-(2-pyrrolidin-1-ylethoxy)phenyl]nicotinonitrile,
4-(1H-indol-6-ylamino)-5-[3-(2-morpholin-4-ylethoxy)phenyl]nicotinonitrile,
4-(1H-indol-5-ylamino)-5-[3-(2-pyrrolidin-1-ylethoxy)phenyl]nicotinonitrile,
4-(1H-indol-5-ylamino)-5-[3-(2-morpholin-4-ylethoxy)phenyl]nicotinonitrile,
5-(3-{2-[(2-hydroxyethyl)amino]ethoxy}phenyl)-4-(1H-indol-5-ylamino)nicotinonitrile,
4-(1H-indol-5-ylamino)-5-(3-{2-[(2-pyrrolidin-1-ylethyl)amino]ethoxy}phenyl)nicotinonitrile,
5-[3-(2-chloroethoxy)-4-methoxyphenyl]-4-(1H-indol-5-ylamino) nicotinonitrile,
5-{3-[2-(diethylamino)ethoxy]-4-methoxyphenyl}-4-(1H-indol-5-ylamino) nicotinonitrile, 5-{3-[2-(diisopropylamino)ethoxy]-4-methoxyphenyl}-4-(1H-indol-5-ylamino) nicotinonitrile,
5-{3-[2-(benzylamino)ethoxy]-4-methoxyphenyl}-4-(1H-indo-5-ylamino) nicotinonitrile,
4-(1H-indol-5-ylamino)-5-(4-methoxy-3-{2-[(2-methoxyethyl)amino]ethoxy}phenyl)nicotinonitrile,
4-(1H-indol-5-ylamino)-5-(4-methoxy-3-{2-[(5-methyl-1,3,4-thiadiazol-2-yl) amino]ethoxy}phenyl)nicotinonitrile,
4-(1H-indol-5-ylamino)-5-(3-{5-[(4-methylpiperazin-1-yl)methyl]-2-thienyl}phenyl)nicotinonitrile,
4-(1H-indol-5-ylamino)-5-{3-[5-(morpholin-4-ylmethyl)-2-thienyl]phenyl}nicotinonitrile,
4-(1H-indol-5-ylamino)-5-{3-[5-(piperidin-1-ylmethyl)-2-thienyl]phenyl}nicotinonitrile,
5-(3-{5-[(dimethylamino)methyl]-2-thienyl}phenyl)-4-(1H-indol-5-ylamino)nicotinonitrile,
5-(3-bromo-4-methoxyphenyl)-4-(1H-indol-5-ylamino) nicotinonitrile,
4-(1H-indol-5-ylamino)-5-[4-methoxy-3-(2-thienyl)phenyl]nicotinonitrile,
5-(4'-chloro-6-methoxybiphenyl-3-yl)-4-(1H-indol-5-ylamino)nicotinonitrile,
5-(3'-chloro-6-methoxybiphenyl-3-yl)-4-(1H-indol-5-ylamino)nicotinonitrile,
5'-[5-cyano-4-(1H-indol-5-ylamino)pyridin-3-yl]-N-cyclopentyl-2'-methoxy biphenyl-4-carboxamide,
5-(2'-chloro-6-methoxybiphenyl-3-yl)-4-(1H-indol-5-ylamino)nicotinonitrile,
5-[3-(benzyloxy)phenyl]-4-(1H-indol-5-ylamino)nicotinonitrile,
5-[4-(benzyloxy)phenyl]-4-(1H-indol-5-ylamino)nicotinonitrile,
3'-[5-cyano-4-(1H-indol-5-ylamino)pyridin-3-yl]-N-methylbiphenyl-4-carboxamide,
N-butyl-3'-[5-cyano-4-(1H-indol-5-ylamino)pyridin-3-yl]biphenyl-4-carboxamide,
3'-[5-cyano-4-(1H-indol-5-ylamino)pyridin-3-yl]-N-(1-ethylpropyl)biphenyl-4-carboxamide,
3'-[5-cyano-4-(1H-indol-5-ylamino)pyridin-3-yl]-N-(2-hydroxyethyl)biphenyl-4-carboxamide,
3'-[5-cyano-4-(1H-indol-5-ylamino)pyridin-3-yl]-N-(2-methoxyethyl)biphenyl-4-carboxamide,
3'-[5-cyano-4-(1H-indol-5-ylamino)pyridin-3-yl]-N-cyclopropylbiphenyl-4-carboxamide,
3'-[5-cyano-4-(1H-indol-5-ylamino)pyridin-3-yl]-N-cyclohexyl)biphenyl-4-carboxamide,
3'-[5-cyano-4-(1H-indol-5-ylamino)pyridin-3-yl]-N-(2-pyrrolidin-1-yl ethyl)biphenyl-4-carboxamide,
N-benzyl-3'-[5-cyano-4-(1H-indol-5-ylamino)pyridin-3-yl]biphenyl-4-carboxamide,
4-(1H-indol-5-ylamino)-5-[4'-(pyrrolidin-1-ylcarbonyl)biphenyl-3-yl]nicotinonitrile,
4-(1H-indol-5-ylamino)-5-[4'-(morpholin-4-ylcarbonyl)biphenyl-3-yl]nicotinonitrile,
4-(1H-indol-5-ylamino)-5-{4'-[(4-methylpiperazin-1-yl)carbonyl]biphenyl-3-yl}nicotinonitrile,
3'-[5-cyano-4-(1H-indol-5-ylamino)pyridin-3-yl]-N-cyclopentylbiphenyl-3-carboxamide,
3'-[5-cyano-4-(1H-indol-5-ylamino)pyridin-3-yl]-N-(4-hydroxybutyl)biphenyl-4-carboxamide,
3'-[5-cyano-4-(1H-indol-5-ylamino)pyridin-3-yl]-N-(3-hydroxypropyl)biphenyl-4-carboxamide,
3'-[5-cyano-4-(1H-indol-5-ylamino)pyridin-3-yl]-N-[2-(methylamino)ethyl]biphenyl-4-carboxamide,
3'-[5-cyano-4-(1H-indol-5-ylamino)pyridin-3-yl]-N-(pyridin-2-ylmethyl) biphenyl-4-carboxamide,
3'-[5-cyano-4-(1H-indol-5-ylamino)pyridin-3-yl]-N-(pyridin-3-ylmethyl) biphenyl-4-carboxamide,
3'-[5-cyano-4-(1H-indol-5-ylamino)pyridin-3-yl]-N-(pyridin-4-ylmethyl) biphenyl-4-carboxamide,
N-butyl-3'-[5-cyano-4-(1H-indol-4-ylamino)pyridin-3-yl]biphenyl-4-carboxamide,
3'-[5-cyano-4-(1H-indol-4-ylamino)pyridin-3-yl]-N-(2-hydroxyethyl)biphenyl-4-carboxamide,
5-(3,4-dimethoxyphenyl)-4-[(7-methyl-1H-indol-5-yl) amino]nicotinonitrile,
5-(3,4-dimethoxyphenyl)-4-[(4-methyl-1H-indol-5-yl) amino]nicotinonitrile,
5-(3,4-dimethoxyphenyl)-4-[1H-indol-5-yl(methyl) amino]nicotinonitrile,
5-(3,4-dimethoxyphenyl)-4-(1H-indol-5-yloxy)nicotinonitrile,
5-(3,4-dimethoxyphenyl)-4-(1H-indol-5-yl)nicotinonitrile,
5-(1-benzofuran-2-yl)-4-[(4-methyl-1H-indol-5-yl) amino]nicotinonitrile,
5-(5-formyl-1-benzothien-2-yl)-4-(1H-indol-4-ylamino) nicotinonitrile,
5-{5-[(dimethylamino)methyl]-1-benzothien-2-yl}-4-(1H-indol-4-ylamino nicotinonitrile,
5-(4-hydroxyphenyl)-4-(1H-indol-4-ylamino)nicotinonitrile,
5-(4-{[(2S)-2-amino-3-phenylpropyl]oxy}phenyl)-4-(1H-indol-4-ylamino) nicotinonitrile,
5-(5-formyl-1-benzothien-2-yl)-4-[(4-methyl-1H-indol-5-yl)amino]nicotinonitrile,
4-[(4-methyl-1H-indol-5-yl)amino]-5-[5-(piperidin-1-ylmethyl)-1-benzothien-2-yl]nicotinonitrile,
5-[5-(hydroxymethyl)-1-benzothien-2-yl]-4-[(4-methyl-1H-indol-5-yl)amino]nicotinonitrile,
4-(1H-indol-5-ylamino)-5-[4-methoxy-3-(2-morpholin-4-ylethoxy)phenyl]nicotinonitrile,
4-(1H-indol-5-ylamino)-5-{4-methoxy-3-[2-(4-methylpiperazin-1-yl)ethoxy]phenyl}nicotinonitrile,
4-(1H-indol-5-ylamino)-5-[4-methoxy-3-(2-piperazin-1-ylethoxy)phenyl]nicotinonitrile,
4-(1H-indol-5-ylamino)-5-[4-methoxy-3-(2-thiomorpholin-4-ylethoxy)phenyl]nicotinonitrile,
5-{3-[2-(4-ethylpiperazin-1-yl)ethoxy]-4-methoxyphenyl}-4-(1H-indol-5-ylamino)nicotinonitrile,
4-(1H-indol-5-ylamino)-5-[4-methoxy-3-(2-piperidin-1-ylethoxy)phenyl]nicotinonitrile,
5-{3-[2-(dimethylamino)ethoxy]-4-methoxyphenyl}-4-(1H-indol-5-ylamino) nicotinonitrile,
5-(3-{2-[bis(2-hydroxyethyl)amino]ethoxy}-4-methoxyphenyl)-4-(1H-indol-5-ylamino)nicotinonitrile,
5-{3-[2-(4-hydroxypiperidin-1-yl)ethoxy]-4-methoxyphenyl}-4-(1H-indol-5-ylamino)nicotinonitrile,
4-(1H-indol-5-ylamino)-5-(4-methoxy-3-{2-[(pyridin-3-ylmethyl)amino]ethoxy}phenyl)nicotinonitrile,
4-(1H-indol-5-ylamino)-5-(4-methoxy-3-{2-[(pyridin-4-ylmethyl)amino]ethoxy}phenyl)nicotinonitrile,
4-(1H-indol-5-ylamino)-5-(4-methoxy-3-{2-[(pyridin-2-ylmethyl)amino]ethoxy}phenyl)nicotinonitrile,
4-(1H-indol-5-ylamino)-5-(4-methoxy-3-{2-[(2-phenylethyl)amino]ethoxy}phenyl)nicotinonitrile,
5-{3-[2-(cyclopentylamino)ethoxy]-4-methoxyphenyl}-4-(1H-indol-5-yl amino) nicotinonitrile,
5-{3-[2-(cyclohexylamino)ethoxy]-4-methoxyphenyl}-4-(1H-indol-5-yl amino) nicotinonitrile,
5-(3-{2-[(2-furylmethyl)amino]ethoxy}-4-methoxyphenyl)-4-(1H-indol-5-yl amino)nicotinonitrile, 5-(2-bromo-4,5-dimethoxyphenyl)-4-(1H-indol-5-ylamino)nicotinonitrile,
5-(2-bromo-4,5-dimethoxyphenyl)-4-[(4-methyl-1H-indol-5-yl)amino]nicotinonitrile,
4-(1H-indol-4-ylamino)-5-[4-methoxy-3-(2-piperidin-1-ylethoxy)phenyl]nicotinonitrile,
5-(3-{2-[(2-hydroxyethyl)amino]ethoxy}-4-methoxyphenyl)-4-(1H-indol-4-yl amino)nicotinonitrile,
4-(1H-indol-5-ylamino)-5-(4-methoxy-3-{2-[(3-phenylpropyl)amino]ethoxy}phenyl)nicotinonitrile,
4-(1H-indol-5-ylamino)-5-(4-methoxy-3-{2-[(2-pyridin-2-ylethyl)amino]ethoxy}phenyl)nicotinonitrile,
4-(1H-indol-5-ylamino)-5-(4-methoxy-3-{2-[(2-pyridin-3-ylethyl)amino]ethoxy}phenyl)nicotinonitrile,
4-(1H-indol-5-ylamino)-5-(4-methoxy-3-{2-[(2-pyridin-4-ylethyl)amino]ethoxy}phenyl)nicotinonitrile.
5-[3-(dimethylamino)phenyl]-4-(1H-indol-4-ylamino)nicotinonitrile,
4-(1H-indol-4-ylamino)-5-[3-(methylsulfonyl)phenyl]nicotinonitrile,
N-{3-[5-cyano-4-(1H-indol-4-ylamino)pyridin-3-yl]phenyl}methane sulfonamide,
4-(1H-indol-5-ylamino)-5-phenylnicotinonitrile,
4-(1H-indol-5-ylamino)-5-(3-thienyl)nicotinonitrile,
4-(1H-indol-5-ylamino)-3,3'-bipyridine-5-carbonitrile,
5-(1,3-benzodioxol-5-yl)-4-(1H-indol-5-ylamino)nicotinonitrile,
4-(1H-indol-5-ylamino)-3,4'-bipyridine-5-carbonitrile,
5-(3-furyl)-4-(1H-indol-5-ylamino)nicotinonitrile,
5-(1H-indol-5-yl)-4-(1H-indol-5-ylamino)nicotinonitrile,
5-(2,3-dihydro-1,4-benzodioxin-6-yl)-4-(1H-indol-5-ylamino)nicotinonitrile,
4-(1H-indol-5-ylamino)-5-pyrimidin-5-ylnicotinonitrile,
4-(1H-indol-5-ylamino)-5-(2-methoxypyrimidin-5-yl)nicotinonitrile,
4-(1H-indol-5-ylamino)-5-(2-thienyl)nicotinonitrile,
5-(1-benzofuran-2-yl)-4-(1H-indol-5-ylamino)nicotinonitrile,
5-(3,5-dimethylisoxazol-4-yl)-4-(1H-indol-5-ylamino)nicotinonitrile,
5-[3-(hydroxymethyl)phenyl]-4-(1H-indol-4-ylamino)nicotinonitrile,
5-{3-(dimethylamino)methy]phenyl}-4-(1H-indol-4-ylamino)nicotinonitrile,
4-(1H-indol-4-ylamino)-5-{5-[(prop-2-yn-1-ylamino)methyl]-1-benzothien-2-yl}nicotinonitrile,
5-{5-[(butylamino)methyl]-1-benzothien-2-yl}-4-(1H-indol-4-ylamino) nicotinonitrile,
5-(5-{[(2-hydroxyethyl)amino]methyl}-1-benzothien-2-O-4-(1H-indol-4-yl amino)nicotinonitrile,
5-(5-{[(3-hydroxypropyl)amino]methyl}-1-benzothien-2-yl)-4-(1H-indol-4-yl amino)nicotinonitrile,
4-(1H-indol-4-ylamino)-5-(5-{[(3-methoxypropyl)amino]methyl}-1-benzothien-2-yl)nicotinonitrile,
5-(5-{[(4-hydroxybutyl)amino]methyl}-1-benzothien-2-yl)-4-(1H-indol-4-ylamino)nicotinonitrile,
5-{5-[(cyclopropylamino)methyl]-1-benzothien-2-yl}-4-(1H-indol-4-ylamino) nicotinonitrile,
5-(5-{[(cyclopropylmethyl)amino]methyl}-1-benzothien-2-yl)-4-(1H-indol-4-ylamino)nicotinonitrile,
4-(1H-indol-4-ylamino)-5-[5-(pyrrolidin-1-ylmethyl)-1-benzothien-2-yl]nicotinonitrile,
4-(1H-indol-4-ylamino)-5-[5-(morpholin-4-ylmethyl)-1-benzothien-2-yl]nicotinonitrile,
4-(1H-indol-4-ylamino)-5-(5-{[(2-morpholin-4-ylethyl)amino]methyl}-1-benzothien-2-yl)nicotinonitrile,
4-(1H-indol-4-ylamino)-5-[5-(piperidin-1-ylmethyl)-1-benzothien-2-yl]nicotinonitrile,
5-(5-{[4-(hydroxymethyl)piperidin-1-yl]methyl}-1-benzothien-2-yl)-4-(1H-indol-4-ylamino)nicotinonitrile,
5-[5-(hydroxymethyl)-1-benzothien-2-yl]-4-(1H-indol-4-ylamino) nicotinonitrile,
5-{5-[(benzylamino)methyl]-1-benzothien-2-yl}-4-(1H-indol-4-ylamino) nicotinonitrile,
4-(1H-indol-4-ylamino)-5-(5-{[(2-phenylethyl)amino]methyl}-1-benzothien-2-yl)nicotinonitrile,
4-(1H-indol-4-ylamino)-5-(5-{[(pyridin-2-ylmethyl)amino]methyl}-1-benzothien-2-yl)nicotinonitrile,
4-(1H-indol-4-ylamino)-5-(5-{[(pyridin-3-ylmethyl)amino]methyl}-1-benzothien-2-yl)nicotinonitrile,
4-(1H-indol-4-ylamino)-5-(5-{[(pyridin-4-ylmethyl)amino]methyl}-1-benzothien-2-yl)nicotinonitrile,
5-(3-bromophenyl)-4-[(4-methyl-1H-indol-5-yl)amino]nicotinonitrile,
4-(1H-indol-4-ylamino)-5-[4-methoxy-3-(2-morpholin-4-ylethoxy)phenyl]nicotinonitrile,
4-(1H-indol-4-ylamino)-5-{4-methoxy-3-[2-(4-methylpiperazin-1-yl)ethoxy]phenyl}nicotinonitrile,
5-{3-[2-(dimethylamino)ethoxy]-4-methoxyphenyl}-4-(1H-indol-4-ylamino) nicotinonitrile,
5-{3-[2-(4-hydroxypiperidin-1H)ethoxy]-4-methoxyphenyl}-4-(1H-indol-4-ylamino)nicotinonitrile,
5-[3-(2-chloroethoxy)-4-methoxyphenyl]-4-(1H-indol-4-ylamino) nicotinonitrile,
4-[(4-methyl-1H-indol-5-yl)amino]-5-[3-(2-thienyl)phenyl]nicotinonitrile,
5-(3,4-dimethoxyphenyl)-4-[(4-ethyl-1H-indol-5-yl)amino]nicotinonitrile,
5-[3-{5-formyl-2-thienyl}phenyl]-4-[(4-methyl-1H-indol-5-yl)amino]nicotinonitrile,
5-(3-{5-[(dimethylamino)methyl]-2-thienyl}phenyl)-4-[(4-methyl-1H-indol-5-yl)amino]nicotinonitrile,
3'-[5-cyano-4-(1H-indol-4-ylamino)pyridin-3-yl]-N-(4-hydroxybutyl)biphenyl-4-carboxamide,
3'-{5-cyano-4-[(4-methyl-1H-indol-5-yl)amino]pyridin-3-yl}-N-(4-hydroxy butyl)biphenyl-4-carboxamide,
4-(1H-indol-4-ylamino)-5-[3-(trifluoromethyl)phenyl]nicotinonitrile,
5-(3-cyanophenyl)-4-(1H-indol-4-ylamino)nicotinonitrile,
3-[5-cyano-4-(1H-indol-4-ylamino)pyridin-3-yl]-N,N-dimethylbenzamide,
3-[5-cyano-4-(1H-indol-4-ylamino)pyridin-3-yl]-N,N-dimethyl benzenesulfonamide,
3-[(5-cyano-4-(1H-indol-4-ylamino)pyridin-3-yl]benzamide,
5-(3-{5-[(dimethylamino)methyl]-2-thienyl}phenyl)-4-(1H-indol-4-yl amino)nicotinonitrile,
2-[5-cyano-4-(1H-indol-4-ylamino)pyridin-3-yl]-N,N-dimethyl benzenesulfonamide,
N-{4-[5-cyano-4-(1H-indol-4-ylamino)pyridin-3-yl]phenyl}methanesulfonamide,
5-(1-benzofuran-2-yl)-4-(1H-indol-4-ylamino)nicotinonitrile,
5-dibenzo[b,d]furan-4-yl-4-(1H-indol-4-ylamino)nicotinonitrile,
4-(1H-indol-4-ylamino)-5-{1-[(4-methylphenyl)sulfonyl]-1H-indol-3-yl}nicotinonitrile,
5-(1-benzothien-2-yl)-4-(1H-indol-4-ylamino)nicotinonitrile,
4-(1H-indol-4-ylamino)-5-(4-methoxyphenyl)nicotinonitrile, 4-(1H-indol-4-ylamino)-5-(2-methoxyphenyl)nicotinonitrile,
5-(1H-indol-2-yl)-4-(1H-indol-4-ylamino)nicotinonitrile,
4-[5-cyano-4-(1H-indol-4-ylamino)pyridin-3-yl]-N,N-dimethyl benzenesulfonamide,
3-[5-cyano-4-(1H-indol-4-ylamino)pyridin-3-yl]benzoic acid,
5-[3-(aminomethyl)phenyl]-4-(1H-indol-4-ylamino)nicotinonitrile,
5-(3,4-dimethoxyphenyl)-4-[(2-oxo-2,3-dihydro-1H-indol-4-yl)amino]nicotinonitrile,
4-[5-cyano-4-(1H-indol-4-ylamino)pyridin-3-yl]-N-(2-methoxyethyl)benzamide,
4-(1H-indol-4-ylamino)-5-(4-methoxy-3-{2-[(3-phenylpropyl)amino]ethoxy}phenyl)nicotinonitrile,
5-[4-(2-chloroethoxy)phenyl]-4-(1H-indol-4-ylamino)nicotinonitrile,
5-[3-(5-formyl-2-thienyl)phenyl]-4-(1H-indol-4-ylamino)nicotinonitrile,
4-(1H-indol-4-ylamino)-5-[(4-(2-morpholin-4-ylethoxy)phenyl]nicotinonitrile,
4-(1H-indol-4-ylamino)-5-{4-[2-(4-methylpiperazin-1-yl)ethoxy]phenyl}nicotinonitrile,
5-(3,4-dimethoxyphenyl)-4-[(5-methyl-1H-indol-4-yl]-amino)nicotinonitrile,
5-(2,4-dimethoxyphenyl)-4-(1H-indol-4-ylamino)nicotinonitrile,
4-(1H-indol-4-ylamino)-5-(4-methoxy-3-(2-[([3-(2-oxopyrrolidin-1-yl)propyl]amino}ethoxy)phenyl]nicotinonitrile,
5-[3-(2-{[2-(1H-imidazol-4-yl)ethyl]amino}ethoxy)-4-methoxyphenyl]-4-(1H-indol-4-ylamino)nicotinonitrile,
4-(1H-indol-4-ylamino)-5-(4-methoxy-3-{2-[(3-pyrrolidin-1-ylpropyl)amino]ethoxy}phenyl)nicotinonitrile,
4-(1H-indol-4-ylamino)-5-[4-methoxy-3-(2-{[2-(1-methylpyrrolidin-2-yl)ethyl]amino}ethoxy)phenyl]nicotinonitrile,
5-(4-methoxy-3-{2-[(3-phenylpropyl)amino]ethoxy}phenyl)-4-[(4-methyl-1H-indol-5-yl)amino]nicotinonitrile,
5-{4-methoxy-3-[2-(4-methylpiperazin-1-yl)ethoxy]phenyl}-4-[(4-methyl-1H-indol-5-yl)amino]nicotinonitrile,
5-(3-methoxy-4-{2-[(3-phenylpropyl)amino]ethoxy}phenyl)-4-[(4-methyl-1H-indol-5-yl)amino]nicotinonitrile,
5-{4-[2-(dimethylamino)ethoxy]-3-methoxyphenyl}-4-[(4-methyl-1H-indol-5-yl)amino]nicotinonitrile,
5-(3-bromophenyl)-4-[(2-oxo-2,3-dihydro-1H-indol-4-yl)amino]nicotinonitrile,
4-(1H-indol-4-ylamino)-5-(4-{2-[(3-phenylpropyl)amino]ethoxy}phenyl)nicotinonitrile,
5-[4-(2-chloroethoxy)phenyl]-4-[(4-methyl-1H-indol-5-yl)amino]nicotinonitrile,
5-(3,4-dimethoxyphenyl)-4-[(2-methyl-1H-indol-4-yl)amino]nicotinonitrile,
4-[(4-methyl-1H-indol-5-yl)amino]-5-{4-[2-(4-methylpiperazin-1-yl)ethoxy]phenyl}nicotinonitrile,
4-[(4-methyl-1H-indol-5-yl)amino]-5-[4-(2-morpholin-4-ylethoxy)phenyl]nicotinonitrile,
5-(1-benzofuran-3-yl)-4-(1H-indol-4-ylamino)nicotinonitrile,
4-(1H-indol-4-ylamino)-5-(4-methoxy-3-{2-[(2-phenylethyl)amino]ethoxy}phenyl)nicotinonitrile,
4-(1H-indol-4-ylamino)-5-(4-methoxy-3-{2-[(2-pyridin-3-ylethyl)amino]ethoxy}phenyl)nicotinonitrile, 4-[(4-methyl-1H-indol-5-yl)amino]-5-(4-{2-[(3-phenylpropyl)amino]ethoxy}phenyl)nicotinonitrile,
6'-[3-(dimethylamino)propoxy]-4-(1H-indol-4-ylamino)-3,3'-bipyridine-5-carbonitrile,
6'-[3-(dimethylamino)propoxy]-4-[(4-methyl-1H-indol-5-yl)amino]-3,3'-bipyridine-5-carbonitrile,
5-(3-hydroxyphenyl)-4-(1H-indol-4-ylamino)nicotinonitrile,
4-(1H-indol-4-ylamino)-5-[5-(piperazin-1-ylmethyl)-1-benzothien-2-yl]nicotinonitrile,
N-({2-[5-cyano-4-(1H-indol-4-ylamino)pyridin-3-yl]-1-benzothien-5-yl}methyl)-b-alaninamide,
4-(1H-indol-4-ylamino)-6'-[(2-morpholin-4-ylethyl)amino]-3,3'-bipyridine-5-carbonitrile,
4-[(4-methyl-1H-indol-5-yl)amino]-6'-[(2-morpholin-4-ylethyl)amino]-1-3,3'-bipyridine-5-carbonitrile,
5-{2-chloro-4-[2-(dimethylamino)ethoxy]phenyl}-4-[(4-methy-1H-indol-5-yl)amino]nicotinonitrile,
4-(1H-indol-4-ylamino)-5-(4-methoxy-3-{2-[(3-morpholin-4-ylpropyl)amino]ethoxy}phenyl)nicotinonitrile,
5-[3-(2-{[3-(1H-imidazol-1-yl)propyl]amino}ethoxy)-4-methoxyphenyl]-4-(1H-indol-4-ylamino)nicotinonitrile,
5-(3-{[(2S)-2-amino-3-phenylpropyl]oxy}phenyl)-4-(1H-indol-4-ylamino) nicotinonitrile,
5-{5-[(benzylamino)methyl]-1-benzothien-2-yl}-4-[(4-methyl-1H-indol-5-yl) amino]nicotinonitrile,
5-{4-[2-(4-butylpiperazin-1-yl)ethoxy]phenyl}-4-[(4-methyl-1H-indol-5-yl) amino]nicotinonitrile,
5-[5-(1,3-dioxan-2-yl)-1-benzofuran-2-yl]-4-(1H-indol-4-ylamino) nicotinonitrile,
5-[5-(1,3-dioxan-2-yl)-1-benzofuran-2-yl]-4-[(4-methyl-1H-indol-5-yl)amino]nicotinonitrile,
5-(2-chloro-4-methoxyphenyl)-4-[(4-methyl-1H-indol-5-yl)amino]nicotinonitrile,
5-[4-(2-chloroethoxy)-3-methoxyphenyl]-4-[(4-methyl-1H-indol-5-yl)amino]nicotinonitrile,
5-(4-hydroxyphenyl)-4-[(4-methyl-1H-indol-5-yl)amino]nicotinonitrile,
5-(2-chloro-6-methoxyphenyl)-4-[(4-methyl-1H-indol-5-yl)amino]nicotinonitrile,
5-[3-methoxy-4-(2-pipendin-1-ylethoxy)phenyl]-4-[(4-methyl-1H-indol-5-yl) amino]nicotinonitrile,
5-{3-methoxy-4-[2-(4-methylpiperazin-1-yl)ethoxy]phenyl}-4-[(4-methyl-1H-indol-5-yl)amino]nicotinonitrile,
5-[3-methoxy-4-(2-morpholin-4-ylethoxy)phenyl]-4-[(4-methyl-1H-indol-5-yl)amino]nicotinonitrile,
5-(2,3-dichlorophenyl)-4-[(4-methyl-1H-indol-5-yl)amino]nicotinonitrile,
5-(4-bromo-2-fluorophenyl)-4-[(4-methyl-1H-indol-5-yl)amino]nicotinonitrile,
5-{5-[(dimethylamino)methyl]-1-benzofuran-2-yl}-4-[(4-methyl-1H-indol-5-yl) amino]nicotinonitrile,
5-(5-{[(2-hydroxyethyl)amino]methyl}-1-benzofuran-2-yl)-4-[(4-methyl-1H-indol-5-yl)amino]nicotinonitrile,
5-(5-{[(3-hydroxypropyl)amino]methyl}-1-benzofuran-2-yl)-4-[(4-methyl-1H-indol-5-yl)amino]nicotinonitrile,
5-(5-{[(2,3-dihydroxypropyl)amino]methyl}-1-benzofuran-2-yl)-4-[(4-methyl-1H-indol-5-yl)amino]nicotinonitrile,
5-(5-{[(2,3-dihydroxypropyl)(methyl)amino]methyl}-1-benzofuran-2-yl)-4-[(4-methyl-1H-indol-5-yl)amino] nicotinonitrile,
5-{5-[(cyclohexylamino)methyl]-1-benzofuran-2-yl}-4-[(4-methyl-1H-indol-5-yl)amino]nicotinonitrile, 4-[(4-methyl-1H-indol-5-yl)amino]-5-[5-(morpholin-4-ylmethyl)-1-benzofuran-2-yl]nicotinonitrile,
4-[(4-methyl-1H-indol-5-yl)amino]-5-[5-(pyrrolidin-1-ylmethyl)-1-benzofuran-2-yl]nicotinonitrile,
4-[(4-methyl-1H-indol-5-yl)amino]-5-(5-{[(2-pyrrolidin-1-ylethyl) amino]methyl}-1-benzofuran-2-yl)nicotinonitrile,
4-[(4-methyl-1H-indol-5-yl)amino]-5-[5-({[(1-methylpiperidin-4-yl)methyl]amino}methyl)-1-benzofuran-2-yl]nicotinonitrile,
5-(5-}[4-(hydroxymethyl)piperidin-1-yl]methyl}-1-benzofuran-2-yl)-4-[(4-methyl-1H-indol-5-yl)amino]nicotinonitrile,
4-[(4-methyl-1H-indol-5-yl)amino]-5-{5-[(4-pyrrolidin-1-ylpiperidin-1H) methyl]-1-benzofuran-2-yl}nicotinonitrile,
5-[5-(1,4'-bipiperidin-t-ylmethyl)-1-benzofuran-2-yl]-4-[(4-methyl-1H-indol-5-yl)amino]nicotinonitrile,
4-[(4-methyl-1H-indol-5-yl)amino]-5-{5-[(4-morpholin-4-ylpiperidin-1-yl) methyl]-1-benzofuran-2-yl}nicotinonitrile,
5-[5-({4-[2-(dimethylamino)ethyl]piperazin-1-yl}-methyl)-1-benzofuran-2-yl]-4-[(4-methyl-1H-indol-5-yl)amino]nicotinonitrile,
4-[(4-methyl-1H-indol-5-yl)amino]-5-{5'[(4-pyridin-2-ylpiperazin-1-yl)methyl]-1-benzofuran-2-yl}nicotinonitrile,
4-[(4-methyl-1H-indol-5-yl)amino]-5-(5-{[(pyridin-2-ylmethyl)amino]methyl}-1-benzofuran-2-yl)nicotinonitrile,
4-[(4-methyl-1H-indol-5-yl)amino]-5-(5-{[(pyridin-3-ylmethyl)amino]methyl}-1-benzofuran-2-yl)nicotinonitrile,
4-[(4-methyl-1H-indol-5-yl)amino]-5-(5-{[(pyridin-4-ylmethyl)amino]methyl}-1-benzofuran-2-yl)nicotinonitrile,
4-[(4-methyl-1H-indol-5-yl)amino]-5-[5-(morpholin-4-ylmethyl)-2-furyl]nicotinonitrile,
4-[(4-methyl-1H-indol-5-yl)amino]-5-[5-(piperidin-1-ylmethyl)-2-furyl]nicotinonitrile,
5-[5-(1,4'-bipiperidin-1-ylmethyl)-2-furyl]-4-[(4-methyl-1H-indol-5-yl) amino]nicotinonitrile,
4-[(4-methyl-1H-indol-5-yl)amino]-5-{5-[(4-pyrrolidin-1-ylpiperidin-1-yl) methyl]-2-furyl}nicotinonitrile,
4-[(4-methyl-1H-indol-5-yl)amino]-5-[5-[(4-morpholin-4-ylpiperidin-1-yl) methyl]-2-furyl]nicotinonitrile,
5-{5-[(diethylamino)methyl]-2-furyl}-4-[(4-methyl-1H-indol-5-yl)amino]nicotinonitrile,
5-{5-[(dibutylamino)methyl]-2-furyl}-4-[(4-methyl-1H-indol-5-yl)amino]nicotinonitrile,
5-{5-[(benzylamino)methyl]-2-furyl}-4-[(4-methyl-1H-indol-5-yl)amino]nicotinonitrile,
4-[(4-methyl-1H-indol-5-yl)amino]-5-(5-{[(3-phenylpropyl)amino]methyl}-2-furyl)nicotinonitrile,
4-[(4-methyl-1H-indol-5-yl)amino]-5-[5-(pyrrolidin-1-ylmethyl)-2-furyl]nicotinonitrile,
4-[(4-methyl-1H-indol-5-yl)amino]-5-[5-(thiomorpholin-4-ylmethyl)-2-furyl]nicotinonitrile,
5-(3,4-dimethoxyphenyl)-4-[(6-methyl-1H-indol-5-yl)amino]nicotinonitrile,
5-(1-benzofuran-2-yl)-4-[(6-methyl-1H-indol-5-yl)amino]nicotinonitrile,
5-(4-{2-[(2-hydroxyethyl)amino]ethoxy}phenyl)-4-[(4-methyl-1H-indol-5-yl) amino]nicotinonitrile,
5-(4-{2-[(3-hydroxypropyl)amino]ethoxy}phenyl)-4-[(4-methyl-1H-indol-5-yl) amino]nicotinonitrile,
5-(4-{2-[(2-ethoxyethyl)amino]ethoxy}phenyl)-4-[(4-methyl-1H-indol-5-yl) amino]nicotinonitrile,
5-[4-(2-{[2-(dimethylamino)ethyl]amino}ethoxy)phenyl]-4-[(4-methyl-1H-indol-5-yl)amino]nicotinonitrile,
4-[(4-methyl-1H-indol-5-yl)amino]-5-[4-(2-pyrrolidin-1-ylethoxy)phenyl]nicotinonitrile,
5-{-4-[2-(benzylamino)ethoxy]phenyl}-4-[(4-methyl-1H-indol-5-yl)amino]nicotinonitrile,
4-[(4-methyl-1H-indol-5-yl)(amino]-5-(4-{2-[(1-methylpiperidin-4-yl)amino]ethoxy}phenyl)nicotinonitrile,
4-[(4-methyl-1H-indol-5-yl)amino]-5-[4-(2-{[(1-methylpiperidin-4-yl)methyl]amino}ethoxy)phenyl]nicotinonitrile,
5-(4-{2-[4-(hydroxymethyl)piperidin-1-yl] ethoxy}phenyl)-4-[(4-methyl-1H-indol-5-yl)amino] nicotinonitrile,
4-[(4-methyl-1H-indol-5-yl)amino]-5-{4-[2-(4-pyrrolidin-1-ylpiperidin-1H) ethoxy]phenyl}nicotinonitrile,
4-[(4-methyl-1H-indol-5-yl)amino]-5-{4-[2-(4-morpholin-4-ylpiperidin-1-yl) ethoxy]phenyl}nicotinonitrile,
5-{4-[2-(4-ethylpiperazin-1-yl)ethoxy]phenyl}-4-[(4-methyl-1H-indol-5-yl) amino]nicotinonitrile,
5-{4-[2-(4-methyl-1,4-diazepan-1-yl)ethoxy]phenyl}-4-[(4-methyl-1H-indol-5-yl)amino]nicotinonitrile,
5-(4-{2-[4-(2-hydroxyethyl)piperazin-1-yl] ethoxy}phenyl)-4-[(4-methyl-1H-indol-5-yl)amino] nicotinonitrile,
5-[4-(2-{4-[2-(dimethylamino)ethyl]piperazin-1-yl}ethoxy)phenyl]-4-[(4-methyl-1H-indol-5-yl)amino] nicotinonitrile,
5-[4-(2-{[3-(1H-imidazol-1-yl)propyl]amino}ethoxy) phenyl]-4-[(4-methyl-1H-indol-5-yl)amino]nicotinonitrile,
4-[(4-methyl-1H-indol-5-yl)amino]-5-{4-[2-(4-pyridin-2-ylpiperazin-1-yl) ethoxy]phenyl}nicotinonitrile,
4-[(4-methyl-1H-indol-5-yl)amino]-5-{4-[2-(4-pyridin-4-ylpiperazin-1-yl) ethoxy]phenyl}nicotinonitrile,
4-[(4-methyl-1H-indol-5-yl)amino]-5-(4-{2-(pyridin-2-ylmethyl)amino]ethoxy}phenyl)nicotinonitrile,
4-[(4-methyl-1H-indol-5-yl)amino]-5-(4-{2-(pyridin-3-ylmethyl)amino]ethoxy}phenyl)nicotinonitrile,
4-[(4-methyl-1H-indol-5-yl)amino]-5-(4-{2-(pyridin-4-ylmethyl)amino]ethoxy}phenyl)nicotinonitrile,
4-[(4-methyl-1H-indol-5-yl)amino]-5-{-4-[2-(4-phenylpiperidin-1-yl)ethoxy]phenyl}nicotinonitrile,
5-(5-{[4-(dimethylamino)piperidin-1-yl]methyl}-2-furyl)-4-[(4-methyl-1H-indol-5-yl)amino]nicotinonitrile,
5-{5-[(4-isopropylpiperazin-1-yl)methyl]-2-furyl}-4-[(4-methyl-1H-indol-5-yl) amino]nicotinonitrile,
4-[(4-methyl-1H-indol-5-yl)amino]-5-{5-[2-(4-methylpiperazin-1-yl)ethoxy]-1-benzofuran-2-yl}nicotinonitrile,
4-[(4-methyl-1H-indol-5-yl)amino]-5-{4-[4-methylpiperazin-1-yl)methyl]phenyl}nicotinonitrile,
4-[(4-methyl-1H-indol-5-yl)amino]-5-[4-(pyrrolidin-1-ylmethyl)phenyl]nicotinonitrile,
4-[(4-methyl-1H-indol-5-yl)amino]-5-[4-(morpholin-4-ylmethyl)phenyl]nicotinonitrile,
5-{4-(dimethylamino)methyl]phenyl}-4-[(4-methyl-1H-indol-5-yl)amino]nicotinonitrile,
4-[(4-methyl-1H-indol-5-yl)amino]-2'-(morpholin-4-ylmethyl)-3,4'-bipyridine-5-carbonitrile,
4-[(4-methyl-1H-indol-5-yl)amino]-5-{3-[(4-methylpiperazin-1-yl)methyl]phenyl}nicotinonitrile,
4-[(4-methyl-1H-indol-5-yl)amino]-5-[3-(pyrrolidin-1-ylmethyl)phenyl]nicotinonitrile, 4-1(4-methyl-1H-indol-5-yl)amino)-5-{3-(morpholin-4-ylmethyl)phenyl}nicotinonitrile,
5-{3-[(dimethylamino)methyl]phenyl}-4-[(4-methyl-1H-indol-5-yl)amino]nicotinonitrile,
5-(4-{[(2R)-2-amino-3-phenylpropyl]oxy}phenyl)-4-(1H-indol-4-ylamino) nicotinonitrile,
5-{2-fluoro-4-[(4-methylpiperazin-1-yl)methyl]phenyl}-4-[(4-methyl-1H-indol-5-yl)amino]nicotinonitrile,
5-[4-(3-chloropropoxy)phenyl]-4-[(4-methyl-1H-indol-5-yl)amino]nicotinonitrile,
4-[(4-methyl-1H-indol-5-yl)amino]-5-[5-(piperidin-1-ylmethyl)-1-benzofuran-2-yl]nicotinonitrile,
4-[(4-methyl-1H-indol-5-yl)amino]-5-{(5-[(4-methylpiperazin-1-yl)methyl]-1-benzofuran-2-yl}nicotinonitrile,
5-(5-formyl-2-thienyl)-4-[(4-methyl-1H-indol-5-yl)amino]nicotinonitrile,
4-[(4-methyl-1H-indol-5-yl)amino]-5-{5-[(4-methylpiperazin-1-yl)methyl]-2-thienyl}nicotinonitrile,
5-(5-formyl-1-benzofuran-2-yl)-4-[(4-methyl-1H-indol-5-yl)amino]nicotinonitrile,
5-(3-methyl-1-benzofuran-2-yl)-4-[(4-methyl-1H-indol-5-yl)amino]nicotinonitrile,
4-[(4-methyl-1H-indol-5-yl)amino]-3,4'-bipyridine-5-carbonitrile,
4-[(4-methyl-1H-indol-5-yl)amino]-5-{5-[(4-methylpiperazin-1-yl)methyl]-2-furyl}nicotinonitrile,
2'-chloro-4-[(4-methyl-1H-indol-5-yl)amino]-3,4'-bipyridine-5-carbonitrile,
5-{2-chloro-4-[2-(4-methylpiperazin-1-yl)ethoxy]phenyl}-4-[(4-methyl-1H-indol-5-yl)amino]nicotinonitrile,
2'-chloro-4-[(4-methyl-1H-indol-5-yl)amino]-3,3'-bipyridine-5-carbonitrile,
4-[(4-methyl-1H-indol-5-yl)amino]-5-{4-[3-(4-methylpiperazin-1-yl)propoxy]phenyl}nicotinonitrile,
4-[(4-methyl-1H-indol-5-yl)amino]-5-[4-(3-morpholin-4-ylpropoxy)phenyl]nicotinonitrile,
4-[(4-methyl-1H-indol-5-yl)amino]-5-[4-(3-piperidin-1-ylpropoxy)phenyl]nicotinonitrile,
5-{4-[3-(dimethylamino)propoxy]phenyl}-4-[(4-methyl-1H-indol-5-yl)amino]nicotinonitrile,
5-[3,4-bis(2-methoxyethoxy)phenyl]-4-[(4-methyl-1H-indol-5-yl)amino]nicotinonitrile,
5-[3-methoxy-4-(2-methoxyethoxy)phenyl]-4-[(4-methyl-1H-indol-5-yl) amino]nicotinonitrile,
5-[5-(hydroxymethyl)-1-benzofuran-2-yl]-4-[(4-methyl-1H-indol-5-yl)amino]nicotinonitrile,
5-[4-(2-methoxyethoxy)phenyl]-4-[(4-methyl-1H-indol-5-yl)amino]nicotinonitrile,
5-[3-(2-methoxyethoxy)phenyl]-4-[(4-methyl-1H-indol-5-yl)amino]nicotinonitrile,
5-(5-formyl-1-benzofuran-2-yl)-4-(1H-indol-5-ylamino)nicotinonitrile,
4-(1H-indol-5-ylamino)-5-{5-[(4-methylpiperazin-1-yl)methyl]-1-benzofuran-2-yl}nicotinonitrile,
5-{5-[(4-cyclopentylpiperazin-1-yl)methyl]-2-furyl}-4-[(4-methyl-1H-indol-5-yl) amino]nicotinonitrile,
5-{5-[(1,1-dioxidothiomorpholin-4-yl)methyl]-2-furyl}-4-[(4-methyl-1H-indol-5-yl)amino]nicotinonitrile,
5-[(5-formyl-2-furyl)-4-[(4-methyl-1H-indol-5-yl)amino] nicotinonitrile,
5-[4-(4-chlorobutoxy)phenyl]-4-[(4-methyl-1H-indol-5-yl)-amino]nicotinonitrile,
4-[(4-methyl-1H-indol-5-yl)amino]-5-{4-[4-(4-methylpiperazin-1-yl)butoxy]phenyl}nicotinonitrile,
5-[4-(2-chloroethoxy)phenyl]-4-[(6-methyl-1H-indol-5-yl)amino]nicotinonitrile,
5-(5-formyl-1-benzofuran-2-yl)-4-[(6-methyl-1H-indol-5-yl)amino]nicotinonitrile,
4-[(6-methyl-1H-indol-5-yl)amino]-5-{4-[2-(4-methylpiperazin-1-yl)ethoxy]phenyl}nicotinonitrile,
4-[(6-methyl-1H-indol-5-yl)amino]-5-{5-[(4-methylpiperazin-1-ylmethyl]-1-benzofuran-2-yl}nicotinonitrile,
4-[(7-chloro-4-methyl-1H-indol-5-yl)amino]-5-(3,4-dimethoxyphenyl)nicotinonitrile,
5-[5-(hydroxymethyl)-1-benzofuran-2-yl]-4-[(6-methyl-1H-indol-5-yl)amino]nicotinonitrile,
5-{5-[(diethylamino)methyl]-1-benzofuran-2-yl}-4-[(6-methyl-1H-indol-5-yl)amino]nicotinonitrile,
5-[3-(4-chlorobutoxy)phenyl]-4-[(4-methyl-1H-indol-5-yl)amino]nicotinonitrile,
4-[(4-methyl-1H-indol-5-yl)amino]-5-{3-[4-(4-methylpiperazin-1-yl)butoxy]phenyl}nicotinonitrile,
4-[(4-methyl-1H-indol-5-yl)amino]-5-{5-[(4-methylpiperazin-1-ylmethyl]-3-furyl}nicotinonitrile,
4-[(6-methyl-1H-indol-5-yl)amino]-5-[4-(2-piperidin-1-ylethoxy)phenyl]nicotinonitrile,
5-{4-[2-(4-hydroxypiperidin-1-yl)ethoxy]phenyl}-4-[(6-methyl-1H-indol-5-yl) amino]nicotinonitrile,
4-[(6-methyl-1H-indol-5-yl)amino]-5-{4-[2-(4-pyrrolidin-1-ylpiperidin-1-yl)ethoxy]phenyl}nicotinonitrile,
4-[(4-methyl-1H-indol-5-yl)amino]-6'-morpholin-4-yl-3,3'-bipyridine-5-carbonitrile,
4-[(4-methyl-1H-indol-5-yl)amino]-6'-piperidin-1-yl-3,3'-bipyridine-5-carbonitrile,
4-[(4-methyl-1H-indol-5-yl)amino]-5-pyrimidin-5-ylnicotinonitrile,
4-[(4-methyl-1H-indol-5-yl)amino]-5-(2-piperidin-1-ylpyrimidin-5-yl) nicotinonitrile,
4-[(4-methyl-1H-indol-5-yl)amino]-5-(2-morpholin-4-ylpyrimidin-5-yl) nicotinonitrile,
4-[(4-methyl-1H-indol-5-yl)amino]-5-(2-pyrrolidin-1-ylpyrimidin-5-yl) nicotinonitrile,
5-[2-(dimethylamino)pyrimidin-5-yl]-4-[(4-methyl-1H-indol-5-yl)amino]nicotinonitrile,
5-(1-benzothien-2-yl)-4-[(4-methyl-1H-indol-5-yl) amino]nicotinonitrile,
5-[4-(2-chloroethoxy)phenyl]-4-(1H-indol-5-ylamino) nicotinonitrile,
5-(5-formyl-3-thienyl)-4-[(4-methyl-1H-indol-5-yl) amino]nicotinonitrile,
5-(4-formyl-2-furyl)-4-[(4-methyl-1H-indol-5-yl)amino] nicotinonitrile,
4-[(4-methyl-1H-indol-5-yl)amino]-5-{5-[(4-methylpiperazin-1-yl)methyl]-3-thienyl}nicotinonitrile,
4-[(4-methyl-1H-indol-5-yl)amino]-3,3'-bipyridine-5-carbonitrile,
4-(1H-indol-5-ylamino)-5-{4-[2-(4-methylpiperazin-1-yl)ethoxy]phenyl}nicotinonitrile,
4-[(4-methyl-1H-indol-5-yl)amino]-5-{5-[(4-methylpiperazin-1-yl)methyl]-1-benzothien-2-yl}nicotinonitrile,
1-butyl-3-(4-{5-cyano-4-[(4-methyl-1H-indol-5-yl)amino]pyridin-3-yl}phenyl)urea,
methyl (4-{5-cyano-[4-[(4-methyl-1H-indol-5-yl)amino]pyridin-3-yl}phenyl)carbamate,
benzyl (4-{5-cyano-4-[(4-methyl-1H-indol-5-yl)amino]pyridin-3-yl}-2-fluorophenyl)carbamate,
4-methoxybenzyl (4-{5-cyano-4-[(4-methyl-1H-indol-5-yl)amino]pyridin-3-yl}-2-fluorophenyl)carbamate,
4-[(7-chloro-4-methyl-1H-indol-5-yl)amino]-5-{5-[(4-methylpiperazin-1-yl) methyl]-1-benzofuran-2-yl}nicotinonitrile,
5-(3,4-dimethoxyphenyl)-4-[(4-methyl-1H-indol-7-yl)amino]nicotinonitrile, 5-(1-benzofuran-2-yl)-4-[(7-chloro-4-methyl-1H-indol-5-yl)amino]nicotinonitrile,
4-[(7-chloro-4-methyl-1H-indol-5-yl)amino]-5-(5-formyl-1-benzofuran-2-yl) nicotinonitrile,
5-[4-(2-chloroethoxy)phenyl]-4-[(7-chloro-4-methyl-1H-indol-5-yl)amino]nicotinonitrile,
4-[(7-chloro-4-methyl-1H-indol-5-yl)amino]-5-{-4-[2-(dimethylamino)ethoxy]phenyl}nicotinonitrile,
4-[(7-chloro-4-methyl-1H-indol-5-yl)amino]-5-{4-[2-(4-methylpiperazin-1-yl)ethoxy]phenyl}nicotinonitrile,
tert-butyl 4-[(2-{5-cyano-4-[(4-methyl-1H-indol-5-yl)amino]pyridin-3-yl}-1-benzofuran-5-yl)methyl]piperazine-1-carboxylate,
5-(2-formyl-1-methyl-1H-imidazol-5-yl)-4-[(4-methyl-1H-indol-5-yl)amino]nicotinonitrile,
4-[4-methyl-1H-indol-5-yl)amino]-5-(5-{[4-(methylsulfonyl)piperazin-1-yl]methyl}-1-benzofuran-2-yl)nicotinonitrile,
4-[(4-methyl-1H-indol-5-yl)amino]-5-{1-methyl-2-[(4-methylpiperazin-1-yl)methyl]-1H-imidazol-5-yl}nicotinonitrile,
4-[(4-methyl-1H-indol-5-yl)amino]-5-[5-(piperazin-1-ylmethyl)-1-benzofuran-2-yl]nicotinonitrile,
4-[(4-methyl-1H-indol-5-yl)amino]-5-(1,3-thiazol-2-yl) nicotinonitrile,
5-(1-methyl-1H-imidazol-2-yl)-4-[(4-methyl-1H-indol-5-yl)amino]nicotinonitrile,
4-[(4-methyl-1H-indol-5-yl)amino]-5-(1,3-thiazol-4-yl) nicotinonitrile,
5-(3,4-dimethoxyphenyl)-4-(1H-indol-7-ylamino)nicotinonitrile,
5-(3,4-dimethoxyphenyl)-4-[(4-methoxy-1H-indol-5-yl)amino]nicotinonitrile,
5-(3,4-dimethoxyphenyl)-4-[(4-fluoro-1H-indol-5-yl)amino]nicotinonitrile,
4-[(7-chloro-4-methyl-1H-indol-5-yl)amino]-5-[5-(piperazin-1-ylmethyl)-1-benzofuran-2-yl]nicotinonitrile,
tert-butyl 4-[(2-{4-[(7-chloro-4-methyl-1H-indol-5-yl)amino]-5-cyanopyridin-3-yl}-1-benzofuran-5-yl)methyl]piperazine-1-carboxylate,
5-(3,4-dimethoxyphenyl)-4-[(2,4-dimethyl-1H-indol-5-yl]-amino]nicotinonitrile,
5-{2-(dimethylamino)methyl]phenyl}-4-[(4-methyl-1H-indol-5-yl)amino]nicotinonitrile,
5-(5-formyl-2-methoxyphenyl)-4-[(4-methyl-1H-indol-5-yl)amino]nicotinonitrile,
5-{2-methoxy-5-[(4-methylpiperazin-1-yl)methyl]phenyl}-4-[(4-methyl-1H-indol-5-yl)amino]nicotinonitrile,
5-{5-[(4-ethylpiperazin-1-yl)methyl]-1-benzofuran-2-yl}-4-[(4-methyl-1H-indol-5-yl)amino]nicotinonitrile,
4-[(4-methyl-1H-indol-5-yl)amino]-5-{5-[(4-methyl-4-oxidopiperazin-1-yl)methyl]-1-benzofuran-2-yl}nicotinonitrile,
5-(3,4-dimethoxyphenyl)-4-[(1,4-dimethyl-1H-indol-5-yl)amino]nicotinonitrile,
3-{5-cyano-4-[(4-methyl-1H-indol-5-yl)amino]pyridin-3-yl}benzoic acid,
5-(2-methoxyphenyl)-4-[(4-methyl-1H-indol-5-yl)amino]nicotinonitrile,
5-(3-methoxyphenyl)-4-[(4-methyl-1H-indol-5-yl)amino]nicotinonitrile,
5-(4-methoxyphenyl)-4-[(4-methyl-1H-indol-5-yl)amino]nicotinonitrile,
4-[(4-methyl-1H-indol-5-yl)amino]-5-phenylnicotinonitrile,
4-[(4-methyl-1H-indol-5-yl)amino]-5-(2-thienyl)nicotinonitrile,
4-[(4-methyl-1H-indol-5-yl)amino]-5-(3-thienyl)nicotinonitrile,
5-(3-furyl)-4-[(4-methyl-1H-indol-5-yl)amino]nicotinonitrile,
H-imidazol-5-yl)-4-[(4-methyl-1H-indol-5-yl)amino] nicotinonitrile,
4'-[(4-methyl-1H-indol-5-yl)amino]-2,3'-bipyridine-5'-carbonitrile,
1-(4-{5-cyano-4-[(4-methyl-1H-indol-5-yl)amino]pyridin-3-yl}phenyl)-3-cyclopropylurea,
1-(4-{5-cyano-4-[(4-methyl-1H-indol-5-yl)amino]pyridin-3-yl}phenyl)-3-methylurea,
3-(4-[5-cyano-4-[(4-methyl-1H-indol-5-yl)amino]pyridin-3-yl}phenyl)-1,1-dimethylurea,
N-(4-{5-cyano-4-[(4-methyl-1H-indol-5-yl)amino]pyridin-3-yl)phenyl) morpholine-4-carboxamide,
4-[(4-methyl-1H-indol-5-yl)amino]-5-(4-nitrophenyl) nicotinonitrile,
5-(4-aminophenyl)-4-[(4-methyl-1H-indol-5-yl)amino] nicotinonitrile,
5-(3-aminophenyl)-4-[(4-methyl-1H-indol-5-yl)amino] nicotinonitrile,
5-(2-aminophenyl)-4-[(4-methyl-1H-indol-5-yl)amino] nicotinonitrile,
5-[4-(dimethylamino)phenyl]-4-[(4-methyl-1H-indol-5-yl)amino]nicotinonitrile,
5-[3-(dimethylamino)phenyl]-4-[(4-methyl-1H-indol-5-yl)amino]nicotinonitrile,
N-(4-{5-cyano-4-[(4-methyl-1H-indol-5-yl)amino]pyridin-3-yl}phenyl)acetamide,
N-(2-{5-cyano-4-[(4-methyl-1H-indol-5-yl)amino]pyridin-3-yl}phenyl)acetamide,
N-(3-{5-cyano-4-[(4-methyl-1H-indol-5-yl)amino]pyridin-3-yl}phenyl)acetamide,
N-(4-{5-cyano-4-[(4-methyl-1H-indol-5-yl)amino]pyridin-3-yl}phenyl)-2-methylpropanamide,
4-{5-cyano-4-[(4-methyl-1H-indol-5-yl)amino]pyridin-3-yl}-N-methyl benzamide,
4-[(4-methyl-1H-indol-5-yl)amino]-5-(1-naphthyl)nicotinonitrile,
4-[4-methyl-1H-indol-5-yl)amino]-5-(2-naphthyl)nicotinonitrile,
4-[(4-methyl-1H-indol-5-yl)amino]-5-(1-methyl-1H-pyrazol-5-yl)nicotinonitrile,
4-[(4-methyl-1H-indol-5-yl)amino]-5-(1H-pyrazol-4-yl) nicotinonitrile,
5-(1-benzothiophen-3-yl)-4-[(4-methyl-1H-indol-5-yl) amino]nicotinonitrile,
H-indol-2-yl)-4-[(4-methyl-1H-indol-5-yl)amino]nicotinonitrile,
5-(1H-indol-5-yl)-4-[(4-methyl-1H-indol-5-yl)amino] nicotinonitrile,
5-(1H-indol-6-yl)-4-[(4-methyl-1H-indol-5-yl)amino] nicotinonitrile,
4-[(4-methyl-1H-indol-5-yl)amino]-5-quinolin-3-ylnicotinonitrile,
4-[(4-methyl-1H-indol-5-yl)amino]-5-quinolin-8-ylnicotinonitrile,
5-(1-benzofuran-5-yl)-4-[(4-methyl-1H-indol-5-yl) amino]nicotinonitrile,
4-(4-methyl-1H-indol-5-ylamino)-5-(quinolin-5-yl)nicotinonitrile,
5-(dibenzo[b,d]thiophen-3-yl)-4-(4-methyl-1H-indol-5-ylamino)nicotinonitrile, 5-(benzo[b]thiophen-5-yl)-4-(4-methyl-1H-indol-5-ylamino)nicotinonitrile, 5-(1H-indol-4-yl)-4-(4-methyl-1H-indol-5-ylamino)nicotinonitrile, 4-[(2,4-dimethyl-1H-indol-5-yl)amino]-5-{5-[(4-methylpiperazin-1-yl)methyl]-1-benzofuran-2-yl}nicotinonitrile, 4-4(2,4-dimethyl-1H-indol-5-yl)amino-1-5-[5-(piperazin-1-ylmethyl)-1-benzofuran-2-yl]nicotinonitrile, 4-[4-methyl-1H-indol-5-yl)amino]-5-[6-[(4-methylpiperazin-1-yl)methyl]-1-benzofuran-2-yl}nicotinonitrile, 4-[(4-methyl-1H-indol-5-yl)amino]-5-[6-(piperazin-1-ylmethyl)-1-benzofuran-2-yl]nicotinonitrile, 4-[(4-methyl-1H-indol-5-yl)amino]-5-{4-(piperazin-1-yl)methyl]phenyl}nicotinonitrile, 4-[(2,4-dimethyl-1H-indol-5-yl)amino]-5-{4-[(4-methylpiperazin-1-yl)methyl]phenyl}nicotinonitrile, 4-(2,4-dimethyl-1H-indol-5-ylamino)-5-{3-[2-(4-methylpiperazin-1-yl)ethoxy]phenyl}nicotinonitrile, 5-{4-[2-(dimethylamino)ethoxy]-3-methoxyphenyl}-4-[(2,4-dimethyl-1H-indol-5-yl)amino]nicotinonitrile, 4-[(2,4-dimethyl-1H-indol-5yl)amino]-5-{4-[2-(4-methylpiperazin-1-yl)ethoxy]phenyl}nicotinonitrile, 4-[(4-methyl-1H-indol-5-yl]-amino]-5-{4-[2-(piperazin-1-yl]ethoxy]phenyl}nicotinonitrile, 4-(4-methyl-1H-indol-5-ylamino)-2'-((4-methylpiperazin-1-yl)methyl)-3,4'-bipyridine-5-carbonitrile, 4-(4-methyl-1H-indol-5-ylamino)-2'-((piperazin-1-yl)methyl)-3,4'-bipyridine-5-carbonitrile, 4'-(4-methyl-1H-indol-5-ylamino)-5-((4-methylpiperazin-1-yl)methyl)-2,3'-bipyridine-5-carbonitrile, 4'-(4-methyl-1H-indol-5-ylamino)-5-(morpholinomethyl)-2,3'-bipyridine-5'-carbonitrile, 4'-(4-methyl-1H-indol-5-ylamino)-5-((4(piperazin-1-yl)methyl)-2,3'-bipyridine-5-carbonitrile, 4'-(4-methyl-1H-indol-5-ylamino)-6-((4-methylpiperazin-1-yl)methyl)-2,3'-bipyridine-5'-carbonitrile, 4'-(4-methyl-1H-indol-5-ylamino)-6-(morpholinomethyl)-2,3'-bipyridine-5-carbonitrile, 4'-(4-methyl-1H-indol-5-ylamino)-6-((piperazin-1-yl)methyl)-2,3'-bipyridine-5'-carbonitrile, 4'-(4-methyl-1H-indol-5-ylamino)-4-(morpholinomethyl)-2,3'-bipyridine-5-carbonitrile, 4'-(4-methyl-1H-indol-5-ylamino)-4-((4-methylpiperazin-1-yl)methyl)-2,3'-bipyridine-5-carbonitrile, 4'-(4-methyl-1H-indol-5-ylamino)-4-((piperazin-1-ylmethyl)-2,3'-bipyridine-5'-carbonitrile, 4-(4-methyl-1H-indol-5-ylamino)-5-4(4-methylpiperazin-1-yl)methyl)-3,3'-bipyridine-5-carbonitrile, 4-(4-methyl-1H-indol-5-ylamino)-5'-((4(piperazin-1-yl)methyl)-3,3'-bipyridine-5-carbonitrile, 4-(4-methyl-1H-indol-5-ylamino)-5-(morpholinomethyl)-3,3'-bipyridine-5-carbonitrile, 4-(4-methyl-1H-indol-5-ylamino)-6'-((4-methylpiperazin-1-yl)methyl)-3,3'-bipyridine-5-carbonitrile.

4-(4-methyl-1H-indol-5-ylamino)-6'-((piperazin-1-yl)methyl)-3,3'-bipyridine-5-carbonitrile, 4-(4-methyl-1H-indol-5-ylamino)-6'-(morpholinomethyl)-3,3'-bipyridine-5-carbonitrile, 4-(4-methyl-1H-indol-5-ylamino)-5-(3-(piperazin-1-ylmethyl)phenyl)nicotinonitrile, 4-(4-methyl-1H-indol-5-ylamino)-5-(4-(piperazin-1-ylmethyl)phenyl)nicotinonitrile, and 5-(3,4-dimethoxyphenyl)-4-(1H-indol-5-ylamino)nicotinonitrile 1-oxide.

18. The compound of any one of claim 1, wherein the compound is in the form of an enantiomer.

19. A pharmaceutical composition comprising the compound of claim 1 and a pharmaceutically acceptable carrier or excipient.

20. The compound of claim 1 or 2 or a pharmaceutically acceptable salt, hydrate, or ester thereof, wherein X is NH or $NCH_3$; $R^1$ is an indolyl group optionally substituted with 1-4 groups selected from halogen, —O—Y—$R^5$, —$NR^6$—Y—$^7$, a $C_{1-10}$ alkyl group and a $C_{1-10}$ haloalkyl group; and $R^2$ is a $C_{6-14}$ aryl group or a 5-14 membered heteroaryl group selected from furyl, thienyl, benzothienyl, benzofuranyl, pyrazolyl, pyridyl, indolyl, quinolinyl, pyrimidinyl, imidazolyl, thiazolyl isothiazolyl, oxazolyl, isoxazolyl, dibenzothienyl, dibenzofuranyl, benzodioxolyl and benzodioxanyl, wherein each group optionally is substituted with 1-4 groups independently selected from —Y—$R^4$ or —O—Y—$R^4$.

\* \* \* \* \*